United States Patent
Harigae et al.

(10) Patent No.: US 10,945,434 B2
(45) Date of Patent: Mar. 16, 2021

(54) AZOLE DERIVATIVE, INTERMEDIATE COMPOUND, METHOD FOR PRODUCING AZOLE DERIVATIVE, AGRICULTURAL OR HORTICULTURAL CHEMICAL AGENT, AND PROTECTIVE AGENT FOR INDUSTRIAL MATERIAL

(71) Applicant: Kureha Corporation, Tokyo (JP)

(72) Inventors: Ryo Harigae, Tokyo (JP); Atsushi Ito, Tokyo (JP); Taiji Miyake, Tokyo (JP); Toru Yamazaki, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 16/636,502

(22) PCT Filed: Nov. 13, 2018

(86) PCT No.: PCT/JP2018/041971
§ 371 (c)(1),
(2) Date: Feb. 4, 2020

(87) PCT Pub. No.: WO2019/093522
PCT Pub. Date: May 16, 2019

(65) Prior Publication Data
US 2020/0288714 A1    Sep. 17, 2020

(30) Foreign Application Priority Data

Nov. 13, 2017    (JP) .............................. JP2017-218655

(51) Int. Cl.
A01N 43/653    (2006.01)
C07D 249/08    (2006.01)

(52) U.S. Cl.
CPC ......... *A01N 43/653* (2013.01); *C07D 249/08* (2013.01)

(58) Field of Classification Search
None
See application file for complete search history.

(56) References Cited

U.S. PATENT DOCUMENTS

| | | | |
|---|---|---|---|
| 4,533,659 A | 8/1985 | Eckhardt et al. | |
| 10,358,426 B2 * | 7/2019 | Dietz | C07D 249/08 |
| 2013/0096299 A1 | 4/2013 | Kusano et al. | |
| 2014/0155262 A1 | 6/2014 | Dietz et al. | |
| 2017/0081296 A1 | 3/2017 | Dietz et al. | |

FOREIGN PATENT DOCUMENTS

| | | |
|---|---|---|
| CN | 103649057 A | 3/2014 |
| EP | 0 099 165 A1 | 1/1984 |
| EP | 2731935 B1 | 3/2016 |
| JP | S58-170770 A | 10/1983 |
| JP | S59-31766 A | 2/1984 |
| JP | 2014-520832 A | 8/2014 |
| WO | 93/11118 A1 | 6/1993 |
| WO | 2011/136268 A1 | 11/2011 |
| WO | 2012/125533 A1 | 9/2012 |
| WO | 2013/007767 A1 | 1/2013 |
| WO | 2014/082871 A1 | 6/2014 |
| WO | 2014/082881 A1 | 6/2014 |
| WO | 2014/095548 A1 | 6/2014 |
| WO | 2014/095672 A1 | 6/2014 |
| WO | 2015/185708 A1 | 12/2015 |
| WO | 2017/029179 A1 | 2/2017 |

OTHER PUBLICATIONS

English translation of Search Report of the Intellectual Property Office of China for CN 201880050458.4 with search date of Jun. 3, 2020.
English translation of Office Action of the Intellectual Property Office of China for CN 201880050458.4 dated Jun. 11, 2020.
Notification of Reason for Refusal of the Intellectual Property Office of Korea for KR 10-2020-7002610 dated May 1, 2020.
English translation of Notification of Reason for Refusal of the Intellectual Property Office of Korea for KR 10-2020-7002610 dated May 1, 2020.
Search Report of the Intellectual Property Office of China for CN 201880050458.4 with search date of Jun. 3, 2020. English-language version to be submitted when available.

(Continued)

*Primary Examiner* — Kamal A Saeed
(74) *Attorney, Agent, or Firm* — Abel Schillinger, LLP

(57) ABSTRACT

It is provided a plant disease controlling agent having low toxicity to human and animals and excellent handling safety, and showing excellent controlling effects on various plant diseases and high antibiotic action to plant disease germs. A compound represented by the following the general formula (I), or an N-oxide or agrochemically acceptable salt thereof.

[Chemical Formula 1]

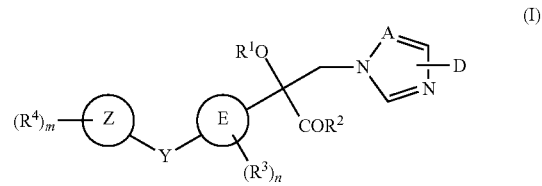

15 Claims, No Drawings

(56) References Cited

OTHER PUBLICATIONS

Office Action of the Intellectual Property Office of China for CN 201880050458.4 dated Jun. 11, 2020. English-language version to be submitted when available.
Translation of the International Preliminary Report on Patentability (Chapter I) for PCT/JP2018/041971 dated May 19, 2020.
Notification of Reasons for Refusal of the Intellectual Property Office of Japan for JP 2019-552425 dated Apr. 7, 2020.
English translation of Notification of Reasons for Refusal of the Intellectual Property Office of Japan for JP 2019-552425 dated Apr. 7, 2020.
Office Action of the Intellectual Property Office of Canada for CA 3,071,569 dated Apr. 6, 2020.
Guo, S. et al., "Metal-free oxidative esterification of acetophenones with alcohols: a facile one-pot approach to α-ketoesters," RSC Advances, published on Oct. 11, 2016, vol. 6, No. 100, retrieved on Nov. 22, 2019, pp. 98422-98426.
Yang, L. et al., "Synthesis of Pelorol and Analogues: Activators of the Inositol 5-Phosphatase SHIP," Organic Letters, published on Feb. 16, 2005, vol. 7, No. 6, pp. 1073-1076.
International Search Report of the International Searching Authority for PCT/JP2018/041971 dated Jan. 15, 2019.
English translation of International Search Report of the International Searching Authority for PCT/JP2018/041971 dated Jan. 15, 2019.
Written Opinion of the International Preliminary Examining Authority of PCT/JP2018/041971 dated Jan. 15, 2019.
English translation of Written Opinion of the International Preliminary Examining Authority of PCT/JP2018/041971 dated Jan. 15, 2019.
Partial Supplementary European Search Report for European Patent Application 18876885.7 dated Aug. 6, 2020, 11 pages.
Yu-Xiu Liu, et al, "Design, synthesis and acaricidal/insecticidal activities of etoxazole analogues", New Journal of Chemistry, vol. 37, No. 6, Jan. 1, 2013, pp. 1803-1810, XP055717562.
Examination Report of the Intellectual Property Office of India for IN 202017003921 dated Jun. 11, 2020 3 pages.
Office Action of the Intellectual Property Office of Eurasian Patent Organization for EA 202090456 dated Jun. 11, 2020, 5 pages.
English translation of Office Action of the Intellectual Property Office of Eurasian Patent Organization for EA 202090456 dated Jun. 11, 2020, 3 pages.
Examination Report of the Intellectual Property Office of India for IN 202017003921 dated Jun. 11, 2020.
Office Action of the Intellectual Property Office of Eurasian Patent Organization for EA 202090456 dated Jun. 11, 2020.
English translation of Office Action of the Intellectual Property Office of Eurasian Patent Organization for EA 202090456 dated Jun. 11, 2020.
Office Action from Patent Application 273066 dated Sep. 29, 2020, 6 pages.
Xiuling Yu, et al, "Design, synthesis and acaricidal/insecticidal . . ." Journal of Agricultural and Food Chemistry, 2016, vol. 64(15), pp. 3034-3040.
Yang, L. et al., "Synthesis of Pelorol and Analogues: Activators of the Inositol 5-Phosphatase Ship", Organic Letters, 2005, vol. 7, No. 6, XP002563127, pp. 1073-1076.
Office Action from Chilean Patent Application No. 2020-00546 dated Nov. 9, 2020, 33 pages.
Office Action from Eurasian Patent Application No. 202090456, dated Nov. 20, 2020, 4 pages.
Office Action from Chinese Patent Application No. 201880050458. 4, dated Nov. 13, 2020, 17 pages.
Atkinson, David C., et al., "Substituted (2-Phenoxyphenyl) Acetic Acids with Antiinflammatory Activity", Journal of Medicinal Chemistry, 1983, vol. 25, No. 10, 8 pages.
Extended European Search Report for European Patent Application No. 18876885.7, 11 pages.
Office Action from Colombian Patent Application No. NC2020/0002329 dated Nov. 24, 2020, 15 pages.
Office Action from Mexican Patent Application No. MX/a/2020/002380 dated Jan. 12, 2021, 9 pages.

\* cited by examiner

AZOLE DERIVATIVE, INTERMEDIATE COMPOUND, METHOD FOR PRODUCING AZOLE DERIVATIVE, AGRICULTURAL OR HORTICULTURAL CHEMICAL AGENT, AND PROTECTIVE AGENT FOR INDUSTRIAL MATERIAL

TECHNICAL FIELD

The present invention relates to a novel azole derivative, an intermediate compound thereof, and a method for producing the azole derivative. The invention also relates to an agricultural or horticultural chemical agent and a protective agent for industrial material, which contain the azole derivative as an active component.

BACKGROUND ART

Agricultural or horticultural chemical agents have hitherto been required which have low toxicity to human and animals, excellent handling safety, and high controlling effects on various plant diseases. Azole-based germicides are known as an agricultural or horticultural chemical agent having the high controlling effect.

PRIOR ART DOCUMENTS

Patent Documents

[Patent Document 1] JP-2014-520832-A (published on Aug. 25, 2014)
[Patent Document 2] JP-58-170770-A (published on Oct. 7, 1983)

SUMMARY OF THE INVENTION

Problems to be Solved by the Invention

It is required to provide a plant disease controlling agent having low toxicity to human and animals and excellent handling safety, and showing excellent controlling effects on various plant diseases and high antibiotic action to plant disease germs.

In view of the problems described above, the present invention has been made, and the objectives thereof is to provide a compound capable of responding the demands described above.

Means for Solving Problem

In order to solve the problem described above, the present inventors have earnestly studied; as a result, they have found the azole derivative shown by the general formula (I) described below has excellent activities and reduced chemical injury, and have completed the present invention.

The azole derivative of the present invention is a compound represented by the general formula (I) described below, an N-oxide thereof, or an agrochemically acceptable salt:

[Chemical Formula 1]

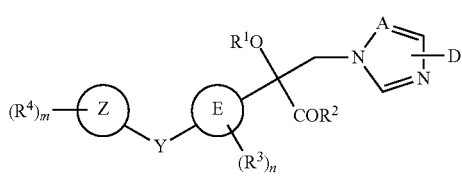

(I)

in the general formula (I),
A is N or CH;
D is a hydrogen, a halogen group, or $SR^D$;
where $R^D$ is hydrogen, a cyano group, a $C_1$-$C_6$-alkyl group, a $C_1$-$C_6$-haloalkyl group, a $C_2$-$C_6$-alkenyl group, a $C_2$-$C_6$-haloalkenyl group, a $C_2$-$C_6$-alkynyl group or a $C_2$-$C_6$-haloalkynyl group;
$R^1$ is a hydrogen, a $C_1$-$C_6$-alkyl group, a $C_2$-$C_6$-alkenyl group, a $C_2$-$C_6$-alkynyl group, a $C_3$-$C_6$-cycloalkyl group, a $C_3$-$C_6$-cycloalkyl-$C_1$-$C_4$-alkyl group, a phenyl group, a phenyl-$C_1$-$C_4$-alkyl group, a phenyl-$C_2$-$C_4$-alkenyl group, a phenyl-$C_2$-$C_4$-alkynyl group, or $COXR^5$;
where $R^5$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group;
X is a single bond, —O—, or —$NR^6$—;
$R^6$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group; and $R^5$ and $R^6$ may form a ring;
$R^2$ is —$OR^7$ or —$NR^8R^9$;
where $R^7$, $R^8$ and $R^9$ are each independently a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group, and $R^8$ and $R^9$ may form a ring,
where aliphatic groups in $R^1$, $R^2$, $R^5$, $R^6$, $R^7$, $R^8$, and $R^9$ may have 1, 2, 3 or the possible maximum number of the same or different groups $R^a$, and $R^a$ is independently selected from a halogen group, a cyano group, a nitro group, a $C_1$-$C_4$-alkoxy group, and a $C_1$-$C_4$-haloalkoxy group;
$R^4$ is a halogen group, a cyano group, a nitro group, an amino group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$;
the cycloalkyl group or phenyl group parts in $R^1$, $R^2$, $R^5$, $R^6$, $R^7$, $R^8$, and $R^9$, or the phenyl group part in $R^4$ may have 1, 2, 3, 4, 5, or the possible maximum number of the same or different groups $R^b$, and $R^b$ is independently selected from a halogen group, a cyano group, a nitro group, a $C_1$-$C_4$-alkyl group, a $C_1$-$C_4$-alkoxy group, a $C_1$-$C_4$-haloalkyl group, and a $C_1$-$C_4$-haloalkoxy group;
$R^3$ is a halogen group, a cyano group, a nitro group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, —$SOR^{10}$, or —$SF_5$;
where $R^{10}$ is a $C_1$-$C_4$-alkyl group or a $C_1$-$C_4$-haloalkyl group;
E is a phenyl group or a 6-membered heteroaromatic ring containing 1 or 2 N atoms;
n $R^3$ are bonded to any substitution sites;
when E is a phenyl group, then n is 0, 1, 2, 3, or 4, and when E is a 6-membered heteroaromatic ring containing 1 or 2 N atoms, then n is 0, 1, or 2;
Y is an oxygen atom, —$CH_2O$—, —$OCH_2$—, —NH—, —N(—$C_1$-$C_4$-alkyl)-, —N(—$C_3$-$C_6$-cycloalkyl)-, or —$S(O)_p$—, which bonds to any sites of E;
where p is 0, 1, or 2;
Z is an aromatic hydrocarbon group which is a phenyl group or a naphthyl group, or a 5-membered or 6-membered heteroaromatic ring or 9-membered or 10-membered heteroaromatic ring formed of 2 rings, containing 1 to 4 heteroatoms selected from O, N, and S; and m $R^4$ are bonded to any substitution sites;

when Z is an aromatic hydrocarbon group, then m is 1, 2, 3, 4, or 5 and when Z is a heteroaromatic ring, then m is 0, 1, 2, 3, or 4.

Effects of the Invention

The azole derivative of the present invention has excellent germicidal action to many germs capable of causing diseases in plants, and has reduced chemical injury to the plants. The chemical agent containing the azole derivative of the present invention as an active ingredient, accordingly, exhibits the high controlling effect on various plant diseases, and exerts effects to reduce the chemical injury.

The agricultural or horticultural chemical agent containing the azole derivative of the present invention as an active ingredient regulates the growth of various farm products or garden plants to increase yields, and exerts effects to increase the quality thereof.

Further, the protective agent for an industrial material containing the azole derivative of the present invention as an active ingredient exerts effects of more effectively protecting industrial materials from various harmful microorganisms attacking the industrial materials.

MODE FOR CARRYING OUT THE INVENTION

Preferable embodiments for carrying out the present invention are explained below. Please note that the described embodiments are just typical embodiments of the present invention and the scope of the present invention should not be limited thereto.

[1. Azole Derivative]

The azole derivative of the present invention is an azole derivative represented by the following general formula (I) (hereinafter referred to as "azole derivative (I)").

[Chemical Formula 2]

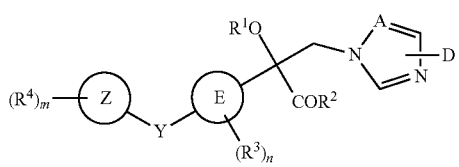

(I)

In the general formula (I), A is N or CH, preferably N. D is a hydrogen, a halogen group, or $SR^D$, and $R^D$ is a hydrogen, a cyano group, a $C_1$-$C_6$-alkyl group, a $C_1$-$C_6$-haloalkyl group, a $C_2$-$C_6$-alkenyl group, a $C_2$-$C_6$-haloalkenyl group, a $C_2$-$C_6$-alkynyl group, or a $C_2$-$C_6$-haloalkynyl group. D is preferably hydrogen.

The $C_1$-$C_6$-alkyl group is a linear or branched alkyl group having 1 to 6 carbon atoms, and includes, for example, a methyl group, an ethyl group, an n-propyl group, an isopropyl group, a 1-methylpropyl group, a 2-methylpropyl group, a 1-ethylpropyl group, an n-butyl group, an isobutyl group, a sec-butyl group, a tert-butyl group, a 2-methylbutyl group, a 3,3-dimethylbutyl group, a 2,2-dimethylbutyl group, a 1,1-dimethylbutyl group, a pentyl group, a 1-methylpentyl group, a neopentyl group, and a 1,1-dimethylethyl group.

The $C_2$-$C_6$-alkenyl group is a linear or branched alkenyl group having 2 to 6 carbon atoms, and includes, for example, an ethenyl group, a 2-propenyl group, a 1-methyl-2-propenyl group, a 2-methyl-2-propenyl group, a 1-butenyl group, a 2-butenyl group, a 3-methyl-2-butenyl group, a 1-methyl-2-butenyl group, a 3-butenyl group, a 1-pentenyl group, a 2-pentenyl group, a 1-hexenyl group, and a 5-hexenyl group.

The $C_2$-$C_6$-alkynyl group is a linear or branched alkynyl group having 2 to 6 carbon atoms, and includes, for example, an ethynyl group, a 1-propynyl group, a 2-propynyl group, a 1-butynyl group, a 2-butynyl group, a 3-butynyl group, a pentynyl group, and a 1-hexynyl group.

The $C_1$-$C_6$-haloalkyl group, the $C_2$-$C_6$-haloalkenyl group, and the $C_2$-$C_6$-haloalkynyl group are groups in which one or more hydrogen atoms are substituted by halogen atoms on substitutable sites on the $C_1$-$C_6$-alkyl group, the $C_2$-$C_6$-alkenyl group, and the $C_2$-$C_6$-alkynyl group described above, respectively, and when two or more halogen groups are substituted, the halogen group may be the same or different. The halogen group may include a chlorine group, a bromine group, an iodine group, and a fluorine group, such as a chloromethyl group, a 2-chloroethyl group, a 2,3-dichloropropyl group, a bromomethyl group, a chlorodifluoromethyl group, a trifluoromethyl group, and a 3,3,3-trifluoropropyl group.

$R^1$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, a phenyl-$C_2$-$C_4$-alkynyl group, or $COXR^5$. The $C_1$-$C_6$-alkyl group, the $C_2$-$C_6$-alkenyl group and the $C_2$-$C_6$-alkynyl group in $R^1$ can be exemplified by the groups shown as examples of the organic group represented by $R^D$. $R^1$ is preferably the hydrogen, the $C_1$-$C_6$-alkyl group, the $C_2$-$C_6$-alkenyl group, the $C_2$-$C_6$-alkynyl group, or the $COXR^5$, more preferably the hydrogen, the $C_1$-$C_6$-alkyl group, or the $COXR^5$, most preferably the hydrogen or the $C_1$-$C_6$-alkyl group.

The $C_3$-$C_8$-cycloalkyl group is a cyclic alkyl having 3 to 8 carbon atoms, and includes, for example, a cyclopropyl group, a cyclobutyl group, a cyclopentyl group, a cyclohexyl group, a cycloheptyl group, and a cyclooctyl group.

The $C_3$-$C_8$-cycloalkyl-$C_1$-$C_4$-alkyl group is a group in which a cyclic cycloalkyl group having 3 to 8 carbon atoms is bonded to a linear or branched alkyl group having 1 to 4 carbon atoms, and includes, for example, a cyclopropylmethyl group, a cyclobutylmethyl group, a cyclopentylmethyl group, a cyclohexylmethyl group, a 2-cyclopropylethyl group, a 1-cyclopropylethyl group, a 2-cyclohexylethyl group, a 3-cyclopropylpropyl group, a 2-cyclopropylpropyl group, and a 4-cyclopropylbutyl group.

The phenyl-$C_1$-$C_4$-alkyl group is a group in which a linear or branched alkyl group having 1 to 4 carbon atoms is substituted by a phenyl group, and includes, for example, a phenylmethyl group, a 2-phenylethyl group, a 3-phenylpropyl group, and a 4-phenylbutyl group.

The phenyl-$C_2$-$C_4$-alkenyl group is a group in which a linear or branched alkenyl group having 2 to 4 carbon atoms is bonded to a phenyl group, and includes, for example, a phenylethenyl group, a phenyl-1-propenyl group, a phenylisopropenyl group, and a phenylbutenyl group.

The phenyl-$C_2$-$C_4$-alkynyl group is a group in which an alkynyl group having 2 to 4 carbon atoms is bonded to a phenyl group, and includes, for example, a phenylethynyl group, a phenyl-1-propynyl group, a phenyl-2-propynyl group, a phenyl-1-butynyl group, a phenyl-2-butynyl group, a phenyl-3-butynyl group, and a phenyl-3-butynyl group.

$R^5$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group. They can be exemplified by the groups shown as examples of the organic groups represented by $R^D$ and $R^1$. $R^5$ is preferably the hydrogen, the $C_1$-$C_6$-alkyl group, the $C_2$-$C_6$-alkenyl group, or the $C_2$-$C_6$-alkynyl group, more preferably the hydrogen or the $C_1$-$C_6$-alkyl group.

X is a single bond, —O—, or —$NR^6$—, and $R^6$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group. They can be exemplified by the groups shown as examples of the organic groups represented by $R^D$ and $R^1$. $R^6$ is preferably the hydrogen, the $C_1$-$C_6$-alkyl group, the $C_2$-$C_6$-alkenyl group, or the $C_2$-$C_6$-alkynyl group, more preferably the hydrogen. $R^5$ and $R^6$ may form a ring.

$R^2$ is —$OR^7$ or —$NR^8R^9$, preferably —$OR^7$. $R^7$, $R^8$, and $R^9$ are each independently a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group. They can be exemplified by the groups shown as examples of the organic groups represented by $R^D$ and 10. $R^8$ and $R^9$ may form a ring.

$R^7$ is preferably the $C_1$-$C_6$-alkyl group.

The aliphatic group in $R^1$, $R^2$, $R^5$, $R^6$, $R^7$, $R^8$, and $R^9$ may have 1, 2, 3, or the possible maximum number of the same or different groups $R^a$, and $R^a$ is independently selected from a halogen group, a cyano group, a nitro group, a $C_1$-$C_4$-alkoxy group, and a $C_1$-$C_4$-haloalkoxy group. The $C_1$-$C_4$-alkoxy group is a linear or branched alkoxy group having 1 to 4 carbon atoms, and includes, for example, a methoxy group, an ethoxy group, an n-propoxy group, an isopropoxy group, an n-butoxy group, a sec-butoxy group, and a tert-butoxy group.

The $C_1$-$C_4$-alkoxy group may be substituted by one or more halogen groups on substitutable sites, and when the two or more halogen groups are substituted, the halogen group may be the same or different.

E is a phenyl group or a 6-membered heteroaromatic ring having one or two N atoms. E is preferably the phenyl group. The form in which E is the phenyl group is represented by the following general formula (I'). The form represented by the following general formula (I") is preferable.

[Chemical Formula 3]

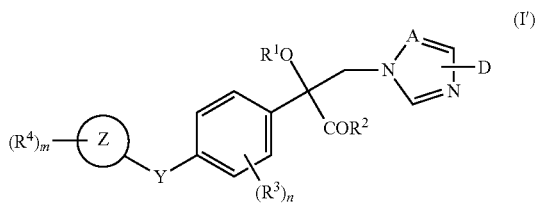

(I')

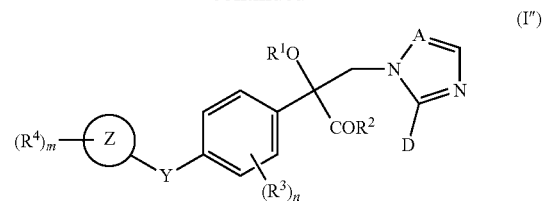

(I")

$R^3$ is a halogen group, a cyano group, a nitro group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, —$SOR^{10}$ or —$SF_5$. The halogen group, the $C_1$-$C_4$-alkyl group, the $C_1$-$C_4$-haloalkyl group, the $C_1$-$C_4$-alkoxy group, and the $C_1$-$C_4$-haloalkoxy group can be exemplified by the groups shown as examples of the organic groups represented by $R^D$, $R^1$, or $R^a$. $R^3$ is preferably the halogen group, the cyano group, the $C_1$-$C_4$-alkyl group, the $C_1$-$C_4$-haloalkyl group, the $C_1$-$C_4$-alkoxy group, —$SOR^{10}$ or —$SF_5$, more preferably the halogen group, the cyano group, the $C_1$-$C_4$-alkyl group, the $C_1$-$C_4$-haloalkyl group, or the $C_1$-$C_4$-alkoxy group. $R^{10}$ is a $C_1$-$C_4$-alkyl group or a $C_1$-$C_4$-haloalkyl group. When E is the phenyl group, the substitution site of $R^3$ is the 2-position, 3-position, 5-position, or 6-position, preferably the 2-position. n is 0, 1, 2, or 3, preferably 1. When E is the 6-membered heteroaromatic ring including one or two N atoms, the substitution site of $R^3$ is the 2-position, 3-position, 5-position, or 6-position, provided that the N atom is not attached, preferably the 2-position. In that case, n is 0, 1, or 2, preferably 1.

$R^4$ is a halogen group, a cyano group, a nitro group, an amino group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$. The halogen group, the $C_1$-$C_4$-alkyl group, the $C_1$-$C_4$-haloalkyl group, the $C_1$-$C_4$-alkoxy group, the $C_1$-$C_4$-haloalkoxy group, and —$SOR^{10}$ can be exemplified by the groups shown as examples of the organic groups represented by $R^D$, $R^1$, and $R^3$. $R^4$ is preferably the halogen group, the nitro group, the amino group, the $C_1$-$C_4$-alkyl group, the $C_1$-$C_4$-haloalkyl group, the $C_1$-$C_4$-alkoxy group, the $C_1$-$C_4$-haloalkoxy group, the $C_1$-$C_4$-alkylamino group, the $C_1$-$C_4$-dialkylamino group, the $C_1$-$C_4$-alkylacylamino group, —$SOR^{10}$ or —$SF_5$, more preferably the halogen group, the $C_1$-$C_4$-alkyl group, the $C_1$-$C_4$-haloalkyl group, the $C_1$-$C_4$-alkoxy group, or the $C_1$-$C_4$-haloalkoxy group.

The $C_1$-$C_4$-alkyl amino group is an amino group in which one of hydrogen atoms in an amino group is substituted by a linear or branched alkyl group having 1 to 4 carbon atoms, and includes, for example, a methylamino group, an ethylamino group, an n-propylamino group, an isopropylamino group, and a tert-butylamino group.

The $C_1$-$C_4$-dialkylamino group is an amino group in which two of hydrogen atoms in an amino group are both substituted by linear or branched alkyl groups having 1 to 4 carbon atoms, and includes, for example, an N,N-dimethylamino group, an N,N-diethylamino group, an N,N-di-n-propylamino group, an N,N-diisopropylamino group, and N,N-di-tert-butylamino group.

The $C_1$-$C_4$-alkylacylamino group is an amino group in which one or two of hydrogen atoms in an amino group are substituted by a linear or branched alkylacyl group having 1 to 4 carbon atoms, and includes, for example, a methylacylamino group, an ethylacylamino group, an n-propylacylamino group, an isopropylacylamino group, a tert-butylacylamino group, an N,N-dimethyl acyl amino group, an N,N-di ethyl acyl amino group, an N,N-di-n-propylacylamino group, an N,N-diisopropylacylamino group, and an N,N-di-tert-butylacylamino group.

The cycloalkyl group or the phenyl group part in $R^1$, $R^2$, $R^5$, $R^6$, $R^7$, $R^8$, and $R^9$, or the phenyl group part in $R^3$ and $R^4$ may have 1, 2, 3, 4, 5, or the possible maximum number of the same or different group $R^b$, and $R^b$ is independently selected from a halogen group, a cyano group, a nitro group, a $C_1$-$C_4$-alkyl group, a $C_1$-$C_4$-alkoxy group, a $C_1$-$C_4$-haloalkyl group, and a $C_1$-$C_4$-haloalkoxy group. The halogen group, the $C_1$-$C_4$-alkyl group, the $C_1$-$C_4$-alkoxy group, the $C_1$-$C_4$-haloalkyl group, and the $C_1$-$C_4$-haloalkoxy group can be exemplified by the groups shown as examples of the organic groups represented by $R^D$, $R^1$, and $R^a$.

Y is an oxygen atom, —CH$_2$O—, —OCH$_2$—, —NH—, —N(—C$_1$-C$_4$-alkyl)-, —N(—C$_3$-C$_6$-cycloalkyl)-, or —S(O)$_p$—, which is attached bonded to any sites of phenyl group to which (R$^3$)$_n$ is bonded, wherein p is 0, 1, or 2, and is preferably the oxygen atom.

Y is bonded to an ortho-position, a meta-position, or a para-position of the phenyl group in which R$^3$ is substituted, and is bonded preferably to the meta-position or the para-position.

Z is an aromatic hydrocarbon group which is a phenyl group or a naphthyl group, or a 5-membered or 6-membered heteroaromatic ring group or a 9-membered or 10-membered heteroaromatic ring group formed of 2 rings, containing 1 to 4 heteroatoms selected from O, N, and S. Z is preferably the phenyl group, or a 5-membered or 6-membered heteroaromatic ring having 1 to 3 heteroatoms selected from N and S, more preferably the phenyl group.

The 5-membered or 6-membered heteroaromatic ring group includes, for example, a furyl group, a pyrazolyl group, a thienyl group, a pyridyl group, a pyrimidinyl group, a pyridazinyl group, a pyrazinyl group, a pyrrolyl group, an imidazolyl group, a pyrazolyl group, a thiazolyl group, an isothiazolyl group, an oxazolyl group, an isooxazolyl group, an oxadiazolyl group, a thiadiazolyl group, a triazolyl group, a tetrazolyl group, and a triazinyl group.

The 9-membered or 10-membered heteroaromatic ring group formed of 2 rings may include an indolyl group, an isoindolyl group, a benzoimidazolyl group, a quinolinyl group, an isoquinolinyl group, a quinoxalinyl group, a cinnolinyl group, a benzopyranyl group, and a pteridinyl group.

m R$^4$ groups are bonded to any substitution sites, and are bonded preferably to a 2-position, a 3-position, a 4-position or a 5-position. When Z is an aromatic hydrocarbon group, then m is 1, 2, 3, 4, or 5; and when Z is a heteroaromatic ring, then m is 0, 1, 2, 3, or 4.

Azole derivatives, which are particularly preferable examples of the azole derivative (I), are shown in Tables 1 to 8 described below.

$R^1$, $R^2$, $R^3$, $R^4$, and Y in Table 1 below correspond to $R^1$, $R^2$, $R^3$, $R^4$, and Y in the following chemical formula (Ia), respectively.

[Chemical Formula 4]

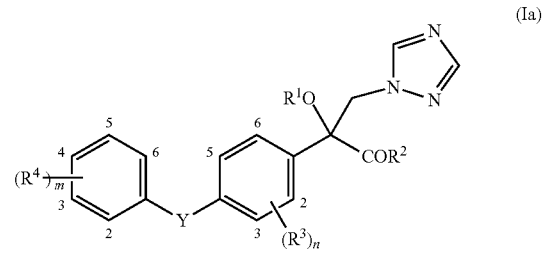

(Ia)

TABLE 1

| COMPOUND NO. | $R^1$ | $R^2$ | $(R^3)_n$ | $(R^4)_m$ | Y |
|---|---|---|---|---|---|
| I-1 | H | OMe | 2-Cl | 4-Cl | —O— |
| I-2 | H | OMe | 2-Me | 4-Cl | —O— |
| I-3 | H | OMe | 2-MeO | 4-Cl | —O— |
| I-4 | H | OMe | 2-CN | 4-Cl | —O— |
| I-5 | H | OMe | H | 4-Cl | —O— |
| I-6 | H | OMe | 3-Cl | 4-Cl | —O— |
| I-7 | H | OMe | 2-OCF$_3$ | 4-Cl | —O— |
| I-8 | H | OMe | 2-SF$_5$ | 4-Cl | —O— |
| I-9 | H | OMe | 3-CF$_5$ | 4-Cl | —O— |
| I-10 | H | OMe | 3-F | 4-Cl | —O— |
| I-11 | H | OMe | 3-Br | 4-Cl | —O— |
| I-12 | H | OMe | 2,3-Cl$_2$ | 4-Cl | —O— |
| I-13 | H | OMe | 2,3-F$_2$ | 4-Cl | —O— |
| I-14 | H | OMe | 2,5-Cl$_2$ | 4-Cl | —O— |
| I-15 | H | OMe | 2,5-Cl$_2$ | 4-Cl | —O— |
| I-16 | H | OMe | 2,6-Cl$_2$ | 4-Cl | —O— |
| I-17 | H | OMe | 2,6-F$_2$ | 4-Cl | —O— |
| I-18 | H | OMe | 2-Cl | 4-MeO | —O— |
| I-19 | H | OMe | 2-Cl | 2-Cl | —O— |
| I-20 | H | OMe | 2-Cl | 3-Cl | —O— |
| I-21 | H | OMe | 2-Cl | 2,4-Cl$_2$ | —O— |
| I-22 | H | OMe | 2-Cl | 4-OCF$_3$ | —O— |
| I-23 | H | OMe | 2-Cl | 4-CF$_3$ | —O— |
| I-24 | H | OMe | 2-Cl | 4-tBu | —O— |
| I-25 | H | OMe | 2-Cl | 4-Br | —O— |
| I-26 | H | OMe | 2-Cl | 4-F | —O— |
| I-27 | H | OMe | 2-Cl | 3,4-Cl$_2$ | —O— |
| I-28 | H | OMe | 2-Cl | 3,4-F$_2$ | —O— |
| I-29 | H | OMe | 2-Cl | 3-F,4-Cl | —O— |
| I-30 | H | OMe | 2-Cl | 3-Cl,4-F | —O— |

TABLE 1-continued

| COMPOUND NO. | R¹ | R² | (R³)ₙ | (R⁴)ₘ | Y |
|---|---|---|---|---|---|
| I-31 | H | OMe | 2-Cl | 2,4-F₂ | —O— |
| I-32 | H | OMe | 2-Cl | 2-F,4-Cl | —O— |
| I-33 | H | OMe | 2-Cl | 4-SF₅ | —O— |
| I-34 | H | OMe | 2-Cl | 4-Me | —O— |
| I-35 | H | OMe | 2-Cl | 4-CN | —O— |
| I-36 | H | OMe | 2-Cl | 3,4,5-Cl₃ | —O— |
| I-37 | H | OMe | 2-Cl | 3,4,5-F₃ | —O— |
| I-38 | H | OMe | 2-Cl | 2,4,6-Cl₃ | —O— |
| I-39 | H | OMe | 2-Cl | 2,4,6-F₃ | —O— |
| I-40 | H | OMe | 2-Cl | 3-F,4-Br | —O— |
| I-41 | H | OMe | 2-Cl | 3-Br,4-F | —O— |
| I-42 | H | OMe | 2-Cl | 2,4-Br₂ | —O— |
| I-43 | H | OMe | 2-Cl | 2-F 4-Br | —O— |
| I-44 | H | OMe | 2-Cl | 3-Cl,4-Br | —O— |
| I-45 | H | OMe | 2-Cl | 3-Br,4-Cl | —O— |
| I-46 | H | OEt | 2-Cl | 4-Cl | —O— |
| I-47 | H | O-iPr | 2-Cl | 4-Cl | —O— |
| I-48 | H | OCH₂(C₃H₅) | 2-Cl | 4-Cl | —O— |
| I-49 | H | O-nPr | 2-Cl | 4-Cl | —O— |
| I-50 | H | O-nBu | 2-Cl | 4-Cl | —O— |
| I-51 | H | O-iBu | 2-Cl | 4-Cl | —O— |
| I-52 | H | O-tBu | 2-Cl | 4-Cl | —O— |
| I-53 | H | O—C₅H₁₂ | 2-Cl | 4-Cl | —O— |
| I-54 | H | NHMe | 2-Cl | 4-Cl | —O— |
| I-55 | H | NMe₂ | 2-Cl | 4-Cl | —O— |
| I-56 | H | NHEt | 2-Cl | 4-Cl | —O— |
| I-57 | H | Net₂ | 2-Cl | 4-Cl | —O— |
| I-58 | H | NH-nPr | 2-Cl | 4-Cl | —O— |
| I-59 | H | H(nPr)₂ | 2-Cl | 4-Cl | —O— |
| I-60 | H | Morphorino- | 2-Cl | 4-Cl | —O— |
| I-61 | H | Piperidino- | 2-Cl | 4-Cl | —O— |
| I-62 | H | Pyrrolidino- | 2-Cl | 4-Cl | —O— |
| I-63 | Me | OMe | 2-Cl | 4-Cl | —O— |
| I-64 | MeCO— | OMe | 2-Cl | 4-Cl | —O— |
| I-65 | tBuCO— | OMe | 2-Cl | 4-Cl | —O— |
| I-66 | PhCO— | OMe | 2-Cl | 4-Cl | —O— |
| I-67 | C₃H₅CO— | OMe | 2-Cl | 4-Cl | —O— |
| I-68 | MeOCO— | OMe | 2-Cl | 4-Cl | —O— |
| I-69 | Me₂NCO— | OMe | 2-Cl | 4-Cl | —O— |
| I-70 | H | OMe | 2-Cl | 4-Cl | —S— |
| I-71 | H | OMe | 2-Cl | 4-Cl | —S(O)— |
| I-72 | H | OMe | 2-Cl | 4-Cl | —S(O)₂— |
| I-73 | H | OMe | 2-Cl | 4-Cl | —NH— |
| I-74 | H | OMe | 2-Cl | 4-C | —NME- |
| I-75 | H | OMe | 2-Cl | 4-C | —N(GH₂PH)— |
| I-76 | H | OMe | 2-Cl | 4-Cl | —CH₂O— |
| I-77 | H | OMe | 2-Cl | 4-Cl | —OCH₂— |
| I-78 | H | OEt | 2-Cl | 4-Br | —O— |
| I-79 | H | O-iPr | 2-Cl | 4-Br | —O— |
| I-80 | H | OCH₂(C₃H₅) | 2-Cl | 4-Br | —O— |
| I-81 | H | O-nPr | 2-Cl | 4-Br | —O— |
| I-82 | H | O-nBu | 2-Cl | 4-Br | —O— |
| I-83 | H | O-tBu | 2-Cl | 4-Br | —O— |
| I-84 | H | NMe₂ | 2-Cl | 4-Br | —O— |
| I-85 | H | Net₂ | 2-Cl | 4-Br | —O— |
| I-86 | H | Morphorino- | 2-Cl | 4-Br | —O— |
| I-87 | H | Piperidino- | 2-Cl | 4-Br | —O— |
| I-88 | Me | OMe | 2-Cl | 4-Br | —O— |
| I-89 | MeCO— | OMe | 2-Cl | 4-Br | —O— |
| I-90 | Me₂NCO— | OMe | 2-Cl | 4-Br | —O— |
| I-91 | H | OMe | 2-Cl | 4-Br | —CH₂O— |
| I-92 | H | OMe | 2-Cl | 4-Br | —OCH₂— |
| I-93 | H | OMe | 2-Cl | 4-CF₃ | —O— |
| I-94 | H | O-iPr | 2-Cl | 4-CF₃ | —O— |
| I-95 | H | OCH₂(C₃H₅) | 2-Cl | 4-CF₃ | —O— |
| I-96 | H | O-nPr | 2-Cl | 4-CF₃ | —O— |
| I-97 | H | O-nBu | 2-Cl | 4-CF₃ | —O— |
| I-98 | H | O-tBu | 2-Cl | 4-CF₃ | —O— |
| I-99 | H | NMe₂ | 2-Cl | 4-CF₃ | —O— |
| I-100 | H | NEt₂ | 2-Cl | 4-CF₃ | —O— |
| I-101 | H | Morphorino- | 2-Cl | 4-CF₃ | —O— |
| I-102 | H | Piperidino- | 2-Cl | 4-CF₃ | —O— |
| I-103 | Me | OMe | 2-Cl | 4-CF₃ | —O— |
| I-104 | MeCO— | OMe | 2-Cl | 4-CF₃ | —O— |
| I-105 | Me₂NCO— | OMe | 2-Cl | 4-CF₃ | —O— |
| I-106 | H | OMe | 2-Cl | 4-CF₃ | —CH₂O— |
| I-107 | H | OMe | 2-Cl | 4-CF₃ | —OCH₂— |

TABLE 1-continued

| COMPOUND NO. | $R^1$ | $R^2$ | $(R^3)_n$ | $(R^4)_m$ | Y |
|---|---|---|---|---|---|
| I-108 | H | OEt | 2-Cl | 4-OCF$_3$ | —O— |
| I-109 | H | O-iPr | 2-Cl | 4-OCF$_3$ | —O— |
| I-110 | H | OCH$_2$(C$_3$H$_5$) | 2-Cl | 4-OCF$_3$ | —O— |
| I-111 | H | O-nPr | 2-Cl | 4-OCF$_3$ | —O— |
| I-112 | H | O-nBu | 2-Cl | 4-OCF$_3$ | —O— |
| I-113 | H | O-tBu | 2-Cl | 4-OCF$_3$ | —O— |
| I-114 | H | NMe$_2$ | 2-Cl | 4-OCF$_3$ | —O— |
| I-115 | H | NEt$_2$ | 2-Cl | 4-OCF$_3$ | —O— |
| I-116 | H | Morphorino- | 2-Cl | 4-OCF$_3$ | —O— |
| I-117 | H | Piperidino- | 2-Cl | 4-OCF$_3$ | —O— |
| I-118 | Me | OMe | 2-Cl | 4-OCF$_3$ | —O— |
| I-119 | MeCO— | OMe | 2-Cl | 4-OCF$_3$ | —O— |
| I-120 | Me$_2$NCO— | OMe | 2-Cl | 4-OCF$_3$ | —O— |
| I-121 | H | OMe | 2-Cl | 4-OCF$_3$ | —CH$_2$O— |
| I-122a | H | OMe | 2-Cl | 4-OCF$_3$ | —OCH$_2$— |
| I-122 | H | OMe | 2-CF$_3$ | 4-Cl | —O— |
| I-123 | H | OMe | 2-CF$_3$ | 4-MeO | —O— |
| I-124 | H | OMe | 2-CF$_3$ | 2-Cl | —O— |
| I-125 | H | OMe | 2-CF$_3$ | 3-Cl | —O— |
| I-126 | H | OMe | 2-CF$_3$ | 24-Cl$_2$ | —O— |
| I-127 | H | OMe | 2-CF$_3$ | 4-OCF$_3$ | —O— |
| I-128 | H | OMe | 2-CF$_3$ | 4-CF$_3$ | —O— |
| I-129 | H | OMe | 2-CF$_3$ | 4-tBu | —O— |
| I-130 | H | OMe | 2-CF$_3$ | 4-Br | —O— |
| I-131 | H | OMe | 2-CF$_3$ | 4-F | —O— |
| I-132 | H | OMe | 2-CF$_3$ | 3,4-Cl$_2$ | —O— |
| I-133 | H | OMe | 2-CF$_3$ | 3,4-F$_2$ | —O— |
| I-134 | H | OMe | 2-CF$_3$ | 3-F,4-Cl | —O— |
| I-135 | II | OMe | 2-CF$_3$ | 3-Cl,4-F | —O— |
| I-136 | H | OMe | 2-CF$_3$ | 2,4-F$_2$ | —O— |
| I-137 | H | OMe | 2-CF$_3$ | 2-F,4-Cl | —O— |
| I-138 | H | OMe | 2-CF$_3$ | 4-SF$_5$ | —O— |
| I-139 | H | OMe | 2-CF$_3$ | 4-Me | —O— |
| I-140 | H | OMe | 2-CF$_3$ | 4-CN | —O— |
| I-141 | H | OMe | 2-CF$_3$ | 3,4,5-Cl$_3$ | —O— |
| I-142 | H | OMe | 2-CF$_3$ | 3,4,5-F$_3$ | —O— |
| I-143 | H | OMe | 2-CF$_3$ | 2,4,6-Cl$_3$ | —O— |
| I-144 | H | OMe | 2-CF$_3$ | 2,4,6-F$_3$ | —O— |
| I-145 | H | OMe | 2-CF$_3$ | 3-F,4-Br | —O— |
| I-146 | H | OMe | 2-CF$_3$ | 3-Br,4-F | —O— |
| I-147 | H | OMe | 2-CF$_3$ | 2,4-Br$_2$ | —O— |
| I-148 | H | OMe | 2-CF$_3$ | 2-F,4-Br | —O— |
| I-149 | H | OMe | 2-CF$_3$ | 3-Cl,4-Br | —O— |
| I-150 | H | OMe | 2-CF$_3$ | 3-Br,4-Cl | —O— |
| I-151 | H | OEt | 2-CF$_3$ | 4-Cl | —O— |
| I-152 | H | O-iPr | 2-CF$_3$ | 4-Cl | —O— |
| I-153 | H | OCH$_2$(C$_3$H$_5$) | 2-CF$_3$ | 4-Cl | —O— |
| I-154 | H | O-nPr | 2-CF$_3$ | 4-Cl | —O— |
| I-155 | H | O-nBu | 2-CF$_3$ | 4-Cl | —O— |
| I-156 | H | O-iBu | 2-CF$_3$ | 4-Cl | —O— |
| I-157 | H | O-tBu | 2-CF$_3$ | 4-Cl | —O— |
| I-158 | H | O—C$_5$H$_{12}$ | 2-CF$_3$ | 4-Cl | —O— |
| I-159 | H | NHMe | 2-CF$_3$ | 4-Cl | —O— |
| I-160 | H | NMe$_2$ | 2-CF$_3$ | 4-Cl | —O— |
| I-161 | H | NHEt | 2-CF$_3$ | 4-Cl | —O— |
| I-162 | H | NEt$_2$ | 2-CF$_3$ | 4-Cl | —O— |
| I-163 | H | NH-nPr | 2-CF$_3$ | 4-Cl | —O— |
| I-164 | H | M(nPr)$_2$ | 2-CF$_3$ | 4-Cl | —O— |
| I-165 | H | Morphorino- | 2-CF$_3$ | 4-Cl | —O— |
| I-166 | H | Piperidino- | 2-CF$_3$ | 4-Cl | —O— |
| I-167 | H | Pyrrolidino- | 2-CF$_3$ | 4-Cl | —O— |
| I-168 | Me | OMe | 2-CF$_3$ | 4-Cl | —O— |
| I-169 | MeCO— | OMe | 2-CF$_3$ | 4-Cl | —O— |
| I-170 | tBuCO— | OMe | 2-CF$_3$ | 4-Cl | —O— |
| I-171 | PhCO— | OMe | 2-CF$_3$ | 4-Cl | —O— |
| I-172 | C$_3$H$_5$CO— | OMe | 2-CF$_3$ | 4-Cl | —O— |
| I-173 | MeOCO— | OMe | 2-CF$_3$ | 4-Cl | —O— |
| I-174 | Me$_2$NCO— | OMe | 2-CF$_3$ | 4-Cl | —O— |
| I-175 | H | OMe | 2-CF$_3$ | 4-Cl | —S— |
| I-176 | H | OMe | 2-CF$_3$ | 4-Cl | —S(O)— |
| I-177 | H | OMe | 2-CF$_3$ | 4-Cl | —S(O)$_2$— |
| I-178 | H | OMe | 2-CF$_3$ | 4-Cl | —NH— |
| I-179 | H | OMe | 2-CF$_3$ | 4-Cl | —NME- |
| I-180 | H | OMe | 2-CF$_3$ | 4-Cl | —N(CH$_2$PH)— |
| I-181 | H | OMe | 2-CF$_3$ | 4-Cl | —CH$_2$O— |
| I-182 | H | OMe | 2-CF$_3$ | 4-Cl | —OCH$_2$— |
| I-183 | H | OEt | 2-CF$_3$ | 4-Br | —O— |

TABLE 1-continued

| COMPOUND NO. | R¹ | R² | (R³)ₙ | (R⁴)ₘ | Y |
|---|---|---|---|---|---|
| I-184 | H | O-iPr | 2-CF₃ | 4-Br | —O— |
| I-185 | H | OCH₂(C₃H₅) | 2-CF₃ | 4-Br | —O— |
| I-186 | H | O-nPr | 2-CF₃ | 4-Br | —O— |
| I-187 | H | O-nBu | 2-CF₃ | 4-Br | —O— |
| I-188 | H | O-tBu | 2-CF₃ | 4-Br | —O— |
| I-189 | H | nMe₂ | 2-CF₃ | 4-Br | —O— |
| I-190 | H | NEt₂ | 2-CF₃ | 4-Br | —O— |
| I-191 | H | Morphorino- | 2-CF₃ | 4-Br | —O— |
| I-192 | H | Piperidino- | 2-CF₃ | 4-Br | —O— |
| I-193 | Me | OMe | 2-CF₃ | 4-Br | —O— |
| I-194 | MeCO— | OMe | 2-CF₃ | 4-Br | —O— |
| I-195 | Me₂NCO— | OMe | 2-CF₃ | 4-Br | —O— |
| I-196 | H | OMe | 2-CF₃ | 4-Br | —CH₂O— |
| I-197 | H | OMe | 2-CF₃ | 4-Br | —OCH₂— |
| I-198 | H | OEt | 2-CF₃ | 4-CF₃ | —O— |
| I-199 | H | O-iPr | 2-CF₃ | 4-CF₃ | —O— |
| I-200 | H | OCH₂(C₃H₅) | 2-CF₃ | 4-CF₃ | —O— |
| I-201 | H | O-nPr | 2-CF₃ | 4-CF₃ | —O— |
| I-202 | H | O-nBu | 2-CF₃ | 4-CF₃ | —O— |
| I-203 | H | O-tBu | 2-CF₃ | 4-CF₃ | —O— |
| I-204 | H | nMe₂ | 2-CF₃ | 4-CF₃ | —O— |
| I-205 | H | NEt₂ | 2-CF₃ | 4-CF₃ | —O— |
| I-206 | H | Morphorino- | 2-CF₃ | 4-CF₃ | —O— |
| I-207 | H | Piperidino- | 2-CF₃ | 4-CF₃ | —O— |
| I-208 | Me | OMe | 2-CF₃ | 4-CF₃ | —O— |
| I-209 | MeCO— | OMe | 2-CF₃ | 4-CF₃ | —O— |
| I-210 | Me₂NCO— | OMe | 2-CF₃ | 4-CF₃ | —O— |
| I-211 | H | OMe | 2-CF₃ | 4-CF₃ | —CH₂O- |
| I-212 | H | OMe | 2-CF₃ | 4-CF₃ | —OCH₂— |
| I-213 | H | OEt | 2-CF₃ | 4-OCF₃ | —O— |
| I-214 | H | O-iPr | 2-CF₃ | 4-OCF₃ | —O— |
| I-215 | H | OCH₂(C₃H₅) | 2-CF₃ | 4-OCF₃ | —O— |
| I-216 | H | O-nPr | 2-CF₃ | 4-OCF₃ | —O— |
| I-217 | H | O-nBu | 2-CF₃ | 4-OCF₃ | —O— |
| I-218 | H | O-tBu | 2-CF₃ | 4-OCF₃ | —O— |
| I-219 | H | nMe₂ | 2-CF₃ | 4-OCF₃ | —O— |
| I-220 | H | NEt₂ | 2-CF₃ | 4-OCF₃ | —O— |
| I-221 | H | Morphorino- | 2-CF₃ | 4-OCF₃ | —O— |
| I-222 | H | Piperidino- | 2-CF₃ | 4-OCF₃ | —O— |
| I-223 | Me | OMe | 2-CF₃ | 4-OCF₃ | —O— |
| I-224 | MeCO— | OMe | 2-CF₃ | 4-OCF₃ | —O— |
| I-225 | Me₂NCO— | OMe | 2-CF₃ | 4-OCF₃ | —O— |
| I-226 | H | OMe | 2-CF₃ | 4-OCF₃ | —CH₂O- |
| I-227 | H | OMe | 2-CF₃ | 4-OCF₃ | —OCH₂— |
| I-228 | H | OMe | 2-Br | 4-Cl | —O— |
| I-229 | H | OMe | 2-Br | 4-MeO | —O— |
| I-230 | H | OMe | 2-Br | 2-Cl | —O— |
| I-231 | H | OMe | 2-Br | 3-Cl | —O— |
| I-232 | H | OMe | 2-Br | 2,4-Cl₂ | —O— |
| I-233 | H | OMe | 2-Br | 4-OCF₃ | —O— |
| I-234 | H | OMe | 2-Br | 4-CF₃ | —O— |
| I-235 | H | OMe | 2-Br | 4-tBu | —O— |
| I-236 | H | OMe | 2-Br | 4-Br | —O— |
| I-237 | H | OMe | 2-Br | 4-F | —O— |
| I-238 | H | OMe | 2-Br | 3,4-Cl₂ | —O— |
| I-239 | H | OMe | 2-Br | 3,4-F₂ | —O— |
| I-240 | H | OMe | 2-Br | 3-F,4-Cl | —O— |
| I-241 | H | OMe | 2-Br | 3-Cl,4-F | —O— |
| I-242 | H | OMe | 2-Br | 2,4-F2 | —O— |
| I-243 | H | OMe | 2-Br | 2-F,4-Cl | —O— |
| I-244 | H | OMe | 2-Br | 4-SF₅ | —O— |
| I-245 | H | OMe | 2-Br | 4-Me | —O— |
| I-246 | H | OMe | 2-Br | 4-CN | —O— |
| I-247 | H | OMe | 2-Br | 3,4,5-Cl₃ | —O— |
| I-248 | H | OMe | 2-Br | 3,4,5-F₃ | —O— |
| I-249 | H | OMe | 2-Br | 2,4,6-Cl₃ | —O— |
| I-250 | H | OMe | 2-Br | 2,4,6-F₃ | —O— |
| I-251 | H | OMe | 2-Br | 3-F,4-Br | —O— |
| I-252 | H | OMe | 2-Br | 3-Br,4-F | —O— |
| I-253 | H | OMe | 2-Br | 2,4-Br₂ | —O— |
| I-254 | H | OMe | 2-Br | 2 F,4-Br | —O— |
| I-255 | H | OMe | 2-Br | 3-Cl,4-Br | —O— |
| I-256 | H | OMe | 2-Br | 3-Br,4-Cl | —O— |
| I-257 | H | OEt | 2-Br | 4-Cl | —O— |
| I-258 | H | O-iPr | 2-Br | 4-Cl | —O— |
| I-259 | H | OCH₂(C₃H₅) | 2-Br | 4-Cl | —O— |
| I-260 | H | O-nPr | 2-Br | 4-Cl | —O— |

TABLE 1-continued

| COMPOUND NO. | R¹ | R² | (R³)ₙ | (R⁴)ₘ | Y |
| --- | --- | --- | --- | --- | --- |
| I-261 | H | O-nBu | 2-Br | 4-Cl | —O— |
| I-262 | H | O-iBu | 2-Br | 4-Cl | —O— |
| I-263 | H | O-tBu | 2-Br | 4-Cl | —O— |
| I-264 | H | O—C₅H₁₂ | 2-Br | 4-Cl | —O— |
| I-265 | H | NHMe | 2-Br | 4-Cl | —O— |
| I-266 | H | NMe₂ | 2-Br | 4-Cl | —O— |
| I-267 | H | NHEt | 2-Br | 4-Cl | —O— |
| I-268 | H | Het₂ | 2-Br | 4-Cl | —O— |
| I-269 | H | NH-nPr | 2-Br | 4-Cl | —O— |
| I-270 | H | N(nPr)₂ | 2-Br | 4-Cl | —O— |
| I-271 | H | Morphorino- | 2-Br | 4-Cl | —O— |
| I-272 | H | Piperidino- | 2-Br | 4-Cl | —O— |
| I-273 | H | Pyrrolidino- | 2-Br | 4-Cl | —O— |
| I-274 | Me | OCH₃ | 2-Br | 4-Cl | —O— |
| I-275 | MeCO— | OCH₃ | 2-Br | 4-Cl | —O— |
| I-276 | tBuCO— | OCH₃ | 2-Br | 4-Cl | —O— |
| I-277 | PhCO— | OCH₃ | 2-Br | 4-Cl | —O— |
| I-278 | C₃H₅CO— | OCH₃ | 2-Br | 4-Cl | —O— |
| I-279 | MeOCO— | OCH₃ | 2-Br | 4-Cl | —O— |
| I-280 | ME₂NCO— | OCH₃ | 2-Br | 4-Cl | —O— |
| I-281 | H | OMe | 2-Br | 4-Cl | —S— |
| I-282 | H | OMe | 2-Br | 4-Cl | —S(O)— |
| I-283 | H | OMe | 2-Br | 4-Cl | —S(O)₂— |
| I-284 | H | OMe | 2-Br | 4-Cl | —NH— |
| I-285 | H | OMe | 2-Br | 4-Cl | —NME- |
| I-286 | H | OMe | 2-Br | 4-Cl | —N(CH₂PH)— |
| I-287 | H | OMe | 2-Br | 4-Cl | —CH₂O— |
| I-288 | H | OMe | 2-Br | 4-Cl | —OCH₂— |
| I-289 | H | OEt | 2-Br | 4-Br | —O— |
| I-290 | H | O-iPr | 2-Br | 4-Br | —O— |
| I-291 | H | OCH₂(C₃H₅) | 2-Br | 4-Br | —O— |
| I-292 | H | O-nPr | 2-Br | 4-B— | —O— |
| I-293 | H | O-nBu | 2-Br | 4-B— | —O— |
| I-294 | H | O-tBu | 2-Br | 4-Br | —O— |
| I-293 | H | nMe₂ | 2-Br | 4-B* | —O— |
| I-296 | H | NEt₂ | 2-Br | 4-Br | —O— |
| I-297 | H | Morphorino- | 2-Br | 4-B— | —O— |
| I-298 | H | Piperidino- | 2-Br | 4 Br | —O— |
| I-299 | Ms | OMe | 2-Br | 4-Br | —O— |
| I-300 | MeCO— | OMe | 2-Br | 4 -Br | —O— |
| I-301 | Me₂NCO— | OMe | 2-Br | 4-Br | —O— |
| I-302 | H | OMe | 2-Br | 4-Br | —CH₂Q- |
| I-303 | H | OMe | 2-Br | 4-Br | —OCH₂— |
| I-304 | H | OEt | 2-Br | 4-CF₃ | —O— |
| I-305 | H | O-iPr | 2-Br | 4-CF₃ | —O— |
| I-306 | H | OCH₂(C₃H₅) | 2-Br | 4-CF₃ | —O— |
| I-307 | H | O-nPr | 2-Br | 4-CF₃ | —O— |
| I-308 | H | O-nBu | 2-Br | 4-CF₃ | —O— |
| I-309 | H | O-tBu | 2-Br | 4-CF₃ | —O— |
| I-310 | H | nMe₂ | 2-Br | 4-CF₃ | —O— |
| I-311 | H | NEt₂ | 2-Br | 4-CF₃ | —O— |
| I-312 | H | Morphorino- | 2-Br | 4-CF₃ | —O— |
| I-313 | H | Piperidino- | 2-Br | 4-CF₃ | —O— |
| I-314 | Me | OMe | 2-Br | 4-CF₃ | —O— |
| I-315 | MeCO— | OMe | 2-Br | 4-CF₃ | —O— |
| I-316 | Me₂NCO— | OMe | 2-Br | 4-CF₃ | —O— |
| I-317 | H | OMe | 2-Br | 4-CF₃ | —CH₂Q- |
| I-318 | H | OMe | 2-Br | 4-CF₃ | —OCH₂— |
| I-319 | H | OEt | 2-Br | 4-OCF₃ | —O— |
| I-320 | H | O-iP— | 2-Br | 4-OCF₃ | —O— |
| I-321 | H | OCH₂(C₃H₅) | 2-Br | 4-OCF₃ | —O— |
| I-322 | H | O-nPr | 2-Br | 4-OCF₃ | —O— |
| I-323 | H | O-nBu | 2-Br | 4-OCF₃ | —O— |
| I-324 | H | O-tBu | 2-Br | 4-OCF₃ | —O— |
| I-325 | H | nMe₂ | 2-Br | 4-OCF₃ | —O— |
| I-326 | H | NEt₂ | 2-Br | 4-OCF₃ | —O— |
| I-327 | H | Morphorino- | 2-Br | 4-OCF₃ | —O— |
| I-328 | H | Piperidino- | 2-Br | 4-OCF₃ | —O— |
| I-329 | Me | OMe | 2-Br | 4-OCF₃ | —O— |
| I-330 | MeCO— | OMe | 2-Br | 4-OCF₃ | —O— |
| I-331 | Me₂NCO— | OMe | 2-Br | 4-OCF₃ | —O— |
| I-332 | H | OMe | 2-Br | 4-OCF₃ | —CH₂Q- |
| I-333 | H | OMe | 2-Br | 4-OCF₃ | —OCH₂— |
| I-334 | H | OMe | 2-F | 4-Cl | —O— |
| I-335 | H | OMe | 2-F | 4-MeO | —O— |

TABLE 1-continued

| COMPOUND NO. | R$^1$ | R$^2$ | (R$^3$)$_n$ | (R$^4$)$_m$ | Y |
|---|---|---|---|---|---|
| I-336 | H | OMe | 2-F | 2-Cl | —O— |
| I-337 | H | OMe | 2-F | 3-Cl | —O— |
| I-338 | H | OMe | 2-F | 2,4-Cl$_2$ | —O— |
| I-339 | H | OMe | 2-F | 4-OCF$_3$ | —O— |
| I-340 | H | OMe | 2-F | 4-CF$_3$ | —O— |
| I-341 | H | OMe | 2-F | 4-tBu | —O— |
| I-342 | H | OMe | 2-F | 4-Br | —O— |
| I-343 | H | OMe | 2-F | 4-F | —O— |
| I-344 | H | OMe | 2-F | 3,4-Cl$_2$ | —O— |
| I-345 | H | OMe | 2-F | 3,4-F$_2$ | —O— |
| I-346 | H | OMe | 2-F | 3-F,4-Cl | —O— |
| I-347 | H | OMe | 2-F | 3-Cl,4-F | —O— |
| I-348 | H | OMe | 2-F | 2,4-F$_2$ | —O— |
| I-349 | H | OMe | 2-F | 2-F,4-Cl | —O— |
| I-350 | H | OMe | 2-F | 4-SF$_5$ | —O— |
| I-351 | H | OMe | 2-F | 4-Me | —O— |
| I-352 | H | OMe | 2-F | 4-CN | —O— |
| I-353 | H | OMe | 2-F | 3,4,5-Cl$_3$ | —O— |
| I-354 | H | OMe | 2-F | 3,4,5-F$_3$ | —O— |
| I-355 | H | OMe | 2-F | 2,4,6-Cl$_3$ | —O— |
| I-356 | H | OMe | 2-F | 2,4,6-F$_3$ | —O— |
| I-357 | H | OMe | 2-F | 3-F,4-Br | —O— |
| I-358 | H | OMe | 2-F | 3-Br,4-F | —O— |
| I-359 | H | OMe | 2-F | 2,4-Br$_2$ | —O— |
| I-360 | H | OMe | 2-F | 2-F,4-Br | —O— |
| I-361 | H | OMe | 2-F | 3-Cl,4-Br | —O— |
| I-362 | H | OMe | 2-F | 3-Br,4-Cl | —O— |
| I-363 | H | OEt | 2-F | 4-Cl | —O— |
| I-364 | H | O-iPr | 2-F | 4-Cl | —O— |
| I-365 | H | OCH$_2$(C$_3$H$_5$) | 2-F | 4-Cl | —O— |
| I-366 | H | O-nPr | 2-F | 4-Cl | —O— |
| I-367 | H | O-nBu | 2-F | 4-Cl | —O— |
| I-368 | H | O-iBu | 2-F | 4-Cl | —O— |
| I-369 | H | O-tBu | 2-F | 4-Cl | —O— |
| I-370 | H | O—C$_5$H$_{12}$ | 2-F | 4-Cl | —O— |
| I-371 | H | NHMe | 2-F | 4-Cl | —O— |
| I-372 | H | NMe$_2$ | 2-F | 4-Cl | —O— |
| I-373 | H | NHEt | 2-F | 4-Cl | —O— |
| I-374 | H | Net$_2$ | 2-F | 4-Cl | —O— |
| I-375 | H | NH-nPr | 2-F | 4-Cl | —O— |
| I-376 | H | N(nPr)$_2$ | 2-F | 4-Cl | —O— |
| I-377 | H | Morphorino- | 2-F | 4-Cl | —O— |
| I-378 | H | Piperidino- | 2-F | 4-Cl | —O— |
| I-379 | H | Pyrrolidino- | 2-F | 4-Cl | —O— |
| I-380 | Me | OCH$_3$ | 2-F | 4-Cl | —O— |
| I-381 | MeCO— | OCH$_3$ | 2-F | 4-Cl | —O— |
| I-382 | tBuCO— | OCH$_3$ | 2-F | 4-Cl | —O— |
| I-383 | PhCO— | OCH$_3$ | 2-F | 4-Cl | —O— |
| I-384 | C$_3$H$_5$CO— | OCH$_3$ | 2-F | 4-Cl | —O— |
| I-385 | MeOCO— | OCH$_3$ | 2-F | 4-Cl | —O— |
| I-386 | ME$_2$NCO— | OCH$_3$ | 2-F | 4-Cl | —O— |
| I-387 | H | OMe | 2-F | 4-Cl | —S— |
| I-388 | H | OMe | 2-F | 4-Cl | —S(O)— |
| I-389 | H | OMe | 2-F | 4-Cl | —S(O)$_2$— |
| I-390 | H | OMe | 2-F | 4-Cl | —NH— |
| I-391 | H | OMe | 2-F | 4-Cl | —NME- |
| I-392 | H | OMe | 2-F | 4-Cl | —N(CH$_2$PH)— |
| I-393 | H | OMe | 2-F | 4-Cl | —CH$_2$O— |
| I-394 | H | OMe | 2-F | 4-Cl | —OCH$_2$— |
| I-395 | H | OEt | 2-F | 4-Br | —O— |
| I-396 | H | O-iPr | 2-F | 4-Br | —O— |
| I-397 | H | OCH$_2$(C$_3$H$_5$) | 2-F | 4-Br | —O— |
| I-398 | H | O-nPr | 2-F | 4-Br | —O— |
| I-399 | H | O-nBu | 2-F | 4-Br | —O— |
| I-400 | H | O-tBu | 2-F | 4-Br | —O— |
| I-401 | H | nMe$_2$ | 2-F | 4-Br | —O— |
| I-402 | H | NEt$_2$ | 2-F | 4-Br | —O— |
| I-403 | H | Morphorino- | 2-F | 4-Br | —O— |
| I-404 | H | Piperidino- | 2-F | 4-Br | —O— |
| I-405 | Me | OMe | 2-F | 4-Br | —O— |
| I-406 | MeCO— | OMe | 2-F | 4-Br | —O— |
| I-407 | Me$_2$NCO— | OMe | 2-F | 4-Br | —O— |
| I-408 | H | OMe | 2-F | 4-Br | —CH$_2$Q- |
| I-409 | H | OMe | 2-F | 4-Br | —OCH$_2$— |
| I-410 | H | OEt | 2-F | 4-CF$_3$ | —O— |

TABLE 1-continued

| COMPOUND NO. | $R^1$ | $R^2$ | $(R^3)_n$ | $(R^4)_m$ | Y |
|---|---|---|---|---|---|
| I-411 | H | O-iPr | 2-F | 4-$CF_3$ | —O— |
| I-112 | H | $OCH_2(C_3H_5)$ | 2-F | 4-$CF_3$ | —O— |
| I-413 | H | O-nPr | 2-F | 4-$CF_3$ | —O— |
| I-414 | H | O-nBu | 2-F | 4-$CF_3$ | —O— |
| I-415 | H | O-tBu | 2-F | 4-$CF_3$ | —O— |
| I-416 | H | $nMe_2$ | 2-F | 4-$CF_3$ | —O— |
| I-417 | H | $NEt_2$ | 2-F | 4-$CF_3$ | —O— |
| I-418 | H | Morphorino- | 2-F | 4-$CF_3$ | —O— |
| I-419 | H | Piperidino- | 2-F | 4-$CF_3$ | —O— |
| I-420 | Me | OMe | 2-F | 4-$CF_3$ | —O— |
| I-421 | MeCO— | OMe | 2-F | 4-$CF_3$ | —O— |
| I-422 | $Me_2NCO$— | OMe | 2-F | 4-$CF_3$ | —O— |
| I-423 | H | OMe | 2-F | 4-$CF_3$ | —$CH_2Q$- |
| I-424 | H | OMe | 2-F | 4-$CF_3$ | —$OCH_2$— |
| I-425 | H | OEt | 2-F | 4-$OCF_3$ | —O— |
| I-426 | H | O-iPr | 2-F | 4-$OCF_3$ | —O— |
| I-427 | H | $OCH_2(C_3H_5)$ | 2-F | 4-$OCF_3$ | —O— |
| I-428 | H | O-nPr | 2-F | 4-$OCF_3$ | —O— |
| I-429 | H | O-nBu | 2-F | 4-$OCF_3$ | —O— |
| I-430 | H | O-tBu | 2-F | 4-$OCF_3$ | —O— |
| I-431 | H | $nMe_2$ | 2-F | 4-$OCF_3$ | —O— |
| I-432 | H | $NEt_2$ | 2-F | 4-$OCF_3$ | —O— |
| I-433 | H | Morphorino- | 2-F | 4-$OCF_3$ | —O— |
| I-434 | H | Piperidino- | 2-F | 4-$OCF_3$ | —O— |
| I-435 | Me | OMe | 2-F | 4-$OCF_3$ | —O— |
| I-436 | MeCO— | OMe | 2-F | 4-$OCF_3$ | —O— |
| I-437 | $Me_2NCO$— | OMe | 2-F | 4-$OCF_3$ | —O— |
| I-438 | H | OMe | 2-F | 4-$OCF_3$ | —$CH_2Q$- |
| I-439 | H | OMe | 2-F | 4-$OCF_3$ | —$OCH_2$— |
| I-440 | H | $NHCH_2Ph$ | 2-Cl | 4-Cl | —O— |
| I-441 | PhNHCO— | OMe | 2-Cl | 4-Cl | —O— |
| I-442 | tBuOCO— | OMe | 2-Cl | 4-Cl | —O— |

$R^1$, $R^2$, $R^3$, $R^4$ and Y in Table 2 below correspond to $R^1$, $R^2$, $R^3$, $R^4$ and Y in the following chemical formula (IIa) and chemical formula (IIb), respectively.

[Chemical Formula 5]

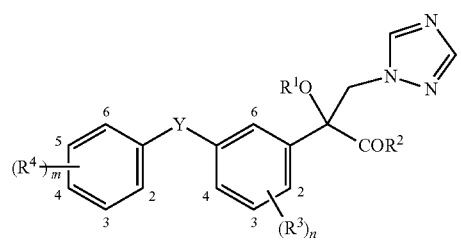

(IIa)

[Chemical Formula 6]

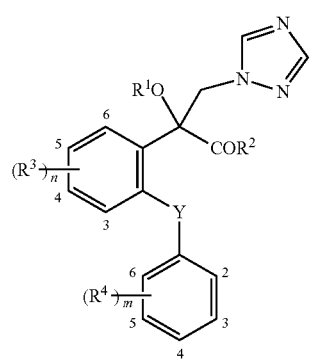

(IIb)

TABLE 2

| COMPOUND NO. | $R^1$ | $R^2$ | $(R^3)_n$ | $(R^4)_m$ | Y |
|---|---|---|---|---|---|
| IIa-1 | H | $OCH_3$ | 2-Cl | 4-Cl | —O— |
| IIa-2 | H | $OCH_3$ | 2-$CF_3$ | 4-Cl | —O— |
| IIa-3 | H | $OCH_3$ | 2-Br | 4-Cl | —O— |
| IIa-4 | H | $OCH_3$ | 2-F | 4-Cl | —O— |
| IIa-5 | H | $OCH_3$ | 2-Cl | 3-Cl | —O— |
| IIa-6 | H | $OCH_3$ | 2-Cl | 4-Br | —O— |
| IIa-7 | H | $OCH_3$ | 2-Cl | 4-$CF_3$ | —O— |
| IIa-8 | H | $OCH_3$ | 2-Cl | 3,4-$Cl_2$ | —O— |
| IIa-9 | H | $OCH_3$ | 2-Cl | 3,4-$F_2$ | —O— |
| IIa-10 | H | OEt | 2-Cl | 4-Cl | —O— |
| IIa-11 | H | $NMe_2$ | 2-Cl | 4-Cl | —O— |
| IIb-12 | H | $OCH_3$ | H | 4-Cl | —O— |
| IIb-13 | H | $OCH_3$ | 4-Cl | 4-Cl | —O— |
| IIb-14 | H | $OCH_3$ | 4-$CF_3$ | 4-Cl | —O— |
| IIb-15 | H | $OCH_3$ | 4-Br | 4-Cl | —O— |
| IIb-16 | H | $OCH_3$ | 6-$CF_3$ | 4-Cl | —O— |
| IIb-17 | H | $OCH_3$ | H | 4-Br | —O— |
| IIb-18 | H | $OCH_3$ | H | 4-$CF_3$ | —O— |
| IIb-19 | H | $OCH_3$ | H | 3,4-$Cl_2$ | —O— |
| IIb-20 | H | $OCH_3$ | H | 3-Cl | —O— |
| IIb-21 | H | OEt | 4-Cl | 3-Cl | —O— |
| IIb-22 | H | $NMe_2$ | 4-$CF_3$ | 3-Cl | —O— |

$R^1$, $R^2$, $R^3$, $R^4$, Y, $Z^2$, $Z^3$, and $Z^4$ in Table 3 below correspond to $R^1$, $R^2$, $R^3$, $R^4$, Y, $Z^2$, $Z^3$ and $Z^4$ in the following chemical formula (IIIa), respectively.

$Z^2$, $Z^3$, and $Z^4$ in the Table show a non-substituted state, before the substitution of $R^4$, as a ring structure, and in the chemical formula (IIIa), a carbon, which is substituted by $R^4$, is also represented by "CH".

[Chemical Formula 7]

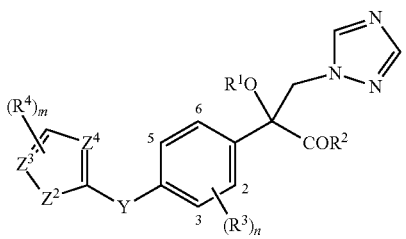

(IIIa)

TABLE 3

| COMPOUND NO. | $R^1$ | $R^2$ | $(R^3)_n$ | Y | $(R^4)_m$ | $Z^2$ | $Z^3$ | $Z^4$ |
|---|---|---|---|---|---|---|---|---|
| IIIa-1 | H | $OCH_3$ | 2-Cl | —O— | — | N—H | CH | CH |
| IIIa-2 | H | $OCH_3$ | 2-Cl | —O— | — | N—Me | CH | CH |
| IIIa-3 | H | $OCH_3$ | 2-Cl | —O— | — | O | CH | CH |
| IIIa-4 | H | $OCH_3$ | 2-Cl | —O— | — | S | CH | CH |
| IIIa-5 | H | $OCH_3$ | 2-Cl | —O— | 4-Cl | S | CH | CH |
| IIIa-6 | H | $OCH_3$ | 2-Cl | —O— | 5-Cl | S | CH | CH |
| IIIa-7 | H | $OCH_3$ | 2-Cl | —O— | 5-Br | S | CH | CH |
| IIIa-8 | H | $OCH_3$ | 2-Cl | —O— | $5-CF_3$ | S | CH | CH |
| IIIa-9 | H | $OCH_3$ | 2-Cl | —O— | $4,5-Cl_2$ | S | CH | CH |
| IIIa-10 | H | $OCH_3$ | $2-CF_3$ | —O— | 5-Cl | S | CH | CH |
| IIIa-11 | H | $OCH_3$ | 2-Br | —O— | 5-Cl | S | CH | CH |
| IIIa-12 | H | $OCH_3$ | 2-F | —O— | 5-Cl | S | CH | CH |
| IIIa-13 | H | $OCH_3$ | 2-Cl | —O— | — | N-H | N | CH |
| IIIa-14 | H | $OCH_3$ | 2-Cl | —O— | — | N—Me | CH | CH |
| IIIa-15 | H | $OCH_3$ | 2-Cl | —O— | 3-Cl | N—Me | CH | CH |
| IIIa-16 | H | $OCH_3$ | 2-Cl | —O— | 4-Cl | N—Me | CH | CH |
| IIIa-17 | H | $OCH_3$ | 2-Cl | —O— | $3-CF_3$ | N—Me | CH | CH |
| IIIa-18 | H | $OCH_3$ | 2-Cl | —O— | 3-Br | N—Me | CH | CH |
| IIIa-19 | H | $OCH_3$ | 2-Cl | —O— | $3-CHF_2$ | N—Me | CH | CH |
| IIIa-20 | H | $OCH_3$ | $2-CF_3$ | —O— | 3-OMe | N—Me | CH | CH |
| IIIa-21 | H | $OCH_3$ | 2-Br | —O— | 3-F | N—Me | CH | CH |
| IIIa-22 | H | $OCH_3$ | 2-F | —O— | 4-F | N—Me | CH | CH |
| IIIa-23 | H | $OCH_3$ | 2-Cl | —O— | — | N—H | CH | N |
| IIIa-24 | H | $OCH_3$ | 2-Cl | —O— | 5-Cl | N—H | CH | N |
| IIIa-25 | H | $OCH_3$ | 2-Cl | —O— | 4-Cl | N—H | CH | N |
| IIIa-26 | H | $OCH_3$ | 2-Cl | —O— | — | N—Me | CH | N |
| IIIa-27 | H | $OCH_3$ | 2-Cl | —O— | 5-Cl | N—Me | CH | N |
| IIIa-28 | H | $OCH_3$ | 2-Cl | —O— | 4-Cl | M-Me | CH | N |
| IIIa-29 | H | $OCH_3$ | 2-Cl | —O— | — | S | CH | N |
| IIIa-30 | H | $OCH_3$ | 2-Cl | —O— | 5-Cl | S | CH | N |
| IIIa-31 | H | $OCH_3$ | 2-Cl | —O— | 4-Cl | S | CH | N |
| IIIa-32 | H | $OCH_3$ | 2-Cl | —O— | — | O | CH | N |
| IIIa-33 | H | $OCH_3$ | 2-Cl | —O— | 5-Cl | O | CH | N |
| IIIa-34 | H | $OCH_3$ | 2-Cl | —O— | 4-Cl | O | CH | N |
| IIIa-35 | H | $OCH_3$ | 2-Cl | —O— | — | N—Me | CH | O |
| IIIa-36 | H | $OCH_3$ | 2-Cl | —O— | 5-Cl | N—Me | CH | O |
| IIIa-37 | H | $OCH_3$ | 2-Cl | —O— | 4-Cl | N—Me | CH | O |
| IIIa-38 | H | $OCH_3$ | 2-Cl | —O— | — | NH | N | N |
| IIIa-39 | H | $OCH_3$ | 2-Cl | —O— | 5-Cl | NH | N | N |
| IIIa-40 | H | $OCH_3$ | 2-Cl | —O— | 4-Cl | NH | N | N |
| IIIa-41 | H | $OCH_3$ | 2-Cl | —O— | — | N—Me | N | N |
| IIIa-42 | H | $OCH_3$ | 2-Cl | —O— | 5-Cl | N—Me | N | N |
| IIIa-43 | H | $OCH_3$ | 2-Cl | —O— | 4-Cl | N—Me | N | N |
| IIIa-44 | H | $OCH_3$ | 2-Cl | —O— | — | S | N | N |
| IIIa-45 | H | $OCH_3$ | 2-Cl | —O— | 5-Cl | S | N | N |
| IIIa-46 | H | $OCH_3$ | 2-Cl | —O— | 4-Cl | S | N | N |

$R^1$, $R^2$, $R^3$, Y, $R^4$, $Z^2$, $Z^3$, $Z^4$, $Z^5$, and $Z^6$ in Table 4 below correspond to $R^1$, $R^2$, $R^3$, Y, $R^4$, $Z^2$, $Z^3$, $Z^4$, $Z^5$, and $Z^6$ in the following chemical formula (TIN, respectively.

$Z^2$, $Z^3$, $Z^4$, $Z^5$, and $Z^6$ in the Table show a non-substituted state, before the substitution of $R^4$, as a ring structure, and in the chemical formula (TIN, a carbon, which is substituted by $R^4$, is also represented by "CH".

[Chemical Formula 8]

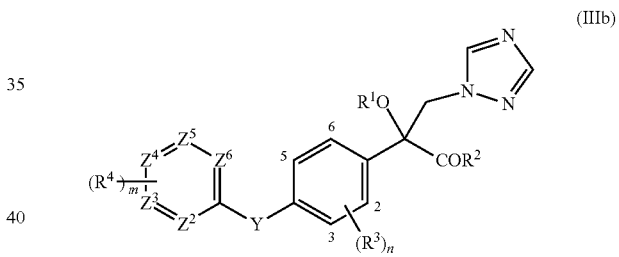

(IIIb)

TABLE 4

| COMPOUND NO. | $R^1$ | $R^2$ | $(R^3)_n$ | Y | $(R^4)_m$ | $Z^2$ | $Z^3$ | $Z^5$ | $Z^5$ | $Z^6$ |
|---|---|---|---|---|---|---|---|---|---|---|
| IIIb-1 | H | $OCH_3$ | 2-Cl | —O— | — | N | CH | CH | CH | CH |
| IIIb-2 | H | $OCH_3$ | 2-Cl | —O— | — | CH | N | CH | CH | CH |
| IIIb-3 | H | $OCH_3$ | 2-Cl | —O— | — | CH | CH | N | CH | CH |
| IIIb-4 | H | $OCH_3$ | 2-Cl | —O— | — | N | CH | CH | CH | N |
| IIIb-5 | H | $OCH_3$ | 2-Cl | —O— | — | N | CH | N | CH | CH |
| IIIb-6 | H | $OCH_3$ | 2-Cl | —O— | — | N | CH | CH | N | CH |
| IIIb-7 | H | $OCH_3$ | 2-Cl | —O— | — | N | N | CH | CH | CH |
| IIIb-8 | H | $OCH_3$ | 2-Cl | —O— | — | N | CH | N | CH | N |
| IIIb-9 | H | $OCH_3$ | 2-Cl | —O— | 4-Cl | N | CH | CH | CH | CH |
| IIIb-10 | H | $OCH_3$ | 2-Cl | —O— | 5-Cl | N | CH | CH | CH | CH |
| IIIb-11 | H | $OCH_3$ | 2-Cl | —O— | 6-Cl | N | CH | CH | CH | CH |
| IIIb-12 | H | $OCH_3$ | 2-Cl | —O— | $4-CF_3$ | N | CH | CH | CH | CH |
| IIIb-13 | H | $OCH_3$ | 2-Cl | —O— | $5-CF_3$ | N | CH | CH | CH | CH |
| IIIb-14 | H | $OCH_3$ | 2-Cl | —O— | $6-CF_3$ | N | CH | CH | CH | CH |
| IIIb-15 | H | $OCH_3$ | 2-Cl | —O— | 4-Br | N | CH | CH | CH | CH |
| IIIb-16 | H | $OCH_3$ | 2-Cl | —O— | 5-Br | N | CH | CH | CH | CH |
| IIIb-17 | H | $OCH_3$ | 2-Cl | —O— | 6-Br | N | CH | CH | CH | CH |
| IIIb-18 | H | $OCH_3$ | 2-Cl | —O— | 4-F | N | CH | CH | CH | CH |
| IIIb-19 | H | $OCH_3$ | 2-Cl | —O— | 5-F | N | CH | CH | CH | CH |
| IIIb-20 | H | $OCH_3$ | 2-Cl | —O— | 6-F | N | CH | CH | CH | CH |
| IIIb-21 | H | $OCH_3$ | 2-Cl | —O— | 4-Cl | CH | N | CH | CH | CH |
| IIIb-22 | H | $OCH_3$ | 2-Cl | —O— | 5-Cl | CH | N | CH | CH | CH |

TABLE 4-continued

| COMPOUND NO. | R¹ | R² | (R³)ₙ | Y | (R⁴)ₘ | Z² | Z³ | Z⁵ | Z⁵ | Z⁶ |
|---|---|---|---|---|---|---|---|---|---|---|
| IIIb-23 | H | OCH₃ | 2-Cl | —O— | 6-Cl | CH | N | CH | CH | CH |
| IIIb-24 | H | OCH₃ | 2-Cl | —O— | 4-CF₃ | CH | N | CH | CH | CH |
| IIIb-25 | H | OCH₃ | 2-Cl | —O— | 5-CF₃ | CH | N | CH | CH | CH |
| IIIb-26 | H | OCH₃ | 2-Cl | —O— | 6-CF₃ | CH | N | CH | CH | CH |
| IIIb-27 | H | OCH₃ | 2-Cl | —O— | 4-Br | CH | N | CH | CH | CH |
| IIIb-28 | H | OCH₃ | 2-Cl | —O— | 5-Br | CH | N | CH | CH | CH |
| IIIb-29 | H | OCH₃ | 2-Cl | —O— | 6-Br | CH | N | CH | CH | CH |
| IIIb-30 | H | OCH₃ | 2-Cl | —O— | 4-F | CH | N | CH | CH | CH |
| IIIb-31 | H | OCH₃ | 2-Cl | —O— | 5-F | CH | N | CH | CH | CH |
| IIIb-32 | H | OCH₃ | 2-Cl | —O— | 6-F | CH | N | CH | CH | CH |
| IIIb-33 | H | OCH₃ | 2-Cl | —O— | 2-Cl | CH | CH | N | CH | CH |
| IIIb-34 | H | OCH₃ | 2-Cl | —O— | 5-Cl | CH | CH | N | CH | CH |
| IIIb-35 | H | OCH₃ | 2-Cl | —O— | 6-Cl | CH | CH | N | CH | CH |
| IIIb-36 | H | OCH₃ | 2-Cl | —O— | 2-CF₃ | CH | CH | N | CH | CH |
| IIIb-37 | H | OCH₃ | 2-Cl | —O— | 5-CF₃ | CH | CH | N | CH | CH |
| IIIb-38 | H | OCH₃ | 2-Cl | —O— | 6-CF₃ | CH | CH | N | CH | CH |
| IIIb-39 | H | OCH₃ | 2-Cl | —O— | 2-Br | CH | CH | N | CH | CH |
| IIIb-40 | H | OCH₃ | 2-Cl | —O— | 5-Br | CH | CH | N | CH | CH |
| IIIb-41 | H | OCH₃ | 2-Cl | —O— | 6-Br | CH | CH | N | CH | CH |
| IIIb-42 | H | OCH₃ | 2-Cl | —O— | 2-F | CH | CH | N | CH | CH |
| IIIb-43 | H | OCH₃ | 2-Cl | —O— | 5-F | CH | CH | N | CH | CH |
| IIIb-44 | H | OCH₃ | 2-Cl | —O— | 6-F | CH | CH | N | CH | CH |
| IIIb-45 | H | OCH₃ | 2-Cl | —O— | 4-Cl | N | CH | CH | CH | N |
| IIIb-46 | H | OCH₃ | 2-Cl | —O— | 5-Cl | N | CH | CH | CH | N |
| IIIb-47 | H | OCH₃ | 2-Cl | —O— | 6-Cl | N | CH | CH | CH | N |
| IIIb-48 | H | OCH₃ | 2-Cl | —O— | 4-CF₃ | N | CH | CH | CH | N |
| IIIb-49 | H | OCH₃ | 2-Cl | —O— | 5-CF₃ | N | CH | CH | CH | N |
| IIIb-50 | H | OCH₃ | 2-Cl | —O— | 6-CF₃ | N | CH | CH | CH | N |
| IIIb-51 | H | OCH₃ | 2-Cl | —O— | 4-Br | N | CH | CH | CH | N |
| IIIb-52 | H | OCH₃ | 2-Cl | —O— | 5-Br | N | CH | CH | CH | N |
| IIIb-53 | H | OCH₃ | 2-Cl | —O— | 6-Br | N | CH | CH | CH | N |
| IIIb-54 | H | OCH₃ | 2-Cl | —O— | 4-F | N | CH | CH | CH | N |
| IIIb-55 | H | OCH₃ | 2-Cl | —O— | 5-F | N | CH | CH | CH | N |
| IIIb-56 | H | OCH₃ | 2-Cl | —O— | 6-F | N | CH | CH | CH | N |
| IIIb-57 | H | OCH₃ | 2-Cl | —O— | 2-Cl | N | CH | N | CH | CH |
| IIIb-58 | H | OCH₃ | 2-Cl | —O— | 5-Cl | N | CH | N | CH | CH |
| IIIb-59 | H | OCH₃ | 2-Cl | —O— | 6-Cl | N | CH | N | CH | CH |
| IIIb-60 | H | OCH₃ | 2-Cl | —O— | 2-CF₃ | N | CH | N | CH | CH |
| IIIb-61 | H | OCH₃ | 2-Cl | —O— | 5-CF₃ | N | CH | N | CH | CH |
| IIIb-62 | H | OCH₃ | 2-Cl | —O— | 6-CF₃ | N | CH | N | CH | CH |
| IIIb-63 | H | OCH₃ | 2-Cl | —O— | 2-Br | N | CH | N | CH | CH |
| IIIb-64 | H | OCH₃ | 2-Cl | —O— | 5-Br | N | CH | N | CH | CH |
| IIIb-65 | H | OCH₃ | 2-Cl | —O— | 6-Br | N | CH | N | CH | CH |
| IIIb-66 | H | OCH₃ | 2-Cl | —O— | 2-F | N | CH | N | CH | CH |
| IIIb-67 | H | OCH₃ | 2-Cl | —O— | 5-F | N | CH | N | CH | CH |
| IIIb-68 | H | OCH₃ | 2-Cl | —O— | 6-F | N | CH | N | CH | CH |
| IIIb-69 | H | OCH₃ | 2-Cl | —O— | 3-Cl | N | CH | CH | N | CH |
| IIIb-70 | H | OCH₃ | 2-Cl | —O— | 5-Cl | N | CH | CH | N | CH |
| IIIb-71 | H | OCH₃ | 2-Cl | —O— | 6-Cl | N | CH | CH | N | CH |
| IIIb-72 | H | OCH₃ | 2-Cl | —O— | 3-CF₃ | N | CH | CH | N | CH |
| IIIb-73 | H | OCH₃ | 2-Cl | —O— | 5-CF₃ | N | CH | CH | N | CH |
| IIIb-74 | H | OCH₃ | 2-Cl | —O— | 6-CF₃ | N | CH | CH | N | CH |
| IIIb-75 | H | OCH₃ | 2-Cl | —O— | 3-Br | N | CH | CH | N | CH |
| IIIb-76 | H | OCH₃ | 2-Cl | —O— | 5-Br | N | CH | CH | N | CH |
| IIIb-77 | H | OCH₃ | 2-Cl | —O— | 6-Br | N | CH | CH | N | CH |
| IIIb-78 | H | OCH₃ | 2-Cl | —O— | 3-F | N | CH | CH | N | CH |
| IIIb-79 | H | OCH₃ | 2-Cl | —O— | 5-F | N | CH | CH | N | CH |
| IIIb-80 | H | OCH₃ | 2-Cl | —O— | 6-F | N | CH | CH | N | CH |
| IIIb-81 | H | OCH₃ | 2-Cl | —O— | 4-Cl | N | N | CH | CH | CH |
| IIIb-82 | H | OCH₃ | 2-Cl | —O— | 5-Cl | N | N | CH | CH | CH |
| IIIb-83 | H | OCH₃ | 2-Cl | —O— | 6-Cl | N | N | CH | CH | CH |
| IIIb-84 | H | OCH₃ | 2-Cl | —O— | 4-CF₃ | N | N | CH | CH | CH |
| IIIb-85 | H | OCH₃ | 2-Cl | —O— | 5-CF₃ | N | N | CH | CH | CH |
| IIIb-86 | H | OCH₃ | 2-Cl | —O— | 6-CF₃ | N | N | CH | CH | CH |
| IIIb-87 | H | OCH₃ | 2-Cl | —O— | 4-Br | N | N | CH | CH | CH |
| IIIb-88 | H | OCH₃ | 2-Cl | —O— | 5-Br | N | N | CH | CH | CH |
| IIIb-89 | H | OCH₃ | 2-Cl | —O— | 6-Br | N | N | CH | CH | CH |
| IIIb-90 | H | OCH₃ | 2-Cl | —O— | 4-F | N | N | CH | CH | CH |
| IIIb-91 | H | OCH₃ | 2-Cl | —O— | 5-F | N | N | CH | CH | CH |
| IIIb-92 | H | OCH₃ | 2-Cl | —O— | 6-F | N | N | CH | CH | CH |
| IIIb-93 | H | OCH₃ | 2-Cl | —O— | 4-Cl | N | CH | N | CH | N |
| IIIb-94 | H | OCH₃ | 2-Cl | —O— | 6-Cl | N | CH | N | CH | N |
| IIIb-95 | H | OCH₃ | 2-Cl | —O— | 4-CF₃ | N | CH | N | CH | N |

TABLE 4-continued

| COMPOUND NO. | $R^1$ | $R^2$ | $(R^3)_n$ | Y | $(R^4)_m$ | $Z^2$ | $Z^3$ | $Z^5$ | $Z^5$ | $Z^6$ |
|---|---|---|---|---|---|---|---|---|---|---|
| IIIb-96 | H | $OCH_3$ | 2-Cl | —O— | 6-$CF_3$ | N | CH | N | CH | N |
| IIIb-97 | H | $OCH_3$ | 2-Cl | —O— | 4-Br | N | CH | N | CH | N |
| IIIb-98 | H | $OCH_3$ | 2-Cl | —O— | 6-Br | N | CH | N | CH | N |
| IIIb-99 | H | $OCH_3$ | 2-Cl | —O— | 4-F | N | CH | N | CH | N |
| IIIb-100 | H | $OCH_3$ | 2-Cl | —O— | 6-F | N | CH | N | CH | N |

$R^2$, $R^3$, $R^4$, $Z^2$, $Z^3$, $Z^6$, $Z^7$, $Z^8$, $Z^9$, and $Z^{10}$ in Table 5 below correspond to $R^2$, $R^3$, $R^4$, $Z^2$, $Z^3$, $Z^6$, $Z^7$, $Z^8$, $Z^9$, and $Z^{10}$ in the following chemical formula (IIIc), respectively.

$Z^6$ in Table shows a non-substituted state, before the substitution of $R^4$, as a ring structure, and in the chemical formula (IIIc), a carbon, which is substituted by $R^4$, is also represented by "CH".

[Chemical Formula 9]

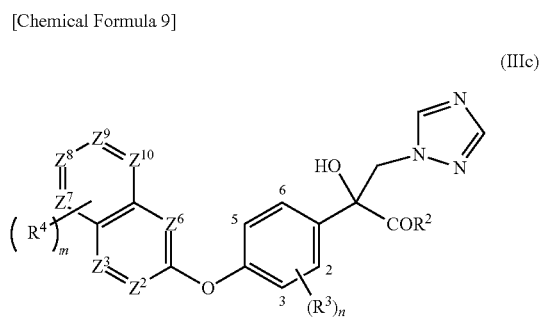

(IIIc)

in the chemical formula (IIId), a carbon, which is substituted by $R^4$, is also represented by "CH".

[Chemical Formula 10]

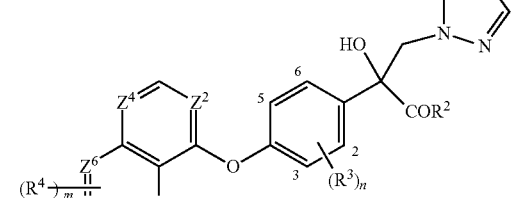

(IIId)

TABLE 5

| COMPOUND NO. | $R^2$ | $(R^3)_n$ | $(R^4)_m$ | $Z^2$ | $Z^3$ | $Z^6$ | $Z^7$ | $Z^8$ | $Z^9$ | $Z^{10}$ |
|---|---|---|---|---|---|---|---|---|---|---|
| IIIc-1 | $OCH_3$ | 2-Cl | — | CH | CH | CH | CH | CH | CH | CH |
| IIIc-2 | $OCH_3$ | 2-Cl | — | CH | N | CH | CH | CH | CH | CH |
| IIIc-3 | $OCH_3$ | 2-Cl | — | CH | CH | N | CH | CH | CH | CH |
| IIIc-4 | $OCH_3$ | 2-Cl | — | CH | CH | CH | N | CH | CH | CH |
| IIIc-5 | $OCH_3$ | 2-Cl | — | CH | CH | CH | CH | CH | CH | N |
| IIIc-6 | $OCH_3$ | 2-Cl | — | CH | CH | CH | N | CH | N | CH |
| IIIc-7 | $OCH_3$ | 2-Cl | — | CH | CH | CH | N | CH | N | N |
| IIIc-8 | $OCH_3$ | 2-Cl | — | N | CH | N | N | CH | N | N |
| IIIc-9 | $OCH_3$ | 2-Cl | — | CH | N | N | N | CH | N | CH |
| IIIc-10 | $OCH_3$ | 2-Cl | 4-Cl | CH | CH | CH | CH | CH | CH | CH |
| IIIc-11 | $OCH_3$ | 2-Cl | 5-Cl | CH | CH | CH | CH | CH | CH | CH |
| IIIc-12 | $OCH_3$ | 2-Cl | 6-Cl | CH | CH | CH | CH | CH | CH | CH |
| IIIc-13 | $OCH_3$ | 2-Cl | 4-Cl | CH | CH | CH | CH | CH | CH | CH |
| IIIc-14 | $OCH_3$ | 2-Cl | 5-Cl | CH | CH | CH | CH | CH | CH | CH |
| IIIc-15 | $OCH_3$ | 2-Cl | 6-Cl | CH | CH | CH | CH | CH | CH | CH |
| IIIc-16 | $OCH_3$ | 2-Cl | 4-Cl | CH | CH | CH | CH | CH | CH | CH |
| IIIc-17 | $OCH_3$ | 2-Cl | 5-Cl | CH | CH | CH | CH | CH | CH | CH |
| IIIc-18 | $OCH_3$ | 2-Cl | 6-Cl | CH | CH | CH | CH | CH | CH | CH |
| IIIc-19 | $OCH_3$ | 2-Cl | 4-Cl | CH | CH | N | CH | CH | CH | CH |
| IIIc-20 | $OCH_3$ | 2-Cl | 5-Cl | CH | CH | N | CH | CH | CH | CH |
| IIIc-21 | $OCH_3$ | 2-Cl | 6-Cl | CH | CH | N | CH | CH | OH | CH |
| IIIc-22 | $OCH_3$ | 2-Cl | 4-Cl | CH | CH | N | CH | CH | CH | CH |
| IIIc-23 | $OCH_3$ | 2-Cl | 5-Cl | CH | CH | N | CH | CH | CH | CH |
| IIIc-24 | $OCH_3$ | 2-Cl | 6-Cl | CH | CH | N | CH | CH | CH | CH |
| IIIc-25 | $OCH_3$ | 2-Cl | 4-F | CH | CH | N | CH | CH | CH | CH |
| IIIc-26 | $OCH_3$ | 2-Cl | 5-F | CH | CH | N | CH | CH | CH | OH |
| IIIc-27 | $OCH_3$ | 2-Cl | 6-F | CH | CH | N | CH | CH | CH | CH |

$R^2$, $R^3$, $R^4$, $Z^2$, $Z^4$, $Z^5$, $Z^6$, and $Z^8$ in Table 6 below correspond to $R^2$, $R^3$, $R^4$, $Z^2$, $Z^4$, $Z^5$, $Z^6$, and $Z^8$ in the following chemical formula (IIId), respectively.

$Z^4$, $Z^5$, $Z^6$, and $Z^8$ in the Table show a non-substituted state, before the substitution of $R^4$, as a ring structure, and

TABLE 6

| COMPOUND NO. | $R^2$ | $(R^3)_n$ | $(R^4)_m$ | $Z^2$ | $Z^4$ | $Z^5$ | $Z^6$ | $Z^8$ |
|---|---|---|---|---|---|---|---|---|
| IIId-1 | $OCH_3$ | 2-Cl | — | CH | CH | CH | CH | CH |
| IIId-2 | $OCH_3$ | 2-Cl | — | CH | CH | CH | CH | N |
| IIId-3 | $OCH_3$ | 2-Cl | — | CH | CH | N | CH | CH |
| IIId-4 | $OCH_3$ | 2-Cl | — | CH | N | CH | CH | CH |
| IIId-5 | $OCH_3$ | 2-Cl | — | N | N | CH | CH | CH |
| IIId-6 | $OCH_3$ | 2-Cl | — | CH | CH | CH | N | N |
| IIId-7 | $OCH_3$ | 2-Cl | — | N | N | N | CH | N |
| IIId-8 | $OCH_3$ | 2-Cl | 4-Cl | CH | CH | CH | CH | CH |
| IIId-9 | $OCH_3$ | 2-Cl | 5-Cl | CH | CH | CH | CH | CH |
| IIId-10 | $OCH_3$ | 2-Cl | 6-Cl | CH | CH | CH | CH | CH |
| IIId-11 | $OCH_3$ | 2-Cl | 4-Cl | CH | CH | CH | CH | CH |
| IIId-12 | $OCH_3$ | 2-Cl | 5-Cl | CH | CH | CH | CH | CH |
| IIId-13 | $OCH_3$ | 2-Cl | 6-Cl | CH | CH | CH | CH | CH |
| IIId-14 | $OCH_3$ | 2-Cl | 4-Cl | CH | CH | CH | CH | CH |
| IIId-15 | $OCH_3$ | 2-Cl | 5-Cl | CH | CH | CH | CH | CH |
| IIId-16 | $OCH_3$ | 2-Cl | 6-Cl | CH | CH | CH | CH | CH |
| IIId-17 | $OCH_3$ | 2-Cl | 4-Cl | CH | CH | CH | CH | N |
| IIId-18 | $OCH_3$ | 2-Cl | 5-Cl | CH | CH | CH | CH | N |
| IIId-19 | $OCH_3$ | 2-Cl | 3-Cl | CH | CH | CH | CH | N |
| IIId-20 | $OCH_3$ | 2-Cl | 4-Cl | CH | CH | CH | CH | N |
| IIId-21 | $OCH_3$ | 2-Cl | 5-Cl | CH | CH | CH | CH | N |
| IIId-22 | $OCH_3$ | 2-Cl | 3-Cl | CH | CH | CH | CH | N |
| IIId-23 | $OCH_3$ | 2-Cl | 4-Cl | CH | CH | CH | CH | N |
| IIId-24 | $OCH_3$ | 2-Cl | 5-Cl | CH | CH | CH | CH | N |
| IIId-25 | $OCH_3$ | 2-Cl | 3-Cl | CH | CH | CH | CH | N |
| IIId-26 | $OCH_3$ | 2-Cl | 7-Cl | CH | N | CH | CH | CH |
| IIId-27 | $OCH_3$ | 2-Cl | 8-Cl | CH | N | CH | CH | CH |
| IIId-28 | $OCH_3$ | 2-Cl | 7-Cl | CH | N | CH | CH | CH |
| IIId-29 | $OCH_3$ | 2-Cl | 8-Cl | CH | N | CH | CH | CH |
| IIId-30 | $OCH_3$ | 2-Cl | 7-Cl | CH | N | CH | CH | CH |
| IIId-31 | $OCH_3$ | 2-Cl | 8-Cl | CH | N | CH | CH | CH |

$R^2$, $R^3$, $R^4$, $Z^2$, $Z^3$, $Z^4$, $Z^5$, $Z^6$, and $Z^7$ in Table 7 below correspond to $R^2$, $R^3$, $R^4$, $Z^2$, $Z^3$, $Z^4$, $Z^5$, $Z^6$, and $Z^7$ in the following chemical formula (IIIe), respectively.

$Z^5$, $Z^6$, and $Z^7$ in the Table show a non-substituted state, before the substitution of $R^4$, as a ring structure, and in the chemical formula (IIIe), a carbon, which is substituted by $R^4$, is also represented by "CH".

[Chemical Formula 11]

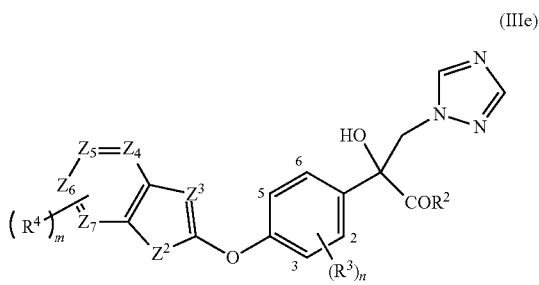

(IIIe)

TABLE 7

| COMPOUND NO. | $R^2$ | $(R^3)_n$ | $(R^4)_m$ | $Z^2$ | $Z^3$ | $Z^4$ | $Z^5$ | $Z^6$ | $Z^7$ |
|---|---|---|---|---|---|---|---|---|---|
| IIIe-1 | OCH$_3$ | 2-Cl | — | N—H | N | CH | CH | CH | CH |
| IIIe-2 | OCH$_3$ | 2-Cl | — | N—Me | N | CH | CH | CH | CH |
| IIIe-3 | OCH$_3$ | 2-Cl | — | O | N | CH | CH | CH | CH |
| IIIe-4 | OCH$_3$ | 2-Cl | — | S | N | CH | CH | CH | CH |
| IIIe-5 | OCH$_3$ | 2-Cl | — | N—H | CH | CH | CH | CH | CH |
| IIIe-6 | OCH$_3$ | 2-Cl | — | N—Me | CH | CH | CH | CH | CH |
| IIIe-7 | OCH$_3$ | 2-Cl | — | N—H | N | N | CH | N | CH |
| IIIe-8 | OCH$_3$ | 2-Cl | — | N—Me | N | N | CH | N | CH |
| IIIe-9 | OCH$_3$ | 2-Cl | — | N—H | N | CH | N | CH | N |
| IIIe-10 | OCH$_3$ | 2-Cl | — | N—Me | N | CH | N | CH | N |
| IIIe-11 | OCH$_3$ | 2-Cl | — | N—H | N | N | CH | CH | CH |
| IIIe-12 | OCH$_3$ | 2-Cl | — | N—Me | N | N | CH | CH | CH |
| IIIe-13 | OCH$_3$ | 2-Cl | — | N—H | N | CH | CH | CH | N |
| IIIe-14 | OCH$_3$ | 2-Cl | — | N—Me | N | CH | CH | CH | N |
| IIIe-15 | OCH$_3$ | 2-Cl | — | N—H | N | CH | N | CH | CH |
| IIIe-16 | OCH$_3$ | 2-Cl | — | N—Me | N | CH | N | CH | CH |
| IIIe-17 | OCH$_3$ | 2-Cl | — | N—H | N | CH | CH | N | CH |
| IIIe-18 | OCH$_3$ | 2-Cl | — | N—Me | N | CH | CH | N | CH |
| IIIe-19 | OCH$_3$ | 2-Cl | 5-Cl | N—Me | N | CH | CH | CH | CH |
| IIIe-20 | OCH$_3$ | 2-Cl | 6-Cl | N—Me | N | CH | CH | CH | CH |
| IIIe-21 | OCH$_3$ | 2-Cl | 7-Cl | N—Me | N | CH | CH | CH | CH |
| IIIe-22 | OCH$_3$ | 2-Cl | 5-Cl | O | N | CH | CH | CH | CH |
| IIIe-23 | OCH$_3$ | 2-Cl | 6-Cl | O | N | CH | CH | CH | CH |
| IIIe-24 | OCH$_3$ | 2-Cl | 7-Cl | O | N | CH | CH | CH | CH |
| IIIe-25 | OCH$_3$ | 2-Cl | 5-Cl | S | N | CH | CH | CH | CH |
| IIIe-26 | OCH$_3$ | 2-Cl | 6-Cl | S | CH | N | CH | CH | CH |
| IIIe-27 | OCH$_3$ | 2-Cl | 7-Cl | S | CH | N | CH | CH | CH |
| IIIe-28 | OCH$_3$ | 2-Cl | — | N—Ph | N | CH | CH | CH | CH |
| IIIe-29 | OCH$_3$ | 2-Cl | — | N—Et | CH | N | CH | CH | CH |
| IIIe-30 | OCH$_3$ | 2-Cl | — | N—Pr | CH | N | CH | CH | CH |
| IIIe-31 | OCH$_3$ | 2-Cl | — | N-Bzl | CH | N | CH | CH | CH |

$R^2$, $R^3$, $R^4$, $Z^2$, $Z^3$, $Z^4$, and $Z^5$ in Table 8 below correspond to $R^2$, $R^3$, $R^4$, $Z^2$, $Z^3$, $Z^4$, and $Z^5$ in the following chemical formula (IIIf), respectively.

$Z^2$ in the Table shows a non-substituted state, before the substitution of $R^3$, as a ring structure, and in the chemical formula (IIIa), a carbon, which is substituted by $R^3$, is also represented by "CH".

[Chemical Formula 12]

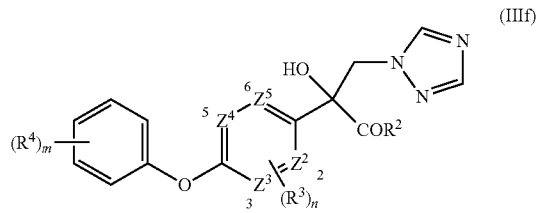

(IIIf)

TABLE 8

| COMPOUND NO. | $R^2$ | $(R^3)_n$ | $(R^4)_m$ | $Z^2$ | $Z^3$ | $Z^4$ | $Z^5$ |
|---|---|---|---|---|---|---|---|
| IIIf-1 | OCH$_3$ | H | 4-Cl | N | CH | CH | CH |
| IIIf-2 | OCH$_3$ | H | 4-Cl | CH | N | CH | CH |
| IIIf-3 | OCH$_3$ | H | 4-Cl | N | CH | CH | N |
| IIIf-4 | OCH$_3$ | H | 4-Cl | CH | N | N | CH |
| IIIf-5 | OCH$_3$ | H | 4-Cl | CH | N | CH | N |
| IIIf-6 | OCH$_3$ | 2-CF$_3$ | 4-Cl | CH | N | CH | CH |
| IIIf-7 | OCH$_3$ | 2-CF$_3$ | 4-Cl | CH | CH | N | CH |
| IIIf-8 | OCH$_3$ | 2-CF$_3$ | 4-Cl | CH | CH | CH | N |
| IIIf-9 | OCH$_3$ | 2-CF$_3$ | 4-Br | CH | N | CH | CH |
| IIIf-10 | OCH$_3$ | 2-CF$_3$ | 4-Br | CH | CH | N | CH |
| IIIf-11 | OCH$_3$ | 2-CF$_3$ | 4-CF$_3$ | CH | N | CH | CH |
| IIIf-12 | OCH$_3$ | 2-CF$_3$ | 4-CF$_3$ | CH | CH | N | CH |
| IIIf-13 | OCH$_3$ | 2-CF$_3$ | 3,4-Cl$_2$ | CH | N | CH | CH |
| IIIf-14 | OCH$_3$ | 2-CF$_3$ | 3,4-Cl$_2$ | CH | CH | N | CH |
| IIIf-15 | OCH$_3$ | 2-CF$_3$ | 3-F,4-Cl | CH | N | CH | CH |
| IIIf-16 | OCH$_3$ | 2-CF$_3$ | 3-F,4-Cl | CH | CH | N | CH |

Agrochemically acceptable salts of the azole derivative (I) include cation salts in which the cation and anion do not particularly exert bad influences on the effects of the azole derivative (I), and acid addition salts of acid thereof. Particularly preferable cation may include ions of alkali metals (preferably sodium and potassium), alkaline earth metals (preferably calcium, magnesium, and barium), and transition metals (preferably manganese, copper, zinc, and iron). If desired, ammonium ions which may have 1 to 4 $C_1$-$C_4$-alkyl substituents and/or one phenyl substituent or benzyl substituent (preferably diisopropyl ammonium, tetramethyl ammonium, tetrabutyl ammonium, trimethylbenzyl ammonium), and phosphonium ions, sulfonium ions (preferably tri($C_1$-$C_4$-alkyl)sulfonium), and sulfoxonium ions (preferably tri($C_1$-$C_4$-alkyl)sulfoxonium) are also preferable. Anions of the useful acid addition salts are mainly chloride ions, bromide ions, fluoride ions, hydrogensulfate ions, sulfate ions, dihyrogen phosphate ions, hydrogen phosphate ions, phosphate ions, nitrate ions, bicarbonate ions, carbonate ions, hexafluorosilicate ions, hexafluorophosphate ions, benzoate ions, and anions of $C_1$-$C_4$-alkanoic acid, preferably formate ions, acetate ions, propionate ions, and butyrate ions. They can be formed by reacting the azole derivative (I) with a corresponding anion acid (preferably hydrochloric acid, hydrobromic acid, sulfuric acid, phosphoric acid, and nitric acid).

[2. Method for Producing Azole Derivative]

The azole derivative (I) can be produced by any of three methods shown below. In the method for producing the azole derivative explained below, explanation is made using a specific aspect of the azole derivative (I) as a matter of convenience, but other aspects can be produced by changing starting materials.

$R^1$, $R^2$, $R^3$, $R^4$, $R^7$, A, and D in the following scheme correspond to $R^1$, $R^2$, $R^3$, $R^4$, $R^7$, A, and D in the general formula (I) described above, respectively.

(1) Method 1 for Producing Azole Derivative

The azole derivative (I) can be produced according to the following whole scheme 1 from compounds obtained by a known technique.

(Whole Scheme 1)

[Chemical Formula 13]

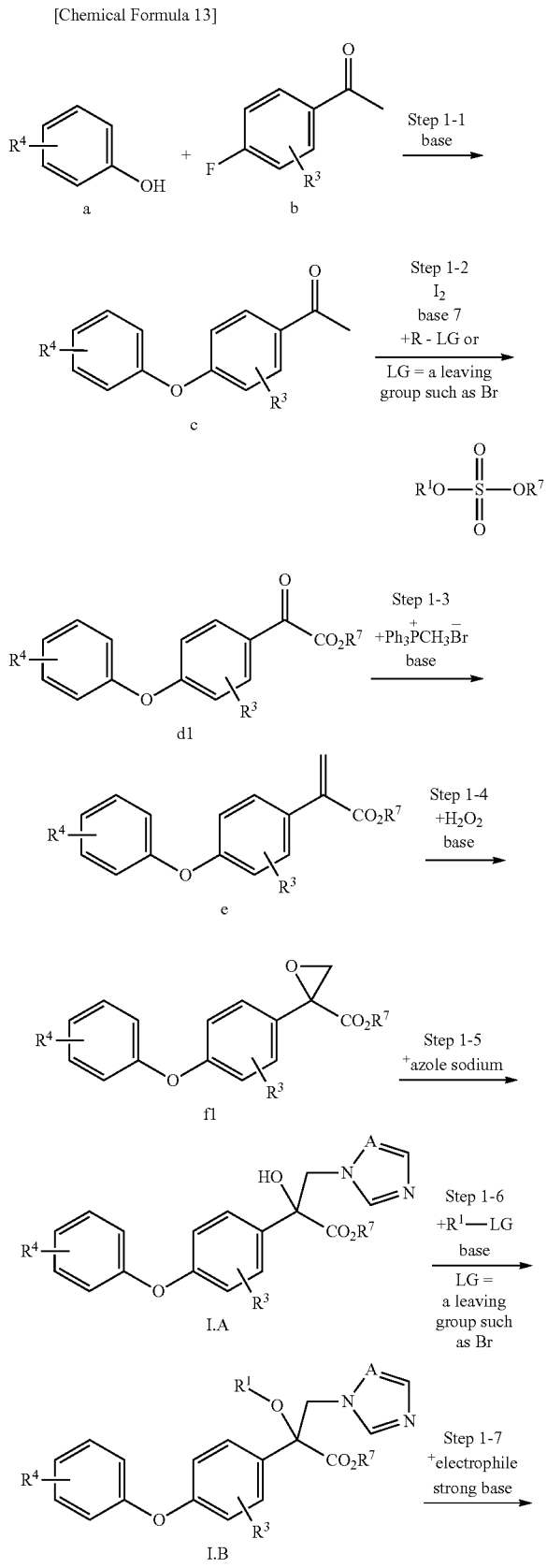
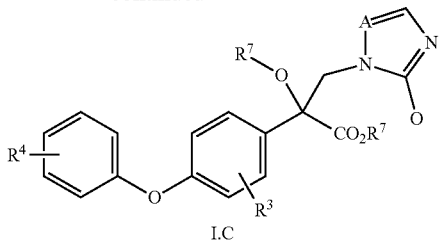

(Step 1-1) In the production method 1, a phenol compound represented by the general formula a (hereinafter referred to as "Phenol a") is reacted with an acetophenone compound represented by the general formula b (hereinafter referred to as "Acetophenone b") in the presence of a base to obtain a compound represented by the general formula c (hereinafter referred to as "Compound c"), in Scheme 1 described above.

(Step 1-2) The obtained Compound c is reacted with iodine in an appropriate solvent, such as dimethyl sulfoxide (DMSO). An appropriate base, such as carbonate, is added thereto, and is reacted with dialkyl sulfate ($R^7OS(=O)_2OR^7$) or $R^7$-LG to obtain a compound represented by the general formula d1 (hereinafter referred to as "Compound d1"). Here, the carbonate includes sodium carbonate, potassium carbonate, cesium carbonate, and lithium carbonate, preferably potassium carbonate. LG is a nucleophilically substitutable leaving group, for example, a leaving group selected from halogen groups, alkylsuflonyloxy groups, and arylsulfonyloxy groups, preferably the halogen groups, more preferably a bromine group and an iodine group.

(Step 1-3) Compound d1 is reacted with a methyltriphenyl phosphonium halide in any solvent, such as toluene, tetrahydrofuran (THF) or DMSO, in the presence of a base, such as potassium tert-butoxide or hydrogenated sodium to obtain an acrylic acid ester compound represented by the general formula e (hereinafter referred to as "Acrylate e").

(Step 1-4) Acrylate e is reacted with an aqueous solution of hydrogen peroxide or a mixture thereof with sodium carbonate or urea in a solvent of methanol or acetonitrile, preferably in the presence of a base, such as sodium hydrogen carbonate or potassium carbonate, to obtain an epoxide compound represented by the general formula f1 (hereinafter referred to as "Epoxide compound f1").

(Step 1-5) Epoxide compound f1 is reacted with an azole sodium in an organic solvent, preferably, dimethyl formamide (DMF), to obtain a compound represented by the general formula I.A, which is a compound represented by the general formula (I) wherein $R^1$ is hydrogen and D is hydrogen (hereinafter referred to as "Compound I.A").

(Step 1-6) In an appropriate case, subsequently Compound I.A is reacted with $R^1$-LG preferably an appropriate solvent, such as THF, in the presence of a base, such as NaH, to obtain a compound represented by the general formula I.B (hereinafter referred to as "Compound I.B"). Here, LG is a nucleophilically substitutable leaving group, for example, a leaving group selected from halogen groups, alkylsulfonyloxy groups, and arylsulfonyloxy groups, preferably a bromine group or an iodine group.

(Step 1-7) Compound I.B is reacted with an electrophile, such as sulfur, iodine, iodine monochloride, or dibromotetrafluoroethane, in the presence of a strong base, such as butyllithium, lithium diisopropylamide, or potassium hexamethyldisilazide to obtain a compound represented by the general formula I.C.

(2) Method 2 for Producing Azole Derivative

The azole derivative (I) of the present invention can be produced according to the following whole scheme 2 from compounds obtained by a known technique.

(Whole Scheme 2)

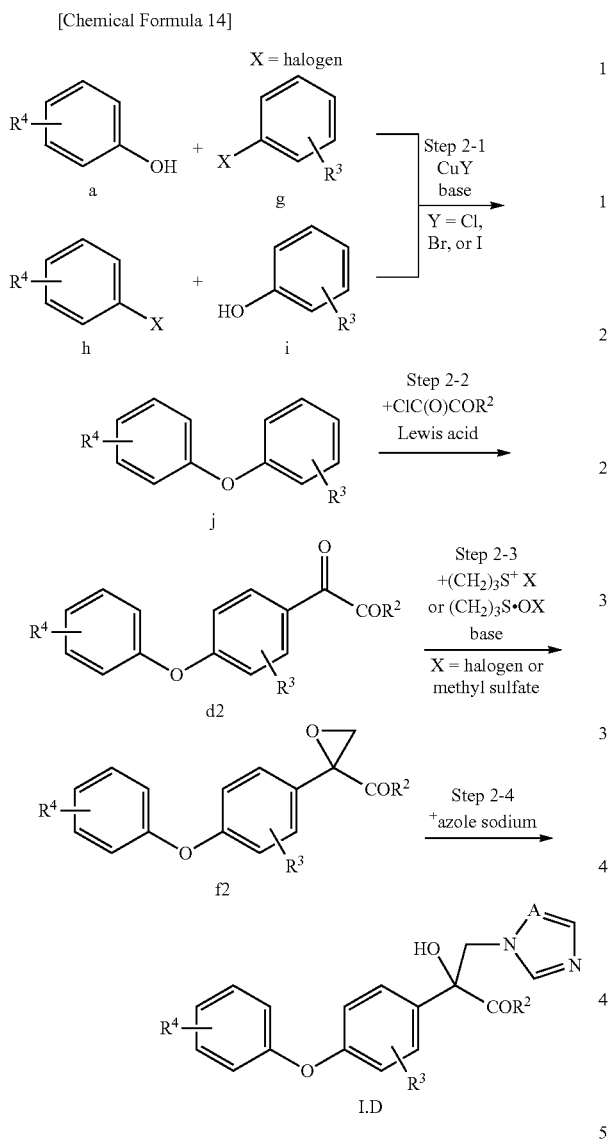

(Step 2-1) In the production method 2, Phenol a is reacted with a halobenzene compound represented by the general formula g, or a phenol compound represented by the general formula i is reacted with a halobenzene compound represented by the general formula h, if desired in the presence of CuX, preferably in the presence of a base to obtain a compound represented by the general formula j (hereinafter referred to as "Compound j"), in the whole Scheme 2 described above. Here, X is a chlorine group, a bromine group, or an iodine group.

(Step 2-2) Compound j is reacted with alkyl chloroglyoxylate in the presence of a Lewis acid, preferably aluminum chloride or iron chloride (III) to obtain Compound d. Compound d may be obtained by the same manner as in the production method 1, or may be introduced into Compound I.A, I.B, or I.C, as in the production method 1.

(Step 2-3) Compound d2 is reacted with a compound selected from trimethylsulfonium halide, trimethylsulfonium methylsulfate, trimethylsulfoxonium halide, and trimethylsulfoxonium methylsulfate in the presence of a base, such as halogenated sodium, sodium tert-butoxide, or cesium carbonate to obtain Epoxide Compound f2.

(Step 2-4) Epoxide Compound f2 is reacted with azole sodium in an organic solvent such as DMF to obtain Compound I.D, which is a compound represented by the general formula (I) wherein $R^1$ is hydrogen and D is hydrogen. Compound I.D may be converted into a derivative.

(3) Method 3 for Producing Azole Derivative

The azole derivative (I) of the present invention can be produced according to the following whole scheme 3 from compounds obtained by a known technique.

(Whole Scheme 3)

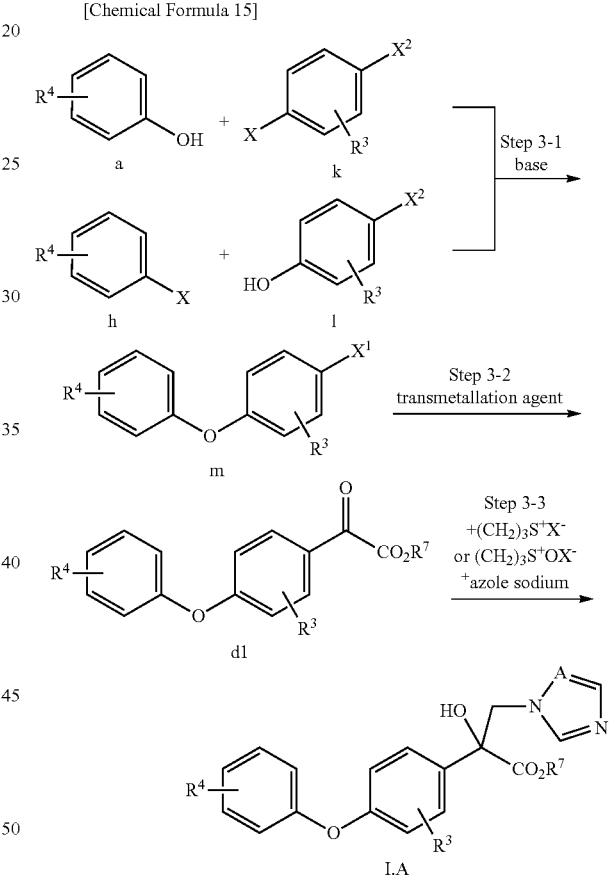

(Step 3-1) In the production method 3, Phenol a is reacted with a halobenzene compound represented by the general formula k, or a phenol compound represented by the general formula l is reacted with a halobenzene compound represented by the general formula h to obtain a compound represented by the general formula m (hereinafter referred to as "Compound m"), in the Whole Scheme 3 described above. Here, $X^1$ is a bromine group or an iodine group.

(Step 3-2) Compound m is converted into an organic metal agent by reacting with a transmetallation agent, such as butyl lithium or isopropyl magnesium chloride, followed by reacting with dialkyl oxalate $(COOR^7)_2$ to obtain Compound d1. Compound d1 may be obtained by the same manner as in the production method 1 or production method 2, or may be introduced into Compound I.A, I.B, I.C, or I.D as in the production method 1 or the production method 2.

(Step 3-3) Compound d1 is reacted with trimethylsulfonium halide, trimethylsulfonium methylsulfate, trimethylsulfoxonium halide, or trimethylsulfoxonium methylsulfate in the presence of azole sodium to obtain Compound I.A, which is a compound represented by the general formula (I) wherein $R^1$ is hydrogen and D is hydrogen. Compound I.A may be converted into a derivative.

[Method for Producing Derivative]

As described above, in the production methods 1 to 3, the explanation is made using the specific aspect of the azole derivative (I) as a matter of convenience, and the present invention is not limited thereto. For example, in the production methods 1 to 3, the embodiment represented by the general formula (I) wherein Z is the phenyl group is explained, but Z is not limited to the phenyl group. For example, when a commercially available compound, in which a naphthyl group, or a 5-membered or 6-membered heteroaromatic ring or a 9-membered or 10 membered heteroaromatic ring formed of 2 rings containing 1 to 4 heteroatoms selected from O, N, and S to which a hydroxyl group and a preferable $R^4$ are bonded, is used as a starting material instead of Phenol a, an azole derivative (I) wherein Z is a group other than the phenyl group can be produced in the same manner as in the production methods 1 to 3.

In the production methods 1 to 3, the embodiment represented by the general formula (I) wherein E is the phenyl group is explained, but E is not limited to the phenyl group. For example, when a compound in which a keto group, a fluoro group, and a preferable $R^3$ are bonded to a 6-membered heteroaromatic ring containing 1 or 2 N atoms is used as a starting material instead of Acetophenone b, an azole derivative (I) in which E is a group other than the phenyl group can be produced in the same manner as in the production method 1.

In addition, according to the following method, an azole derivative (I) wherein E is a group other than the phenyl group can be produced in the same manner as in the production method 2.

To use a compound in which a chlorine group, a bromine group, or an iodine group, and a preferable $R^3$ are bonded to a 6-membered heteroaromatic ring containing 1 or 2 N atoms instead of the halobenzene compound represented by the general formula g.

To use a compound in which a hydroxyl group and preferable $R^3$ are bonded to a 6-membered heteroaromatic ring containing 1 or 2 N atoms instead of the phenol compound represented by the general formula i.

In addition, according to the following method, an azole derivative (I) wherein E is a group other than the phenyl group can be produced in the same manner as in the production method 3.

To use a compound in which a first halogen group selected from a chlorine group, a bromine group, and an iodine group, a second halogen group selected from a bromine group and an iodine group, and preferable $R^3$ are bonded to a 6-membered heteroaromatic ring containing 1 or 2 N atoms instead of the halobenzene compound represented by the general formula k.

To use a compound in which a bromine group or an iodine group, a hydroxyl group, and preferable $R^3$ are bonded to a 6-membered heteroaromatic ring containing 1 or 2 N atoms instead of the phenol compound represented by the general formula l.

In the production methods 1 to 3, Y in the general formula (I) is an oxygen atom, but Y is not limited to the oxygen atom. For example, when a commercially available compound in which —$CH_2OH$, —$OCH_3$, —$NH_2$, —N(—$C_1$-$C_4$-alkyl)H, —N(—$C_3$-$C_6$-cycloalkyl)H, or —S(O)$_p$H is bonded to Z in the general formula (I) is used as a starting material instead of Phenol a, an azole derivative (I) in which Y is a group other than oxygen atom can be produced in the same manner as in the production methods 1 to 3.

[3. Method for Producing N-Oxide Form of Azole Derivative]

N-oxide form can be produced from Compound I according to a conventional oxidation method, for example, by treating Compound I with an organic acid peroxide such as meth-chloroperoxybenzoic acid (see WO 03/64572 or J. Med. Chem. 38(11), 1892 to 903, 1995), hydrogen peroxide, which is an inorganic oxidizing agent (see J. Heterocyc. Chem. 18 (7), 1305 to 8, 1981), or oxone (see J. Am. Chem. Soc. 123 (25), 5962 to 5973, 2001). This oxidation can provide pure mono-N-oxide or a mixture of different N-oxides. The mixture of N-oxides can be separated by using a conventional method such as chromatography.

[4. Intermediate Compound of Azole Derivative]

Preferable intermediate compounds in the production of the azole derivative may include compounds represented by the following general formula (IV) (hereinafter referred to as "Intermediate Compound (IV)").

[Chemical Formula 16]

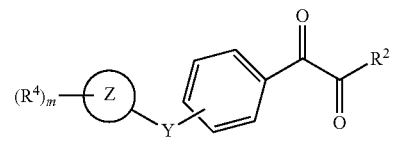

(IV)

Here, $R^2$, $R^4$, Y, Z, and m in the general formula (IV) are the same as $R^2$, $R^4$, Y, Z, and m in the general formula (I), respectively.

Compound d1 in Scheme 1 and Compound d2 in Schemes 2 and 3 are one aspect of Intermediate Compound (IV). When Intermediate Compound (IV) is used, accordingly, an azole derivative (I) can be produced referring to Schemes 1 to 3 described above.

As shown in Scheme 1 described above, the compound represented by the general formula (IV) wherein $R^2$ is a group represented by —$OR^7$ (hereinafter referred to as "Intermediate Compound (VI)") can be produced from a compound represented by the following general formula (V) (hereinafter referred to as "Intermediate Compound (V)").

[Chemical Formula 17]

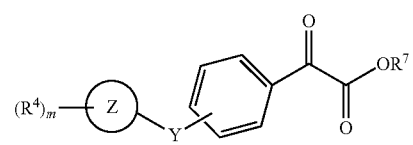

(VI)

[Chemical Formula 18]

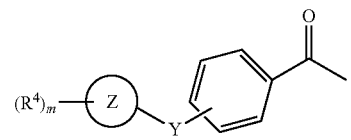

(V)

Here, $R^7$, $R^4$, Y, Z, and m in the general formula (VI) are the same as $R^7$, $R^4$, Y, Z, and m in the general formula (I), respectively. Similarly, $R^4$, Y, Z, and m in the general formula (V) are the same as $R^4$, Y, Z, and m in the general formula (I), respectively.

Specifically, Intermediate Compound (VI) can be produced in a manner in which using an $R^7$-halogenated compound, iodine, and a carbonate, Intermediate Compound (V) is changed to Intermediate Compound (VI) in dimethyl sulfoxide.

[5. Agricultural or Horticultural Chemical Agent]

The azole derivative (I) has an imidazolyl group or a 1,2,4-triazolyl group, and thus can form an acid addition salt of an inorganic acid or an organic acid, or a metal complex. The derivative, accordingly, can be used as a part of an acid addition salt or metal complex in an agricultural or horticultural chemical agent, or the like, as an active ingredient.

(1) Plant Disease Controlling Effect

The agricultural or horticultural chemical agent in the present embodiment shows the controlling effect on various plant diseases.

Examples of the applicable diseases may include diseases described below. In parentheses described after each disease, main pathogenic germs, which cause the disease, are described: asian soybean rust (*Phakopsora pachyrhizi, Phakopsora meibomiae*), soybean brown spot (*Zymoseptoria glycines*), soybean purpora (*Cercospora kikuchii*), soybean brown leaf spot (*Alternaria* sp.), soybean anthrax (*Collectotrichum truncatum*), soybean Frogeye leaf spot (*Cercocpora sojina*), soybean *Rhizoctonia* root rot (*Rhizoctonia solani*), soybean leaf rot (*Rhizoctonia solani*), soybean melanose (*Diaporthe phaseolorum*), soybean stem *Phytophthora* rot (*Phytophthora sojae*), rapeseed *Phoma* leaf spot/stem canker (*Leptosphaeria maculans, Leptosphaeria biglobosa*), rapeseed Light leaf spot (*Pyrenopeziza brassicae*), rapeseed Clubroot (*Plasmodiophora brassicae*), rapeseed *Verticillium* wilt (*Verticillium longisporum*), rapeseed Blackspot (*Alternaria* spp), rice blast (*Pyricularia oryzae*), rise *Helminthosporium* leaf spot (*Cochliobolus miyabeanus*), rice plant germsl leaf (*Xanthomonas oryzae*), rice sheath blight disease (*Rhizoctonia solani*), rice stem-rot (*Helminthosporium sigmoideun*), rice "Bakanae" disease (*Gibberella fujikuroi*), rice seeding blight (*Pythium aphanidermatum*), rice damping-off (*Pythium graminicola*), barley powdery mildew (*Erysiphe graminis* f. sp *hordei*), barley stem rust (*Puccinia graminis*), barley stripe rust (*Puccinia striiformis*), barley mottle leaf (*Pyrenophora graminea*), barley scald (*Rhynchosporium secalis*), barley loose kernel smut (*Ustilago nuda*), barley net blotch (*Pyrenophora teres*), barley *Fusarium* head blight (*Fusarium graminearum, Microdochium nivale*), wheat powdery mildew (*Erysiphe graminis* f. sp *tritici*), wheat leaf rust (*Puccinia recondita*), wheat stripe rust (*Puccinia striiformis*), wheat eye spot (*Pseudocercosporella herpotrichoides*), wheat *Fusarium* head blight (*Fusarium graminearum, Microdochium nivale*), wheat glume blotch (*Phaeosphaeria nodorum*), wheat speckled leaf blotch (*Zymoseptoria tritici*), wheat *Fusarium* snow blight (*Microdochium nivale*), wheat damping-off (*Gaeumannomyces graminis*), wheat glume spot (*Epicoccum* spp), wheat yellow spot (*Pyrenophora tritici-repentis*), wheat snow-rot (*Typhula incarnate, Typhula ishikariensis*), grass dollarspot disease (*Sclerotinia homoeocarpa*), grass largepatchdisease (*Rhizoctonia solani*), brown patch disease (*Rhizoctonia solani*), grass anthrax (*Colletotrichum graminicola*), grass Gray leaf Spot (*Pyricularia grisea*), grass necrotic ring spot (*Ophiosphaerella korrae*), grass Red thread (*Laetisaria fuciformis*), grass rust (*Puccinia zoysiae*), grass summer patch (*Magnaporthe poae*), grass Root decline of warm-season grasses (*Gaeumannomyces graminis*), grass brown ring patch (*Waitea circinata*), grass fairy ring disease (*Agaricus, Calvatia, Chlorophyllum, Clitocybe, Lepiota, Lepista, Lycoperdon, Marasmius, Scleroderma, Tricholoma*, and the like), grass *Fusarium* snow blight (*Microdochium nivale*), grass snow-rot (*Typhula incarnate, Typhula ishikariensis*), grass *Curvularia* speckled leaf blotch (*Curvularia* sp.), grass *Rhizoctonia* patch (*Ceratobasidium* sp.), grass damping-off (*Zoysia* decline), corn smut (*Ustilago maydis*), corn anthrax (*Colletotrichum graminicola*), corn brown spot (*Kabatiella zeae*), corn gray leaf spot (*Cercospora zeae-maydis*), corn sooty blotch (*Setosphaeria turcica*), corn North leaf spot (*Cochliobolus carbonum*), corn leaf spot (*Physoderma maydis*), corn rust (*Puccinia* spp), corn *Helminthosporium* leaf spot (*Bipolaris maydis*), corn yellow *Helminthosporium* leaf spot (*Phyllosticta maydis*), corn *Fusarium* head blight (*Gibberella zeae*), sugarcane rust (*Puccinia* spp), gourd family powdery mildew (*Sphaerotheca fuliginea*), gourd family anthracnose (*Colletotrichum lagenarium, Glomerella cingulata*), cucumber Downy mildew (*Pseudoperonospora cubensis*), cucumber gray *Phytophthora* rot (*Phytophthora capsici*), cucumber *Fusarium* wilt (*Fusarium oxysporum* f. sp. *cucumerinum*), watermelon *Fusarium* wilt (*Fusarium oxysporum* f. sp. *niveum*), apple powdery mildew (*Podosphaera leucotricha*), apple black spot (*Venturia inaequalis*), apple *Monilia* (*Monilinia mali*), apple *Alternaria* blotch (*Alternaria alternata*), apple *Valsa* canker (*Valsa mali*), pear black spot (*Alternaria kikuchiana*), pear powdery mildew (*Phyllactinia pyri*), pear chocolate spot (*Gymnosporangium asiaticum*), pear black spot (*Venturia nashicola*), strawberry powdery mildew (*Sphaerotheca humuli*), Stone fruit tree brown rot (*Monilinia fructicola*), citrus blue mold (*Penicillium italicum*), grape powdery mildew (*Uncinula necator*), grape Downy mildew (*Plasmopara viticola*), grape ripe rot (*Glomerella cingulata*), grape rust (*Phakopsora ampelopsidis*), mottle leaf (Black sigatoka) (*Mycosphaerella fijiensis, Mycosphaerella musicola*), tomato powdery mildew (*Erysiphe cichoracearum*), tomato early blight (*Alternaria solani*), eggplant powdery mildew (*Erysiphe cichoracearum*), potato summer *Phytophthora* rot (*Alternaria solani*), potato anthrax (*Colletotrichum coccodes*), potato powdery mildew (*Erysiphe* spp, *Leveillula taurica*), potato *Phytophthora* rot (*Phytophthora infestans*), tobacco powdery mildew (*Erysiphe cichoracearum*), tobacco chocolate spot (*Alternaria longipes*), sugar beet brown spot (*Cercospora beticola*), sugar beet powdery mildew (*Erysiphe betae*), sugar beet leaf rot (*Thanatephorus cucumeris*), sugar beet root rot (*Thanatephorus cucumeris*), sugar beet black root rot (*Aphanomyces cochlioides*), Japanses radish chlorosis (*Fusarium oxysporum* f. sp. *raphani*), tea leaf anthrax (*Discula theae-sinensis*), tea leaf blister blight (*Exobasidium vexans*), tea leaf *Paracercospora egenula* (*Pseudocercospora ocellata, Cercospora chaae*), tea leaf ring spot (*Pestalotiopsis longiseta, Pestalotiopsis theae*), tea leaf net blister blight (*Exobasidium reticulatum*), cotton black spot *Alternaria* leaf spot (*Alternaria* spp), cotton anthrax (*Glomerella* spp), cotton ring spot (*Ascochyta gossypii*), cotton rust (*Puccinia* spp, *Phykopsora* spp), cotton *Cercospora* blight and leaf spot (*Cercospora* spp), cotton *Diplopia* boll rot (*Diplopia* spp), cotton Hard lock (*Fusarium* spp), cotton *Phoma* blight (*Phoma* spp), cotton *Stemphyllium* leaf spot (*Stemphyllium* spp), peanut black leaf blight (*Cercosporidium* personatum), peanut brown spot (*Cercospora arachidicola*), peanut southern blight (*Sclerotium rolfsii*), peanut rust (*Puccinia arachidis*), gray mold (*Botrytis*

*cinerea*) attacking various crops, diseases by the genus *Pythium* (*Pythium* spp), secerotial diseases (*Sclerotinia sclerotiorum*), and the like. Also seed infectious diseases or diseases in early growth of various plants, caused by *Aspergillus* sp., *Cochliobolus* sp., *Corticium* sp., *Diplodia* sp., *Penicillium* sp., *Fusarium* sp., *Gibberella* sp., *Mucor* sp., *Phoma* sp., *Phomopsis* sp., *Pyrenophora* sp., *Pythium* sp., *Rhizoctonia* sp., *Rhizopus* sp., *Thielaviopsis* sp., *Tilletia* sp., *Trichoderma* sp., and *Ustilago* sp. are included.

The agricultural or horticultural chemical agent of the present embodiment can be used for a germicide. The agricultural or horticultural chemical agent of the present embodiment show the particularly excellent controlling effect on the wheat family *Fusarium* head blight diseases such as wheat speckled leaf blotch and barley leaf rust, among the diseases described above. For that reason, the agricultural or horticultural chemical agent is preferably used for controlling the wheat family, but is not limited thereto.

The agricultural or horticultural chemical agent of the present embodiment can be utilized in all of plants. Examples of the applicable plant may include the followings: Gramineae familaysuch as rice, wheat, barley, rye, oat, triticale, corn, sorghum, sugarcane, grass, bentgrass, bermudagrass, fescue, and ryegrass; Leguminosae family such as soybean, peanut, kidney bean, pea, small red bean, and alfalfa; Convolvulaceae family such as sweet potato; Solanaceae family such as red pepper, pimento, tomato, eggplant, potato, and tobacco; Polygonaceae family such as buck wheat; Asteraceae family such as sunflower; Araliaceae family such as *ginseng*; Brassicaceae family such as rapeseed, Chinese cabbage, turnip, cabbage, and Japanses radish; Chenopodiaceae family such as sugar beet; Malvaceae family such as cotton; Rubiaceae family such as coffee tree; Sterculiaceae family such as cacao; Theaceae family such as tea leaf; Gourd family such as watermelon, melon, cucumber, and pumpkin; Liliaceae family such as onion, green onion, and garlic; Rosaceae family such as strawberry, apple, almond, apricot, plum, yellow peach, Japanese plum, peach, and pear; Apiaceae family such as carrot; Araceae family such as taro; Anacardiaceae family such as mango; Bromeliaceae family such as pineapple; Caricaceae family such as *papaya*; Ebenaceae family such as persimmon; Ericaceae family such as blueberry; Juglandaceae family such as pecan; Musaceae family such as banana; Oleaceae family such as olive; Arecaceae family such as coconut and date palm; Rutaceae family such as mandarine orange, orange, grapefruit, and lemon; Vitaceae family such as grape; flowers and ornamental plants; and trees other than fruit trees, and other ornamental plants. The plant may also include wild plants, plant cultivars, plants and plant cultivars obtained by a conventional breeding method such as crossbreeding or plasmogamy, and gene recombination plants and plant cultivars obtained by a gene manipulation. The gene recombination plants and plant cultivars may include, for example, herbicide-resistant crops, pest-resistant crops into which insecticidal protein-producing genes are integrated, disease-resistant crops into which genes capable of producing substance inducing disease resistance, taste-increasing crops, yield-increasing crops, preserving property-improving crops, yield-increasing corps, and the like. The specific gene recombination plant cultivars may include products containing a registered trademark such as Roundup Ready, Liberty Link, B.t., BXN, Poast Compatible, Agri Sure, Genuity, Optimum, Powercore, DroughtGard, YieldGard, Herculex, WideStrike, Twinlink, VipCot, GlyTol, Newleaf, or Bollgard.

(3) Effect of Protecting Industrial Material

Further, the azole derivative (I) shows the excellent effect of effectively protecting industrial materials from various harmful microorganisms attacking the industrial materials, and thus can be used as a protective agent for industrial materials. Examples of the microorganism may include microorganisms described below.

*Aspergillus* sp., which are paper/pulp-deteriorating microorganisms (including slime-forming germs); *Aspergillus* sp. which are fiber-deteriorating microorganisms such as *Trichoderma* sp., *Penicillium* sp., *Geotrichum* sp., *Chaetomium* sp., *Cadophora* sp., *Ceratostomella* sp., *Cladosporium* sp., *Corticium* sp., *Lentinus* sp., *Lenzites* sp., *Phoma* sp., *Polysticus* sp., *Pullularia* sp., *Stereum* sp., *Trichosporium* sp., *Aerobacter* sp., *Bacillus* sp., *Desulfovibrio* sp., *Pseudomonas* sp., *Flavobacterium* sp., and *Micrococcus* sp.; *Tyromyces palustris* which are wood-degrading germs such as *Penicillium* sp., *Chaetomium* sp., *Myrothecium* sp., *Curvularia* sp., *Gliomastix* sp., *Memnoniella* sp., *Sarcopodium* sp., *Stschybotrys* sp., *Stemphylium* sp., *Zygorhynchus* sp., *bacillus* sp., and *Staphylococcus* sp.; *Aspergillus* sp. which are leather-deteriorating microorganisms such as *Coriolus versicolor, Aspergillus* sp., *Penicillium* sp., *Rhizopus* sp., *Aureobasidium* sp., *Gliocladum* sp., *Cladosporium* sp., *Chaetomium* sp., and *Trichoderma* sp.; *Aspergillus* sp. which are rubber/plastic-deteriorating microorganisms such as *Penicillium* sp., *Chaetomium* sp., *Cladosporium* sp., *Mucor* sp., *Paecilomyces* sp., *Pilobus* sp., *Pullularia* sp., *Trichosporon* sp., and *Tricothecium* sp.; *Aspergillus* sp. which are coating-deteriorating microorganisms such as *Penicillium* sp., *Rhizopus* sp., *Trichoderma* sp., *Chaetomium* sp., *Myrothecium* sp., *Streptomyces* sp., *Pseudomonas* sp., *Bacillus* sp., *Micrococcus* sp., *Serratia* sp., *Margarinomyces* sp., and *Monascus* sp.; *Penicillium* sp., *Cladosporium* sp., *Aureobasidium* sp., *Gliocladium* sp., *Botryodiplodia* sp., *IIIacrosporium* sp., *Monilia* sp., *Phoma* sp., *Pullularia* sp., *Sporotrichum* sp., *Trichoderma* sp., *bacillus* sp., *Proteus* sp., *Pseudomonas* sp., *Serratia* sp., and the like.

The present invention is not limited to each embodiment described above, and various alterations can be made within the scope shown in claims. Further, embodiments in which technical means which are disclosed in different embodiments are suitably combined are encompassed in the technical scope of the present invention.

(4) Pharmaceutical Preparation

The agricultural or horticultural chemical agent is used by mixing the azole derivative (I), which is the active ingredient, with a solid carrier or liquid carrier (diluent), a surfactant, and other pharmaceutical preparation adjuvants, and the like and forming into pharmaceutical preparation in various states, for example, a powder agent, a hydrating agent, a granular agent, and an emulsion.

The pharmaceutical preparation is prepared so that the azole derivative (I) is contained in an amount of 0.1 to 95% by weight, preferably 0.5 to 90% by weight, more preferably 2 to 80% by weight as the active ingredient. Examples of the solid carrier, the liquid carrier, and the surfactant, which are used as the pharmaceutical preparation adjuvant, are described below. First, the solid carrier is used as a powdery carrier or a granular carrier. Examples thereof may include minerals such as clay, talc, diatom earth, zeolite, montmorillonite, bentonite, acid clay, activated clay, attapulgite, calcite, vermiculite, pearlite, pumice, and silica sand; synthetic organic substances such as urea; salts such as calcium carbonate, sodium carbonate, sodium sulfate, hydrated lime, and sodium bicarbonate; synthetic inorganic substances such as amorphous silica including white carbon, and titanium dioxide; plant carriers such as wood powder, corn stalk (corncob), walnut shell (skins of nuts), fruit cores, chaff, sawdust, wheat bran, soy flour, powdered cellulose, starch, dextrin, and saccharides; various polymer carriers, for example, water-soluble polymer gels such as crosslinked lignin, cation gel, gelation capable of gelling by heating or with a multivalent metal salt and agar, and chlorinated polyethylene, chlorinated polypropylene, polyvinyl acetate, polyvinyl chloride, ethylene-vinyl acetate copolymer, and urea-aldehyde resin, and the like.

The liquid carrier may include aliphatic solvents (paraffin), aromatic solvents (xylene, alkyl benzene, alkyl naphthalene, and the like), mixed solvents (coal oil), machine oil (purified high boiling temperature aliphatic hydrocarbon), alcohols (ethanol, isopropanol, cyclohexanol, and the like), polyhydric alcohols (ethylene glycol, diethylene glycol, propylene glycol, hexylene glycol, polyethylene glycol, polypropylene glycol, and the like), polyhydric alcohol derivatives (propylene-based glycol ether, and the like), ketones (acetone, cyclohexanone, ±-butyrolactone, and the like), esters (fatty acid methyl esters (coconut oil fatty acid methyl ester), ethylhexyl lactate, propylene carbonate, dibasic acid methyl ester (succinic acid dimethyl ester, glutamic acid dimethyl ester, adipic acid dimethyl ester, and the like)), nitrogen-containing carriers (N-alkyl pyrrolidones), oils and fats (coconut oil, soybean oil, rape seed oil, and the like), amide-based solvents (dimethyl formamide, (N,N-dimethyl octanamide, N,N-dimethyldecane-1-amide, 5-(dimethyl-amino)-4-methyl-5-oxo-valeric acid methyl ester, N-acyl morpholine-based solvent (CAS No. 887947-29-7, and the like)), dimethyl sulfoxide, acetonitrile, and water, and the like.

Examples of the surfactant are described below. The non-ionic surfactant may include, for example, sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether formalin condensate, polyoxyethylene/polyoxypropylene block polymer, alkyl polyoxyethylene/polyoxypropylene block polymer ether, polyoxyethylenealkylamine, polyoxyethylene fatty acid amide, polyoxyethylene fatty acid bisphenyl ether, polyoxyethylene benzylphenyl (or phenylphenyl) ether, polyoxyethylene styrylphenyl (or phenylphenyl) ether, polyoxyethylene ether, and ester-type silicone and fluorine-based surfactants, polyoxyethylene castor oil, polyoxyethylene hydrogenated castor oil, and the like. The anionic surfactant may include sulfate salts such as alkyl sulfate, polyoxyethylene alkyl ether sulfate, polyoxyethylene alkylphenyl ether sulfate, polyoxyethylene benzyl (or styryl) phenyl(or phenylphenyl) ether sulfate, polyoxyethylene, polyoxypropylene block polymersulfate; sulfonate salts such as paraffin (alkane) sulfonate, α-olefin sulfonate, dialkyl sulfosuccinate, alkyl benzenesulfonate, mono or dialkyl naphthalenesulfonate, naphthalenesulfonate-formalin condensate, alkyl diphenyl ether disufonate, lignin sulfonate, polyoxyethylene alkylphenyl ether sulfonate, and polyoxyethylene alkyl ether sulfosuccinic acid halfester; fatty acid salts such as fatty acid, N-methyl fatty acid sarcosinate, and resin acid; phosphate salts such as polyoxyethylene alkyl ether phosphate, polyoxyethylene mono or di-alkyl phenyl ether phosphate, polyoxyethylene benzylate (or styrylate) phenyl (or phenylphenyl) ether phosphate, polyoxyethylene/polyoxypropylene block polymer, phosphatidylcholine phosphatidyl ethanolimine (lecithin), and alkyl phosphate. The cationic surfactant may include ammonium salts such as alkyl trimethyl ammonium chloride, methyl polyoxyethylene alkyl ammonium chloride, alkyl N-methyl pyridium bromide, mono or di-alkylmethylated ammonium chloride, and alkyl pentamethyl propylene diamine dichloride; benzalkonium salts such as alkyl dimethyl benzalkonium chloride, and benzethomium chloride (octylphenoxyethoxyethyl dimethyl benzyl ammonium chloride).

Other adjuvants for the pharmaceutical preparation may include inorganic salts such as sodium and potassium, which are used as a pH-controlling agent; fluorine- or silicone-based defoaming agents; water-soluble salts such as sodium chloride; water-soluble polymers such as xanthan gum, guar gum, carboxymethyl cellulose, polyvinyl pyrrolidone, carboxyvinyl polymer, acrylic polymers, polyvinyl alcohol, starch derivatives and polysaccharides, algic acid and salts thereof, which are used as a thickener; metal salts of stearic acid, sodium tripolyphosphate, sodium hexametaphosphorate; and preservatives, coloring agents, antioxidants, ultraviolet absorbing agents, chemical injury-reducing agents, and the like.

The pharmaceutical preparation may be used as it is, or used by diluting it with a diluent such as water to adjust a pre-determined concentration. When it is diluted, the concentration of the azole derivative (I) is desirably within a range of 0.001 to 1.0%.

The amount of the azole derivative (I) used is from 20 to 5000 g, more preferably from 50 to 2000 g per hectare (h) of the agricultural or horticultural land such as a farm, a paddy field, a fruit farm, or a green house. The concentration and amount of use vary depending on the dosage form, the time when it is used, the usage, the location of use, and the target crop, and thus it is possible to increase or decrease them without adhering to the range described above.

The agricultural or horticultural chemical agent in the present embodiment can be used in a state in which it is combined with a known other active ingredient to increase the performance as the agricultural or horticultural chemical agent. Examples of the known other active ingredient may include known active ingredients contained in a germicide, an insecticides, a miticide, a nematicide, or a plant growth regulator.

(5-1) Active Ingredient for Use of Germicide

The active ingredient suitable for the germicide use may include, for example, sterol biosynthesis-inhibiting compounds, benzimidazole-based compounds, succinate dehydrogenase-inhibiting compounds (SDHI compounds), strobilurin-based compounds, phenylamide-based compounds, dicarboxyimide-based compounds, anilinopyrimidine-based compounds, compounds having multiple reactive points, antibiotics, carbamate-based compounds, quinoline-based compounds, organic phosphorus-based compound, carboxyamide-based compounds, and the like.

The sterol biosynthesis-inhibiting compound may include azaconazole, bitertanol, bromuconazole, difenoconazole, cyproconazole, diniconazole, fenbuconazole, fluquin-conazole, flutriafol, hexaconazole, imazalil, imibenconazole, metconazole, ipconazole, myclobutanil, pefurazoate, penconazole, prochloraz, propiconazole, prothioconazole, epoxiconazole, simeconazole, tebuconazole, tetraconazole, triadimefon, triadimenol, triflumizole, triticonazole, flusilazole, oxpoconazol, mephentrifluconazole, ipfentrifluconazole, 1-((1H-1,2,4-triazole-1-yl)methyl)-5-(4-chlorobenzyl)-2-(chloromethyl)-2-meth ylcyclopentane-1-ol, methyl 2-((1H-1,2,4-triazole-1-yl)methyl)-3-(4-chlorobenzyl)-2-hydrox-1-methylcyclo pentane-1-carboxylate, fenpropimorph, fenpropidin, spiroxamine, tridemorph, bupirimate, fenarimol, pyrifenox, triforine, and the like.

The benzimidazole-based compound may include carbendazim, benomyl, thiabendazole, thiophanate-methyl, fuberidazole, and the like.

The succinate dehydrogenase-inhibiting compounds (SDHI compounds) may include bixafen, benzovindiflupyr, boscalid, fluopyram, flutolanil, fluxapyroxad, furametpyr, isofetamid, isopyrazam, mepronil, penflufen, penthiopyrad, sedaxane, thifluzamide, fluindapyr, pyraziflumid, pydiflumetofen, benodanil, carboxin, pyrapropoyne, inpyrfluxam, isoflucypram, and oxycarboxin.

The strobilurin-based compound may include azoxystrobin, dimoxystrobin, enestrobin, fenamistrobin, fluoxastrobin, kresoxim-methyl, metominostrobin, orysastrobin, picoxystrobin, pyraclostrobin, trifloxystrobin, madestrobin, pyribencarb, pyraoxystrobin, pyrametostrobin, flufenoxystrobin, enoxastrobin, coumoxystrobin, triclopyricarb, and the like.

The phenylamide-based compound may include benalaxyl, benalaxyl M or kiralaxyl, metalaxyl, metalaxyl M or mefenoxam, and oxadixyl, and the like.

The dicarboxyimide-based compound may include procymidone, iprodione, vinclozolin, and the like.

The anilinopyrimidine-based compound may include cyprodinil, mepanipyrim, pyrimethanil, and the like.

The compound having multiple reactive points may include mancozeb, maneb, metiram, propineb, thiram (thiuram), zineb, ziram, amobam, anilazine, dithianon, fluazinam, pencycuron, quintozene, trifluanid, dodain, guazatine, iminoctadine (iminoctadine acetate, iminoctadine albesilate), copper compounds (for example, copper oxychloride, cupric hydroxide, basic copper sultphate, copper sulfate, organic copper (oxide-copper), copper nonylphenolsulfonate, DBEDC, and the like), hydrogencarbonates (sodium hydrogen carbonate, potassium hydrogen carbonate), silver metal, fentin, sulfur, captan, chlorothalonil (TPN), folpet, and the like.

The antibiotic may include kasugamycin, polyoxin, streptomycin, validamycin, oxytetracycline, and the like.

The carbamate-based compound may include benthiavalicarb (benthiavalicarb isopropyl), diethofencarb, iprovalicarb, propamocarb, tolprocarb, and the like.

The quinoline-based compound may include oxolinic acid, pyroquilone, quinoxyfen, tebufloquin, and the like.

The organic phosphorus-based compound may include dinocap, edifenphos (EDDP), phosethyl (phosethyl-aluminum), iprobenfos (IBP), meptyldinocap, tolclofos-methyl, and the like.

The carboxyamide-based compound may include carpropamide, ethaboxam, fenoxanil, silthiofam, tiadinil, isotianil, and the like.

The other compounds for germicide use may include ametoctradin, amisulbrom, cyazofamid, cyflufenamide, cymoxanil, diclocymet, diclomezine, famoxadone, fenamidone, fenhexamid, fenitropan, fludioxonil, fluopicolide, flusulfamide, flutianil, halpin, isoprothiolane, isotianyl, mandipropamid, metrafenone, oxathiapiprolin, fthalide, proquinazid, valifenalate, zoxamide, dichlobentiazox, fenpicoxamid, picarbutrazox, quinofumelin, diemthomorph, flumorph, bupirimate, ferimzone, acibenzolar (acibenzolar-S-methyl), etridiazole, hymexazol, probenazole, tricyclazole, fenpyrazamine, tecloftalam, hydroxyisoxazole, fluoroimide, pyriofenone, diflumetorim, quinomethionate, aminopyrifen, dichlobentiazox, lentinula hypha extract, biotic pesticides (*Agrobacterium radiobacter, Pseudomonas fluorescens, Pseudomonas rhodesiae, Bacillus subtilis, Bacillus simplex, Bacillus amyloliquefaciens*, nonpathogenic *Erwinia carotovora, Lactobacillus plantalum, Variovarax paradoxus*), and the like.

(5-2) Active Ingredient for Insecticide

The preferable active ingredient for the insecticide use may include, for example, organic phosphorus-based compounds, carbamate-based compounds, pyrethroid-based compounds, Neres toxin-based compounds, neonicotinoid-based compounds, benzoylurea-based compounds, and other insect growth-controlling compounds, organic chlorinated compounds, naturally derived compounds, and the like.

The organic phosphorus-based compounds includes acephate, azinphos-methyl, cadusafos, chloroethoxyfos, chlorfenvinphos, chlorpyrifos, cyanophos, demeton-S-methyl, diazinon, dichlorvos (DDVP), dicrotophos, dimethoate, disulfoton, ethion, ethoprophos, EPN, fenamiphos, fenitrothion (MEP), fention (MPP), fosthiazate, imicyafos, isofenphos, isoxathion, malathion, methamidophos, methidathion, mevinphos, monocrotophos, Omethoate, oxydementon methyl, parathion, parathion-methyl, phenthoate, phorate, phosalone, phosmet, phosphamidon, phoxim, pyrimiphos-methyl, profenofos, prothiofos, pyraclofos, pyridaphenthion, quinalphos, tebupirimfos, terbufos, triazophos, trichlorfon (DEP), and the like.

The carbamate-based compound includes alanycarb, aldicarb, benfuracarb, BPMC, carbaryl (NAC), carbofuran, carbosulfan, cartap, fenoxycarb (BPMC), formetanate, isoisoprocarb (MIPC), methiocarb, methomyl, oxamyl, pirimicarb, thiodicarb, XMC, bendiocarb, ethiofencarb, fenobcarb, phenothiocarb, furathiocarbo, metolcarb, xylylcarb, and the like.

The pyrethroid-based compound may include acrinathrin, allethrin, cypermethrin, bifenthrin, cycloprothrin, cyfluthrin, cypermethrin, deltamethrin, dimefluthrin, esfenvalerate, etofenprox, fenpropathrin, fenvalerate, flubrocythrinate, fulcythrinate, fluvalinate, halfenprox, cyhalothrin, metofluthrin, momfluorothrin, permethrin, profluthrin, tefluthrin, tralomethrin, cyfluthrin, kappa-bifenthrin, imiprothrin, pyrethrin, chloroprallethrin, epsilon-metofluthrin, cyphenothrin, and the like.

The Neres toxin compound may include cartap, bensultap, thiocyclam, monosultap, bisultap, and the like.

The neonicotinoid compound may include acetamiprid, clothianidin, dinotefran, imidacloprid, nitenpyram, thiacloprid, thiamethoxam, and the like.

The benzoylurea compound may include bistrifluron, chlorfluazuron, diflubenzuron, flucycloxuron, flufenoxuron, hexaflumuron, lufenuroN, NovaluroN, Noviflumuron, teflubenzuron, triflumuron, and the like.

The other insect growth-controlling compound may include buprofezin, chromafenozide, cyromazine, halofenozide, methoxyfenozide, tebufenozide, pyriproxyfen, and the like.

The organic chlorinated compound may include aldrin, dieldrin, endosulfan, methoxychlor, lindane, DDT, and the like.

The naturally derived compound may include abamection, *Bacillus thuringiensis*-derived viable spores and production crystal toxins, and mixtures thereof, bensultap, emamectin benzoate, Lepimectin, Milbemectin, spinetoram, spinosad, machine oils, starch, saccharified reduced starch, rapeseed oil, sodium oleate, propylene glycol monofatty acid esters, fatty acid glyceride, ferric phosphate, and the like.

The other compounds for the insecticide use may include avermection, chlorantraniliprole, chlorfenapyr, cyantraniliprole, diafenthiuron, ethiprole, fipronil, flonicamid, flubendiamide, fluensulfone, flupyradifurone, indoxacarb, metaflumizone, meta-aldehyde, pymetrozine, pyridaryl, pyrifluquinazon, silafluofen, spirotetramat, Sulfoxaflor, tolfenpyrad, afidopyropen, broflanilide, Cyclaniliprole, dichloromezotiaz, furometokin, fluazaindolizine, fluhexafon, fluxametamide, Pyriprole, tetraniliprole, triflumezopyrim, methoprene, tyclopyrazoflor, flupyrimin, spiropidion, benzpyrimoxan, cyhalodiamide, Sulfluramid, and the like.

(5-3) Active Ingredient for Miticide Use

The preferable active ingredient for the miticide use (acaricidal active component) may include, for example, acequinocyl, amidoflumet, amitraz, azocyclo tin, bifenazate, bromopropionate, propylate, chlorfeson, quinomethionate, phenisobromolate, benzoximate, Clofentezine, cyenopyrafen, cyflumetofen, cyhexatin, diflovidazin, dienochlor, etoxazole, Fenazaquin, fenbutatin oxide, fenpyroximate, phenothiocarb, fluacrypyrim, hexythiazox, propargite (BPPS), pyflubumide, pyridaben, pyrimidifen, spirodiclofen, spiromesifen, Tebufenpyrad, tetratetradifon, acynonapyr, combined oil, and the like.

(5-4) Active Ingredient for Nematicide Use

The preferable active ingredient for the nematicide use (nematicide active component) may include, for example D-D (1,3-dichloropropene), DCIP (dichlorodiisopropyl ether), methyl isothiocyanate, carbam sodium salt, cadusfos, fosthiazate, imicyafos, morantel tartarate, levamisole hydrochloride, Nemadectin, thioxazafen, and the like.

(5-5) Active Ingredient for Plant Growth Regulator Use

The optimum active ingredient for the plant growth regulator use may include, for example, aminoethoxyvinyl glycine, chlormequat, chlorpropham, cyclanilide, dikegulac, daminozide, ethephon, flurprimidol, flumetralin, forchlorfenuron, gibberellin, maleic hydrazide salt, mepiquat chloride, methyl cyclopropene, benzylaminopurine, paclobutrazol, prohexadion, thidiazuron, tributyl phosphorotrithioate, trinexapac-ethyl, uniconazole, and the like.

[Method for Removing Plant Disease]

The agricultural or horticultural chemical agent in the present embodiment can be used in farmlands such as farms, paddy fields, lawns, and fruit farms, and non-farmlands. The agricultural or horticultural chemical agent in the present embodiment can also be used, in addition to the treatments of stems and leaves such as a foliage application, by seed treatments including treatments of bulbs and tubers, irrigation treatments, and non-foliage treatments such as a water surface treatment. The plant disease-controlling method in the present embodiment, accordingly, is a method including procedures of performing the foliage treatment or non-foliage treatment using the agricultural or horticultural chemical agent described above. When the non-foliage treatment is performed, the labor can be reduced compared to a case where the foliage treatment is performed.

When the agent is used in the seed treatment, the chemical agent is stuck to the seeds by mixing the hydrating agent and the powder agent with and stirring them, or immersing the seeds in the diluted hydrating agent. The treatment includes a seed coating treatment. In the seed treatment, the amount of the active ingredient used is, for example, from 0.01 to 10000 g to 100 kg of the seeds, preferably from 0.1 to 1000 g. The seed treated with the agricultural or horticultural chemical agent are utilized in the same manner as in usual seeds.

When the agent is used in the irrigation treatment, planting holes and peripheries thereof are treated with the granular agent when seedlings are transplanted, or the like. The soil around the seeds or plants are treated with the granular agent and the hydrating agent. When the irrigation treatment is performed, the amount of the active ingredient used is, for example, from 0.01 to 10000 g, preferably from 0.1 to 1000 g, per square meter ($m^2$) of the agricultural or horticultural land.

When the agent is used in the water-surface treatment, the water surface of the paddy field is treated with the granular agent, or the like. When the water surface treatment is performed, the amount of the active ingredient used is, for example, from 0.1 to 10000 g per 10 acres (a) of the paddy field, preferably from 1 to 1000 g.

When the agent is used in the forage application, the amount of the active ingredient used is, for example, from 20 to 5000, more preferably from 50 to 2000 g, per hectare (ha) of the agricultural or horticultural land such as the farm, paddy field, fruit farm, or green house.

The concentration and the amount of use vary depending on the dosage form, the time when it is used, the usage, the location of use, and the target crop, and thus it is possible to increase or decrease them without adhering to the range described above.

The protective agent for industrial material containing the azole derivative (I) as the active ingredient may contain various components in addition to the azole derivative (I). The protective agent for industrial material containing the azole derivative (I) as the active ingredient can be used by dissolving or dispersing it in an appropriate liquid carrier, or mixing it with a solid carrier. The protective agent for industrial material containing the azole derivative (I) as the active ingredient may contain, if necessary, an emulsifier, a dispersant, a spreader, a penetrating agent, a wetting agent, a stabilizer, and the like. Examples of the dosage form of the protective agent for industrial material containing the azole derivative (I) as the active ingredient may include a hydrating agent, a powder agent, a granular agent, a tablet, a paste, a suspension, an aerosol, and the like. The protective agent for industrial material containing the azole derivative (I) as the active ingredient may contain other germicides, insecticides, deterioration preventing agents, and the like.

The liquid carrier is not particularly limited so long as it is not reacted with the active ingredient. The liquid carrier may include, for example, water, alcohols (for example, methyl alcohol, ethyl alcohol, ethylene glycol, cellosolve, and the like), ketones (for examples, acetone, methyl ethyl ketone, and the like), ethers (for examples, dimethyl ether, diethyl ether, dioxane, tetrahydrofuran, and the like), aromatic hydrocarbons (for examples, benzene, toluene, xylene, methyl naphthalene, and the like), aliphatic hydrocarbons (for examples, gasoline, kerosene, coal oil, machine oil, fuel oil, and the like), acid amides (for examples, dimethyl formamide, N-methyl pyrrolidone, and the like), halogenated hydrocarbons (for examples, chloroform, tetrachloromethane, and the like), esters (for examples, ethyl acetate ester, glycerin ester of fatty acid, and the like), nitriles (for examples, acetonitrile, and the like), dimethyl sulfoxide, and the like.

As the solid carrier, it is possible to use a fine powder or granular material of kaolin, bentonite, acid clay, pyrophyllite, talc, diatom earth, calcite, urea, or ammonium sulfate.

As the emulsifier or the dispersant, it is possible to use surfactants such as soaps, alkyl sulfonates, alkylaryl sulfonates, dialkyl sulfosuccinate, quaternary ammonium salts, oxyalkyl amines, fatty acid esters, polyalkylene oxides, anhydrosorbitols, and the like.

When the azole derivative (I) is contained in the pharmaceutical preparation as the active ingredient, the content thereof depends on the dosage form and the intended purpose, but it may be adjusted to 0.1 to 99.9% by weight based on the whole amount of the pharmaceutical preparation. When it is actually used, it is preferable that a solvent, a diluent, or an extender is appropriately added thereto so that the treatment concentration is usually to 0.005 to 5% by weight, preferably 0.01 to 1% by weight.

As explained above, the azole derivative (I) shows the excellent germicidal action on many germs which cause plant diseases. The agricultural or horticultural disease-controlling agent containing the azole derivative (I) as the active ingredient has the low toxicity to human and animals and the high handling safety, and can show the high controlling effect on the various plant diseases.
(Supplementary Information)

The present invention is not limited to the embodiments described above, and various alterations can be made within the scope shown in claims. Embodiments, obtained by combining technical means which are appropriately changed within the scope shown in claims, are, thus, encompassed in the technical scope of the present invention.

SUMMARY

The azole derivative of the present invention is preferably a compound or salt thereof, represented by the general formula (I) wherein
$R^1$ is a hydrogen, a $C_1$-$C_6$-alkyl group, a $C_2$-$C_6$-alkenyl group, a $C_2$-$C_6$-alkynyl group, or $COXR^5$;
$R^2$ is —$OR^7$;
$R^5$ is a hydrogen, a $C_1$-$C_6$-alkyl group, a $C_2$-$C_6$-alkenyl group, or a $C_2$-$C_6$-alkynyl group;
$R^6$ is a hydrogen, a $C_1$-$C_6$-alkyl group, a $C_2$-$C_6$-alkenyl group, or a $C_2$-$C_6$-alkynyl group;
$R^3$ is a halogen group, a cyano group, a $C_1$-$C_4$-alkyl group, a $C_1$-$C_4$-haloalkyl group, a $C_1$-$C_4$-alkoxy group, —$SOR^{10}$, or —$SF_5$; and
$R^4$ is a halogen group, a nitro group, a cyano group, an amino group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$.

The azole derivative of the present invention is preferably a compound or salt thereof represented by the general formula (I) wherein
$R^1$ is a hydrogen, a $C_1$-$C_6$-alkyl group, or $COXR^5$;
$R^5$ is a hydrogen or a $C_1$-$C_6$-alkyl group;
$R^6$ is a hydrogen;
$R^3$ is a halogen group, a cyano group, a $C_1$-$C_4$-alkyl group, a $C_1$-$C_4$-haloalkyl group, a $C_1$-$C_4$-alkoxy group, —$SOR^{10}$, or —$SF_5$; and
$R^4$ is a halogen group, a nitro group, a cyano group, an amino group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$.

The azole derivative of the present invention is preferably a compound or salt thereof represented by the general formula (I) wherein
$R^1$ is a hydrogen or a $C_1$-$C_6$-alkyl group;
$R^7$ is a $C_1$-$C_6$-alkyl group;
$R^3$ is a halogen group, a cyano group, a $C_1$-$C_4$-alkyl group, a $C_1$-$C_4$-haloalkyl group, or a $C_1$-$C_4$-alkoxy group; and
$R^4$ is a halogen group, a cyano group, a $C_1$-$C_4$-alkyl group, a $C_1$-$C_4$-haloalkyl group, a $C_1$-$C_4$-alkoxy group, or a $C_1$-$C_4$-haloalkoxy group.

The azole derivative of the present invention is preferably a compound or salt thereof represented by the general formula (I) wherein E is a phenyl group.

The azole derivative of the present invention is preferably a compound or salt thereof represented by the general formula (I) wherein Z is a phenyl group, a naphthyl group, or a 5-membered or 6-membered heteroaromatic ring containing 1 to 3 heteroatoms selected from N and S.

The azole derivative of the present invention is preferably a compound or salt thereof represented by the general formula (I) wherein Z is a phenyl group.

The azole derivative of the present invention is preferably a compound or salt thereof represented by the general formula (I) wherein Y is an oxygen atom.

The azole derivative of the present invention is preferably a compound or salt thereof represented by the general formula (I) wherein A is N, and D is hydrogen.

The azole derivative of the present invention is preferably a compound or salt thereof represented by the following general formula (II).

[Chemical Formula 19]

(II)

The method for producing the azole derivative of the present invention is preferably the method for producing the compound represented by the general formula (I) described above containing a step of converting a compound represented by the following general formula (V) into a compound represented by the following general formula (VI) using a dialkyl sulfate represented by the following general formula (VII) or $R^7$-LG in which LG is a nucleophilically substitutable leaving group, iodine, and a carbonate in dimethyl sulfoxide. LG is preferably a halogen group.

[Chemical Formula 20]

(VII)

[Chemical Formula 21]

(V)

[Chemical Formula 22]

(VI)

The present invention contains a method for producing a compound represented by the general formula (VI) described above, which is a production method containing converting a compound represented by the general formula (V) into a compound represented by the general formula (VI) using a dialkyl sulfate represented by the general formula (VII) described above or IC-LG, iodine, and a carbonate in a dimethyl sulfoxide. Here, LG is a nucleophilically substitutable leaving group.

An agricultural or horticultural chemical agent or a protective agent for industrial material containing the azole derivative of the present invention as an active ingredient is encompassed within the scope of the present invention.

EXAMPLE

Hereinafter, the present invention will be described in detail with reference to production examples, preparation examples, and test examples. It is to be noted that the present invention is not limited to the following production examples, preparation examples, and test examples as long as the present invention does not deviate from the gist.

<Synthesis Example 1. Synthesis of Control Compound B (Compound Described in Patent Literature 2)

Synthesis of methyl 2-oxo-2-(4-phenoxyphenyl)acetate 1.00 g of diphenyl ether commercially available was dissolved in 12 ml of methylene chloride, and the solution was cooled in an ice bath. The solution was added with 0.936 g of aluminum chloride and then dropped with 0.864 g of methyl chloroglyoxylate for 30 minutes. After stirring the mixture at the same temperature for 30 minutes, the mixture was poured into a mixed solution of ice+concentrated hydrochloric acid. The mixture was extracted with methylene chloride, and the organic layer was washed with 2M hydrochloric acid, water, and a saturated saline solution, and dried with anhydrous sodium sulfate. After a solvent was distilled off, the residue was purified by column chromatography (20 g of silica gel, hexane/ethyl acetate=10/1), thereby obtaining 0.973 g of the title compound as a colorless liquid. A yield was 64.6%.

$^1$HNMR (400 MHz, CDCl$_3$) δ: 8.00 (d, J=9.0 Hz, 2H), 7.42 (dd, J=8.5, 7.6 Hz, 2H), 7.26-7.21 (m, 1H), 7.08 (dd, J=8.5, 7.5 Hz, 2H), 7.02 (d, J=9.0 Hz, 2H), 3.96 (s, 3H).

Synthesis of methyl 2-(4-phenoxyphenyl)acrylate 184 mg of sodium hydride was weighed in a 25 ml three-necked flask and 7 ml of dimethylsulfoxide (hereinafter, referred to as DMSO) was added thereto. After stirring the mixture at a room temperature for 20 minutes, the mixture was cooled to 10° C., and added with 1.75 g of methyltriphenylphosphine bromide (MTPB) little by little. After the mixture returned to a room temperature and was again stirred for 30 minutes, 0.938 g of methyl 2-oxo-2-(4-phenoxyphenyl)acetate synthesized in the preceding paragraph was dissolved in 2 ml of DMSO and dropped for 5 minutes, and the mixture was stirred at a room temperature for 1 hour. After the completion of the reaction, the mixture was added with water and extracted with toluene. The organic layer was washed with water and a saturated saline solution and dried with anhydrous sodium sulfate. A solvent was distilled off, and the residue was purified by column chromatography (15 g of silica gel, hexane/ethyl acetate=10/1), thereby obtaining 0.595 g of the title compound as a colorless liquid. A yield was 63.9%.

$^1$HNMR (400 MHz, CDCl$_3$) δ: 7.39 (d, J=8.8 Hz, 2H), 7.34 (dd, J=8.6, 7.4 Hz, 2H), 7.15-7.10 (m, 1H), 7.04 (dd, J=8.5, 1.0 Hz, 2H), 6.98 (d, J=8.8 Hz, 2H), 3.83 (s, 3H).

Synthesis of methyl 2-hydroxy-2-(4-phenoxyphenyl)-3-(1H-1,2,4-triazol-1-yl)propanoate (Control Compound B)

0.590 g of methyl 2-(4-phenoxyphenyl)acrylate synthesized in the preceding paragraph was dissolved in 6 ml of acetonitrile and 6 ml of methanol, and the solution was cooled to 0° C. The solution was added with 0.767 g of urea-hydrogen peroxide adduct and 0.385 g of potassium carbonate and stirred at a room temperature for 7.25 hours. The mixture was added with 0.100 g of potassium carbonate and further stirred at a room temperature for 1 hour. After the completion of the reaction, the mixture was added with water and extracted with toluene, and the organic layer was washed with water and a saturated saline solution and dried with anhydrous sodium sulfate. The solvent was distilled off to obtain 0.585 g of crude as a colorless liquid. 0.560 g of crude was dissolved in 8 ml of dimethylformamide (DMF), and the mixture was added with 0.144 g of triazole and 0.189 g of sodium triazole and stirred at 50° C. for 1.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/4), thereby obtaining 0.484 g of the title compound as a white solid. A yield was 61.4%.

$^1$HNMR (400 MHz, CDCl$_3$) δ: 8.17 (s, 1H), 7.91 (s, 1H), 7.60 (d, J=8.9 Hz, 2H), 7.39-7.34 (m, 2H), 7.17-7.12 (m, 1H), 7.04-6.99 (m, 2H), 7.01 (d, J=8.9 Hz, 2H), 5.03 (d, J=14.0 Hz, 1H), 4.44 (d, J=14.0 Hz, 1H), 4.36 (s, 1H), 3.83 (s, 3H).

Synthesis Example 2. Synthesis of Compound I-5

Synthesis of methyl 2-(4-(4-chlorophenoxy)phenyl)-2-oxoacetate

By the same operation as the synthesis of methyl 2-oxo-2-(4-phenoxyphenyl)acetate of Synthesis Example 1, 0.998 g of the title compound was obtained as a colorless liquid from 1.21 g of 4-chlorodiphenyl ether. A yield was 58.0%.

$^1$HNMR (400 MHz, CDCl$_3$) δ: 8.02 (d, J=9.0 Hz, 2H), 7.38 (d, J=9.0 Hz, 2H), 7.06-7.00 (m, 4H), 3.97 (s, 3H).

Synthesis of methyl 2-(4-(4-chlorophenoxy)phenyl)acrylate

By the same operation as the synthesis of methyl 2-(4-phenoxyphenyl)acrylate of Synthesis Example 1, 0.431 g of the title compound was obtained as a colorless liquid from 0.980 g of methyl 2-(4-(4-chlorophenoxy)phenyl)-2-oxoacetate. A yield was 44.3%.

$^1$HNMR (400 MHz, CDCl$_3$) δ: 7.39 (d, J=8.8 Hz, 2H), 7.30 (d, J=9.0 Hz, 2H), 6.99-6.94 (m, 4H), 3.83 (s, 3H).

Synthesis of methyl 2-(4-(4-chlorophenoxy)phenyl)-2-hydroxy-3-(1H-1,2,4-triazol-1-yl)propanoate (I-5)

By the same operation as the synthesis of the control compound B of Synthesis Example 1, 0.276 g of the title compound was obtained as a white solid from 0.413 g of methyl 2-(4-(4-chlorophenoxy)phenyl)acrylate. A yield was 51.6%.

$^1$HNMR (400 MHz, CDCl$_3$) δ: 8.16 (s, 1H), 7.91 (s, 1H), 7.62 (d, J=8.9 Hz, 2H), 7.31 (d, J=8.9 Hz, 2H), 6.99 (d, J=8.9 Hz, 2H), 6.96 (d, J=8.9 Hz, 2H), 5.02 (d, J=14.0 Hz, 1H), 4.44 (s, 1H), 4.43 (d, J=14.0 Hz, 1H), 3.83 (s, 3H).

Synthesis Example 3. Synthesis of Compound I-21

Synthesis of 1-(2-chloro-4-(2,4-dichlorophenoxy)phenyl)ethan-1-on 1.54 g of 2-chloro-4-fluoroacetophenone was dissolved in 16 ml of DMF, and the solution was added with 1.47 g of 2,4-dichlorophenol and 1.48 g of potassium carbonate and stirred at 100° C. for 0.75 hours. A temperature of a bath was raised to 120° C., and the mixture was further stirred for 2 hours. The mixture was added with 0.144 g of 2,4-dichlorophenol and further stirred for 2 hours. After the completion of the reaction, the mixture was added with toluene, and the organic layer was washed with water and a saturated saline solution, and dried with anhydrous sodium sulfate. The solvent was distilled off and the residue was purified by column chromatography (75 g of silica gel, hexane/ethyl acetate=10/1), thereby obtaining 1.922 g of the title compound as a colorless viscous liquid. A yield was 68.3%.

$^1$HNMR (400 MHz, CDCl$_3$) δ: 7.64 (d, J=8.7 Hz, 1H), 7.51 (d, J=2.5 Hz, 1H), 7.29 (dd, J=8.7, 2.5 Hz, 1H), 7.06 (d, J=8.7 Hz, 1H), 6.92 (d, J=2.5 Hz, 1H), 6.83 (dd, J=8.7, 2.5 Hz, 1H), 2.65 (s, 3H).

Synthesis of methyl-2-(2-chloro-4-(2,4-dichlorophenoxy)phenyl)-2-oxoacetate 1.86 g of 1-(2-chloro-4-(2,4-dichlorophenoxy)phenyl)ethan-1-on synthesized in the preceding paragraph was weighed in a 100 ml eggplant flask and added 24 ml of DMSO to be dissolved. The mixture was added with 4.76 g of iodine and stirred at 100° C. for 0.5 hours in an oil bath. After the completion of the reaction, the mixture was cooled to 60° C., added with 5.69 g of potassium carbonate, and stirred at 100° C. for 0.5 hours. The mixture was cooled to 35° C., added with 1.17 ml of iodomethane, and stirred at 35° C. for 1.5 hours. After the completion of the reaction, excess iodine was quenched with 60 ml of saturated sodium sulfite aqueous solution, 60 ml of toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layer was dried with anhydrous sodium sulfate, and the solvent was distilled off. The residue was purified by column chromatography (60 g of silica gel, hexane/ethyl acetate=7/1), thereby obtaining 1.2786 g of the title compound as a light yellow liquid. A yield was 60.5%.

$^1$HNMR (400 MHz, CDCl$_3$) δ: 7.82 (d, J=8.7 Hz, 1H), 7.53 (d, J=2.5 Hz, 1H), 7.32 (dd, J=8.7, 2.5 Hz, 1H), 7.10 (d, J=8.7 Hz, 1H), 6.92 (d, J=2.5 Hz, 1H), 6.89 (dd, J=8.7, 2.5 Hz, 1H), 3.95 (s, 3H).

Synthesis of methyl-2-(2-chloro-4-(2,4-dichlorophenoxy)phenyl)-2-hydroxy-3-(1H-1,2,4-triazol-1-yl)propanoate (I-21)

0.525 g of methyl-2-(2-chloro-4-(2,4-dichlorophenoxy)phenyl)-2-oxoacetate obtained in the preceding paragraph was dissolved in 3 mL of dimethylacetamide (DMAc), and the solution was added with 0.387 g of trimethylsulfoxonium iodide (TMSOI) and 0.174 g of triazole sodium and stirred at 40° C. for 0.75 hours and at 50° C. for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/4), thereby obtaining 0.235 g of the title compound as a light yellow solid. A yield was 36.3%.

$^1$HNMR (400 MHz, CDCl$_3$) δ: 8.00 (s, 1H), 7.88 (s, 1H), 7.49 (d, J=2.5 Hz, 1H), 7.41 (d, J=8.8 Hz, 1H), 7.26 (dd, J=8.7, 2.5 Hz, 1H), 7.00 (d, J=8.7 Hz, 1H), 6.94 (d, J=2.5 Hz, 1H), 6.76 (dd, J=8.8, 2.5 Hz, 1H), 5.02 (d, J=14.3 Hz, 1H), 4.92 (d, J=14.3 Hz, 1H), 4.90 (brs, 1H), 3.79 (s, 3H).

Synthesis Example 4. Synthesis of Compound I-18

Synthesis of 1-(2-chloro-4-(4-methoxyphenoxy)phenyl)ethan-1-on 2.015 g of 2-chloro-4-fluoroacetophenone was dissolved in 21 ml of DMF, and the solution was added with 1.462 g of 4-methoxyphenol and 1.935 g of potassium carbonate and stirred at 80° C. for 3.5 hours. The mixture was added with 0.435 g of 4-methoxyphenol and 0.484 g of potassium carbonate and further stirred for 2.5 hours. After the completion of the reaction, the mixture was added with toluene, and the organic layer was washed with water and a saturated saline solution, and dried with anhydrous sodium sulfate. The solvent was distilled off and the residue was purified by column chromatography (75 g of silica gel, hexane/ethyl acetate=10/1), thereby obtaining 2.367 g of the title compound as a colorless viscous liquid. A yield was 73.3%.

$^1$HNMR (400 MHz, CDCl$_3$) δ: 7.62 (d, J=8.7 Hz, 1H), 7.00 (d, J=9.2 Hz, 2H), 6.94-6.91 (m, 3H), 6.84 (dd, J=8.7, 2.4 Hz, 1H), 3.83 (s, 3H), 2.64 (s, 3H).

Synthesis of methyl 2-(2-chloro-4-(4-methoxyphenoxy)phenyl)-2-oxoacetate 2.0879 g of 1-(2-chloro-4-(4-methoxyphenoxy)phenyl)ethan-1-on synthesized in the preceding paragraph was weighed in a 100 ml eggplant flask and added 30 ml of DMSO to be dissolved. The mixture was added with 6.151 g of iodine and stirred for 0.5 hours in an oil bath of 100° C. After the completion of the reaction, the mixture was cooled to 60° C., added with 7.35 g of potassium carbonate, and stirred at 100° C. for 0.5 hours. The mixture was cooled to 35° C., added with 1.50 ml of iodomethane, and stirred at 35° C. for 1.5 hours. After the completion of the reaction, 60 ml of saturated sodium sulfite aqueous solution and 60 ml of toluene were added to the mixture, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (60 g of silica gel, hexane/ethyl acetate=7/1), thereby obtaining 1.6922 g of the title compound as a colorless solid. A yield was 69.9%.

¹HNMR (400 MHz, CDCl₃) δ: 7.81 (d, J=9.0 Hz, 1H), 7.02 (d, J=9.2 Hz, 2H), 6.97-6.89 (m, 4H), 3.94 (s, 3H), 3.83 (s, 3H).

Synthesis of methyl 2-(2-chloro-4-(4-methoxyphenoxy)phenyl)acrylate 210 mg of sodium hydride was weighed in a 25 ml three-necked flask, and 8 ml of DMSO was added thereto. After stirring the mixture at a room temperature for 20 minutes, the mixture was cooled with ice and added with 1.91 g of MTPB little by little. After the mixture returned to a room temperature and was again stirred for 30 minutes, 1.34 g of methyl 2-(2-chloro-4-(4-methoxyphenoxy)phenyl)-2-oxoacetate synthesized in the preceding paragraph was dissolved in 2 ml of DMSO and dropped for 2 minutes, and the mixture was stirred at a room temperature for 1 hour. After the completion of the reaction, the mixture was added with water and extracted with toluene. The organic layer was washed with water and a saturated saline solution and dried with anhydrous sodium sulfate. A solvent was distilled off, and the residue was purified by column chromatography (30 g of silica gel, hexane/ethyl acetate=7/1), thereby obtaining 1.05 g of the title compound as a colorless viscous liquid. A yield was 79.1%.
¹HNMR (400 MHz, CDCl₃) δ: 7.16 (d, J=8.5 Hz, 1H), 7.02 (d, J=9.0 Hz, 2H), 6.91 (d, J=9.0 Hz, 2H), 6.94-6.81 (m, 1H), 6.83 (dd, J=8.5, 2.5 Hz, 1H), 6.48 (d, J=1.5 Hz, 1H), 5.76 (d, J=1.5 Hz, 1H), 3.82 (s, 3H), 3.78 (s, 3H).

Synthesis of methyl 2-(2-chloro-4-(4-chlorophenoxy)phenyl)oxirane-2-carboxylate 0.8681 g of methyl 2-(2-chloro-4-(4-methoxyphenoxy)phenyl)acrylate synthesized in the preceding paragraph was dissolved in 7 ml of acetonitrile and 9.4 ml of methanol, and the solution was cooled to 0° C. The solution was added with 0.898 g of urea-hydrogen peroxide adduct and 0.383 g of potassium carbonate and stirred at a room temperature for 5.5 hours. The mixture was added with 0.388 g of potassium carbonate and further stirred at a room temperature for 1 hour. After the completion of the reaction, the mixture was added with water and extracted with toluene, and the organic layer was washed with water and a saturated saline solution and dried with anhydrous sodium sulfate. The solvent was distilled off to obtain 0.827 g of crude of oxirane as a colorless liquid.

Synthesis of methyl-2-(2-chloro-4-(4-methoxyphenoxy)phenyl)-2-hydroxy-3-(1H-1,2,4-triazol-1-yl) propanoate (I-18)

0.796 g of methyl 2-(2-chloro-4-(4-chlorophenoxy)phenyl)oxirane-2-carboxylate synthesized in the preceding paragraph was dissolved in 9.5 ml of DMF, and the solution was added with 0.167 g of triazole and 0.222 g of triazole sodium and stirred at 50° C. for 1.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/4→ethyl acetate→chloroform methanol 20/1), thereby obtaining 0.693 g of the title compound as a white solid. A yield was 63.0%.

¹HNMR (400 MHz, CDCl₃) δ: 7.99 (s, 1H), 7.88 (s, 1H), 7.35 (d, J=8.8 Hz, 1H), 6.98 (d, J=9.2 Hz, 2H), 6.93-6.89 (m, 3H), 6.76 (dd, J=8.8, 2.5 Hz, 1H), 5.01 (d, J=14.3 Hz, 1H), 4.92 (d, J=14.3 Hz, 1H), 4.83 (s, 1H), 3.82 (s, 3H), 3.79 (s, 3H).

Synthesis Example 5. Synthesis of Compound I-1

Synthesis of 2-(2-chloro-4-(4-chlorophenoxy)phenyl)-2-oxoacetic acid

After 761 mg of 1-(2-chloro-4-(4-chlorophenoxy)phenyl)-ethan-1-on commercially available and 10.8 mL of DMSO were added to and dissolved in a 100 mL eggplant flask, the mixture was added with 2.21 g of iodine, heated to 100° C., and stirred. After 3 hours from the start of the reaction, the mixture was added with a saturated sodium sulfite aqueous solution to stop the reaction, and extracted with toluene three times. The extract was washed with water three times and washed with a saturated saline solution once. After the extract was dried with anhydrous sodium sulfate, a solvent was distilled off and 181 mg of orange liquid crude product was obtained but no target product was contained in the mixture. A water layer was added with a 1N HCl aqueous solution to be acidic, extracted with ethyl acetate three times, and washed with a saturated saline solution once. After dried with anhydrous sodium sulfate, the solvent was distilled off, and the title compound was obtained as a white solid crude product (551.1 mg, yield of 65.4%).
¹HNMR (400 MHz, DMSO-d₆) δ: 7.78 (d, J=8.4 Hz, 1H), 7.50 (d, J=8.8 Hz, 2H), 7.18 (d, J=8.8 Hz, 2H), 7.05 (d, J=2.4 Hz, 1H), 7.00 (dd, J=8.4, 2.4 Hz, 1H).

Synthesis of methyl 2-(2-chloro-4-(4-chlorophenoxy)phenyl)-2-oxoacetate

After 177 mg of 2-(2-chloro-4-(4-chlorophenoxy)phenyl)-2-oxoacetic acid and 1.1 mL of DMF were added to and dissolved in a 100 mL eggplant flask, the mixture was added with 223 mg of cesium carbonate and 57 μL of methyl iodide and stirred. After 1 hour from the start of the reaction, the mixture was added with a saturated aqueous ammonium chloride solution to stop the reaction and extracted with toluene three times. The extract was washed with water three times and washed with a saturated saline solution once. After the extract was dried with anhydrous sodium sulfate, a solvent was distilled off to obtain 171.5 mg of colorless liquid crude product of α-ketoester. By purification by column chromatography (5 g of silica gel, hexane:ethyl acetate=9:1), the title compound was obtained as 161.4 mg of colorless viscous liquid compound (yield of 87.1%).
¹HNMR (400 MHz, CDCl₃) δ: 7.87 (d, J=8.7 Hz, 1H), 7.36 (d, J=8.9 Hz, 2H), 7.03-6.97 (m, 3H), 6.87 (dd, J=8.7, 2.5 Hz, 1H), 3.91 (s, 3H).¹³CNMR (100 MHz, CDCl₃) δ: 165.3, 160.5, 153.6, 135.8, 133.4, 130.2, 129.7, 124.0, 121.5, 120.2, 119.8, 115.5, 52.3.

Synthesis of methyl 2-(2-chloro-4-(4-chlorophenoxy)phenyl)oxirane-2-carboxylate

After 130.4 mg of methyl 2-(2-chloro-4-(4-chlorophenoxy)phenyl)-2-oxoacetate, 68 μL of diiodomethane and 1.0 mL of THF were added to and dissolved in a 50 mL eggplant flask, the mixture was cooled in a dry ice acetone bath, added with 0.68 mL of isopropylmagnesium chloride and continuously stirred. After 0.5 hours from the start of the reaction, the mixture was added with a saturated aqueous ammonium chloride solution to stop the reaction, and extracted with ethyl acetate three times. The extract was washed with water once and washed with a saturated saline solution once. After the extract was dried with anhydrous sodium sulfate, a solvent was distilled off to obtain 187.1 mg of colorless liquid crude product of methyl 2-(2-chloro-4-(4-chlorophenoxy)phenyl)oxirane-2-carboxylate. By purification by column chromatography (6 g of silica gel, hexane:ethyl acetate=9:1), the title compound was obtained as 91.6 mg of colorless viscous liquid mixture.

Synthesis of methyl 2-hydroxy-2-(2-chloro-4-(4-chlorophenoxy)phenyl)-3-(1H-1,2,4-triazol-1-yl)propanoate (I-1)

After 91.6 mg of mixture of methyl 2-(2-chloro-4-(4-chlorophenoxy)phenyl)oxirane-2-carboxylate and 1.2 mL of DMF were added to and dissolved in a 100 mL eggplant flask, the mixture was added with 43.7 mg of triazole sodium salt, heated to 40° C., and stirred. The reaction was appropriately sampled and tracked by HPLC. After 4 hours from the start of the reaction, the mixture was added with a saturated aqueous ammonium chloride solution to stop the reaction and was extracted with toluene three times. The extract was washed with water three times and washed with a saturated saline solution once. After the extract was dried with anhydrous sodium sulfate, a solvent was distilled off to obtain 187 mg of colorless liquid crude product. By purification by column chromatography (2 g of silica gel, hexane:ethyl acetate=1:1), 27.0 mg of colorless viscous liquid mixture was obtained. The mixture was crystallized with toluene to obtain the title compound (I-1) as 12.8 mg of white solid.

$^1$HNMR (400 MHz, CDCl$_3$) δ: 8.00 (s, 1H), 7.88 (s, 1H), 7.40 (d, J=8.8 Hz, 1H), 7.34 (d, J=8.7 Hz, 2H), 6.99-6.95 (m, 3H), 6.81 (dd, J=8.8 Hz, 1H), 5.0 (d, J=14.3 Hz, 1H), 4.93 (d, J=14.3 Hz, 1H), 4.88 (br, 1H), 3.80 (s, 3H).

Synthesis Example 6. Synthesis of Compound I-46

Synthesis of methyl-2-(2-chloro-4-(4-chlorophenoxy)phenyl)-2-hydroxy-3-(1H-1,2,4-triazol-1-yl)propanoate (I-46)

46.4 mg of compound (I-1) synthesized in Synthesis Example 5 was dissolved in 2 ml of ethyl acetate. The mixture was added with 19.0 mg of a 20% sodium ethoxide/ethanol solution and stirred at a room temperature for 2 hours. The mixture was added with 11.6 mg of sodium tert-butoxide (STB) and stirred at a room temperature for 1 hour, and added with 2 ml of ethanol and stirred for 2 hours. After the completion of the reaction, the mixture was added with a saturated ammonium chloride aqueous solution and extracted with chloroform. The organic layer was washed with water and then dried with anhydrous sodium sulfate. The solvent was distilled off, and 45.4 mg of the title compound was obtained as a white solid by vacuum drying. A yield was 94.6%.

$^1$HNMR (400 MHz, CDCl$_3$) δ: 8.00 (s, 1H), 7.87 (s, 1H), 7.40 (d, J=8.8 Hz, 1H), 7.34 (d, J=9.0 Hz, 2H), 6.98-6.94 (m, 3H), 6.80 (dd, J=8.8, 2.6 Hz, 1H), 5.02 (d, J=14.3 Hz, 1H), 4.97 (d, J=14.3 Hz, 1H), 4.76 (s, 1H), 4.25-4.19 (m, 2H), 1.27 (t, J=7.5 Hz, 3H).

Synthesis Example 7. Synthesis of Compound I-22

Synthesis of 1-(2-chloro-4-(4-(trifluoromethoxy)phenoxy)phenyl)ethan-1-on 1.50 g of 2-chloro-4-fluoroacetophenone was dissolved in 16 ml of DMF, and the solution was added with 1.704 g of 4-trifluoromethoxyphenol and 1.44 g of potassium carbonate and stirred at 120° C. for 2.5 hours. After the completion of the reaction, the mixture was added with toluene, and the organic layer was washed with water and a saturated saline solution, and dried with anhydrous sodium sulfate. A solvent is distilled off, and the residue was purified by column chromatography (75 g of silica gel, hexane/ethyl acetate=10/1), thereby obtaining 2.627 g of the title compound as a colorless viscous liquid. A yield was 91.3%.

$^1$HNMR (400 MHz, CDCl$_3$) δ: 7.65 (d, J=8.6 Hz, 1H), 7.26 (d, J=9.0 Hz, 2H), 7.08 (d, J=9.0 Hz, 2H), 7.01 (d, J=2.4 Hz, 1H), 6.90 (dd, J=8.6, 2.5 Hz, 1H), 2.66 (s, 3H).

Synthesis of methyl 2-(2-chloro-4-(4-(trifluoromethoxy)phenoxy)phenyl)-2-oxoacetate 2.61 g of 1-(2-chloro-4-(4-(trifluoromethoxy)phenoxy)phenyl)ethan-1-on synthesized in the preceding paragraph was weighed in a 100 ml eggplant flask and added with 25 ml of DMSO to be dissolved. The mixture was added with 6.418 g of iodine and stirred for 0.5 hours in an oil bath of 100° C. After the completion of the reaction, the mixture was cooled to 60° C., added with 7.65 g of potassium carbonate, and stirred at 100° C. for 0.5 hours. The mixture was cooled to 35° C., added with 1.58 ml of iodomethane, and stirred at 35° C. for 1.5 hours. After the completion of the reaction, a saturated sodium sulfite aqueous solution and toluene were added to the mixture, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (60 g of silica gel, hexane/ethyl acetate=7/1), thereby obtaining 1.879 g of the title compound as a light yellow liquid. A yield was 63.5%.

$^1$HNMR (400 MHz, CDCl$_3$) δ: 7.82 (d, J=8.7 Hz, 1H), 7.28 (d, J=9.1 Hz, 2H), 7.12 (d, J=9.1 Hz, 2H), 7.00 (d, J=2.4 Hz, 1H), 6.95 (dd, J=8.7, 2.4 Hz, 1H), 3.95 (s, 3H).

Synthesis of methyl 2-(2-chloro-4-(4-trifluoromethoxy)phenoxy)phenyl)-2-hydroxy-3-(1H-1,2,4-triazol-1-yl)propanoate (1-22)

0.563 g of methyl 2-(2-chloro-4-(4-(trifluoromethoxy)phenoxy)phenyl)-2-oxoacetate obtained in the preceding paragraph was dissolved in 3 ml of DMF, and the solution was added with 0.320 g of trimethylsulfoxonium bromide (TMSOB) and 0.177 g of sodium triazole and stirred at 50° C. for 2.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/4), thereby obtaining 0.172 g of the title compound (I-22) as a while solid. A yield was 25.1%.

$^1$HNMR (400 MHz, CDCl$_3$) δ: 8.00 (s, 1H), 7.88 (s, 1H), 7.41 (d, J=8.8 Hz, 1H), 7.23 (brd, J=9.1 Hz, 2H), 7.03 (d, J=9.1 Hz, 2H), 7.00 (d, J=2.5 Hz, 1H), 6.81 (dd, J=8.8, 2.5 Hz, 1H), 5.02 (d, J=14.3 Hz, 1H), 4.94 (d, J=14.3 Hz, 1H), 4.89 (brs, 1H), 3.80 (s, 3H).

Synthesis Example 8. Synthesis of Compound I-23

Synthesis of 1-(2-chloro-4-(4-(trifluoromethyl)phenoxy)phenyl)ethan-1-on 1.53 g of 2-chloro-4-fluoroacetophenone was dissolved in 16 ml of N-methyl-2-pyrrolidone (NMP), and the solution was added with 2.15 g of 4-trifluoromethylphenol and 4.99 g of potassium carbonate and stirred at 140° C. for 1 hour. After the completion of the reaction, the mixture was added with toluene, and the organic layer was washed with water and a saturated saline solution, and dried with anhydrous sodium sulfate. A solvent was distilled off, and the residue was purified by column chromatography (75 g of silica gel, hexane/ethyl acetate=10/1), thereby obtaining 1.58 g of the title compound as a colorless viscous liquid. A yield was 56.6%.

$^1$HNMR (400 MHz, CDCl$_3$) δ: 7.68-7.62 (m, 3H), 7.13 (d, J=8.4 Hz, 2H), 7.06 (d, J=2.4 Hz, 2H), 6.95 (dd, J=8.6, 2.5 Hz, 1H), 2.67 (s, 3H).

Synthesis of methyl 2-(2-chloro-4-(4-(trifluoromethyl)phenoxy)phenyl)-2-oxoacetate 1.56 g of 1-(2-chloro-4-(4-(trifluoromethyl)phenoxy)phenyl)ethan-1-on synthesized in the preceding paragraph was weighed in a 100 ml eggplant flask and added with 20 ml of DMSO to be dissolved. The mixture was added with 4.01 g of iodine and stirred for 0.5 hours in an oil bath of 100° C. After the completion of the reaction, the mixture was cooled to 60° C., added with 4.76 g of potassium carbonate, and stirred at 100° C. for 0.5 hours. The mixture was cooled to 35° C., added with 1.0 ml of iodomethane, and stirred at 35° C. for 1.5 hours. After the completion of the reaction, a saturated sodium sulfite aqueous solution and toluene were added to the mixture, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (37 g of silica gel, hexane/ethyl acetate=10/1), thereby obtaining 1.064 g of the title compound as a light yellow liquid. A yield was 60.0%.

$^1$HNMR (400 MHz, CDCl$_3$) δ: 7.84 (d, J=8.6 Hz, 1H), 7.69 (d, J=8.5 Hz, 2H), 7.19 (d, J=8.4 Hz, 2H), 7.04 (d, J=2.4 Hz, 1H), 7.00 (dd, J=8.6, 2.4 Hz, 1H), 3.96 (s, 3H).

Synthesis of methyl 2-(2-chloro-4-(4-trifluoromethyl)phenoxy)phenyl)-2-hydroxy-3-(1H-1,2,4-triazol-1-yl)propanoate (1-23)

0.508 g of methyl 2-(2-chloro-4-(4-(trifluoromethyl)phenoxy)phenyl)-2-oxoacetate obtained in the preceding paragraph was dissolved in 2.6 ml of DMF, and the solution was added with 0.270 g of TMSOB and 0.170 g of triazole sodium and stirred at 50° C. for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/3), thereby obtaining 0.160 g of the title compound as light yellow to white solids. A yield was 25.5%.

$^1$HNMR (400 MHz, CDCl$_3$) δ: 8.01 (s, 1H), 7.89 (s, 1H), 7.63 (d, J=8.6 Hz, 2H), 7.46 (d, J=8.8 Hz, 1H), 7.08 (d, J=8.6 Hz, 2H), 7.05 (d, J=2.5 Hz, 1H), 6.88 (dd, J=8.8, 2.5 Hz, 1H), 5.03 (d, J=14.3 Hz, 1H), 4.95 (d, J=14.3 Hz, 1H), 4.90 (brs, 1H), 3.81 (s, 3H).

Synthesis Example 9. Synthesis of Compound I-24

Synthesis of 1-(4-(4-(tert-butyl)phenoxy)-2-chlorophenyl)ethan-1-on 1.51 g of 2-chloro-4-fluoroacetophenone was dissolved in 16 ml of DMF, and the solution was added with 1.45 g of 4-tert-butylphenol and 1.45 g of potassium carbonate and stirred at 110° C. for 2.5 hours. After the completion of the reaction, the mixture was added with toluene, and the organic layer was washed with water and a saturated saline solution, and dried with anhydrous sodium sulfate. A solvent was distilled off, and the residue was purified by column chromatography (75 g of silica gel, hexane/ethyl acetate=10/1), thereby obtaining 1.60 g of the title compound as a colorless viscous liquid. A yield was 60.4%.

$^1$HNMR (400 MHz, CDCl$_3$) δ: 7.63 (d, J=8.7 Hz, 1H), 7.40 (d, J=8.8 Hz, 2H), 6.99 (d, J=8.8 Hz, 2H), 6.99 (d, J=2.4 Hz, 2H), 6.89 (dd, J=8.7, 2.5 Hz, 1H), 2.65 (s, 3H), 1.34 (s, 9H).

Synthesis of methyl 2-(4-(4-(tert-butyl)phenoxy)-2-chlorophenyl)-2-oxoacetate 1.586 g of 1-(4-(4-(tert-butyl)phenoxy)-2-chlorophenyl)ethan-1-on synthesized in the preceding paragraph was weighed in a 100 ml eggplant flask and added with 18 ml of DMSO to be dissolved. The mixture was added with 4.21 g of iodine and stirred for 0.5 hours in an oil bath of 100° C. After the completion of the reaction, the mixture was cooled to 60° C., added with 5.07 g of potassium carbonate, and stirred at 100° C. for 0.5 hours. The mixture was cooled to 35° C., added with 1.05 ml of iodomethane, and stirred at 35° C. for 1.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (37 g of silica gel, hexane/ethyl acetate=10/1), thereby obtaining 1.22 g of the title compound as a light yellow liquid. A yield was 62.3%.

$^1$HNMR (400 MHz, CDCl$_3$) δ: 7.80 (d, J=8.7 Hz, 1H), 7.43 (d, J=8.8 Hz, 2H), 7.00 (d, J=8.8 Hz, 2H), 6.97 (d, J=2.4 Hz, 1H), 6.94 (dd, J=8.7, 2.4 Hz, 1H), 3.94 (s, 3H), 1.35 (s, 9H).

Synthesis of methyl 2-(4-(4-(tert-butyl)phenoxy)-2-chlorophenyl)oxirane-2-carboxylate 0.465 g of methyl 2-(4-(4-(tert-butyl)phenoxy)-2-chlorophenyl)-2-oxoacetate obtained in the preceding paragraph was dissolved in 2.5 ml of DMF, and the solution was added with 0.280 g of TMSOB and 0.135 g of sodium tert-butoxide, stirred at a room temperature for 0.5 hours, and stirred at 50° C. for 0.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=7/1), thereby obtaining 0.0905 g of the title compound as light yellow to white liquid. A yield was 18.7%.

$^1$HNMR (400 MHz, CDCl$_3$) δ: 7.38 (d, J=8.6 Hz, 1H), 7.36 (d, J=8.8 Hz, 2H), 6.99 (d, J=2.4 Hz, 1H), 6.97 (d, J=8.8 Hz, 2H), 6.89 (dd, J=8.6, 2.4 Hz, 1H), 3.77 (s, 3H), 3.57 (d, J=6.4 Hz, 1H), 3.03 (d, J=6.4 Hz, 1H), 1.33 (s, 9H).

Synthesis of methyl 2-(4-(4-(tert-butyl)phenoxy)-2-chlorophenyl)-2-hydroxy-3-(1H-1,2,4-triazol-1-yl)propanoate (I-24)

89.5 mg of methyl 2-(4-(4-(tert-butyl)phenoxy)-2-chlorophenyl)oxirane-2-carboxylate obtained in the preceding paragraph was dissolved in 1 ml of DMF, and the solution was added with 17.4 mg of triazole and 23.0 mg of triazole sodium and stirred at 50° C. for 3 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (3 g of silica gel, hexane/ethyl acetate=1/3), thereby obtaining 78.5 mg of the title compound as a white solid. A yield was 75.4%.

$^1$HNMR (400 MHz, CDCl$_3$) δ: 8.00 (s, 1H), 7.89 (s, 1H), 7.38 (d, J=8.8 Hz, 2H), 7.37 (d, J=8.8 Hz, 1H), 6.98 (d, J=2.5 Hz, 1H), 6.95 (d, J=8.8 Hz, 2H), 6.82 (dd, J=8.8, 2.5 Hz, 1H), 5.02 (d, J=14.2 Hz, 1H), 4.92 (d, J=14.2 Hz, 1H), 4.79 (brs, 1H), 3.79 (s, 3H), 1.33 (s, 9H).

Synthesis Example 10. Synthesis of Compound I-80

Synthesis of tert-butyl 2-(4-(4-bromophenoxy)-2-chlorophenyl)-2-hydroxy-3-(1H-1,2,4-triazol-1-yl)propanoate (I-80)

37.6 mg of tert-butyl 2-(2-chloro-4-((4-chlorobenzyl)oxy)phenyl)-2-oxoacetate was dissolved in 0.5 ml of DMF, and the solution was added with 11.3 mg of triazole sodium and 8.9 mg of triazole and stirred at 50° C. for 8 hours. After the completion of the reaction, the mixture was added with ethyl acetate, and the organic layer was washed with water and a saturated saline solution and dried with anhydrous sodium sulfate. A solvent was distilled off, and the residue was purified by column chromatography (3 g of silica gel, hexane/ethyl acetate=1/3), thereby obtaining 36.5 mg of the title compound as a white solid. A yield was 82.7%.

$^1$HNMR (400 MHz, CDCl$_3$) δ: 8.04 (s, 1H), 7.85 (s, 1H), 7.48 (d, J=9.0 Hz, 2H), 7.37 (d, J=8.8 Hz, 1H), 6.99 (d, J=2.5 Hz, 1H), 6.90 (d, J=9.0 Hz, 2H), 6.80 (dd, J=8.8, 2.5 Hz, 1H), 4.99 (d, J=14.3 Hz, 1H), 4.95 (d, J=14.3 Hz, 1H), 4.53 (s, 1H), 1.46 (s, 9H).

Synthesis Example 11. Synthesis of Compound I-47

Synthesis of 2-(2-chloro-4-(4-chlorophenoxy)phenyl)2-hydroxy-3-(1H-1,2,4-triazol-1-yl) propanoic acid 135 mg of the compound (I-1) synthesized in Synthesis Example 5 was dissolved in 1 ml of methanol, and the solution was added with 2 ml of 2 mol/L sodium hydroxide aqueous solution and stirred at a room temperature for 6.5 hours. After the completion of the reaction, the mixture was adjusted with 1 mol/L hydrochloric acid to have a pH of 3 to 4 and extracted with ethyl acetate. The organic layer was washed with a saturated saline solution and dried with anhydrous sodium sulfate. The solvent was distilled off, and 115 mg of the title compound was obtained as a white solid by vacuum drying.

Synthesis of isopropyl 2-(2-chloro-4-(4-chlorophenoxy)phenyl)-2-hydroxy-3-(1H-1,2,4-triazol-1-yl)propanoate (I-47)

49.9 mg of 2-(2-chloro-4-(4-chlorophenoxy)phenyl)2-hydroxy-3-(1H-1,2,4-triazol-1-yl)propanoic acid obtained in the preceding paragraph was dissolved in 1 ml of DMF, and the solution was added with 58.7 mg of cesium carbonate. The mixture was added with 26.1 mg of 2-iodopropane and stirred at 50° C. for 2 hours. The mixture was added with 17.0 mg of 2-iodopropane and further stirred at the same temperature for 3.5 hours. After the completion of the reaction, the mixture was added with ethyl acetate, and the organic layer was washed with water and a saturated saline solution, and dried with anhydrous sodium sulfate. A solvent was distilled off, and the residue was purified by column chromatography (2.5 g of silica gel, hexane/ethyl acetate=1/3), thereby obtaining 51.6 mg of the title compound as a white solid. A yield was 93.4%.

$^1$HNMR (400 MHz, CDCl$_3$) δ: 8.02 (s, 1H), 7.86 (s, 1H), 7.39 (d, J=8.8 Hz, 1H), 7.34 (d, J=9.0 Hz, 2H), 6.98 (d, J=2.5 Hz, 1H), 6.96 (d, J=9.0 Hz, 2H), 6.80 (dd, J=8.8, 2.5 Hz, 1H), 5.10 (sept, J=6.3 Hz, 1H), 5.01 (d, J=14.3 Hz, 1H), 4.94 (d, J=14.3 Hz, 1H), 4.74 (s, 1H), 1.26 (d, J=6.3 Hz, 3H), 1.23 (d, J=6.3 Hz, 3H).

Synthesis Example 12. Synthesis of Compound I-48

Synthesis of cyclopropylmethyl 2-(2-chloro-4-(4-chlorophenoxy)phenyl)-2-hydroxy-3-(1H-1,2,4-triazol-1-yl)propanoate (I-48)

54.5 mg of 2-(2-chloro-4-(4-chlorophenoxy)phenyl)2-hydroxy-3-(1H-1,2,4-triazol-1-yl)propanoic acid obtained in the preceding paragraph was dissolved in 1 ml of DMF, and the solution was added with 68.7 mg of cesium carbonate. The mixture was added 16 μL of cyclopropylmethyl bromide and stirred at 50° C. for 3 hours. The mixture was added with 16 μL of cyclopropylmethyl bromide and further stirred at the same temperature for 2 hours. After the completion of the reaction, the mixture was added with ethyl acetate, and the organic layer was washed with water and a saturated saline solution, and dried with anhydrous sodium sulfate. A solvent was distilled off, and the residue was purified by column chromatography (3 g of silica gel, hexane/ethyl acetate=1/2), thereby obtaining 38.2 mg of the title compound as a white solid. A yield was 61.6%.

$^1$HNMR (400 MHz, CDCl$_3$) δ: 8.02 (s, 1H), 7.87 (s, 1H), 7.41 (d, J=8.8 Hz, 1H), 7.34 (d, J=9.0 Hz, 2H), 6.98 (d, J=2.5 Hz, 1H), 6.96 (d, J=9.0 Hz, 2H), 6.81 (dd, J=8.8, 2.5 Hz, 1H), 5.02 (d, J=14.3 Hz, 1H), 4.96 (d, J=14.3 Hz, 1H), 4.76 (s, 1H), 4.03 (d, J=7.4 Hz, 2H), 1.17-1.08 (m, 1H), 0.58-0.53 (m, 1H), 0.31-0.24 (m, 1H).

Synthesis Example 13. Synthesis of Compound I-27

Synthesis of 1-(2-chloro-4-(3,4-dichlorophenoxy)phenyl)ethan-1-on 1.560 g of 2-chloro-4-fluoroacetophenone was dissolved in 16 ml of DMF, and the solution was added with 1.615 g of 3,4-dichlorophenol and 1.510 g of potassium carbonate and stirred at 90° C. for 6 hours. After the completion of the reaction, the mixture was added with toluene and the organic layer was washed with water and a saturated saline solution, and dried with anhydrous sodium sulfate. A solvent was distilled off, and the residue was purified by column chromatography (60 g of silica gel, hexane/ethyl acetate=10/1), thereby obtaining 1.701 g of the title compound as a colorless viscous liquid. A yield was 62.1%.

Synthesis of methyl 2-(2-chloro-4-(3,4-dichlorophenoxy)phenyl)-2-oxoacetate 1.70 g of 1-(2-chloro-4-(3,4-dichlorophenoxy)phenyl)ethan-1-on synthesized in the preceding paragraph was weighed in a 100 ml eggplant flask and added with 20 ml of DMSO to be dissolved. The mixture was added with 4.37 g of iodine and stirred for 0.5 hours in an oil bath of 100° C. After the completion of the reaction, the mixture was cooled to 60° C., added with 5.212 g of potassium carbonate, and stirred at 100° C. for 0.5 hours. The mixture was cooled to 35° C., added with 1.1 ml of iodomethane, and stirred at 35° C. for 1.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (60 g of silica gel, hexane/ethyl acetate=10/1), thereby obtaining 1.175 g of the title compound as a light yellow liquid. A yield was 60.6%.

$^1$HNMR (400 MHz, CDCl$_3$) δ: 7.82 (d, J=8.6 Hz, 1H), 7.49 (d, J=8.8 Hz, 1H), 7.22 (d, J=2.8 Hz, 1H), 7.00 (d, J=2.4 Hz, 1H), 6.97 (dd, J=8.6, 2.4 Hz, 1H), 6.96 (dd, J=8.8, 2.8 Hz, 1H), 3.96 (s, 3H).

Synthesis of methyl 2-(2-chloro-4-(3,4-dichlorophenoxy)phenyl)-2-hydroxy-3-(1H-1,2,4-triazol-1-yl)propanoate (I-27)

0.813 g of methyl 2-(2-chloro-4-(3,4-dichlorophenoxy)phenyl)-2-oxoacetate obtained in the preceding paragraph was dissolved in 4.5 ml of DMF, and the solution was added with 0.548 g of trimethylsulfoxonium iodide (TMSOI) and 0.247 g of triazole sodium salt at 0° C., and stirred for 30 minutes while returning to a room temperature. The mixture was put in a bath of 50° C. and stirred for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/3), thereby obtaining 0.242 g of the title compound as a white solid. A yield was 24.2%.

$^1$HNMR (400 MHz, CDCl$_3$) δ: 8.01 (s, 1H), 7.88 (s, 1H), 7.43 (d, J=8.8 Hz, 2H), 7.13 (d, J=2.8 Hz, 1H), 7.00 (d, J=2.5 Hz, 1H), 6.89 (dd, J=8.8, 2.8 Hz, 1H), 6.83 (dd, J=8.8, 2.5 Hz, 1H), 5.02 (d, J=14.3 Hz, 1H), 4.98 (s, 1H), 4.93 (d, J=14.3 Hz, 1H), 3.80 (s, 3H).

Synthesis Example 14. Synthesis of Compound I-7

Synthesis of 1-(4-chlorophenoxy)-3-(trifluoromethoxy)benzene 2.67 g of 3-trifluoromethoxyfluorobenzene was dissolved in 18 ml of NMP, and the solution was added with 2.39 g of 4-chloroiodobenzene, 6.55 g of cesium carbonate, 0.205 g of copper iodide and 0.401 g of dimethylglycine hydrochloride (DMG) and stirred at 90° C. for 6 hours. After the completion of the reaction, the mixture was added with toluene, and the organic layer was washed with water and a saturated saline solution, and dried with anhydrous sodium sulfate. A solvent was distilled off, and the residue was purified by column chromatography (75 g of silica gel, hexane/ethyl acetate=10/1), thereby obtaining 1.171 g of the title compound as a colorless viscous liquid. A yield was 40.6%.

$^1$HNMR (400 MHz, CDCl$_3$) δ: 7.35-7.28 (m, 3H), 7.00-6.94 (m, 3H), 6.93-6.88 (m, 1H), 6.86-6.84 (m, 1H).

Synthesis of methyl 2-(4-(4-chlorophenoxy)-2-(trifluoromethoxy)phenyl)-2-oxoacetate 1.17 g of 1-(4-chlorophenoxy)-3-(trifluoromethoxy)benzene synthesized in the preceding paragraph was weighed in a 100 ml eggplant flask and dissolved in 5.0 ml of methylene chloride. The solution was cooled to −20° C. and added with 0.523 g of aluminum chloride. In addition, the mixture was cooled to −40° C. and dropped with a solution obtained by dropping 0.487 g of methylglyoxalylic acid chloride in 5 ml of methylene chloride for 9 minutes. The mixture was heated over 1 hour to be −5° C. After the completion of the reaction, the mixture was added with ice+concentrated hydrochloric acid and extracted with ethyl acetate. The extract was washed water and a saturated saline solution and dried with anhydrous sodium sulfate. A solvent was distilled off, and the residue was again dissolved in 5.0 ml of methylene chloride. The mixture was cooled to −5° C. and added with 0.548 g of aluminum chloride. The mixture was dropped with a solution, in which 0.499 g of methylglyoxalic acid chloride is dissolved in 5 ml of methylene chloride, for 1 minute. The mixture was stirred for 2 hours while being heated to a room temperature. After the completion of the reaction, the mixture was added with ice+concentrated hydrochloric acid and extracted with ethyl acetate. The extract was washed with water and a saturated saline solution and dried with anhydrous sodium sulfate. A solvent was distilled off, and the residue was purified by column chromatography (30 g of silica gel, hexane/ethyl acetate=10/1), thereby obtaining 0.287 g of the title compound as a colorless viscous liquid. A yield was 22.1%.

$^1$HNMR (400 MHz, CDCl$_3$) δ: 7.94 (d, J=9.3 Hz, 1H), 7.41 (d, J=8.9 Hz, 2H), 7.04 (d, J=8.9 Hz, 2H), 6.93-6.89 (m, 2H), 3.94 (s, 3H).

Synthesis of methyl 2-(4-(4-chlorophenoxy)-2-(trifluoromethoxy)phenyl)-2-hydroxy-3-(1H-1,2,4-triazol-1-yl)propanoate (I-7)

0.259 g of methyl 2-(4-(4-chlorophenoxy)-2-(trifluoromethoxy)phenyl)-2-oxoacetate obtained in the preceding paragraph was dissolved in 1.5 ml of DMAc, and the solution was added with 0.171 g of TMSOI and 0.076 g of triazole sodium and stirred at a room temperature for 0.5 hours and at 50° C. for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (9 g of silica gel, hexane/ethyl acetate=1/3), thereby obtaining 0.108 g of the title compound as a white solid. A yield was 34.2%.

$^1$HNMR (400 MHz, CDCl$_3$) δ: 8.06 (s, 1H), 7.88 (s, 1H), 7.45 (d, J=8.8 Hz, 1H), 7.35 (d, J=8.9 Hz, 2H), 6.98 (d, J=8.9 Hz, 2H), 6.98-6.93 (m, 1H), 6.77 (dd, J=8.8, 2.4 Hz, 1H), 5.01 (d, J=14.2 Hz, 1H), 4.76 (d, J=14.2 Hz, 1H), 4.70 (s, 1H), 3.79 (s, 3H).

Synthesis Example 15. Synthesis of Compound I-4

Synthesis of 1-bromo-4-(4-chlorophenoxy)-2-cyanobenzene

In a nitrogen atmosphere, 10.494 g of 1-bromo-2-cyano-4-fluorobenzene and 0.337 g of 4-chlorophenol were dissolved in 4.5 mL of NMP, and the solution was added with 0.420 g of potassium carbonate at a room temperature, heated to 100° C., stirred for 23 hours, and then stirred at 160° C. for 1 hour. Thereafter, the reaction was stopped by adding water, the mixture was extracted with ethyl acetate, the organic layer was washed with water and a saturated saline solution, and then dried with anhydrous sodium sulfate. The solvent was distilled off, and 0.845 g of crude obtained was purified by column chromatography (20 g of silica gel, hexane/ethyl acetate=19/1) to obtain a mixture containing the title compound as a main product as 0.656 g of colorless oil.

$^1$HNMR (400 MHz, CDCl$_3$) δ: 7.60 (d, J=8.8 Hz, 1H), 7.39-7.36 (m, 2H), 7.21 (d, J=2.8 Hz, 1H), 7.08 (dd, J=8.8, 2.8 Hz, 1H), 6.98-6.95 (m, 2H).

Synthesis of methyl 3-bromo-2-(4-(4-chlorophenoxy)-2-cyanophenyl)-2-hydroxypropanoate In a nitrogen atmosphere, 3 mL of tetrahydrofuran (THF) solution of 0.195 g of 1-bromo-4-(4-chlorophenoxy)-2-cyanobenzene obtained in the preceding paragraph was cooled to 0° C., added with 0.5 ml of a THF solution of iPrMgCl·LiCl, heated to a room temperature, and then stirred for 20 minutes. Next, the solution was cooled to 0° C. once, added with a THF solution of 0.08 ml of methyl 3-bromopyruvate, heated to a room temperature, and stirred for 1 hour. Thereafter, the solution was added with 1N hydrochloric acid aqueous solution to stop the reaction, the mixture was extracted with ethyl acetate, and the organic layer was washed with saturated sodium bicarbonate water and a saturated saline solution and then dried with anhydrous sodium sulfate. The solvent was distilled off, and 0.243 g of crude obtained was purified by column chromatography (10.0 g of silica gel, hexane/ethyl acetate=9/1), thereby obtaining 0.055 g of the title compound as light yellow oil. A yield was 21.0%.

$^1$HNMR (400 MHz, CDCl$_3$) δ: 7.63 (brs, 1H), 7.50 (d, J=8.4 Hz, 1H), 7.36-7.34 (m, 3H), 7.26 (dd, J=8.0, 2.0 Hz, 1H), 7.00 (d, J=8.8 Hz, 2H), 4.12 (d, J=12.0 Hz, 1H), 3.83 (s, 3H), 3.72 (d, J=11.6 Hz, 1H).

Synthesis of methyl 2-(4-(4-chlorophenoxy)-2-cyanophenyl)-2-hydroxy-3-(1H-1,2,4-triazol-1-yl)propanoate (I-4)

In a nitrogen atmosphere, 0.011 g of triazole sodium was added to 2 mL of DMF solution of 0.039 g of bromohydrin, and the mixture was heated to 40° C. and stirred for 1 hour, and then stirred at 50° C. for 2 hours. After the mixture is cooled to a room temperature, the mixture was added with 0.004 g of triazole sodium, heated to 50° C. and stirred for 1 hour. Thereafter, the mixture was added with a saturated ammonium chloride aqueous solution to stop the reaction and extracted with chloroform, and the organic layer was washed with a saturated saline solution and then dried with anhydrous sodium sulfate. The solvent was distilled off, and 0.052 g of crude obtained was purified by column chromatography (6.3 g of silica gel, hexane/ethyl acetate=1/1→1/4→0/1), thereby obtaining 0.005 g of the title compound as light yellow solid. A yield was 10.4%.

$^1$HNMR (400 MHz, CDCl$_3$) δ: 8.08 (s, 1H), 7.83 (s, 1H), 7.57 (d, J=9.2 Hz, 2H), 7.36-7.34 (m, 3H), 7.29-7.25 (m, 1H), 6.98 (d, J=8.8 Hz, 1H), 5.04 (d, J=14.4 Hz, 1H), 4.78 (d, J=14.4 Hz, 1H), 3.81 (s, 3H).

Synthesis Example 16. Synthesis of Compound I-122

Synthesis of 1-(4-(4-chlorophenoxy)-2-(trifluoromethyl)phenyl)ethan-1-on

After 825 mg of 4-fluoro-2-(trifluoromethyl)acetophenone and 7.2 mL of DMF were added to and dissolved in a 25 mL eggplant flask, the mixture was added with 567 mg of 4-chlorophenol and 663 mg of potassium carbonate and heated and stirred in an oil bath of 120° C. After 1.5 hours from the start of the reaction, the mixture was added with water to stop the reaction and extracted with toluene three times. The extract was washed with water three times and washed with a saturated saline solution once. After the extract was dried with anhydrous sodium sulfate, a solvent was distilled off to obtain 1.33 g of the title compound as a brown liquid.

Synthesis of methyl 2-(4-(4-chlorophenoxy)-2-(trifluoromethyl)phenyl)-2-oxoacetate 1.3257 g of 1-(4-(4-chlorophenoxy)-2-(trifluoromethyl)phenyl)ethan-1-on and 16 mL of DMSO were added to and dissolved in a 100 mL eggplant flask, the mixture was added with 3.2500 g of iodine and heated and stirred in an oil bath of 100° C. After 0.5 hours from the start of the reaction, the reaction solution was cooled to a room temperature and then added with 3.8714 g of potassium carbonate, and heated and stirred in an oil bath at 100° C. again. After 0.5 hours, the reaction solution was cooled to a room temperature, added with 0.80 mL of methyl iodide and continuously stirred. After 3.5 hours, the mixture was heated and stirred in a water bath of 35° C. After 1 hour, the mixture was added with a saturated sodium sulfite aqueous solution to stop the reaction, filtered, added with water, and extracted with toluene three times. The extract was washed with water three times and washed with a saturated saline solution once. After the extract was dried with anhydrous sodium sulfate, a solvent was distilled off to obtain 1.3677 g of brown liquid crude product of ketoester. By purification by column chromatography (50 g of silica gel, hexane:ethyl acetate=9:1), 840.2 mg of the title compound was obtained as an orange liquid compound.

$^1$HNMR (400 MHz, CDCl$_3$) δ: 7.66 (d, J=8.6 Hz, 1H), 7.41 (d, J=9.0 Hz, 2H), 7.34 (d, J=2.4 Hz, 1H), 7.14 (dd, J=8.6, 2.4 Hz, 1H), 7.04 (d, J=9.0 Hz, 2H), 3.94 (s, 3H).

Synthesis of methyl 2-(4-(4-chlorophenoxy)-2-(trifluoromethyl)phenyl)-2-hydroxy propanoate 840 mg of methyl 2-(4-(4-chlorophenoxy)-2-(trifluoromethyl)phenyl)-2-oxoacetate and 12.2 mL of THF were added to a 50 mL three-necked flask and cooled to −78° C. in an acetone bath, the mixture was dropped with 3.11 mL of methyl magnesium bromide and continuously stirred. After two hours from the completion of the dropping, the mixture was added with 5 mL of 1 N hydrochloric acid, the water layer was separated, and THF of the organic layer was distilled off. The water layer was extracted with toluene twice, combined with the organic layer distilled off THF, washed with water once, and washed with a saturated saline solution once. After the mixture was dried with anhydrous sodium sulfate, a solvent was distilled off to obtain 900 mg of a yellow liquid crude product of hydroxy ester. By purification by column chromatography (30 g of silica gel, hexane:ethyl acetate=4:1), 689 mg of the title compound was obtained as a yellow liquid compound. A yield was 78.5%.

$^1$HNMR (400 MHz, CDCl$_3$) δ: 7.60 (d, J=8.8 Hz, 1H), 7.37 (d, J=2.7 Hz, 1H), 7.34 (d, J=9.0 Hz, 2H), 7.09 (dd, J=8.8, 2.7 Hz, 1H), 6.98 (d, J=9.0 Hz, 2H), 3.74 (s, 3H), 3.66 (s, 1H), 1.87 (s, 3H).

Synthesis of methyl 2-(4-(4-chlorophenoxy)-2-(trifluoromethyl)phenyl)acrylate

After 651 mg of methyl 2-(4-(4-chlorophenoxy)-2-(trifluoromethyl)phenyl)-2-hydroxypropanoate and 13.0 mL of toluene were added to and dissolved in a 50 mL eggplant flask, the mixture was added with 165 mg of tosylate monohydrate and connected to a Dean-Stark tube to be dehydrated and refluxed. A saturated sodium hydrogen carbonate aqueous solution was added after 1.5 hours and extracted with toluene three times. The extract was washed with a saturated saline solution once. After the extract was dried with anhydrous sodium sulfate, a solvent was distilled off to obtain 669 mg of black liquid mixture. After 8.7 mL of toluene was added to and dissolved in a 50 mL eggplant flask, the mixture was added with 90 µL of concentrated sulfuric acid and connected to a Dean-Stark tube to be dehydrated and refluxed. After 1 hour, the mixture was added with a saturated sodium hydrogen carbonate aqueous solution and extracted with toluene three times. The extract was washed with a saturated saline solution once. After the extract was dried with anhydrous sodium sulfate, a solvent was distilled off to obtain 592 mg of black liquid mixture. By purification by column chromatography (20 g of silica gel, hexane:ethyl acetate=9:1), 689 mg of the title compound was obtained as a yellow liquid compound. A yield was 94.4%.

$^1$HNMR (400 MHz, CDCl$_3$) δ: 7.35 (d, J=8.9 Hz, 2H), 7.28 (d, J=2.4 Hz, 1H), 7.22 (d, J=8.4 Hz, 1H), 7.10 (dd, J=8.4, 2.4 Hz, 1H), 7.01 (d, J=8.9 Hz, 2H), 6.60 (d, J=1.1 Hz, 1H), 5.76 (d, J=1.1 Hz, 1H), 3.74 (s, 3H).

Synthesis of methyl 2-(4-(4-chlorophenoxy)-2-(trifluoromethyl)phenyl)oxirane-2-carboxylate After 570.0 mg of methyl 2-(4-(4-chlorophenoxy)-2-(trifluoromethyl)phenyl)acrylate (9) and 4.0 mL of acetonitrile were added to and dissolved in a 100 mL eggplant flask, the mixture was added with 452 mg of potassium carbonate, 452 mg of hydrogen peroxide urea, and 4.0 mL of methanol and stirred. After 2 hours, the mixture was added with a saturated sodium sulfite aqueous solution and 1N hydrochloric acid, and extracted with toluene three times. The extract was washed with water once and washed with a saturated saline solution once. After the extract was dried with anhydrous sodium sulfate, a solvent was distilled off to obtain 590 mg of colorless liquid crude product of oxirane. By purification by column chromatography (15 g of silica gel, hexane:ethyl acetate=9:1), 459.5 mg of the title compound was obtained as a colorless liquid compound. A yield was 77.2%.

$^1$HNMR (400 MHz, CDCl$_3$) δ: 7.58 (d, J=8.6 Hz, 1H), 7.36 (d, J=9.0 Hz, 2H), 7.26 (d, J=2.2 Hz, 1H), 7.12 (dd, J=8.6, 2.2 Hz, 1H), 7.01 (d, J=9.0 Hz, 2H), 3.74 (s, 3H), 3.64 (d, J=6.2 Hz, 1H), 3.05 (d, J=6.2 Hz, 1H).

Synthesis of methyl 2-(4-(4-chlorophenoxy)-2-(trifluoromethyl)phenyl)-2-hydroxy-3-(1H-1,2,4-triazol-1-yl)propanoate (1-122)

After 454.6 mg of methyl 2-(4-(4-chlorophenoxy)-2-(trifluoromethyl)phenyl)oxirane-2-carboxylate and 1.22 mL of DMF were added to and dissolved in a 100 mL eggplant flask, the mixture was added with 26.0 mg of sodium carbonate, and heated and stirred in an oil bath of 60° C.

After 2 hours, the mixture was added with 22.3 mg of triazole sodium and continuously stirred. After 1.5 hours, the mixture was added with 103.5 mg of sodium carbonate and continuously stirred. After 2 hours, the mixture was added with 55.8 mg of triazole sodium and continuously stirred. After 4 hours, the mixture was extracted with saturated ammonium chloride aqueous solution and toluene three times. The extract was washed with water twice and washed with a saturated saline solution once. After the extract was dried with anhydrous sodium sulfate, a solvent was distilled off to obtain 474 mg of colorless liquid crude product of azole. By purification by column chromatography (15 g of silica gel, hexane:ethyl acetate=1:1→chloroform:ethyl acetate=1:1), 314 mg of the title compound (I-122) was obtained as a white solid compound. A yield was 58.2%.

$^1$HNMR (400 MHz, CDCl$_3$) δ: 8.11 (s, 1H), 7.89 (s, 1H), 7.62 (d, J=8.9 Hz, 1H), 7.38 (d, J=2.7 Hz, 1H), 7.36 (d, J=9.0 Hz, 2H), 7.06 (dd, J=8.9, 2.7 Hz, 1H), 6.98 (d, J=9.0 Hz, 2H), 5.08 (d, J=14.1 Hz, 1H), 4.70 (d, J=14.1 Hz, 1H), 4.67 (s, 1H), 3.80 (s, 3H).

Synthesis Example 17. Synthesis of Compound I-228

Synthesis of 1-(2-bromo-4-(4-chlorophenoxy)phenyl)ethan-1-on

After 869 mg of 2-bromo-4-fluoroacetophenone and 7.2 mL of DMF were added to and dissolved in a 25 mL eggplant flask, the mixture was added with 567 mg of p-chlorophenol and 665 mg of potassium carbonate and heated and stirred in an oil bath of 120° C. After 2.5 hours from the start of the reaction, the mixture was added with water to stop the reaction and extracted with toluene three times. The extract was washed with water three times and washed with a saturated saline solution once. After the extract was dried with anhydrous sodium sulfate, a solvent was distilled off to obtain 1.33 g of the title compound as a brown liquid.

$^1$HNMR (400 MHz, CDCl$_3$) δ: 7.55 (d, J=8.6 Hz, 1H), 7.36 (d, J=8.8 Hz, 2H), 7.20 (d, J=2.4 Hz, 1H), 7.00 (d, J=8.8 Hz, 2H), 6.94 (dd, J=8.6, 2.4 Hz, 1H), 2.64 (s, 3H).

Synthesis of methyl 2-(2-bromo-4-(4-chlorophenoxy)phenyl)-2-oxoacetate (6)

After 1.33 g of 1-(2-bromo-4-(4-chlorophenoxy)phenyl)ethan-1-on and 16 mL of DMSO were added to and dissolved in a 100 mL eggplant flask, the mixture was added with 3.25 g of iodine and heated and stirred in an oil bath of 100° C. After 0.5 hours from the start of the reaction, the reaction solution was cooled to a room temperature and then added with 3.87 g of potassium carbonate, and continuously stirred. After 0.5 hours, the reaction solution was cooled to a room temperature and then added with 0.80 mL of methyl iodide, heated with a water bath of 35° C., and stirred. After 1 hour, the mixture was added with a saturated sodium sulfite aqueous solution to stop the reaction, filtered, added with water, and extracted with toluene three times. The extract was washed with water three times and washed with a saturated saline solution once. After the mixture was dried with anhydrous sodium sulfate, a solvent was distilled off to obtain 1.49 g of brown liquid crude product of ketoester. By purification by column chromatography (50 g of silica gel, hexane:ethyl acetate=9:1), 1.05 g of the title compound was obtained as an orange liquid compound. A yield was 71.2%.

$^1$HNMR (400 MHz, CDCl$_3$) δ: 7.82 (d, J=8.7 Hz, 1H), 7.52 (dd, J=8.0, 1.6 Hz, 1H), 7.35 (td, J=7.9, 1.6 Hz, 1H), 7.25 (td, J=7.9, 1.6 Hz, 1H), 7.16 (dd, J=8.0, 1.6 Hz, 1H), 6.92 (d, J=2.4 Hz, 1H), 6.89 (dd, J=8.7, 2.4 Hz, 1H), 3.95 (s, 3H).

Synthesis of methyl 2-(2-bromo-4-(4-chlorophenoxy)phenyl)-2-hydroxypropanoate

After 1.0149 g of methyl 2-(2-bromo-4-(4-chlorophenoxy)phenyl)-2-oxoacetate and 14.3 mL of THF were added to a 50 mL three-necked flask and cooled to −78° C. in an acetone bath, the mixture was dropped with 3.64 mL of methyl magnesium bromide and continuously stirred. After two hours from the completion of the dropping, the mixture was added with 5 mL of 2N hydrochloric acid, the water layer was separated, and THF of the organic layer was distilled off. The water layer was extracted with toluene twice, combined with the organic layer distilled off THF, washed with water once, and washed with a saturated saline solution once. After the mixture was dried with anhydrous sodium sulfate, a solvent was distilled off to obtain 1.04 g of a yellow liquid crude product of hydroxy ester. By purification by column chromatography (35 g of silica gel, hexane:ethyl acetate=4:1), 718.7 mg of the title compound was obtained as a colorless liquid compound. A yield was 67.9%.

$^1$HNMR (400 MHz, CDCl$_3$) δ: 7.55 (d, J=8.7 Hz, 1H), 7.33 (d, J=9.0 Hz, 2H), 7.19 (d, J=2.6 Hz, 1H), 6.97 (d, J=9.0 Hz, 2H), 6.94 (dd, J=8.7, 2.6 Hz, 1H), 3.79 (s, 3H), 3.70 (s, 1H), 1.85 (s, 3H).

Synthesis of methyl 2-(2-bromo-4-(4-chlorophenoxy)phenyl)acrylate

After 701 mg of methyl 2-(2-bromo-4-(4-chlorophenoxy)phenyl)-2-hydroxypropanoate (8), 13.6 mL of toluene were added to and dissolved in a 50 mL eggplant flask, the mixture was added with 174 mg of tosylate monohydrate and connected to a Dean-Stark tube to be dehydrated and refluxed. A saturated sodium hydrogen carbonate aqueous solution was added after 1.5 hours and extracted with toluene three times. The extract was washed with water once and washed with a saturated saline solution once. After the extract was dried with anhydrous sodium sulfate, a solvent was distilled off to obtain 656 mg of black liquid crude product of unsaturated ester. By purification by column chromatography (20 g of silica gel, hexane:ethyl acetate=9:1), 634 mg of the title compound was obtained as a yellow liquid compound. A yield was 94.4%.

$^1$HNMR (400 MHz, CDCl$_3$) δ: 7.34 (d, J=9.0 Hz, 2H), 7.21 (d, J=8.4 Hz, 1H), 7.19 (d, J=2.5 Hz, 1H), 7.00 (d, J=9.0 Hz, 2H), 6.93 (dd, J=8.4, 2.5 Hz, 1H), 6.51 (d, J=1.3 Hz, 1H), 5.77 (d, J=1.3 Hz, 1H), 3.79 (s, 3H).

Synthesis of methyl 2-(2-bromo-4-(4-chlorophenoxy)phenyl)oxirane-2-carboxylate

After 596.0 mg of methyl 2-(2-bromo-4-(4-chlorophenoxy)phenyl)acrylate and 3.88 mL of acetonitrile were added to and dissolved in a 100 mL eggplant flask, the mixture was added with 666 mg of potassium carbonate, 441 mg of hydrogen peroxide urea, and 3.88 mL of methanol and stirred. After 2 hours, the mixture was added with a saturated sodium sulfite aqueous solution and 2 N hydrochloric acid, and extracted with toluene three times. The extract was washed with water once and washed a saturated saline solution once. After the extract was dried with anhydrous sodium sulfate, a solvent was distilled off to obtain 465 mg of colorless liquid crude product of oxirane. By purification by column chromatography (15 g of silica gel, hexane:ethyl acetate=9:1), 439 mg of the title compound was obtained as a colorless liquid compound. A yield was 70.6%.

$^1$HNMR (400 MHz, CDCl$_3$) δ: 7.38 (d, J=8.5 Hz, 1H), 7.34 (d, J=8.8 Hz, 2H), 7.18 (d, J=2.4 Hz, 1H), 6.99 (d, J=8.8 Hz, 2H), 6.94 (dd, J=8.5, 2.4 Hz, 1H), 3.78 (s, 3H), 3.62 (d, J=6.3 Hz, 1H), 3.01 (d, J=6.3 Hz, 1H).

Synthesis of methyl 2-(2-bromo-4-(4-chlorophenoxy)phenyl)-2-hydroxy-3-(1H-1,2,4-triazol-1-yl)propanoate (I-228)

After 455 mg of methyl 2-(2-bromo-4-(4-chlorophenoxy)phenyl)oxirane-2-carboxylate and 1.22 mL of DMF were added to and dissolved in a 100 mL eggplant flask, the mixture was added with 22.3 mg of triazole sodium and heated and stirred in an oil bath of 60° C. After 1.5 hours, the mixture was extracted with saturated ammonium chloride aqueous solution and toluene three times. The extract was washed with water three times and washed with a saturated saline solution once. After the extract was dried with anhydrous sodium sulfate, a solvent was distilled off to obtain 474 mg of colorless liquid crude product of azole. By purification by column chromatography (12 g of silica gel, chloroform:ethyl acetate=1:1), 292 mg of the title compound (I-228) was obtained as a white solid compound. A yield was 57.2%.

$^1$HNMR (400 MHz, CDCl$_3$) δ: 7.97 (s, 1H), 7.88 (s, 1H), 7.40 (d, J=8.8 Hz, 1H), 7.34 (d, J=8.9 Hz, 2H), 7.18 (d, J=2.5

Hz, 1H), 6.96 (d, J=8.9 Hz, 2H), 6.85 (dd, J=8.8, 2.5 Hz, 1H), 5.02 (s, 2H), 4.86 (s, 1H), 3.80 (s, 3H).

Synthesis Example 18. Synthesis of Compound I-334

Synthesis of 1-(4-chlorophenoxy)-3-fluorobenzene

After 674 mg of m-fluorophenol, 954.0 mg of p-chloroiodobenzene (3), and 6.0 mL of NMP were added to and dissolved in a 25 mL eggplant flask, the mixture was added with 76.5 mg of copper iodide, and 2.61 g of cesium carbonate and heated and stirred in an oil bath of 160° C. After 4.5 hours from the start of the reaction, the mixture was added with a saturated ammonium chloride aqueous solution to stop the reaction and was extracted with toluene three times. The extract was washed with water three times and washed with a saturated saline solution once. After the extract was dried with anhydrous sodium sulfate, a solvent was distilled off to obtain 1.39 g of black liquid crude product of diaryl ether. By purification by column chromatography (70 g of silica gel, hexane), 355 mg of the title compound was obtained as a colorless liquid compound. A yield was 39.8%.

$^1$HNMR (400 MHz, CDCl$_3$) δ: 7.32 (d, J=9.0 Hz, 2H), 7.28 (d, J=6.6 Hz, 1H), 6.97 (d, J=9.0 Hz, 2H), 6.81 (tdd, J=8.3, 2.4, 0.8 Hz, 1H), 6.76 (dd, J=8.3, 2.3 Hz, 1H), 6.69 (td, J=10.1, 2.4 Hz, 1H).

Synthesis of 1-(4-(4-chlorophenoxy)-2-fluorophenyl)ethan-1-on

After 111 mg of 1-(4-chlorophenoxy)-3-fluorobenzene and 0.5 mL of dichloromethane were added to and dissolved in 10 mL eggplant flask, the mixture was added with 42 μL of acetyl chloride and 80.6 mg of aluminum chloride and stirred. After 1.5 hours from the start of the reaction, the mixture was added with 2N hydrochloric acid to stop the reaction and extracted with dichloromethane three times. 129 mg of colorless liquid crude product of phenoxy ketone was obtained. By purification by column chromatography (6.5 g of silica gel, hexane:ethyl acetate=19:1), 97.7 mg of the title compound was obtained as a colorless liquid compound. A yield was 86.7%.

$^1$HNMR (400 MHz, CDCl$_3$) δ: 7.89 (t, J=8.7 Hz, 1H), 7.38 (d, J=9.0 Hz, 2H), 7.03 (d, J=9.0 Hz, 2H), 6.79 (dd, J=8.7, 2.3 Hz, 1H), 6.66 (dd, J=12.3, 2.3 Hz, 1H), 2.61 (d, J=5.1 Hz, 3H).

Synthesis of methyl 2-(4-(4-chlorophenoxy)-2-fluorophenyl)-2-oxoacetate 289 mg of 1-(4-(4-chlorophenoxy)-2-fluorophenyl)ethan-1-on and 4.4 mL of DMSO were added to and dissolved in a 50 mL eggplant flask, the mixture was added with 888 mg of iodine and heated and stirred in an oil bath of 100° C. After 0.5 hours from the start of the reaction, the reaction solution was cooled to a room temperature and then added with 1.0597 g of potassium carbonate, and heated and stirred in an oil bath of 100° C. again. After 0.5 hours, the reaction solution was cooled to a room temperature and then added with 218 μL of methyl iodide, and heated with a water bath of 35° C. and stirred. After 1 hour, the mixture was added with a saturated sodium sulfite aqueous solution to stop the reaction, filtered, added with water, and extracted with toluene three times. The extract was washed with water three times and washed with a saturated saline solution once. After the extract was dried with anhydrous sodium sulfate, a solvent was distilled off to obtain 266.7 mg of yellow liquid crude product of ketoester. By purification by column chromatography (13 g of silica gel, hexane:ethyl acetate=9:1), 176.3 mg of the title compound was obtained as a yellow liquid compound. A yield was 52.3%.

$^1$HNMR (400 MHz, CDCl$_3$) δ: 7.92 (d, J=8.7 Hz, 1H), 7.41 (d, J=9.0 Hz, 2H), 7.04 (d, J=9.0 Hz, 2H), 6.85 (ddd, J=8.7, 2.3, 0.6 Hz, 1H), 6.65 (dd, J=12.1, 2.3 Hz, 1H), 3.95 (s, 3H).

Synthesis of methyl 2-(4-(4-chlorophenoxy)-2-fluorophenyl)-2-hydroxypropanoate

After 176 mg of methyl 2-(4-(4-chlorophenoxy)-2-fluorophenyl)-2-oxoacetate and 3.0 mL of THF were added to a 25 mL three-necked flask and cooled to −78° C. in an acetone bath, the mixture was dropped with 0.76 mL of MeMgBr and continuously stirred. After 1.5 hours from the completion of the dropping, the mixture was dropped with 2N hydrochloric acid and extracted with ethyl acetate three times. The extract was washed with water once and washed a saturated saline solution once. After the extract was dried with anhydrous sodium sulfate, a solvent was distilled off to obtain 184 mg of a yellow liquid crude product of hydroxy ester. By purification by column chromatography (30 g of silica gel, hexane:ethyl acetate=4:1), 119.4 mg of the title compound was obtained as a colorless liquid compound. A yield was 64.4%.

$^1$HNMR (400 MHz, CDCl$_3$) δ: 7.47 (t, J=8.8 Hz, 1H), 7.33 (d, J=9.0 Hz, 2H), 6.98 (d, J=9.0 Hz, 2H), 6.76 (ddd, J=8.7, 2.5, 0.9 Hz, 1H), 6.66 (dd, J=12.4, 2.5 Hz, 1H), 3.79 (s, 3H), 3.70 (d, J=1.2 Hz, 1H), 2.04 (s, 3H).

Synthesis of methyl 2-(4-(4-chlorophenoxy)-2-fluorophenyl)acrylate

After 119 mg of methyl 2-(4-(4-chlorophenoxy)-2-fluorophenyl)-2-hydroxypropanoate and 2.8 mL of toluene were added to and dissolved in a 50 mL eggplant flask, the mixture was added with 35.4 mg of tosylate monohydrate and connected to a Dean-Stark tube to be dehydrated and refluxed. A saturated sodium hydrogencarbonate aqueous solution was added after 1.25 hours and extracted with toluene three times. The extract was washed with water once and washed a saturated saline solution once. After the extract was dried with anhydrous sodium sulfate, a solvent was distilled off to obtain 109.7 mg of the title compound as a brown liquid.

$^1$HNMR (400 MHz, CDCl$_3$) δ: 7.34 (d, J=8.9 Hz, 2H), 7.23 (t, J=8.4 Hz, 1H), 7.00 (d, J=8.9 Hz, 2H), 6.76 (ddd, J=8, 4, 2.4, 0.7 Hz, 1H), 6.69 (dd, J=11.1, 2.4 Hz, 1H), 6.49 (d, J=1.1 Hz, 1H), 5.87 (d, J=1.1 Hz, 1H), 3.81 (s, 3H).

Synthesis of methyl 2-(4-(4-chlorophenoxy)-2-(fluorophenyl)oxirane-2-carboxylate After 110 mg of methyl 2-(4-(4-chlorophenoxy)-2-(fluorophenyl)acrylate and 0.92 mL of acetonitrile were added to and dissolved in a 100 mL eggplant flask, the mixture was added with 158 mg of potassium carbonate, 104 mg of hydrogen peroxide urea, and 0.92 mL of methanol and stirred. After 2 hours, the mixture was added with a saturated sodium sulfite aqueous solution and extracted with toluene three times. The extract was washed with water once and washed a saturated saline solution once. After the extract was dried with anhydrous sodium sulfate, a solvent was distilled off to obtain 124 mg of yellow liquid crude product of oxirane. By purification by column chromatography (6 g of silica gel, hexane:ethyl acetate=9:1), 68.3 mg of the title compound was obtained as a colorless liquid compound. A yield was 54.4%.

$^1$HNMR (400 MHz, CDCl$_3$) δ: 7.34 (t, J=8.4 Hz, 1H), 7.34 (d, J=8.9 Hz, 2H), 6.99 (d, J=8.9 Hz, 2H), 6.76 (ddd, J=8.4, 2.4, 0.8 Hz, 1H), 6.70 (dd, J=10.9, 2.4 Hz, 1H), 3.78 (s, 3H), 3.51 (d, J=6.4 Hz, 1H), 3.05 (d, J=6.4 Hz, 1H).

Synthesis of methyl 2-(4-(4-chlorophenoxy)-2-fluorophenyl)-2-hydroxy-3-(1H-1,2,4-triazol-1-yl)propanoate (I-334)

After 68.3 mg of methyl 2-(4-(4-chlorophenoxy)-2-fluorophenyl)oxirane-2-carboxylate and 0.63 mL of DMF were added to and dissolved in a 50 mL eggplant flask, the mixture was added with 24.1 mg of triazole sodium, and heated and stirred in an oil bath of 50° C. After 1 hour, the mixture was added with saturated ammonium chloride aqueous solution and extracted with toluene three times. The extract was washed with water three times and washed with a saturated saline solution once. After the extract was dried with anhydrous sodium sulfate, a solvent was distilled off to obtain 46.9 mg of colorless liquid crude product of azole. By purification by column chromatography (2.5 g of silica gel, chloroform:ethyl acetate=1:1), 25.4 mg of the title compound (I-334) was obtained as a white solid compound. A yield was 30.6%.

$^1$HNMR (400 MHz, CDCl$_3$) δ: 8.13 (s, 1H), 7.89 (s, 1H), 7.47 (t, J=8.8 Hz, 1H), 7.35 (d, J=8.9 Hz, 2H), 6.98 (d, J=8.9 Hz, 2H), 6.74 (dd, J=8.8, 2.5 Hz, 1H), 6.68 (dd, J=12.7, 2.5 Hz, 1H), 5.11 (d, J=14.1 Hz, 1H), 4.74 (d, J=14.1 Hz, 1H), 4.61 (s, 1H), 3.82 (s, 3H).

Synthesis Example 19. Synthesis of Compound I-2

Synthesis of 1-(4-chlorophenoxy)-3-methylbenzene

After 541 mg of m-cresol and 7.5 mL of DMF were added to and dissolved in a 25 mL eggplant flask, the mixture was added with 1.79 g of p-chloroiodobenzene, 3.26 g of cesium carbonate, and 95.6 mg of copper iodide (I), and heated and stirred in an oil bath of 90° C. After 6 hours from the start of the reaction, the mixture was added with a saturated aqueous ammonium chloride solution to stop the reaction and extracted with hexane three times. The extract was washed with water twice and was washed with a saturated saline solution once. After the extract was dried with anhydrous sodium sulfate, a solvent was distilled off to obtain 1.61 g of brown liquid crude product of diaryl ether. By purification by column chromatography (50 g of silica gel, hexane), 314.4 mg of the title compound was obtained as a colorless liquid compound. A yield was 28.7%.

$^1$HNMR (400 MHz, CDCl$_3$) δ: 7.28 (d, J=8.8 Hz, 2H), 7.22 (t, J=7.8 Hz, 1H), 6.94-6.90 (m, 3H), 6.82-6.78 (m, 2H), 2.33 (s, 3H).

Synthesis of methyl 2-(4-(4-chlorophenoxy)-2-methylphenyl)-2-oxoacetate

After 314 mg of 1-(4-chlorophenoxy)-3-methylbenzene and 1.44 mL of dichloromethane were added to and dissolved in 50 mL eggplant flask, the mixture was added with 158 μL of methyl chloroglyoxylate and 231 mg of aluminum chloride and stirred. After 1 hour from the start of the reaction, the mixture was added with water to stop the reaction and extracted with chloroform three times. 436 mg of colorless liquid crude product of ketoester was obtained. By purification by column chromatography (6.5 g of silica gel, hexane:ethyl acetate=9:1), 323 mg of the title compound was obtained as a colorless liquid. A yield was 73.7%.

$^1$HNMR (400 MHz, CDCl$_3$) δ: 7.88 (d, J=8.0 Hz, 1H), 7.35 (d, J=8.9 Hz, 2H), 7.00 (d, J=8.9 Hz, 2H), 6.85-6.81 (m, 1H), 6.64 (s, 1H), 3.70 (s, 3H), 2.34 (s, 3H).

Synthesis of methyl-2-(4-(4-chlorophenoxy)-2-methylphenyl)acrylate

After 53.7 mg of 55% sodium hydride and 1.8 mL of DMSO were added to a 25 mL eggplant flask and cooled in an ice bath, the mixture was added with 492 mg of methyltriphenylphosphonium bromide (MTPB), heated to a room temperature, and stirred. After 30 minutes, the mixture was dropped with a DMSO solution (0.5 mL) of 323 mg of methyl 2-(4-(4-chlorophenoxy)-2-methylphenyl)-2-oxoacetate and continuously stirred. After 1 hour, the mixture was added with saturated aqueous ammonium chloride solution and extracted with toluene three times. The extract was washed with water three times and washed with a saturated saline solution once. After the extract was dried with anhydrous sodium sulfate, a solvent was distilled off to obtain 636 mg of orange solid crude product of unsaturated ester. By purification by column chromatography (30 g of silica gel, hexane:ethyl acetate=9:1), 240 mg of the title compound was obtained as a colorless liquid compound. A yield was 74.7%.

$^1$HNMR (400 MHz, CDCl$_3$) δ: 7.31-7.20 (m, 2H), 6.89-6.93 (m, 2H), 6.90 (d, J=9.0 Hz, 2H), 6.68 (s, 1H), 6.30 (d, J=1.4 Hz, 1H), 5.77 (d, J=1.4 Hz, 1H), 3.62 (s, 3H), 2.30 (s, 3H).

Synthesis of methyl 2-(4-(4-chlorophenoxy)-2-methylphenyl)oxirane-2-carboxylate

After 239.7 mg of methyl-2-(4-(4-chlorophenoxy)-2-methylphenyl)acrylate, 1.98 mL of acetonitrile and 1.98 mL of methanol were added to a 100 mL eggplant flask and cooled in an ice bath, the mixture was added with 110 mg of potassium carbonate and 232 mg of hydrogen peroxide urea, heated to a room temperature, and stirred. After 22 hours, the mixture was added with a saturated sodium sulfite aqueous solution and extracted with toluene three times. The extract was washed with water once and was washed with a saturated saline solution once. After the extract was dried with anhydrous sodium sulfate, a solvent was distilled off to obtain 179 mg of the title compound as a yellow liquid.

Synthesis of methyl 2-(4-(4-chlorophenoxy)-2-methylphenyl)-2-hydroxy-3-(1H-1,2,4-triazol-1-yl) propanoate (I-2)

After 179 mg of crude methyl 2-(4-(4-chlorophenoxy)-2-methylphenyl)oxirane-2-carboxylate and 2.25 mL of DMF were added to and dissolved in a 100 mL eggplant flask, the mixture was added with 38.8 mg of triazole and 51.5 mg of triazole sodium and heated and stirred in an oil bath of 50° C. After 2.5 hours, the mixture was added with saturated aqueous ammonium chloride solution and extracted with toluene three times. The extract was washed with water three times and washed with a saturated saline solution once. After the extract was dried with anhydrous sodium sulfate, a solvent was distilled off to obtain 212 mg of colorless liquid crude product of azole. By purification by column chromatography (10 g of silica gel, chloroform:ethyl acetate=1:1), 25.4 mg of the title compound (I-2) was obtained as a white solid compound. 2 process yield was 23.8%.

$^1$HNMR (400 MHz, CDCl$_3$) δ: 8.06 (s, 1H), 7.87 (s, 1H), 7.33-7.27 (m, 3H), 6.94-6.88 (m, 3H), 6.66 (s, 1H), 5.01 (d, J=14.1 Hz, 1H), 4.85 (d, J=14.1 Hz, 1H), 4.42 (s, 1H), 3.55 (s, 3H), 2.27 (s, 3H).

Synthesis Example 20. Synthesis of Compound I-3

Synthesis of
1-(4-chlorophenoxy)-3-methoxybenzene

After 621 mg of m-methoxyphenol and 7.5 mL of DMF were added to and dissolved in a 25 mL eggplant flask, the mixture was added with 1.7888 g of p-chloroiodobenzene, 3.27 g of cesium carbonate, 95.6 mg of copper iodide (I) and heated and stirred in an oil bath of 90° C. After 6 hours from the start of the reaction, the mixture was added with a saturated aqueous ammonium chloride solution to stop the reaction and extracted with hexane three times. The extract was washed with water twice and was washed with a saturated saline solution once. After the extract was dried with anhydrous sodium sulfate, a solvent was distilled off to obtain 1.58 g of brown liquid crude product of diaryl ether. By purification by column chromatography (50 g of silica gel, hexane), 303 mg of the title compound was obtained as a colorless liquid compound. A yield was 25.8%.

$^1$HNMR (400 MHz, CDCl$_3$) δ: 7.29 (d, J=9.0 Hz, 2H), 7.23 (t, J=8.3 Hz, 1H), 6.95 (d, J=9.0 Hz, 2H), 6.67 (ddd, J=8.3, 2.4, 0.8 Hz, 1H), 6.59-6.54 (m, 2H), 3.78 (s, 3H).

Synthesis of methyl 2-(4-(4-chlorophenoxy)-2-methylphenyl)-2-oxoacetate

After 303 mg of 1-(4-chlorophenoxy)-3-methoxybenzene and 1.29 mL of dichloromethane were added to and dissolved in 50 mL eggplant flask, the mixture was added with 142 µL of methyl chloroglyoxylate and 231 mg of aluminum chloride and stirred. After 1 hour from the start of the reaction, the mixture was added with water to stop the reaction and extracted with chloroform three times. 424 mg of colorless liquid crude product of ketoester was obtained. By purification by column chromatography (21 g of silica gel, hexane:ethyl acetate=7:1), 206 mg of the title compound was obtained as a colorless liquid compound. A yield was 49.8%.

$^1$HNMR (400 MHz, CDCl$_3$) δ: 7.98 (d, J=8.9 Hz, 1H), 7.35 (d, J=9.0 Hz, 2H), 7.02 (d, J=9.0 Hz, 2H), 6.76 (dd, J=8.9, 2.3 Hz, 1H), 6.27 (d, J=2.3 Hz, 1H), 3.78 (s, 3H), 3.70 (s, 3H).

Synthesis of methyl
2-(4-(4-chlorophenoxy)-2-methoxyphenyl)acrylate

After 32.8 mg of 55% sodium hydride and 1.1 mL of DMSO were added to a 10 mL eggplant flask and cooled in an ice bath, the mixture was added with 299 mg of MTPB, heated to a room temperature, and stirred. After 30 minutes, the mixture was dropped with a DMSO (0.3 mL) solution of 206 mg of methyl 2-(4-(4-chlorophenoxy)-2-methoxyphenyl)-2-oxoacetate and continuously stirred. After 1 hour, the mixture was added with saturated aqueous ammonium chloride solution and extracted with toluene three times. The extract was washed with water three times and washed with a saturated saline solution once. After the extract was dried with anhydrous sodium sulfate, a solvent was distilled off to obtain 411 mg of brown solid crude product of unsaturated ester. By purification by column chromatography (20 g of silica gel, hexane:ethyl acetate=7:1), 139 mg of the title compound was obtained as a colorless liquid compound. A yield was 68.1%.

$^1$HNMR (400 MHz, CDCl$_3$) δ: 7.30-7.24 (m, 3H), 6.92 (d, J=9.0 Hz, 2H), 6.69 (dd, J=8, 5, 2.5 Hz, 1H), 6.40 (d, J=2.5 Hz, 1H), 6.28 (d, J=1.4 Hz, 1H), 5.87 (d, J=1.4 Hz, 1H), 3.75 (s, 3H), 3.62 (s, 3H).

Synthesis of methyl 2-(4-(4-chlorophenoxy)-2-methoxyphenyl)oxirane-2-carboxylate After 139.4 mg of 2-(4-(4-chlorophenoxy)-2-methoxyphenyl)acrylate, 1.09 mL of acetonitrile and 1.09 mL of methanol were added to a 50 mL eggplant flask and cooled in an ice bath, the mixture was added with 60.9 mg of potassium carbonate and 128 mg of hydrogen peroxide urea, heated to a room temperature, and stirred. After 22 hours, the mixture was added with a saturated sodium sulfite aqueous solution and extracted with toluene three times. The extract was washed with water once and washed with a saturated saline solution once. After the extract was dried with anhydrous sodium sulfate, a solvent was distilled off to obtain 104 mg of the title compound as a yellow liquid.

Synthesis of methyl 2-(4-(4-chlorophenoxy)-2-methoxyphenyl)-2-hydroxy-3-(1H-1,2,4-triazol-1-yl) propanoate (I-3)

After 104 mg of methyl 2-(4-(4-chlorophenoxy)-2-methylphenyl)oxirane-2-carboxylate and 1.24 mL of DMF were added to and dissolved in a 100 mL eggplant flask, the mixture was added with 21.5 mg of triazole and 28.3 mg of triazole sodium and heated and stirred in an oil bath of 50° C. After 2.5 hours, the mixture was added with a saturated ammonium chloride aqueous solution and extracted with toluene three times. The extract was washed with water three times and washed with a saturated saline solution once. After the extract was dried with anhydrous sodium sulfate, a solvent was distilled off to obtain 119 mg of colorless liquid crude product of azole. By purification by column chromatography (10 g of silica gel, chloroform:ethyl acetate=1:1), 101 mg of the title compound (I-3) was obtained as a colorless viscous liquid compound. 2 process yield was 59.8%.

$^1$HNMR (400 MHz, CDCl$_3$) δ: 8.07 (s, 1H), 7.87 (s, 1H), 7.35 (d, J=8.8 Hz, 1H), 7.31 (d, J=9.0 Hz, 2H), 6.92 (d, J=9.0 Hz, 2H), 6.64 (dd, J=8.8, 2.5 Hz, 1H), 6.37 (d, J=2.5 Hz, 1H), 5.00 (d, J=14.1 Hz, 1H), 4.84 (d, J=14.1 Hz, 1H), 4.40 (s, 1H), 3.71 (s, 3H), 3.56 (s, 3H).

Synthesis Example 21. Synthesis of Compound I-19

Synthesis of 1-(2-chloro-4-(2-chlorophenoxy)phenyl)ethan-1-on

After 692 mg of 2-chloro-4-fluoroacetophenone and 7.2 mL of DMF were added to and dissolved in a 25 mL eggplant flask, the mixture was added with 568 mg of 2-chlorophenol and 664 mg of potassium carbonate and heated and stirred in an oil bath of 120° C. After 1.5 hours from the start of the reaction, the mixture was added with water to stop the reaction and extracted with toluene three times. The extract was washed with water three times and washed with a saturated saline solution once. After the extract was dried with anhydrous sodium sulfate, a solvent was distilled off to obtain 1.1159 g of the title compound as a brown liquid.

$^1$HNMR (400 MHz, CDCl$_3$) δ: 7.65 (d, J=8.7 Hz, 1H), 7.51 (dd, J=8.0, 1.6 Hz, 1H), 7.32 (td, J=7.5, 1.6 Hz, 1H), 7.22 (td, J=7.5, 1.6 Hz, 1H), 7.12 (dd, J=8.0, 1.6 Hz, 1H), 6.93 (d, J=2.4 Hz, 1H), 6.83 (dd, J=8.7, 2.4 Hz, 1H), 2.65 (s, 3H).

Synthesis of methyl 2-(2-chloro-4-(2-chlorophenoxy)phenyl)-2-oxoacetate

After 1.12 g of 1-(2-chloro-4-(2-chlorophenoxy)phenyl)ethan-1-on and 16 mL of DMSO were added to and dissolved in a 100 mL eggplant flask, the mixture was added with 3.25 g of iodine and heated and stirred in an oil bath of 100° C. After 0.5 hours from the start of the reaction, the reaction solution was cooled to a room temperature and then added with 3.87 g of potassium carbonate, and heated and stirred in an oil bath of 100° C. again. After 0.5 hours, the reaction solution was cooled to a room temperature and then added with 0.80 mL of methyl iodide, heated with a water bath of 35° C., and stirred. After 1 hour, the mixture was added with a saturated sodium sulfite aqueous solution to stop the reaction, filtered, added with water, and extracted with toluene three times. The extract was washed with water three times and washed with a saturated saline solution once. After the extract was dried with anhydrous sodium sulfate, a solvent was distilled off to obtain 946 mg of brown liquid crude product of ketoester. By purification by column chromatography (45 g of silica gel, hexane:ethyl acetate=9:1), 474.9 mg of the title compound was obtained as orange liquid. 2 process yield was 36.5%.

$^1$HNMR (400 MHz, CDCl$_3$) δ: 7.82 (d, J=8.7 Hz, 1H), 7.52 (dd, J=8.0, 1.6 Hz, 1H), 7.35 (td, J=7.9, 1.6 Hz, 1H), 7.25 (td, J=7.9, 1.6 Hz, 1H), 7.16 (dd, J=8.0, 1.6 Hz, 1H), 6.92 (d, J=2.4 Hz, 1H), 6.89 (dd, J=8.7, 2.4 Hz, 1H), 3.95 (s, 3H).

Synthesis of methyl 2-(2-chloro-4-(2-chlorophenoxy)phenyl)oxirane-2-carboxylate

After 26.9 mg of 55% sodium hydride, 1.0 mL of DMSO, and 133 mg of trimethylsulfoxonium iodide were added to a 25 mL eggplant flask and stirred in an ice bath, the mixture was added with 1.5 mL of DMSO solution of methyl 2-(2-chloro-4-(2-chlorophenoxy)phenyl)-2-oxoacetate and continuously stirred at a room temperature. After 1.5 hours, the mixture was added with a saturated aqueous ammonium chloride solution to stop the reaction and extracted with toluene three times. The extract was washed with water three times and washed with a saturated saline solution once. After the extract was dried with anhydrous sodium sulfate, a solvent was distilled off to obtain 208 mg of brown liquid crude product of oxirane. By purification by column chromatography (10 g of silica gel, hexane:ethyl acetate=9:1), 59.2 mg of the title compound was obtained as a colorless liquid compound. A yield was 34.5%.

$^1$HNMR (400 MHz, CDCl$_3$) δ: 7.49 (dd, J=8.0, 1.6 Hz, 1H), 7.38 (d, J=8.5 Hz, 1H), 7.29 (td, J=7.6, 1.5 Hz, 1H), 7.18 (td, J=7.6, 1.6 Hz, 1H), 7.09 (dd, J=8.0, 1.5 Hz, 1H), 6.96 (d, J=2.5 Hz, 1H), 6.84 (dd, J=8.5, 2.5 Hz, 1H), 3.77 (s, 3H), 3.51 (d, J=6.4 Hz, 1H), 3.05 (d, J=6.4 Hz, 1H).

Synthesis of methyl 2-(2-chloro-4-(2-chlorophenoxy)phenyl)-2-hydroxy-3-(1H-1,2,4-triazol-1-yl)propanoate (I-19)

After 59.2 mg of methyl 2-(2-chloro-4-(2-chlorophenoxy)phenyl)oxirane-2-carboxylate and 0.70 mL of DMF were added to and dissolved in a 100 mL eggplant flask, the mixture was added with 12.8 mg of triazole and 16.0 mg of triazole sodium and heated and stirred in an oil bath of 50° C. After 2 hours, the oil bath was heated to 60° C. and continuously stirred. After 1 hour, the mixture was added with saturated aqueous ammonium chloride solution and extracted with toluene three times. The extract was washed with water once and washed with a saturated saline solution once. After the extract was dried with anhydrous sodium sulfate, a solvent was distilled off to obtain 64.3 mg of colorless liquid crude product of azole. By purification by column chromatography (3 g of silica gel, chloroform:ethyl acetate=1:1), 59.0 mg of the title compound (I-19) was obtained as a white solid compound. A yield was 82.8%.

$^1$HNMR (400 MHz, CDCl$_3$) δ: 8.00 (s, 1H), 7.88 (s, 1H), 7.48 (dd, J=8.0, 1.6 Hz, 1H), 7.40 (d, J=8.8 Hz, 1H), 7.29 (td, J=8.1, 1.7 Hz, 1H), 7.18 (td, J=8.0, 1.5 Hz, 1H), 7.07 (dd, J=8.1, 1.5 Hz, 1H), 6.94 (d, J=2.6 Hz, 1H), 6.77 (dd, J=8.8, 2.6 Hz, 1H), 5.03 (d, J=14.3 Hz, 1H), 4.92 (d, J=14.3 Hz, 1H), 4.83 (s, 1H), 3.79 (s, 3H).

Synthesis Example 22. Synthesis of Compound I-20

Synthesis of 1-(2-chloro-4-(3-chlorophenoxy)phenyl)ethan-1-on

After 691 mg of 2-chloro-4-fluoroacetophenone and 7.2 mL of DMF were added to and dissolved in a 25 mL eggplant flask, the mixture was added with 568 mg of 3-chlorophenol and 665 mg of potassium carbonate and heated and stirred in an oil bath of 120° C. After 1.5 hours from the start of the reaction, the mixture was added with water to stop the reaction and extracted with toluene three times. The extract was washed with water three times and washed with a saturated saline solution once. After the extract was dried with anhydrous sodium sulfate, a solvent was distilled off to obtain 1.18 g of the title compound as a brown liquid.

$^1$HNMR (400 MHz, CDCl$_3$) δ: 7.65 (d, J=8.6 Hz, 1H), 7.33 (t, J=8.1 Hz, 1H), 7.20 (ddd, J=8.1, 2.2, 1.0 Hz, 1H), 7.06 (t, J=2.2 Hz, 1H), 7.02 (d, J=2.4 Hz, 1H), 6.95 (ddd, J=8.1, 2.2, 1.0 Hz, 1H), 6.92 (dd, J=8.7, 2.4 Hz, 1H), 2.66 (s, 3H).

Synthesis of methyl 2-(2-chloro-4-(3-chlorophenoxy)phenyl)-2-oxoacetate

After 1.18 g of 1-(2-chloro-4-(3-chlorophenoxy)phenyl)ethan-1-on and 16 mL of DMSO were added to and dissolved in a 100 mL eggplant flask, the mixture was added with 3.25 g of iodine and heated and stirred in an oil bath of 100° C. After 0.5 hours from the start of the reaction, the reaction solution was cooled to a room temperature and then added with 3.87 g of potassium carbonate, and heated and stirred in an oil bath of 100° C. again. After 0.5 hours, the reaction solution was cooled to a room temperature and then added with 0.80 mL of methyl iodide, heated with a water bath of 35° C., and stirred. After 1 hour, the mixture was added with a saturated sodium sulfite aqueous solution to stop the reaction, filtered, added with water, and extracted with toluene three times. The extract was washed with water three times and washed with a saturated saline solution once. After the extract was dried with anhydrous sodium sulfate, a solvent was distilled off to obtain 1.13 g of brown liquid crude product of ketoester. By purification by column chromatography (45 g of silica gel, hexane:ethyl acetate=9:1), 427.6 mg of the title compound was obtained as an orange liquid compound. A yield was 32.8%.

¹HNMR (400 MHz, CDCl₃) δ: 7.83 (d, J=8.6 Hz, 1H), 7.36 (t, J=8.1 Hz, 1H), 7.24 (ddd, J=8.1, 2.0, 0.9 Hz, 1H), 7.11 (t, J=2.0 Hz, 1H), 7.01-6.95 (m, 3H), 3.96 (s, 3H).

Synthesis of methyl 2-(2-chloro-4-(3-chlorophenoxy)phenyl)-2-hydroxy-3-(1H-1,2,4-triazol-1-yl)propanoate (I-20)

After 261 mg of methyl 2-(2-chloro-4-(3-chlorophenoxy)phenyl)-2-oxoacetate and 1.20 mL of DMAc were added to and dissolved in a 50 mL eggplant flask, the mixture was added with 95.5 mg of triazole sodium and 212.5 mg of trimethylsulfoxonium iodide and heated and stirred in an oil bath of 50° C. After 2.5 hours, the mixture was added with a saturated aqueous ammonium chloride solution to stop the reaction and extracted with toluene three times. The extract substance was washed with water once and washed with a saturated saline solution once. After the extract was dried with anhydrous sodium sulfate, a solvent was distilled off to obtain 331 mg of orange liquid crude product of azole. By purification by column chromatography (14 g of silica gel, chloroform:ethyl acetate=1:1), 146.9 mg of the title compound (I-20) was obtained as a colorless viscous liquid compound. A yield was 44.9%.

¹HNMR (400 MHz, CDCl₃) δ: 8.01 (s, 1H), 7.89 (s, 1H), 7.43 (d, J=8.8 Hz, 1H), 7.30 (t, J=8.2 Hz, 1H), 7.16 (ddd, J=8.2, 2.3, 0.9 Hz, 1H), 7.03 (t, J=2.3 Hz, 1H), 7.01 (d, J=2.5 Hz, 1H), 6.91 (ddd, J=8.2, 2.3, 0.9 Hz, 1H), 6.85 (dd, J=8.8, 2.5 Hz, 1H), 5.03 (d, J=14.3 Hz, 1H), 4.93 (d, J=14.3 Hz, 1H), 4.85 (s, 1H), 3.80 (s, 3H).

Synthesis Example 23. Synthesis of Compound I-6

Synthesis of 1-chloro-2-(4-chlorophenoxy)benzene

After 1.20 g of p-iodochlorobenzene, 965 mL of o-chlorophenol, and 10.0 mL of DMF were added to and dissolved in a 25 mL eggplant flask, the mixture was added with 3.26 g of cesium carbonate, 95.7 mg of copper iodide (I), and 210 mg of N,N-dimethylglycine hydrochloride and heated and stirred in an oil bath of 90° C. After 1 hour from the start of the reaction, the oil bath was heated to 135° C. After 5 hours, the oil bath returned to a room temperature and was washed with water through a short column twice. After the mixture was dried with anhydrous sodium sulfate, a solvent was distilled off to obtain 674 mg of brown liquid crude product of diaryl ether. By purification by column chromatography (20 g of silica gel, hexane), 392.4 mg of the title compound was obtained as a colorless liquid compound. A yield was 32.7%.

¹HNMR (400 MHz, CDCl₃) δ: 7.47 (dd, J=8.0, 1.6 Hz, 1H), 7.28 (d, J=9.0 Hz, 2H), 7.24 (td, J=8.0, 1.6 Hz, 1H), 7.12 (td, J=7.7, 1.5 Hz, 1H), 7.00 (dd, J=8.1, 1.5 Hz, 1H), 6.89 (d, J=9.0 Hz, 2H).

Synthesis of methyl 2-(3-chloro-4-(4-chlorophenoxy)phenyl)-2-oxoacetate

After 392 mg of 1-chloro-2-(4-chlorophenoxy)benzene and 1.64 mL of dichloromethane were added to and dissolved in 100 mL eggplant flask, the mixture was added with 181 μL of methyl chlorogloyoxylate and 266 mg of aluminum chloride and stirred. After 1.5 hours from the start of the reaction, the mixture was added with 2N hydrochloric acid to stop the reaction and extracted with methylene chloride three times. After the mixture was dried with anhydrous sodium sulfate, a solvent was distilled off to obtain 534 mg of colorless liquid crude product of ketoester. By purification by column chromatography (21 g of silica gel, hexane:ethyl acetate=9:1), 460.8 mg of the title compound was obtained as a colorless liquid compound. A yield was 86.4%.

¹HNMR (400 MHz, CDCl₃) δ: 8.19 (d, J=2.1 Hz, 1H), 7.89 (dd, J=8.7, 2.1 Hz, 1H), 7.39 (d, J=9.0 Hz, 2H), 7.02 (d, J=9.0 Hz, 2H), 6.90 (d, J=8.7 Hz, 1H), 3.98 (s, 3H).

Synthesis of methyl 2-(3-chloro-4-(4-chlorophenoxy)phenyl)oxirane-2-carboxylate

After 461 mg of methyl 2-(3-chloro-4-(4-chlorophenoxy)phenyl)-2-oxoacetate and 2.1 mL of DMAC were added to and dissolved in a 100 mL eggplant flask, the mixture was added with 558 mg of cesium carbonate and 295 mg of trimethylsulfoxonium bromide and stirred. After 2 hours, the mixture was heated in an oil bath of 50° C. After 1 hour, the mixture was added with a saturated aqueous ammonium chloride solution to stop the reaction and extracted with toluene three times. The extract was washed with water three times and washed with a saturated saline solution once. After the extract was dried with anhydrous sodium sulfate, a solvent was distilled off to obtain 474.7 mg of yellow liquid crude product of oxirane. By purification by column chromatography (silica gel, hexane:ethyl acetate=9:1®7:3), 75.2 mg of the title compound was obtained as a colorless liquid compound. A yield was 15.6%.

¹HNMR (400 MHz, CDCl₃) δ: 7.64 (d, J=2.2 Hz, 1H), 7.39 (dd, J=8.5, 2.2 Hz, 1H), 7.30 (d, J=9.0 Hz, 2H), 6.95 (d, J=8.5 Hz, 1H), 6.91 (d, J=9.0 Hz, 2H), 3.81 (s, 3H), 3.45 (d, J=6.3 Hz, 1H), 2.96 (d, J=6.3 Hz, 1H).

Synthesis of methyl 2-(3-chloro-4-(4-chlorophenoxy)phenyl)-2-hydroxy-3-(1H-1,2,4-triazol-1-yl)propanoate (I-6)

After 75.2 mg of methyl 2-(3-chloro-4-(4-chlorophenoxy)phenyl)oxirane-2-carboxylate and 0.70 mL of DMF were added to and dissolved in a 50 mL eggplant flask, the mixture was added with 15.7 mg of triazole and 20.6 mg of triazole sodium and heated and stirred in an oil bath of 60° C. After 1 hour, the mixture was added with saturated aqueous ammonium chloride solution and extracted with toluene three times. The extract was washed with water once and washed with a saturated saline solution once. After the extract was dried with anhydrous sodium sulfate, a solvent was distilled off to obtain 65.8 mg of colorless liquid crude product of azole. By purification by column chromatography (3 g of silica gel, chloroform:ethyl acetate=1:1), 55.2 mg of the title compound (I-6) was obtained as a colorless viscous liquid compound. A yield was 61.0%.

¹HNMR (400 MHz, CDCl₃) δ: 8.17 (s, 1H), 7.92 (s, 1H), 7.80 (d, J=2.3 Hz, 1H), 7.52 (dd, J=8.7, 2.3 Hz, 1H), 7.31 (d, J=9.0 Hz, 2H), 6.97 (d, J=8.7 Hz, 1H), 6.91 (d, J=9.0 Hz, 2H), 5.01 (d, J=14.0 Hz, 1H), 4.42 (d, J=14.0 Hz, 1H), 4.40 (s, 1H), 3.85 (s, 3H).

Synthesis Example 24. Synthesis of Compound IIa-1

Synthesis of 2-bromo-1-chloro-4-(4-chlorophenoxy)benzene

After 1.05 g of 2-bromo-1-fluorobenzene and 9.0 mL of NMP were added to and dissolved in a 25 mL eggplant flask, the mixture was added with 706 mg of 4-chlorophenol and 829 mg of potassium carbonate, and heated and stirred in an oil bath of 160° C. After 6.5 hours from the start of the reaction, the mixture was added with water to stop the reaction and extracted with toluene three times. The extract was washed with water three times and washed with a saturated saline solution once. After the extract was dried with anhydrous sodium sulfate, 1.93 g of brown liquid crude product of aryl bromide was obtained. By purification by column chromatography (55 g of silica gel, hexane), 903 mg of the title compound was obtained as a colorless liquid compound. A yield was 56.8%.

$^1$HNMR (400 MHz, CDCl$_3$) δ: 7.39 (d, J=8.8 Hz, 1H), 7.33 (d, J=9.0 Hz, 2H), 7.23 (d, J=2.8 Hz, 1H), 6.95 (d, J=9.0 Hz, 2H), 6.89 (dd, J=8.8, 2.8 Hz, 1H).

Synthesis of methyl 2-(2-chloro-5-(4-chlorophenoxy)phenyl)-2-oxoacetate

After 897 mg of 2-bromo-1-chloro-4-(4-chlorophenoxy) benzene, 402 mg of dimethyl oxalate and 14.1 mL of tetrahydrofuran were added to and dissolved in a 25 mL eggplant flask, the mixture was cooled to −78° C. in a dry ice acetone bath, added with 1.16 mL of n-butyllithium, and stirred. After 1 hour from the start of the reaction, the mixture was added with 2N hydrochloric acid to stop the reaction and extracted with chloroform three times. After the extract was dried with anhydrous sodium sulfate, a solvent was distilled off to obtain 1.11 g of colorless liquid crude product of ketoester. By purification by column chromatography (silica gel, hexane:ethyl acetate=92:8-71:29), 625 mg of the title compound was obtained as a colorless liquid compound. A yield was 68.1%.

$^1$HNMR (400 MHz, CDCl$_3$) δ: 7.40 (d, J=8.8 Hz, 1H), 7.35 (d, J=8.9 Hz, 2H), 7.33 (d, J=3.0 Hz, 1H), 7.15 (dd, J=8.8, 3.0 Hz, 1H), 6.98 (d, J=8.9 Hz, 2H), 3.96 (s, 3H).

Synthesis of methyl 2-(2-chloro-5-(4-chlorophenoxy)phenyl)oxirane-2-carboxylate After 621 mg of methyl 2-(2-chloro-5-(4-chlorophenoxy) phenyl)-2-oxoacetate and 2.86 mL of dichloromethane were added to and dissolved in a 25 mL eggplant flask, the mixture was added with 398 mg of trimethylsulfoxonium bromide and 100 mg of sodium hydride and stirred. After 1 hour, the mixture was added with a saturated ammonium chloride aqueous solution to stop the reaction and extracted with dichloromethane three times. After the extract was dried with anhydrous sodium sulfate, a solvent was distilled off to obtain 716 mg of yellow liquid crude product of oxirane. By purification by column chromatography (silica gel, hexane:ethyl acetate=97:3→76:24), 243 mg of the title compound was obtained as a colorless liquid compound. A yield was 37.5%.

$^1$HNMR (400 MHz, CDCl$_3$) δ: 7.33 (d, J=8.8 Hz, 1H), 7.32 (d, J=8.9 Hz, 2H), 7.09 (d, J=2.9 Hz, 1H), 6.97-6.92 (m, 3H), 3.78 (s, 3H), 3.61 (d, J=6.3 Hz, 1H), 2.99 (d, J=6.3 Hz, 1H).

Synthesis of methyl 2-(2-chloro-5-(4-chlorophenoxy)phenyl)-2-hydroxy-3-(1H-1,2,4-triazol-1-yl)propanoate After 223 mg of methyl 2-(2-chloro-5-(4-chlorophenoxy) phenyl)oxirane-2-carboxylate and 2.63 mL of DMF were added to and dissolved in a 100 mL eggplant flask, the mixture was added with 45.7 mg of triazole and 60.3 mg of triazole sodium and heated and stirred in an oil bath of 60° C. After 2 hours, the mixture was added with saturated ammonium chloride aqueous solution and extracted with toluene three times. The extract was washed with water three times and washed with a saturated saline solution once. After the extract was dried with anhydrous sodium sulfate, a solvent was distilled off to obtain 267 mg of colorless liquid crude product of azole. By purification by column chromatography (8 g of silica gel, chloroform:ethyl acetate=1:1), 205 mg of the title compound (II-1) was obtained as a white solid compound. A yield was 76.3%.

$^1$HNMR (400 MHz, CDCl$_3$) δ: 7.92 (s, 1H), 7.86 (s, 1H), 7.32 (d, J=8.6 Hz, 1H), 7.30 (d, J=8.9 Hz, 2H), 7.07 (d, J=2.9 Hz, 1H), 6.88 (dd, J=8.6, 2.9 Hz, 1H), 6.80 (d, J=8.9 Hz, 2H), 4.99 (s, 1H), 4.98 (s, 1H), 4.94 (s, 1H), 3.80 (s, 3H).

Synthesis Example 25. Synthesis of Compound I-26

Synthesis of methyl 2-(2-chloro-4-(4-fluorophenoxy)phenyl)-2-oxoacetate

After 0.54 mL of 2-chloro-4-fluoroacetophenone and 7.2 mL of dehydrated DMF were added to and dissolved in a 25 mL eggplant flask, the mixture was added with 0.448 g of p-fluorophenol (1) and 0.663 g of potassium carbonate, and heated and stirred in an oil bath of 120° C. After 1.5 hours from the start of the reaction, the mixture was added with water to stop the reaction and extracted with toluene three times. The extract was washed with water twice and washed with a saturated saline solution once. After the extract was dried with anhydrous sodium sulfate, a solvent was distilled off to obtain a crude product of diaryl ether body. After the crude diaryl ether body and 16 mL of dehydrated DMSO were added to and dissolved in a 100 mL eggplant flask, the mixture was added with 3.25 g of iodine and heated and stirred in an oil bath of 100° C. After 0.5 hours from the start of the reaction, the reaction solution was cooled to a room temperature and then added with 3.87 g of potassium carbonate and heated and stirred in an oil bath at 100° C. again. After 0.5 hours, the reaction solution was cooled to a room temperature, and then added with 0.80 mL of methyl iodide, heated with a water bath of 35° C., and stirred. After 0.5 hours, the mixture was added with a saturated sodium sulfite aqueous solution to stop the reaction, filtered, added with water, and extracted with toluene three times. The extract was washed with water three times and washed with a saturated saline solution once. After the extract was dried with anhydrous sodium sulfate, a solvent was distilled off to obtain 1.14 g of brown liquid crude product of ketoester body (4). By purification by column chromatography (50 g of silica gel, hexane:ethyl acetate=9:1), 0.506 g of the title compound was obtained as a yellow liquid compound. 2 process yield was 41%.

$^1$HNMR (400 MHz, CDCl$_3$) δ: 7.81 (d, J=8.9 Hz, 1H), 7.16-7.04 (m, 4H), 6.95-6.91 (m, 2H), 3.95 (s, 3H).

Synthesis of methyl 2-(2-chloro-4-(4-fluorophenoxy)phenyl)-2-hydroxy-3-(1H-1,2,4-triazol-1-yl)propanoate (I-26)

Under an argon atmosphere, 0.506 g of methyl 2-(2-chloro-4-(4-fluorophenoxy)phenyl)-2-oxoacetate and 3.0 mL of dehydrated DMAc were added to and dissolved in a 50 mL eggplant flask, and the mixture was added with 0.189 g of t-BuONa and 0.302 mg of trimethylsulfoxonium bromide and stirred at a room temperature. After 0.5 hours, the mixture was added with a saturated ammonium chloride aqueous solution to stop the reaction and extracted with toluene three times. The extract was washed with water three times and washed with a saturated saline solution once. After the extract was dried with anhydrous sodium sulfate, a solvent was distilled off to obtain 0.239 g of yellow liquid crude product. By purification by column chromatography (10 g of cica silica gel, hexane:ethyl acetate=9:1), 0.054 g of the title compound was obtained as a colorless liquid compound. The mixture was added to 0.47 mL of dehydrated DMF and dissolved in a 50 mL eggplant flask, and was added with 0.011 g of triazole and 0.015 g of triazole sodium and heated and stirred in an oil bath of 60° C. After 2.0 hours, the mixture was added with saturated sodium hydrogencarbonate aqueous solution and extracted with toluene three times. The mixture was washed with water three times and washed with a saturated saline solution once. After the extract was dried with anhydrous sodium sulfate, a solvent was distilled off to obtain 0.077 g of colorless liquid crude product of azole body. By purification by column chromatography (10 g of silica gel, chloroform:ethyl acetate=1:1), 0.022 g of the title compound (I-26) was obtained as a white liquid compound.

$^1$HNMR (400 MHz, CDCl$_3$) δ: 8.00 (s, 1H), 7.88 (s, 1H), 7.38 (d, J=8.8 Hz, 1H), 7.08 (t, J=9.2 Hz, 2H), 7.00 (dd, J=9.2, 4.5 Hz, 2H), 6.94 (d, J=2.5 Hz, 1H), 6.78 (dd, J=8.8, 2.5 Hz, 1H), 5.02 (d, J=14.3 Hz, 1H), 4.93 (d, J=14.3 Hz, 1H), 4.87 (s, 1H), 3.78 (s, 3H).

Synthesis Example 26. Synthesis of Compound I-25

Synthesis of 1-(4-(4-bromophenoxy)-2-chlorophenyl)ethan-1-on

After 691 mg of 2-chloro-4-fluoroacetophenone and 7.2 mL of dehydrated DMF were added to and dissolved in a 25 mL eggplant flask, the mixture was added with 767 mg of p-bromophenol and 666 mg of potassium carbonate and heated and stirred in an oil bath of 120° C. After 1.5 hours from the start of the reaction, the mixture was added with 10 mL of water to stop the reaction and extracted with toluene. An organic layer was separately washed with water and a saturated saline solution and then dried with anhydrous sodium sulfate. A solvent was distilled off to obtain 1,330 mg of the title compound as a brown liquid crude product.

$^1$HNMR (400 MHz, CDCl$_3$) δ: 7.65 (d, J=8.6 Hz, 1H), 7.52 (d, J=8.9 Hz, 2H), 6.99 (d, J=2.4 Hz, 1H), 6.95 (d, J=8.9 Hz, 2H), 6.90 (dd, J=8.6, 2.4 Hz, 1H), 2.65 (s, 3H).

Synthesis of methyl 2-(4-(4-bromophenoxy)-2-chlorophenyl)-2-oxoacetate 1,330 mg of 1-(4-(4-bromophenoxy)-2-chlorophenyl)ethan-1-on and 16 mL of dehydrated DMSO were added to and dissolved in a 100 mL eggplant flask, the mixture was added with 1,657 mg of iodine, and heated and stirred in an oil bath of 100° C. After 0.5 hours from the start of the reaction, the reaction solution was cooled to a room temperature and then added with 3,870 mg of potassium carbonate and heated and stirred in an oil bath at 100° C. again. After 0.5 hours, the reaction solution was cooled to a room temperature, and then added with 0.80 mL of methyl iodide, heated with a water bath of 35° C., and stirred. After 47 minutes, the reaction solution was added with 10 mL of saturated sodium sulfite aqueous solution to stop the reaction, filtered, and then extracted with toluene. An organic layer was separately washed with water and a saturated saline solution and then dried with anhydrous sodium sulfate. A solvent was distilled off to obtain 1.24 g of brown liquid crude product of ketoester. By purification by column chromatography (50 g of silica gel, hexane:ethyl acetate=9:1), 700.9 mg of the title compound was obtained as a yellow liquid compound. 2 process yield was 48.0%.

$^1$HNMR (400 MHz, CDCl$_3$) δ: 7.81 (d, J=8.5 Hz, 1H), 7.55 (d, J=8.9 Hz, 2H), 7.01-6.93 (m, 4H), 3.95 (s, 3H).

Synthesis of methyl 2-(4-(4-bromophenoxy)-2-chlorophenyl)oxirane-2-carboxylate and tert-butyl 2-(4-(4-bromophenoxy)-2-chlorophenyl)oxirane-2-carboxylate 2.0 mL of dehydrated DMAc solution of 700.9 mg of methyl 2-(4-(4-bromophenoxy)-2-chlorophenyl)-2-oxoacetate was added in a 25 mL eggplant flask, and stirred at 0° C. under an argon atmosphere. The mixture was added with 507.6 mg of trimethylsulfoxonium iodide and 218.8 mg of STB in order and stirred. After 12 minutes, the mixture was added with 10 mL of saturated ammonium chloride aqueous solution to stop the reaction. The organic layer was extracted with toluene, separately washed with a saturated ammonium chloride aqueous solution, water and a saturated saline solution, and dried with sodium sulfate. A solvent was distilled off to obtain 691.0 mg of brown liquid crude product of oxirane. By purification by column chromatography (30 g of cica silica gel, hexane:ethyl acetate=5:1), the title compound was obtained as 129.4 mg of methyl 2-(4-(4-bromophenoxy)-2-chlorophenyl)oxirane-2-carboxylate as a colorless liquid compound. A yield was 17.8%. In addition, 42.3 mg of tert-butyl 2-(4-(4-bromophenoxy)-2-chlorophenyl)oxirane-2-carboxylate was obtained by another fraction. A yield was 5.2%.

Methyl 2-(4-(4-bromophenoxy)-2-chlorophenyl)oxirane-2-carboxylate $^1$HNMR (400 MHz, CDCl$_3$) δ: 7.49 (d, J=9.0 Hz, 2H), 7.40 (d, J=8.5 Hz, 1H), 7.00 (d, J=2.4 Hz, 1H), 6.94 (d, J=9.0 Hz, 2H), 6.89 (dd, J=8.5, 2.4 Hz, 1H), 3.78 (s, 3H), 3.59 (d, J=6.3 Hz, 1H), 3.02 (d, J=6.3 Hz, 1H).

tert-butyl 2-(4-(4-bromophenoxy)-2-chlorophenyl)oxirane-2-carboxylate $^1$HNMR (400 MHz, CDCl$_3$) δ: 7.50 (d, J=9.0 Hz, 2H), 7.39 (d, J=8.5 Hz, 1H), 7.01 (d, J=2.4 Hz, 1H), 6.94 (d, J=9.0 Hz, 2H), 6.89 (dd, J=8.5, 2.4 Hz, 1H), 3.52 (d, J=6.3 Hz, 1H), 2.95 (d, J=6.3 Hz, 1H), 1.44 (s, 9H).

Synthesis of methyl 2-(2-chloro-4-(4-bromophenoxy)phenyl)-2-hydroxy-3-(1H-1,2,4-triazol-1-yl)propanoate (I-25)

After 129.4 mg of methyl 2-(4-(4-bromophenoxy)-2-chlorophenyl)oxirane-2-carboxylate and 1.3 mL of dehydrated DMF were added to and dissolved in a 25 mL eggplant flask, the mixture was added with 23.5 mg of triazole and 31.2 mg of triazole sodium salt, and heated and stirred in an oil bath of 60° C. After 2 hours, the mixture was added with 10 mL of saturated ammonium chloride aqueous solution and extracted with toluene. An organic layer was separately washed with water and a saturated saline solution and then dried with anhydrous sodium sulfate. A solvent was distilled off to obtain 114.6 mg of colorless liquid crude product of azole. By purification by column chromatography (5 g of silica gel, chloroform:ethyl acetate=1:1), 82.2 mg of the title compound was obtained as a colorless solid. The obtained solid was re-dissolved in 1.0 mL of toluene of 80° C. and re-crystallized at a room temperature, and the obtained crystal was washed with toluene of 0° C. Thereafter, drying was performed to obtain the title compound (I-25) as 60.1 mg of colorless crystal.

$^1$HNMR (400 MHz, CDCl$_3$) δ: 8.00 (s, 1H), 7.88 (s, 1H), 7.49 (d, J=8.9 Hz, 2H), 7.41 (d, J=8.8 Hz, 1H), 6.98 (d, J=2.5 Hz, 1H), 6.91 (d, J=8.9 Hz, 2H), 6.82 (dd, J=8.8, 2.5 Hz, 1H), 5.02 (d, J=14.3 Hz, 1H), 4.94 (d, J=14.3 Hz, 1H), 4.87 (s, 1H), 3.80 (s, 3H).

Synthesis Example 27. Synthesis of Compound I-28

Synthesis of 1-(2-chloro-4-(3,4-difluorophenoxy) phenyl)ethan-1-on 1.35 g of 2-chloro-4-fluoroacetophenone was dissolved in 10 ml of DMF, and the mixture was added with 1.13 g of 3,4-difluorophenol and 1.31 g of potassium carbonate and stirred at 90° C. for 6 hours. After the completion of the reaction, the mixture was added with toluene, and the organic layer was washed with water and a saturated saline solution, and dried with anhydrous sodium sulfate. A solvent is distilled off, and the residue was purified by column chromatography (60 g of silica gel, hexane/ethyl acetate=10/1), thereby obtaining 1.528 g of the title compound as a colorless viscous liquid. A yield was 69.0%.

$^1$HNMR (400 MHz, CDCl$_3$) δ: 7.65 (d, J=8.8 Hz, 1H), 7.24-7.16 (m, 1H), 6.99 (d, J=2.4 Hz, 1H), 6.94-6.88 (m, 1H), 6.90 (dd, J=8.8, 2.4 Hz, 1H), 6.83-6.78 (m, 1H), 2.65 (s, 3H).

Synthesis of methyl 2-(2-chloro-4-(3,4-difluorophenoxy)phenyl)-2-oxoacetate 1.453 g of 1-(2-chloro-4-(3,4-difluorophenoxy)phenyl) ethan-1-on synthesized in the preceding paragraph was weighed in a 100 ml eggplant flask and added with 20 ml of DMSO to be dissolved. The mixture was added with 4.19 g of iodine and stirred for 0.5 hours in an oil bath of 100° C. After the completion of the reaction, the mixture was cooled to 60° C., added with 4.967 g of potassium carbonate, and stirred at 100° C. for 0.5 hours. The mixture was cooled to 35° C., added with 1.05 ml of iodomethane, and stirred at 35° C. for 1.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (30 g of silica gel, hexane/ethyl acetate=10/1), thereby obtaining 0.962 g of the title compound as a colorless liquid. A yield was 57.3%.

$^1$HNMR (400 MHz, CDCl$_3$) δ: 7.82 (d, J=8.8 Hz, 1H), 7.27-7.19 (m, 1H), 6.99-6.93 (m, 3H), 6.87-6.82 (m, 1H), 3.96 (s, 3H).

Synthesis of methyl 2-(2-chloro-4-(3,4-difluorophenoxy)phenyl)-2-hydroxy-3-(1H-1,2,4-triazol-1-yl) propanoate (I-28)

0.610 g of methyl 2-(2-chloro-4-(3,4-difluorophenoxy) phenyl)-2-oxoacetate obtained in the preceding paragraph was dissolved in 3.5 ml of DMF, and the mixture was added with 0.355 g of TMSOB and 0.207 g of triazole sodium at −20° C., and stirred for 1 hour while returning to a room temperature. The mixture was put in a bath of 50° C. and stirred for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/3), thereby obtaining 0.180 g of the title compound as a white solid. A yield was 24.4%.

$^1$HNMR (400 MHz, CDCl$_3$) δ: 8.00 (s, 1H), 7.88 (s, 1H), 7.43 (d, J=8.8 Hz, 1H), 7.17 (dt, J=9.7, 9.0 Hz, 1H), 6.97 (d, J=2.5 Hz, 1H), 6.87 (ddd, J=10.8, 6.6, 2.9 Hz, 1H), 6.81 (dd, J=8.8, 2.5 Hz, 1H), 6.74-6.79 (m, 1H), 5.02 (d, J=14.3 Hz, 1H), 4.94 (d, J=14.3 Hz, 1H), 4.89 (s, 1H), 3.80 (s, 3H).

Synthesis Example 28. Synthesis of Compound I-76

Synthesis of 1-bromo-2-chloro-4-((4-chlorobenzyl)oxy)benzene 1.156 g of 4-bromo-3-chlorophenol was dissolved in 10 ml of DMF, and the solution was added with 0.924 g of p-chlorobenzylchloride and 0.937 g of potassium carbonate and stirred at 80° C. for 1 hour. After the completion of the reaction, the mixture was added with toluene and the organic layer was washed with water and a saturated saline solution, and dried with anhydrous sodium sulfate. A solvent was distilled off to obtain 1.808 g of the title compound of crude product as a light yellow viscous liquid. A yield was 97.7%.

$^1$HNMR (400 MHz, CDCl$_3$) δ: 7.47 (d, J=8.9 Hz, 1H), 7.36 (d, J=8.6 Hz, 2H), 7.32 (d, J=8.6 Hz, 2H), 7.06 (d, J=2.9 Hz, 1H), 6.73 (dd, J=8.9, 2.4 Hz), 4.98 (s, 2H).

Synthesis of methyl 2-(2-chloro-4-((4-chlorobenzyl) oxy)phenyl)-2-oxoacetate 1.000 g of 1-bromo-2-chloro-4-((4-chlorobenzyl)oxy) benzene synthesized in the preceding paragraph was weighed in a 25 ml four-necked flask and dissolved in 6.0 ml of THF. The solution was cooled to an internal temperature of −70° C. and dropped with 1.25 ml of 2.67 M/n-butyl-lithium/hexane solution for 4 minutes. After the mixture was stirred at the same temperature for 30 minutes, the mixture was dropped with a solution in which 0.427 g of dimethyl oxalate for 3 minutes and stirred for 0.75 hours. After the completion of the reaction, the mixture was added with concentrated hydrochloric acid and extracted with ethyl acetate. The extract was washed with water and a saturated saline solution and dried with anhydrous sodium sulfate. A solvent is distilled off, and the residue was purified by column chromatography (30 g of silica gel, hexane/ethyl acetate=7/1), thereby obtaining 0.635 g of the title compound as a colorless viscous liquid. A yield was 62.2%.

¹HNMR (400 MHz, CDCl₃) δ: 7.82 (d, J=8.8 Hz, 1H), 7.38 (d, J=8.6 Hz, 2H), 7.34 (d, J=8.6 Hz, 2H), 7.02 (d, J=2.4 Hz, 1H), 6.95 (dd, J=8.8, 2.4 Hz, 1H), 5.10 (s, 2H), 3.95 (s, 3H).

Synthesis of methyl 2-(2-chloro-4-((4-chlorobenzyl)oxy)phenyl)-2-hydroxy-3-(1H-1,2,4-triazol-1-yl)propanoate (I-76)

0.604 g of methyl 2-(2-chloro-4-((4-chlorobenzyl)oxy)phenyl)-2-oxoacetate obtained in the preceding paragraph was dissolved in 3.5 ml of DMAc, and the solution was added with 0.336 g of TMSOB and 0.195 g of triazole sodium and stirred at a room temperature for 0.5 hours and at 50° C. for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/4), thereby obtaining 0.192 g of the title compound as a white solid. A yield was 25.5%.

¹HNMR (400 MHz, CDCl₃) δ: 7.97 (s, 1H), 7.86 (s, 1H), 7.38-7.31 (m, 5H), 6.98 (d, J=2.6 Hz, 1H), 6.77 (dd, J=8.8, 2.5 Hz, 1H), 4.99 (d, J=14.2 Hz, 1H), 4.98 (s, 2H), 4.93 (d, J=14.2 Hz, 1H), 4.85 (s, 1H), 3.78 (s, 3H).

Synthesis Example 29. Synthesis of Compound IIIc-1

Synthesis of 1-(2-chloro-4-(naphthalen-2-yloxy)phenyl)ethan-1-on 1.23 g of 2-chloro-4-fluoroacetophenone was dissolved in 11 ml of DMF, and the solution was added with 1.12 g of 2-naphthol and 1.18 g of potassium carbonate and stirred at 90° C. for 4 hours. After the completion of the reaction, the mixture was added with toluene, and the organic layer was washed with water and a saturated saline solution, and dried with anhydrous sodium sulfate. A solvent is distilled off, and the residue was purified by column chromatography (40 g of silica gel, hexane/ethyl acetate=10/1), thereby obtaining 0.968 g of the title compound as a colorless viscous liquid. A yield was 45.9%.

¹HNMR (400 MHz, CDCl₃) δ: 7.89 (d, J=8.9 Hz, 1H), 7.86 (d, J=8.8 Hz, 1H), 7.77 (d, J=8.0 Hz, 1H), 7.65 (d, J=8.6 Hz, 1H), 7.54-7.45 (m, 3H), 7.23 (dd, J=8.9, 2.4 Hz, 1H), 7.04 (d, J=2.4 Hz, 1H), 6.95 (dd, J=8.6, 2.4 Hz, 1H), 2.66 (s, 3H).

Synthesis of methyl 2-(2-chloro-4-(4-naphthalen-2-yloxy)phenyl)-2-oxoacetate 0.952 g of 1-(2-chloro-4-(naphthalen-2-yloxy)phenyl)ethan-1-on synthesized in the preceding paragraph was weighed in a 100 ml eggplant flask and added with 10 ml of DMSO to be dissolved. The mixture was added with 2.60 g of iodine and stirred for 0.5 hours in an oil bath of 100° C. After the completion of the reaction, the mixture was cooled to 60° C., added with 3.11 g of potassium carbonate, and stirred at 100° C. for 0.5 hours. The mixture was cooled to 35° C., added with 0.65 ml of iodomethane, and stirred at 35° C. for 1.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (30 g of silica gel, hexane/ethyl acetate=10/1), thereby obtaining 0.579 g of the title compound as a colorless liquid. A yield was 53.0%.

¹HNMR (400 MHz, CDCl₃) δ: 7.91 (d, J=8.9 Hz, 1H), 7.87 (d, J=8.9 Hz, 1H), 7.81 (dd, J=8.4, 0.5 Hz, 1H), 7.79 (d, J=7.8 Hz, 1H), 7.56-7.47 (m, 3H), 7.23 (dd, J=8.9, 2.4 Hz, 1H), 7.03-6.98 (m, 2H), 3.95 (s, 3H).

Synthesis of methyl 2-(2-chloro-4-(naphthalen-2-yloxy)phenyl)-2-hydroxy-3-(1H-1,2,4-triazol-1-yl)propanoate (IIIc-1)

0.530 g of methyl 2-(2-chloro-4-(4-naphthalen-2-yloxy)phenyl)-2-oxoacetate obtained in the preceding paragraph was dissolved in 3 ml of DMF, and the solution was added with 0.345 g of TMSOI and 0.157 g of triazole sodium and stirred at a room temperature for 0.5 hours. The mixture was put in a bath at 50° C. and stirred for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (9 g of silica gel, hexane/ethyl acetate=1/3), thereby obtaining 0.402 g of the title compound as a white solid. A yield was 28.4%.

¹HNMR (400 MHz, CDCl₃) δ: 8.01 (s, 1H), 7.89 (s, 1H), 7.89-7.84 (m, 2H), 7.76 (d, J=8.0 Hz, 1H), 7.53-7.40 (m, 4H), 7.21 (dd, J=8.9, 2.4 Hz, 1H), 7.03 (d, J=2.5 Hz, 1H), 6.88 (dd, J=8.7, 2.5 Hz, 1H), 5.04 (d, J=14.3 Hz, 1H), 4.95 (d, J=14.3 Hz, 1H), 4.90 (s, 1H), 3.80 (s, 3H).

Synthesis Example 30. Synthesis of Compound I-35

Synthesis of 1-(2-chloro-4-(4-cyanophenoxy)phenyl)ethan-1-on 1.21 g of 2-chloro-4-fluoroacetophenone was dissolved in 15 ml of N-methyl-2-pyrrolidone (NMP), and the solution was added with 1.26 g of 4-cyanophenol and 3.89 g of cesium carbonate and stirred at 130° C. for 1 hour. After the completion of the reaction, the mixture was added with toluene, and the organic layer was washed with water and a saturated saline solution, and dried with anhydrous sodium sulfate. A solvent is distilled off, and the residue was purified by column chromatography (75 g of silica gel, hexane/ethyl acetate=10/1), thereby obtaining 1.466 g of the title compound as a colorless viscous liquid. A yield was 73.9%.

¹HNMR (400 MHz, CDCl₃) δ: 7.70-7.67 (m, 3H), 7.12-7.09 (m, 3H), 6.99 (ddj=8.5, 2.4 Hz, 1H), 2.67 (s, 3H).

Synthesis of methyl 2-(2-chloro-4-(4-cyanophenoxy)phenyl)-2-oxoacetate 1.43 g of 1-(2-chloro-4-(4-cyanophenoxy)phenyl)ethan-1-on synthesized in the preceding paragraph was weighed in a 100 ml eggplant flask and added with 20 ml of DMSO to be dissolved. The mixture was added with 3.894 g of iodine and stirred for 0.5 hours in an oil bath of 100° C. After the completion of the reaction, the mixture was cooled to 60° C., added with 4.66 g of potassium carbonate, and stirred at 100° C. for 0.5 hours. The mixture was cooled to 35° C., added with 1.0 ml of iodomethane, and stirred at 35° C. for 2.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. After the residue was purified by column chromatography (35 g of silica gel, toluene/ethyl acetate=5/1), recrystallization was performed by hexane/ethyl acetate to obtain 0.643 g of the title compound as a colorless solid. A yield was 38.8%.

$^1$HNMR (400 MHz, CDCl$_3$) δ: 7.85 (d, J=8.6 Hz, 1H), 7.48 (d, J=8.9 Hz, 2H), 7.16 (d, J=8.9 Hz, 2H), 7.08 (d, J=2.3 Hz, 1H), 7.03 (dd, J=8.6, 2.3 Hz, 1H), 3.97 (s, 3H).

Synthesis of methyl 2-(2-chloro-4-(4-cyanophenoxy)phenyl)-2-hydroxy-3-(1H-1,2,4-triazol-1-yl)propanoate (I-35)

0.620 g of methyl 2-(2-chloro-4-(4-cyanophenoxy)phenyl)-2-oxoacetate obtained in the preceding paragraph was dissolved in 4.5 ml of DMF, and the solution was added with 0.374 g of TMSOB and 0.216 g of triazole sodium and stirred at a room temperature for 0.5 hours and then stirred at 50° C. for 1.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (15 g of silica gel, hexane/ethyl acetate=1/4), thereby obtaining 0.202 g of the title compound as a white solid. A yield was 25.8%.

$^1$HNMR (400 MHz, CDCl$_3$) δ: 8.01 (s, 1H), 7.88 (s, 1H), 7.66 (d, J=8.9 Hz, 2H), 7.48 (d, J=8.7 Hz, 1H), 7.08 (d, J=2.5 Hz, 1H), 7.05 (d, J=8.9 Hz, 2H), 6.90 (dd, J=8.7, 2.5 Hz, 1H), 5.03 (d, J=14.3 Hz, 1H), 5.00 (s, 1H), 4.96 (d, J=14.3 Hz, 1H), 3.81 (s, 3H).

Synthesis Example 31. Synthesis of Compound I-29

Synthesis of 1-(2-chloro-4-(4-chloro-3-fluorophenoxy)phenyl)ethan-1-on 1.43 g of 2-chloro-4-fluoroacetophenone was dissolved in 15 ml of DMF, and the mixture was added with 1.50 g of 4-chloro-3-fluorophenol and 1.62 g of potassium carbonate and stirred at 100° C. for 3 hours. After the completion of the reaction, the mixture was added with toluene, and the organic layer was washed with water and a saturated saline solution, and dried with anhydrous sodium sulfate. A solvent is distilled off, and the residue was purified by column chromatography (60 g of silica gel, hexane/ethyl acetate=10/1), thereby obtaining 2.222 g of the title compound as a colorless viscous liquid. A yield was 89.4%.

$^1$HNMR (400 MHz, CDCl$_3$) δ: 7.65 (d, J=8.6 Hz, 1H), 7.41 (t, J=8.7 Hz, 1H), 7.02 (d, J=2.4 Hz, 1H), 6.93 (dd, J=8.6, 2.4 Hz, 1H), 6.88 (dd, J=9.6, 2.7 Hz, 1H), 6.83 (ddd, J=8.7, 2.7, 1.3 Hz), 2.66 (s, 3H).

Synthesis of methyl 2-(2-chloro-4-(4-chloro-3-fluorophenoxy)phenyl)-2-oxoacetate 1.508 g of 1-(2-chloro-4-(4-chloro-3-fluorophenoxy)phenyl)ethan-1-on synthesized in the preceding paragraph was weighed in a 100 ml eggplant flask and added with 20 ml of DMSO to be dissolved. The mixture was added with 4.09 g of iodine and stirred in an oil bath of 100° C. for 0.5 hours. After the completion of the reaction, the mixture was cooled to 60° C., added with 4.85 g of potassium carbonate, and stirred at 100° C. for 0.5 hours. The mixture was cooled to 35° C., added with 1.0 ml of iodomethane, and stirred at 35° C. for 3.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (33 g of silica gel, hexane/ethyl acetate=6/1), thereby obtaining 1.064 g of the title compound as a light yellow liquid. A yield was 61.5%.

$^1$HNMR (400 MHz, CDCl$_3$) δ: 7.83 (d, J=8.6 Hz, 1H), 7.45 (t, J=8.7 Hz, 1H), 7.02 (d, J=2.4 Hz, 1H), 6.98 (dd, J=8.6, 2.4 Hz, 1H), 6.92 (dd, J=9.4, 2.7 Hz, 1H), 6.86 (ddd, J=8.7, 2.7, 1.3 Hz), 3.96 (s, 3H).

Synthesis of methyl 2-(2-chloro-4-(4-chloro-3-fluorophenoxy)phenyl)-2-hydroxy-3-(1H-1,2,4-triazo 1-1-yl)propanoate (I-29)

1.05 g of methyl 2-(2-chloro-4-(4-chloro-3-fluorophenoxy)phenyl)-2-oxoacetate obtained in the preceding paragraph was dissolved in 6 ml of DMF, and the solution was added with 0.579 g of TMSOB and 0.335 g of triazole sodium at 0° C., and stirred for 30 minutes while returning to a room temperature. The mixture was stirred in a bath of 50° C. for 2.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (20 g of silica gel, hexane/ethyl acetate=1/4), thereby obtaining 0.380 g of the title compound as a light yellow solid. A yield was 29.3%. $^1$HNMR (400 MHz, CDCl$_3$) δ: 8.01 (s, 1H), 7.87 (s, 1H), 7.43 (d, J=8.8 Hz, 1H), 7.38 (t, J=8.7 Hz, 1H), 7.02 (d, J=2.5 Hz, 1H), 6.87-6.82 (m, 2H), 6.76 (ddd, J=8.7, 2.7, 1.3 Hz), 5.02 (d, J=14.3 Hz, 1H), 5.01 (s, 1H), 4.94 (d, J=14.3 Hz, 1H), 3.80 (s, 3H).

Synthesis Example 32. Synthesis of Compound IIb-12

Synthesis of 1-(2-(4-chlorophenoxy)phenyl)ethan-1-on 1.24 g of 2-fluoroacetophenone was dissolved in 15 ml of DMF, and the solution was added with 1.269 g of 4-chlorophenol and 3.82 g of cesium carbonate and stirred at 100° C. for 5.5 hours. After the completion of the reaction, the mixture was added with toluene, and the organic layer was washed with water and a saturated saline solution, and dried with anhydrous sodium sulfate. A solvent is distilled off, and the residue was purified by column chromatography (30 g of silica gel, hexane/ethyl acetate=7/1), thereby obtaining 1.30 g of the title compound as a colorless viscous liquid. A yield was 58.7%.

$^1$HNMR (400 MHz, CDCl$_3$) δ: 7.83 (dd, J=7.8, 1.8 Hz, 1H), 7.45 (ddd, J=8.3, 7.3, 1.8 Hz, 1H), 7.32 (d, J=9.0 Hz, 2H), 7.20 (ddd, J=7.8, 7.3, 1.1 Hz, 1H), 6.95 (d, J=9.0 Hz, 2H), 6.90 (dd, J=8.3, 1.1 Hz, 1H), 2.61 (s, 3H).

Synthesis of methyl 2-(2-(4-chlorophenoxy)phenyl)-2-oxoacetate 1.28 g of 1-(2-(4-chlorophenoxy)phenyl)ethan-1-on synthesized in the preceding paragraph was weighed in a 100 ml eggplant flask and added with 20 ml of DMSO to be dissolved. The mixture was added with 4.20 g of iodine and stirred in an oil bath of 100° C. for 0.5 hours. After the completion of the reaction, the mixture was cooled to 60° C., added with 5.00 g of potassium carbonate, and stirred at 100° C. for 0.5 hours. The mixture was cooled to 35° C., added with 1.05 ml of iodomethane, and stirred at 35° C. for 2 hours. After the completion of the reaction, a saturated sodium sulfite aqueous solution and toluene were added to the mixture, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (32 g of silica gel, hexane/ethyl acetate=7/1), thereby obtaining 1.011 g of the title compound as a light yellow liquid. A yield was 67.2%.

$^1$HNMR (400 MHz, CDCl$_3$) δ: 7.96 (dd, J=7.8, 1.8 Hz, 1H), 7.55 (ddd, J=8.5, 7.3, 1.8 Hz, 1H), 7.35 (d, J=8.9 Hz, 2H), 7.26-7.22 (m, 1H), 7.00 (d, J=8.9 Hz, 2H), 6.86 (d, J=8.3 Hz, 1H), 3.72 (s, 3H).

Synthesis of methyl 2-(2-(4-chlorophenoxy)phenyl)-2-hydroxy-3-(1H-1,2,4-triazol-1-yl)propanoate (IIb-12)

1.01 g of methyl 2-(2-(4-chloro-phenoxy)phenyl)-2-oxoacetate obtained in the preceding paragraph was dissolved in 7 ml of DMF, and the solution was added with 0.660 g of TMSOB and 0.381 g of triazole sodium at 0° C., and stirred for 30 minutes while returning to a room temperature. The mixture was stirred in a bath of 50° C. for 2.5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (20 g of silica gel, hexane/ethyl acetate=1/3), thereby obtaining 0.273 g of the title compound as a white solid. A yield was 21.0%.

$^1$HNMR (400 MHz, CDCl$_3$) δ: 8.05 (s, 1H), 7.85 (s, 1H), 7.44 (dd, J=7.8, 1.6 Hz, 1H), 7.32-7.27 (m, 1H), 7.30 (d, J=9.0 Hz, 2H), 7.20 (ddd, J=8.6, 7.3, 1.1 Hz, 1H), 6.90 (d, J=9.0 Hz, 2H), 6.86 (dd, J=8.1, 1.0 Hz, 1H), 5.03 (d, J=14.1 Hz, 1H), 4.87 (d, J=14.1 Hz, 1H), 4.59 (s, 1H), 3.55 (s, 3H).

Synthesis Example 33. Synthesis of Compound IIIb-10

Synthesis of 2-(4-bromo-3-chlorophenoxy)-5-chloropyridine

After 741.3 mg of 2,5-dichloropyridine and 9.0 mL of N-methyl pyrrolidone were added to and dissolved in a 25 mL eggplant flask, the mixture was added with 1.14 g of 4-bromo-3-chlorophenol and 1.96 g of potassium carbonate, and heated and stirred in an oil bath of 160° C. After 5 hours, the mixture was added with an ammonium chloride aqueous solution and extracted with toluene three times. The extract was washed with water three times and washed with a saturated saline solution once. After the extract was dried with anhydrous sodium sulfate, a solvent was distilled off to obtain 1.91 g of brown liquid crude product of diaryl ether. By purification by column chromatography (silica gel, hexane:ethyl acetate=100:0→95:5), 1.53 g of 2-(4-bromo-3-chlorophenoxy)-5-chloropyridine which is the title compound was obtained as a colorless liquid compound. A yield was 95.9%.

$^1$HNMR (400 MHz, CDCl$_3$) δ: 8.12 (dd, J=2.7, 0.6 Hz, 1H), 7.68 (dd, J=8.7, 2.7 Hz, 1H), 7.62 (d, J=8.7 Hz, 1H), 7.27 (d, J=2.7 Hz, 1H), 6.94 (dd, J=8.7, 2.7 Hz, 1H), 6.93 (dd, J=8.7, 0.6 Hz, 1H).

Synthesis of methyl 2-(2-chloro-4-((5-chlorobenzyl-2-yl)oxy)phenyl)-2-oxoacetate After 640 mg of 2-(4-bromo-3-chlorophenoxy)-5-chloropyridine, 284 mg of dimethyl oxalate and 5.0 mL of tetrahydrofuran were added to and dissolved in a 25 mL eggplant flask, the mixture was cooled to -78° C. in a dry ice acetone bath, added with 0.82 mL (2.67 M) of n-butyllithium, and stirred. After 1.5 hours from the start of the reaction, the mixture was added with 2N hydrochloric acid to stop the reaction and extracted with chloroform three times. After the extract was dried with anhydrous sodium sulfate, a solvent was distilled off to obtain 748 mg of orange liquid crude product of ketoester. By purification by column chromatography (silica gel, hexane:ethyl acetate=88:12 to 67:33), 338 mg of methyl 2-(2-chloro-4-((5-chloropyridine-2-yl)oxy)phenyl)-2-oxoacetate which is the title compound was obtained as a colorless liquid compound. A yield was 51.6%.

$^1$HNMR (400 MHz, CDCl$_3$) δ: 8.17 (dd, J=2.7, 0.6 Hz, 1H), 7.87 (d, J=8.6 Hz, 1H), 7.74 (dd, J=8.7, 2.7 Hz, 1H), 7.25 (d, J=2.2 Hz, 1H), 7.17 (dd, J=8.6, 2.2 Hz, 1H), 7.00 (dd, J=8.7, 0.6 Hz, 1H), 3.96 (s, 3H).

Synthesis of 2-(2-chloro-4-((5-chlorobenzyl-2-yl)oxy)phenyl)-2-hydroxy-3-(1H-1,2,4-triazol-1-yl)propanoate (compound IIIb-10)

After 313 mg of methyl 2-(2-chloro-4-(5-chloropyridine-2-yl)oxy)phenyl)-2-oxoacetate obtained in the preceding paragraph and 1.44 mL of N,N-dimethylacetamide were added to and dissolved in a 50 mL eggplant flask, the mixture was added with 114 mg of triazole sodium and 200 mg of TMSOB and heated and stirred in an oil bath of 50° C. After 3 hours from the start of the reaction, the mixture was added with an ammonium chloride aqueous solution and extracted with toluene three times. The extract was washed with water once and was washed with a saturated saline solution once. After the extract was dried with anhydrous sodium sulfate, a solvent was distilled off to obtain 338 mg of yellow liquid crude product of azole. By purification by column chromatography (silica gel, chloroform:ethyl acetate=47:53→0:100) to obtain 166 mg of 2-(2-chloro-4-((5-chloropyridine-2-yl)oxy)phenyl)-2-hydroxy-3-(1H-1,2,4-triazole-1-yl)propanoate, which is the title compound, as a colorless viscous substance. A yield was 42.3%.

$^1$HNMR (400 MHz, CDCl$_3$) δ: 8.14 (d, J=2.7 Hz, 1H), 8.03 (s, 1H), 7.89 (s, 1H), 7.69 (dd, J=8.6, 2.7 Hz, 1H), 7.50 (d, J=8.7 Hz, 1H), 7.20 (d, J=2.4 Hz, 1H), 7.02 (dd, J=8.7, 2.4 Hz, 1H), 6.92 (d, J=8.6 Hz, 1H), 5.06 (d, J=14.2 Hz, 1H), 4.91 (d, J=14.2 Hz, 1H), 4.89 (s, 1H), 3.79 (s, 3H).

Synthesis Example 34. Synthesis of Compound I-33

Synthesis of (4-(4-bromo-3-chlorophenoxy)phenyl) pentafluoro-λ$^6$-sulfane

After 890.8 mg of 4-fluorophenylsulfur pentafluoride and 7.2 mL of DMF were added to and dissolved in a 30 mL centrifuge tube, the mixture was added with 914.8 mg of 4-bromo-3-chlorophenol and 1.5680 g of cesium carbonate and heated and stirred in an oil bath at 120° C. After 4 hours from the start of the reaction, the mixture was added with a saturated ammonium chloride aqueous solution to stop the reaction and extracted with benzene three times. The extract was washed with water once and washed with a saturated saline solution twice. After the extract was dried with anhydrous sodium sulfate, 1.5400 g of brown liquid crude product of aryl bromide was obtained. By purification by column chromatography (silica gel, hexane), 1.3452 g of (4-(4-bromo-3-chlorophenoxy)phenyl)pentafluoro-λ$^6$-sulfan which is the title compound was obtained as a colorless liquid compound. A yield was 81.9%.

$^1$HNMR (400 MHz, CDCl$_3$) δ: 7.74 (d, J=9.1 Hz, 2H), 7.62 (d, J=8.8 Hz, 1H), 7.18 (d, J=2.8 Hz, 1H), 7.03 (d, J=9.1 Hz, 2H), 6.85 (dd, J=8.8, 2.8 Hz, 1H).

Synthesis of 2-(2-chloro-4-(4-pentafluoro-λ$^6$-sulfanyl)phenoxy)phenyl)-2-methyl oxoacetate 409.9 mg of (4-(4-bromo-3-chlorophenoxy)phenyl)pentafluoro-λ$^6$-sulphane obtained in the preceding paragraph and 1.5 mL of tetrahydrofuran were added to and dissolved in a 25 mL eggplant flask and then cooled with water, and the mixture was added with 1.18 mL (1.27 M) of isopropyl magnesium chloride.lithium chloride complex and stirred. After 30 minutes, the mixture was added with 0.15 mL of methyl chloroglyoxylate and continuously stirred. After 1 hour, the mixture was added with 2N hydrochloric acid to stop the reaction and extracted with chloroform three times. After the extract was dried with anhydrous sodium sulfate, a solvent was distilled off to obtain 524.6 mg of orange liquid crude product. By purification by column chromatography (silica gel, hexane/ethyl acetate=91/9→70/30), 59.2 mg of 2-(2-chloro-4-(4-pentafluoro-λ$^6$-sulfanyl)phenoxy)phenyl)-2-methyl oxoacetate which is the title compound was obtained as a colorless liquid compound. A yield was 14.2%.

$^1$HNMR (400 MHz, CDCl$_3$) δ: 7.85 (d, J=8.6 Hz, 1H), 7.82 (d, J=9.1 Hz, 2H), 7.14 (d, J=9.1 Hz, 2H), 7.07 (d, J=2.3 Hz, 1H), 7.03 (dd, J=8.6, 2.3 Hz, 1H), 3.97 (s, 3H).

Synthesis of 2-(2-chloro-4-(4-(pentafluoro-λ$^6$-sulfanyl)phenoxy)phenyl)-2-hydroxy-3-(1H-1,2,4-triazol-1-yl)methyl propionate (Compound I-33)

After 59.2 mg of 2-(2-chloro-4-(4-pentafluoro-λ$^6$-sulfanyl)phenoxy)phenyl)-2-methyl oxoacetate obtained in the preceding paragraph and 0.2 mL of DMAc were added to and dissolved in a 50 mL eggplant flask, the mixture was added with 16.9 mg of triazole sodium and 29.5 mg of TMSOB and heated and stirred in an oil bath of 50° C. After 3 hours, the mixture was added with an ammonium chloride aqueous solution and extracted with toluene three times. The extract was washed with water once and was washed with a saturated saline solution once. After the extract was dried with anhydrous sodium sulfate, a solvent was distilled off to obtain 59.1 mg of yellow liquid crude product. By purification by column chromatography (silica gel, chloroform/ethyl acetate=1/1), 25.1 mg of 2-(2-chloro-4-(4-(pentafluoro-λ$^6$-sulfanyl)phenoxy)phenyl)-2-hydroxy-3-(1H-1,2,4-triazol-1-yl)methyl propionate which is the title compound was obtained as a colorless liquid compound. A yield was 35.3%.

$^1$HNMR (400 MHz, CDCl$_3$) δ: 8.00 (s, 1H), 7.89 (s, 1H), 7.76 (d, J=9.1 Hz, 2H), 7.48 (d, J=8.8 Hz, 1H), 7.07 (d, J=2.5 Hz, 1H), 7.03 (d, J=9.1 Hz, 2H), 6.90 (dd, J=8.8, 2.5 Hz, 1H), 5.03 (d, J=14.3 Hz, 1H), 4.96 (d, J=14.3 Hz, 1H), 4.87 (s, 1H), 3.81 (s, 3H).

Synthesis Example 35. Synthesis of Compound I-31

Synthesis of 1-(2-chloro-4-(2,4-dichlorophenoxy) phenyl)ethan-1-on 1.31 g of 2-chloro-4-fluoroacetophenone was dissolved in 14 ml of NMP, and the solution was added with 1.02 g of 2,4-difluorophenol and 1.27 g of potassium carbonate and stirred at 100° C. for 5.5 hours. After the completion of the reaction, the mixture was added with toluene, and the organic layer was washed with water and a saturated saline solution, and dried with anhydrous sodium sulfate. A solvent is distilled off, and the residue was purified by column chromatography (silica gel, hexane/ethyl acetate=9/1), thereby obtaining 1.65 g of the title compound as a colorless viscous liquid. A yield was 77.3%.

$^1$HNMR (400 MHz, CDCl$_3$) δ: 7.64 (d, J=8.7 Hz, 1H), 7.16 (td, J=8.9, 5.5 Hz, 1H), 7.02-6.90 (m, 3H), 7.01 (dd, J=8.7, 2.5 Hz, 1H), 2.64 (s, 3H).

Synthesis of 2-(2-chloro-4-(2,4-difluorophenoxy) phenyl)-2-methyl oxoacetate 1.652 g of 1-(2-chloro-4-(2,4-difluorophenoxy)phenyl) ethan-1-on synthesized in the preceding paragraph and 20 mL of DMSO were added to and dissolved in a 100 ml eggplant flask. The mixture was added with 5.70 g of iodine and stirred in an oil bath of 100° C. for 0.5 hours. After the completion of the reaction, the mixture was cooled to 60° C., added with 5.76 g of potassium carbonate, and stirred at 100° C. for 0.5 hours. The mixture was cooled to 35° C., added with 1.2 mL of iodomethane, and stirred at 35° C. for 2.5 hours. After the completion of the reaction, excess iodine was quenched with a saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (30 g of silica gel, hexane/ethyl acetate=5/1), thereby obtaining 1.20 g of the title compound as a colorless liquid. A yield was 62.7%.

$^1$HNMR (400 MHz, CDCl$_3$) δ: 7.81 (d, J=8.7 Hz, 1H), 7.17 (td, J=8.9, 5.4 Hz, 1H), 7.04-6.90 (m, 4H), 3.95 (s, 3H).

Synthesis of 2-(2-chloro-4-(2,4-difluorophenoxy)phenyl)-2-hydroxy-3-(1H-1,2,4-triazol-1-yl)methyl propanoate (compound I-31)

1.20 g of 2-(2-chloro-4-(2,4-difluorophenoxy)phenyl)-2-methyl oxoacetate obtained in the preceding paragraph was dissolved in 5.5 ml of DMAc, and the solution was added with 0.757 g of TMSOB and 0.434 g of triazole sodium and stirred at a room temperature for 0.5 hours. The mixture was put in a bath of 50° C. and stirred for 4 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/3), thereby obtaining 0.402 g of the title compound as a white solid. A yield was 24.0%.

$^1$HNMR (400 MHz, CDCl$_3$) δ: 7.99 (1H,$), 7.88 (1H,$), 7.39 (d, J=8.8 Hz, 1H), 7.11 (td, J=8.9, 5.5 Hz, 1H), 7.00-6.90 (m, 3H), 6.76 (dd, J=8.8, 2.6 Hz, 1H), 5.02 (d, J=14.3 Hz, 1H), 4.90 (d, J=14.3 Hz, 1H), 4.83 (s, 1H), 3.79 (s, 3H).

Synthesis Example 36. Synthesis of Compound I-236

Synthesis of 1-(2-bromo-4-(4-bromophenoxy)phenyl)ethan-1-on 1.26 g of 2-bromo-4-fluoroacetophenone was dissolved in 10 ml of DMF, and the solution was added with 1.11 g of 4-bromophenol and 2.46 g of cesium carbonate and stirred at 100° C. for 1 hour. After the completion of the reaction, the mixture was added with toluene, and the organic layer was washed with water and a saturated saline solution, and dried with anhydrous sodium sulfate. A solvent is distilled off, and the residue was purified by column chromatography (silica gel, hexane/ethyl acetate=9/1), thereby obtaining 1.93 g of the title compound as a colorless viscous liquid. A yield was 89.2%.

$^1$HNMR (400 MHz, CDCl$_3$) δ: 7.57-7.49 (m, 3H), 7.20 (d, J=2.4 Hz, 1H), 7.10-6.93 (m, 3H), 2.64 (s, 3H).

Synthesis of 2-(2-bromo-4-(4-bromophenoxy)phenyl)-2-methyl oxoacetate 1.91 g of 1-(2-bromo-4-(4-bromophenoxy)phenyl)ethan-1-on synthesized in the preceding paragraph and 20 mL of DMSO were added to and dissolved in a 100 ml eggplant flask. The mixture was added with 4.20 g of iodine and stirred in an oil bath of 100° C. for 0.5 hours. After the completion of the reaction, the mixture was cooled to 60° C., added with 5.00 g of potassium carbonate, and stirred at 100° C. for 0.5 hours. The mixture was cooled to 35° C., added with 1.05 mL of iodomethane, and stirred at 35° C. for 3.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 1.38 g of the title compound as a light yellow liquid. A yield was 64.7%.

$^1$HNMR (400 MHz, CDCl$_3$) δ: 7.73 (d, J=8.7 Hz, 1H), 7.54 (d, J=8.9 Hz, 2H), 7.18 (d, J=2.4 Hz, 1H), 7.01-6.96 (m, 3H), 3.95 (s, 3H).

Synthesis of 2-(2-bromo-4-(bromophenoxy)phenyl)-2-hydroxy-3-(1H-1,2,4-triazol-1-yl)methyl propanoate (Compound I-236)

1.38 g of 2-(2-bromo-4-(4-bromophenoxy)phenyl)-2-methyl oxoacetate obtained in the preceding paragraph was dissolved in 5 ml of DMF, and the mixture was added with 0.696 g of TMSOB and 0.397 g of triazole sodium and stirred for 30 hours while returning to a room temperature. The mixture was stirred in a bath of 50° C. for 3 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/3), thereby obtaining 0.335 g of the title compound as a yellow solid. A yield was 20.2%.

$^1$HNMR (400 MHz, CDCl$_3$) δ: 7.97 (s, 1H), 7.87 (s, 1H), 7.48 (d, J=8.9 Hz, 2H), 7.39 (d, J=8.8 Hz, 1H), 7.18 (d, J=2.5 Hz, 1H), 6.91 (d, J=8.9 Hz, 2H), 6.85 (dd, J=8.8, 2.5 Hz, 1H), 5.02 (s, 2H), 4.98 (s, 1H), 3.80 (s, 3H).

Synthesis Example 37. Synthesis of Compound I-130

Synthesis of 1-(4-(4-bromophenoxy)-2-(trifluoromethyl)phenyl)ethan-1-on 1.61 g of 2-trifluoromethyl-4-fluoroacetophenone was dissolved in 10 ml of DMF, and the mixture was added with 1.48 g of 4-bromophenol and 3.27 g of potassium carbonate and stirred at 100° C. for 1 hour. After the completion of the reaction, the mixture was added with toluene, and the organic layer was washed with water and a saturated saline solution, and dried with anhydrous sodium sulfate. The solvent was distilled off, and 2.50 g of the title compound was obtained as a colorless viscous liquid by vacuum drying. A yield was 89.3%.

$^1$HNMR (400 MHz, CDCl$_3$) δ: 7.55-7.49 (m, 3H), 7.31 (d, J=2.4 Hz, 1H), 7.12 (dd, J=8.5, 2.4 Hz, 1H), 6.95 (d, J=8.9 Hz, 2H), 2.58 (s, 3H).

Synthesis of 2-(4-(4-bromophenoxy)-2-(trifluoromethyl)phenyl)-2-methyl oxoacetate 2.48 g of 1-(4-(4-bromophenoxy)-2-(trifluoromethyl)phenyl)ethane-1-on and 15 mL of DMSO were added to and dissolved in a 100 ml eggplant flask. The mixture was added with 5.61 g of iodine and stirred in an oil bath of 100° C. for 0.5 hours. After the completion of the reaction, the mixture was cooled to 60° C., added with 6.70 g of potassium carbonate, and stirred at 100° C. for 0.5 hours. The mixture was cooled to 35° C., added with 1.05 mL of iodomethane, and stirred at 35° C. for 3.5 hours. After the completion of the reaction, a saturated sodium sulfite aqueous solution and toluene were added to the mixture, and the precipitated solution was filtrated with celite. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 1.38 g of the title compound as a light yellow liquid. A yield was 49.5%.

$^1$HNMR (400 MHz, CDCl$_3$) δ: 7.66 (d, J=8.6 Hz, 1H), 7.55 (d, J=8.9 Hz, 2H), 7.34 (d, J=2.4 Hz, 1H), 7.14 (dd, J=8.6, 2.4 Hz, 1H), 6.99 (d, J=8.9 Hz, 2H), 3.94 (s, 3H).

Synthesis of 2-(4-(4-bromophenoxy)-2-(trifluoromethyl)phenyl)-2-hydroxy-3-(1H-1,2,4-triazol-1-yl) methyl propanoate (Compound I-130)

1.38 g of 2-(4-(4-bromophenoxy)-2-(trifluoromethyl)phenyl)-2-methyl oxoacetate obtained in the preceding paragraph was dissolved in 5 ml of DMF, and the mixture was added with 0.707 g of TMSOB and 0.406 g of triazole sodium and stirred for 30 minutes while returning to a room temperature. The mixture was stirred in a bath of 50° C. for 5 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/3), thereby obtaining 0.147 g of the title compound as a yellow solid. A yield was 4.3%.

$^1$HNMR (400 MHz, CDCl$_3$) δ: 8.11 (s, 1H), 7.89 (s, 1H), 7.62 (d, J=8.9 Hz, 1H), 7.50 (d, J=8.8 Hz, 2H), 7.39 (d, J=2.7 Hz, 1H), 7.06 (dd, J=8.9, 2.8 Hz), 6.93 (d, J=8.8 Hz), 5.08 (d, J=14.1 Hz, 1H), 4.72 (d, J=14.1 Hz, 1H), 4.68 (s, 1H), 3.80 (s, 3H).

Synthesis Example 38. Synthesis of Compound I-234

Synthesis of 1-(2-bromo-4-(4-(trifluoromethyl)phenoxy)phenyl)ethan-1-on 1.24 g of 2-bromo-4-fluoroacetophenone was dissolved in 10 ml of NMP, and the mixture was added with 1.10 g of 4-trifluorophenol and 2.46 g of potassium carbonate and stirred at 100° C. for 0.5 hours, 120° C. for 1 hour, and 140° C. for 1.5 hours. After the completion of the reaction, the mixture was added with toluene, and the organic layer was washed with water and a saturated saline solution, and dried with anhydrous sodium sulfate. A solvent is distilled off, and the residue was purified by column chromatography (silica gel, hexane/ethyl acetate=9/1), thereby obtaining 1.04 g of the title compound as a colorless viscous liquid. A yield was 50.9%.

$^1$HNMR (400 MHz, CDCl$_3$) δ: 7.65 (d, J=8.6 Hz, 2H), 7.58 (d, J=8.5 Hz, 1H), 7.27 (d, J=2.4 Hz, 1H), 7.12 (d, J=8.6 Hz, 2H), 7.01 (dd, J=8.5, 2.4 Hz, 1H), 2.65 (s, 3H).

Synthesis of 2-(2-bromo-4-(4-trifluoromethyl)phenoxy)phenyl)-2-methyl oxoacetate 1.02 g of 1-(2-bromo-4-(4-(trifluoromethyl)phenoxy)phenyl)ethan-1-on obtained in the preceding paragraph was weighed and 11.5 mL of DMSO were added to and dissolved in a 100 ml eggplant flask. The mixture was added with 2.33 g of iodine and stirred at 100° C. for 0.5 hours in an oil bath. After the completion of the reaction, the mixture was cooled to 60° C., added with 2.76 g of potassium carbonate, and stirred at 100° C. for 0.5 hours. The mixture was cooled to 35° C., added with 0.60 mL of iodomethane, and stirred at 35° C. for 3 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 0.677 g of the title compound as a light yellow liquid. A yield was 58.9%.

$^1$HNMR (400 MHz, CDCl$_3$) δ: 7.76 (d, J=8.6 Hz, 1H), 7.69 (d, J=8.9 Hz, 2H), 7.25 (d.J=2.4 Hz, 1H), 7.18 (d, J=8.9 Hz, 2H), 7.05 (dd, J=8.6, 2.4 Hz, 1H), 3.96 (s, 3H).

Synthesis of 2-(2-bromo-4-(4-(trifluoromethyl)phenoxy)phenyl)-2-hydroxy-3-(1H-1,2,4-triazol-1-yl) methyl propionate (compound I-234)

0.663 g of 2-(2-bromo-4-(4-trifluoromethyl)phenoxy)phenyl)-2-methyl oxoacetate obtained in the preceding paragraph was dissolved in 4.5 ml of DMF, and the mixture was added with 0.344 g of TMSOB and 0.195 g of triazole sodium and stirred for 30 hours while returning to a room temperature. The mixture was stirred in a bath of 50° C. for 4 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/3), thereby obtaining 0.142 g of the title compound as a yellow solid. A yield was 17.8%.

$^1$HNMR (400 MHz, CDCl$_3$) δ: 7.98 (s, 1H), 7.88 (s, 1H), 7.63 (d, J=8.6 Hz, 2H), 7.45 (d, J=8.8 Hz, 1H), 7.25 (d, J=2.5 Hz, 1H), 7.07 (d, J=8.6 Hz, 2H), 6.91 (dd, J=8.8, 2.5 Hz, 1H), 5.04 (s, 2H), 5.00 (s, 1H), 3.81 (s, 3H).

Synthesis Example 39. Synthesis of Compound I-128

Synthesis of 1-(2-(trifluoromethyl)-4-(4-(trifluoromethyl)phenoxy)phenyl)ethan-1-on 1.20 g of 2-trifluoromethyl-4-fluoroacetophenone was dissolved in 10 ml of NMP, and the mixture was added with 1.16 g of 4-tribromophenol and 2.48 g of potassium carbonate and stirred at 120° C. for 1.5 hours. After the completion of the reaction, the mixture was added with toluene, and the organic layer was washed with water and a saturated saline solution, and dried with anhydrous sodium sulfate. A solvent is distilled off, and the residue was purified by column chromatography (silica gel, hexane/ethyl acetate=7/1), thereby obtaining 1.31 g of the title compound as a colorless viscous liquid. A yield was 64.5%.

$^1$HNMR (400 MHz, CDCl$_3$) δ: 7.66 (d, J=8.7 Hz, 2H), 7.53 (d, J=8.5 Hz, 1H), 7.38 (d, J=2.4 Hz, 1H), 7.20 (dd, J=8.5, 2.4 Hz, 1H), 7.13 (d, J=8.7 Hz, 2H), 2.59 (s, 3H).

Synthesis of 2-(2-(trifluoromethyl)-4-(4-(trifluoromethyl)phenoxy)phenyl)-2-methyl oxoacetate 1.30 g of 1-(2-triflouromethyl)-4-(4-(trifluoromethyl)phenoxy)phenyl)ethan-1-on obtained in the preceding paragraph was weighed and 15 mL of DMSO were added to and dissolved in a 100 ml eggplant flask. The mixture was added with 3.03 g of iodine and stirred at 100° C. for 0.5 hours in an oil bath. After the completion of the reaction, the mixture was cooled to 60° C., added with 3.61 g of potassium carbonate, and stirred at 100° C. for 0.5 hours. The mixture was cooled to 35° C., added with 0.75 mL of iodomethane, and stirred at 35° C. for 2 hours. After the completion of the reaction, a saturated sodium sulfite aqueous solution and toluene were added to the mixture, and the precipitated solution was filtrated with celite. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 0.755 g of the title compound as a light yellow liquid. A yield was 51.6%.

$^1$HNMR (400 MHz, CDCl$_3$) δ: 7.70 (d, J=8.9 Hz, 2H), 7.69 (d, J=8.7 Hz, 1H), 7.40 (d, J=2.3 Hz, 1H), 7.23-7.17 (m, 3H), 3.95 (s, 3H).

Synthesis of 2-hydroxy-2-(2-(trifluoromethyl)-4-(4-(trifluoromethyl)phenoxy)phenyl) methyl propionate After 0.386 g of 2-(2-(trifluoromethyl)-4-(4-(trifluoromethyl)phenoxy)phenyl)-2-methyl oxoacetate obtained in the preceding paragraph was dissolved in 4 mL of dichloroethane and cooled to −15° C., the mixture was dropped with 1.4 mL (1.4 M) of a trimethylaluminum-hexane solution for 10 minutes. After the mixture was stirred at the same temperature for 30 minutes, the mixture was added with a hydrochloric acid aqueous solution and extracted with chloroform. After the organic layer was washed with hydrochloric acid, water, and a saturated saline solution, the organic layer was dried with anhydrous sodium sulfate, and the solvent was distilled off. 0.392 g of the title compound was obtained as a colorless liquid by vacuum drying.

Synthesis of 2-(2-(trifluoromethyl)-4-(4-(trifluoromethyl)phenoxy)phenyl)methyl acrylate 0.392 g of 2-hydroxy-2-(2-(trifluoromethyl)-4-(4-(trifluoromethyl)phenoxy)phenyl)methyl propionate obtained in the preceding paragraph was dissolved in 5 mL of toluene, and the mixture was added with 94.8 mg of p-toluenesulfonic acid monohydrate and refluxed for 1 hour. The mixture was added with 91.8 mg of p-toluenesulfonic acid monohydrate for 1 hour, 0.5 g of molecular sieves 4A for 30 minutes, and 109 mg of p-toluenesulfonic acid monohydrate for 1 hour, and refluxed for 1 hour. After the completion of the reaction, a solid matter was removed by filtration and the mixture was washed with a sodium hydrogen carbonate aqueous solution, water and a saturated saline solution. After the organic layer was dried with anhydrous sodium sulfate, the solvent was distilled off and the residue was purified by column chromatography (silica gel, hexane/ethyl acetate=10/1), thereby obtaining 0.258 g of the title compound as a colorless liquid. A yield was 68.8%.

$^1$HNMR (400 MHz, CDCl$_3$) δ: 7.64 (d, J=8.8 Hz, 2H), 7.35 (d, J=2.5 Hz, 1H), 7.27 (d, J=8.4 Hz, 1H), 7.17 (dd, J=8.4, 2.5 Hz, 1H), 7.12 (d, J=8.8 Hz, 2H), 6.62 (s, 1H), 5.79 (s, 1H), 3.77 (s, 1H).

Synthesis of 2-(2-(trifluoromethyl)-4-(4-(trifluoromethyl)phenoxy)phenyl)oxirane-2-methyl carboxylate After 0.250 g of methyl 2-(2-(trifluoromethyl)-4-(4-(trifluoromethyl)phenoxy)phenyl)methyl acrylate synthesized in the preceding paragraph was dissolved in 1.6 mL of acetonitrile and 1.6 mL of methanol and cooled in an ice bath, the mixture was added with 184 mg of hydrogen peroxide-urea adduct and 89.2 mg of potassium carbonate and stirred at a room temperature for 6.5 hours. After the completion of the reaction, the mixture was added with 2N hydrochloric acid and extracted with ethyl acetate. After the organic layer was washed with water and a saturated saline solution, the solvent was distilled off. The residue was purified by column chromatography (silica gel, hexane/ethyl acetate=7/1), thereby obtaining 0.239 g of the title compound as a colorless liquid. A yield was 91.7%.

$^1$HNMR (400 MHz, CDCl$_3$) δ: 7.64 (d, J=8.6 Hz, 2H), 7.63 (d, J=8.6 Hz, 1H), 7.33 (d, J=2.5 Hz, 1H), 7.20 (dd, J=8.6, 2.5 Hz, 1H), 7.12 (d, J=8.6 Hz, 2H), 3.76 (s, 3H), 3.66 (d, J=6.2 Hz, 1H), 3.06 (d, J=6.2 Hz, 1H).

Synthesis of 2-hydroxy-3-(1H-1,2,4-triazole-1-yl)-2-(2-(trifluoromethyl)-4-(4-trifluorometh yl)phenoxy)phenyl)methyl propionate (Compound I-128)

0.230 g of 2-(2-(trifluoromethyl)-4-(4-(trifluoromethyl)phenoxy)phenyl)oxirane-2-methyl carboxylate obtained in the preceding paragraph was dissolved in 2 mL of DMF, and the mixture was added with 51.7 mg of triazol and 39.4 mg of triazole sodium and stirred at 50° C. for 3 hours and at 60° C. for 3 hours. After the completion of the reaction, the mixture was added with a saturated ammonium chloride aqueous solution and extracted with ethyl acetate. The organic layer was washed with water and a saturated saline solution, and then dried with anhydrous sodium sulfate. A solvent is distilled off, and the residue was purified by column chromatography (silica gel, hexane/ethyl acetate=1/3), thereby obtaining 0.187 g of the title compound as a white solid. A yield was 69.5%.

$^1$HNMR (400 MHz, CDCl$_3$) δ: 8.12 (s, 1H), 7.89 (s, 1H), 7.70-7.64 (m, 3H), 7.45 (d, J=2.7 Hz, 1H), 7.13 (dd, J=9.0, 2.7 Hz, 1H), 7.10 (d, J=9.0 Hz, 2H), 5.09 (d, J=14.1 Hz, 1H), 4.74 (s, 1H), 4.73 (d, J=14.1 Hz, 1H), 3.81 (s, 3H).

Synthesis Example 40. Synthesis of Compound I-40

Synthesis of 1-(4-(4-bromo-3-fluorophenoxy)-2-chlorophenyl)ethan-1-on 1.30 g of 2-chloro-4-fluoroacetophenone was dissolved in 10 ml of DMF, and the mixture was added with 1.60 g of 4-bromo-3-fluorophenol and 3.17 g of potassium carbonate and stirred at 80° C. for 3 hour. After the completion of the reaction, the mixture was added with toluene, and the organic layer was washed with water and a saturated saline solution, and dried with anhydrous sodium sulfate. A solvent is distilled off, and the residue was purified by column chromatography (silica gel, hexane/ethyl acetate=9/1), thereby obtaining 2.03 g of the title compound as a colorless viscous liquid. A yield was 78.3%.

$^1$HNMR (400 MHz, CDCl$_3$) δ: 7.65 (d, J=8.6 Hz, 1H), 7.56 (dd, J=8.8, 8.0 Hz, 1H), 7.03 (d, J=2.4 Hz, 1H), 6.94 (dd, J=8.6, 2.4 Hz, 1H), 6.84 (dd, J=9.2, 2.7 Hz, 1H), 6.77 (ddd, J=8.8, 2.7, 0.9 Hz, 1H), 2.66 (s, 3H).

Synthesis of 2-(4-(4-bromo-3-fluorophenoxy)-2-chlorophenyl)-2-methyl oxoacetate 2.01 g of 1-4-(4-bromo-3-fluorophenoxy)-2-chlorophenyl)ethan-1-on obtained in the preceding paragraph was added to and dissolved in 11.5 mL of DMSO. The mixture was added with 4.74 g of iodine and stirred at 100° C. for 0.5 hours in an oil bath. After the completion of the reaction, the mixture was cooled to 60° C., added with 56.8 g of potassium carbonate, and stirred at 100° C. for 0.5 hours. The mixture was cooled to 35° C., added with 1.2 mL of iodomethane, and stirred at 35° C. for 2.5 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 1.36 g of the title compound as a light yellow liquid. A yield was 59.8%.

$^1$HNMR (400 MHz, CDCl$_3$) δ: 7.83 (d, J=8.6 Hz, 1H), 7.59 (dd, J=8.7, 7.8 Hz, 1H), 7.02 (d, J=2.3 Hz, 1H), 6.99 (dd, J=8.6, 2.3 Hz, 1H), 6.90 (dd, J=9.0, 2.7 Hz, 1H), 6.80 (ddd, J=8.7, 2.7, 1.2 Hz, 1H), 3.96 (s, 3H).

Synthesis of 2-(4-(4-bromo-3-fluorophenoxy)-2-(chlorophenyl)-2-hydroxy-3-(1H-1,2,4-triazol-1-yl) methyl propionate (Compound I-40)

1.11 g of 2-(4-(4-bromo-3-fluorophenoxy)-2-chlorophenyl)-2-methyl oxoacetate obtained in the preceding paragraph was dissolved in 6 ml of DMAc, and the mixture was added with 0.603 g of TMSOB and 0.345 g of triazole sodium and stirred at a room temperature for 30 minutes. The mixture was stirred in a bath of 50° C. for 2 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/3), thereby obtaining 0.365 g of the title compound as a light yellow solid. A yield was 27.2%.

$^1$HNMR (400 MHz, CDCl$_3$) δ: 8.01 (s, 1H), 7.88 (s, 1H), 7.52 (dd, J=8.7, 7.9 Hz, 1H), 7.45 (d, J=8.8 Hz, 1H), 7.02 (d, J=2.5 Hz, 1H), 6.86 (dd, J=8.8, 2.5 Hz, 1H), 6.81 (dd, J=9.3, 2.7 Hz, 1H), 6.72 (ddd, J=8.7, 2.7, 1.1 Hz, 1H), 5.03 (d, J=14.3 Hz, 1H), 4.94 (d, J=14.3 Hz, 1H), 4.88 (s, 3H), 3.80 (s, 3H).

Synthesis Example 41. Synthesis of Compound I-133

Synthesis of 1-(4-(3,4-difluorophenoxy)-2-(trifluoromethyl)phenyl)ethan-1-on 1.85 g of 2-trifluoromethyl-4-fluoroacetophenone was dissolved in 15 ml of DMAc, and the mixture was added with 1.40 g of 3,4-difluorophenol and 3.81 g of potassium carbonate and stirred at 90° C. for 1 hour. After the completion of the reaction, the mixture was added with toluene, and the organic layer was washed with water and a saturated saline solution, and dried with anhydrous sodium sulfate. The solvent was distilled off, and 2.75 g of the title compound was obtained as a colorless viscous liquid. A yield was 96.6%.

$^1$HNMR (400 MHz, CDCl$_3$) δ: 7.51 (d, J=8.5 Hz, 1H), 7.31 (d, J=2.5 Hz, 1H), 7.25-7.15 (m, 1H), 7.13 (dd, J=8.5, 2.5 Hz, 1H), 6.92 (ddd, J=10.7, 6.6, 2.9 Hz, 1H), 6.83-6.77 (m, 1H), 2.58 (s, 3H).

Synthesis of 2-(4-(3,4-difluorophenoxy)-2-(trifluoromethyl)phenyl)-2-methyl oxoacetate 2.73 g of 1-(4-(3,4-difluorophenoxy)-2-(trifluoromethyl)phenyl)ethan-1-on synthesized in the preceding paragraph was weighed and added with 35 ml of DMSO to be dissolved. The mixture was added with 6.91 g of iodine and stirred at 100° C. for 0.5 hours in an oil bath. After the completion of the reaction, the mixture was cooled to 60° C., added with 8.35 g of potassium carbonate, and stirred at 100° C. for 0.5 hours. The mixture was cooled to 35° C., added with 1.7 mL of iodomethane, and stirred at 35° C. for 2 hours. After the completion of the reaction, a saturated sodium sulfite aqueous solution and toluene were added to the mixture, and the precipitated solution was filtrated with celite. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 1.60 g of the title compound as a light yellow liquid. A yield was 51.3%.

$^1$HNMR (400 MHz, CDCl$_3$) δ: 7.67 (d, J=8.6 Hz, 1H), 7.34 (d, J=2.5 Hz, 1H), 7.28-7.20 (m, 1H), 7.15 (dd, J=8.6, 2.5 Hz), 6.96 (ddd, J=10.5, 6.6, 2.9 Hz, 1H), 6.87-6.82 (m, 1H), 3.95 (s, 3H).

Synthesis of 2-(4-(3,4-difluorophenoxy)-2-(trifluoromethyl)phenyl)methyl acrylate After 1.59 g of 2-(4-(3,4-difluorophenoxy)-2-(trifluoromethyl)phenyl)-2-methyl oxoacetate obtained in the preceding paragraph was dissolved in 17.6 mL of dichloroethane and cooled to −15° C., the mixture was dropped with 6.3 mL (1.4 M) of a trimethylaluminum-hexane solution for 6 minutes. After the mixture was stirred at the same temperature for 30 minutes, the mixture was added with a hydrochloric acid aqueous solution and extracted with chloroform. After the organic layer was washed with hydrochloric acid, water, and a saturated saline solution, the organic layer was dried with anhydrous sodium sulfate, and the solvent was distilled off.

This solution was dissolved in 15 mL of toluene, added with 426 mg of 98% sulfuric acid, and refluxed for 0.5 hours. After the completion of the reaction, this solution was dropped to a saturated sodium bicarbonate aqueous solution and washed with water and a saturated saline solution. After the organic layer was dried with anhydrous sodium sulfate, the solvent was distilled off and the residue was purified by column chromatography (silica gel, hexane/ethyl acetate=10/1), thereby obtaining 0.757 g of the title compound as a colorless liquid. A yield was 77.9%.

$^1$HNMR (400 MHz, CDCl$_3$) δ: 7.28 (d, J=2.5 Hz, 1H), 7.23 (d, J=8.4 Hz, 1H), 7.22-7.14 (m, 1H), 7.10 (dd, J=8.4, 2.5 Hz, 1H), 6.91 (ddd, J=10.9, 6.6, 2.9 Hz, 1H), 6.83-6.77 (m, 1H), 6.60 (d, J=1.0 Hz, 1H), 5.77 (d, J=1.0 Hz, 1H), 3.76 (s, 3H).

Synthesis of 2-(4-(3,4-difluorophenoxy)-2-(trifluoromethyl)phenyl)-2-hydroxy-3-(1H-1,2,4-triazol-1-yl)methyl propanoate (Compound I-133)

After 0.726 g of 2-(4-(3,4-difluorophenoxy)-2-(trifluoromethyl)phenyl)methyl acrylate synthesized in the preceding paragraph was dissolved in 4.6 mL of acetonitrile and 4.6 mL of methanol and cooled in an ice bath, the mixture was added with 532 mg of hydrogen peroxide-urea adduct and 258 mg of potassium carbonate and stirred at a room temperature for 7 hours. After the completion of the reaction, the mixture was added with 2N hydrochloric acid and extracted with ethyl acetate. After the organic layer was washed with water and a saturated saline solution, the organic layer was dried with anhydrous sodium sulfate, and the solvent was distilled off. This solution was dissolved in 5 mL of DMF, added with 130 mg of triazole and 170 mg of triazole sodium, and stirred at 60° C. for 5 hours. After the completion of the reaction, the mixture was added with a saturated ammonium chloride aqueous solution and extracted with ethyl acetate. The organic layer was washed with water and a saturated saline solution, and then dried with anhydrous sodium sulfate. A solvent is distilled off, and the residue was purified by column chromatography (silica gel, hexane/ethyl acetate=1/3), thereby obtaining 0.187 g of the title compound as a white solid. A yield was 79.4%.

$^1$HNMR (400 MHz, CDCl$_3$) δ: 8.11 (s, 1H), 7.88 (s, 1H), 7.64 (d, J=8.9 Hz, 1H), 7.38 (d, J=2.7 Hz, 1H), 7.22-7.15 (m, 1H), 7.06 (dd, J=8.9, 2.7 Hz, 1H), 6.89 (ddd, J=10.7, 6.6, 2.9 Hz, 1H), 5.08 (d, J=14.1 Hz, 1H), 4.76 (s, 1H), 4.72 (d, J=14.1 Hz, 1H), 3.79 (s, 3H).

Synthesis Example 42. Synthesis of Compound IIIc-4

Synthesis of 1-(2-chloro-4-(quinolin-6-yloxy)phenyl)ethan-1-on 1.01 g of 2-chloro-4-fluoroacetophenone was dissolved in 10 ml of NMP, and the mixture was added with 1.02 g of 6-quinolinol and 2.46 g of potassium carbonate and stirred at 80° C. for 3.5 hours. After the completion of the reaction, the mixture was added with toluene, and the organic layer was washed with a 2N sodium hydroxide aqueous solution, water, and a saturated saline solution, and dried with anhydrous sodium sulfate. A solvent is distilled off, and the residue was purified by column chromatography (silica gel, hexane/ethyl acetate=2/3), thereby obtaining 1.19 g of the title compound as a colorless viscous liquid. A yield was 68.1%.

$^1$HNMR (400 MHz, CDCl$_3$) δ: 8.91 (dd, J=4.2, 1.7 Hz, 1H), 8.16 (d, J=9.1 Hz, 1H), 8.09 (dd, J=8.4, 1.7 Hz, 1H), 7.68 (d, J=8.6 Hz, 1H), 7.48 (dd, J=9.1, 2.7 Hz, 1H), 7.43 (dd, J=8.4, 4.2 Hz, 1H), 7.39 (d, J=2.7 Hz, 1H), 7.08 (d, J=2.4 Hz, 1H), 6.99 (dd, J=8.6, 2.4 Hz, 1H), 2.67 (s, 3H).

Synthesis of 2-(2-chloro-4-(quinolin-6-yloxy)phenyl)-2-methyl oxoacetate 1.18 g of 1-(2-chloro-4-(quinolin-6-yloxy)phenyl)ethan-1-on obtained in the preceding paragraph is added to and dissolved in 15 mL of DMSO. The mixture was added with 3.24 g of iodine and stirred at 100° C. for 0.5 hours in an oil bath. After the completion of the reaction, the mixture was cooled to 60° C., added with 3.84 g of potassium carbonate, and stirred at 100° C. for 0.5 hours. The mixture was cooled to 35° C., added with 0.8 mL of iodomethane, and stirred at 35° C. for 3 hours. After the completion of the reaction, excess iodine was quenched with saturated sodium sulfite aqueous solution, toluene was added, and the precipitated solution was filtrated with celite. The filtered solid was decanted with toluene and added to the previous solution. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=1/3), thereby obtaining 242 mg of the title compound as a light orange liquid. A yield was 17.8%.

Synthesis of 2-(2-chloro-4-(quinolin-6-yloxy)phenyl)-2-hydroxy-3-(1H-1,2,4-triazol-1-yl)methyl propionate (Compound IIIc-4)

239 mg of 2-(2-chloro-4-(quinolin-6-yloxy)phenyl)-2-methyl oxoacetate obtained in the previous process was dissolved in 2.1 ml of DMAc, and the mixture was added with 148 mg of TMSOB and 83.1 mg of triazole sodium and stirred at a room temperature for 30 hours. The mixture was stirred in a bath of 50° C. for 6 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate and then the solvent was distilled off, and the residue was purified by column chromatography (silica gel, chloroform/methanol=20/1) and then is re-crystallized from ethyl acetate, thereby obtaining 37.4 mg of the title compound as a white solid. A yield was 12.6%.

$^1$HNMR (400 MHz, CDCl$_3$) δ: 8.89 (dd, J=4.2, 1.7 Hz, 1H), 8.13 (d, J=9.1 Hz, 1H), 8.08 (d, J=8.3 Hz, 1H), 8.02 (s, 1H), 7.90 (s, 1H), 7.46 (dd, J=9.1, 2.7 Hz, 1H), 7.45 (d, J=8.8 Hz, 1H), 7.42 (dd, J=8.3, 4.2 Hz, 1H), 7.33 (d, J=2.7 Hz, 1H), 7.07 (d, J=2.5 Hz, 1H), 6.91 (dd, J=8.8, 2.5 Hz, 1H), 5.04 (d, J=14.1 Hz, 1H), 4.97 (s, 1H), 4.97 (d, J=14.3 Hz, 1H), 3.81 (s, 3H).

Synthesis Example 43. Synthesis of Compound IIId-1

Synthesis of 1-(2-chloro-4-(naphthalen-1-yloxy)phenyl)ethan-1-on 1.20 g of 2-trifluoromethyl-4-fluoroacetophenone was dissolved in 10 ml of NMP, and the mixture was added with 1.21 g of 1-naphthol and 2.96 g of cesium carbonate and stirred at 100° C. for 4 hours. After the completion of the reaction, the mixture was added with toluene, and the organic layer was washed with water and a saturated saline solution, and dried with anhydrous sodium sulfate. The solvent was distilled off, and 1.37 g of the title compound was obtained as a light orange solid. A yield was 58.7%.

$^1$HNMR (400 MHz, CDCl$_3$) δ: 7.99 (d, J=8.3 Hz, 1H), 7.92 (d, J=8.2 Hz, 1H), 7.75 (d, J=8.3 Hz, 1H), 7.63 (d, J=8.7 Hz, 1H), 7.57-7.44 (m, 3H), 7.14 (dd, J=7.5, 0.8 Hz, 1H), 7.01 (d, J=2.4 Hz), 6.89 (dd, J=8.7, 2.4 Hz), 2.64 (s, 3H).

Synthesis of 2-(2-chloro-4-(naphthalen-1-yloxy)phenyl)-2-methyl oxoacetate 1.36 g of 1-(2-chloro-4-(naphthalen-1-yloxy)phenyl)ethan-1-on obtained in the preceding paragraph was weighed and added with 15 mL of DMSO to be dissolved. The mixture was added with 3.48 g of iodine and stirred at 100° C. for 0.5 hours in an oil bath. After the completion of the reaction, the mixture was cooled to 60° C., added with 4.09 g of potassium carbonate, and stirred at 100° C. for 0.5 hours. The mixture was cooled to 35° C., added with 0.95 ml of iodomethane, and stirred at 35° C. for 3 hours. After the completion of the reaction, a saturated sodium sulfite aqueous solution and toluene were added to the mixture, and the precipitated solution was filtrated with celite. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=7/1), thereby obtaining 1.07 g of the title compound as a light yellow solid. A yield was 69.0%.

$^1$HNMR (400 MHz, CDCl$_3$) δ: 7.92 (d, J=8.3 Hz, 2H), 7.80 (d, J=8.7 Hz, 1H), 7.79 (d, J=8.3 Hz, 1H), 7.58-7.47 (m, 3H), 7.18 (d, J=7.5 Hz, 1H), 6.99 (d, J=2.4 Hz, 1H), 6.95 (dd, J=8.7, 2.4 Hz, 1H), 3.94 (s, 3H).

Synthesis of 2-(2-chloro-4-(naphthalen-1-yloxy)phenyl)-2-hydroxy-3-(1H-1,2,4-triazol-1-yl) methyl propionate (compound IIId-1)

2-(2-chloro-4-(naphthalen-1-yloxy)phenyl)-2-methyl oxoacetate obtained in the preceding paragraph was dissolved in 6 ml of DMAc, and the mixture was added with 0.641 g of TMSOB and 0.368 g of triazole sodium and stirred at a room temperature for 30 minutes. The mixture was stirred in a bath of 50° C. for 3 hours. After the completion of the reaction, the mixture was added with a saturated ammonium chloride aqueous solution and extracted with ethyl acetate. The organic layer was washed with water three times and then washed with a saturated saline solution. After the organic layer was dried with anhydrous sodium sulfate, the solvent was distilled off and the residue was purified by column chromatography (silica gel, hexane/ethyl acetate=1/3), thereby obtaining 0.368 g of the title compound as a white solid. A yield was 27.9%.

$^1$HNMR (400 mHz, CDCl$_3$) δ: 8.02 (brd, J=8.0 Hz, 1H), 8.01 (s, 1H), 7.99 (brd, J=9.3 Hz, 1H), 7.88 (s, 1H), 7.70 (d, J=8.3 Hz, 1H), 7.57-7.47 (m, 2H), 7.44 (dd, J=8.1, 7.7 Hz, 1H), 7.39 (d, J=8.8 Hz, 1H), 7.01 (d, J=2.5 Hz, 1H), 6.86 (dd, J=8.8, 2.5 Hz, 1H), 5.02 (d, J=14.2 Hz, 1H), 4.92 (d, J=14.2 Hz, 1H), 4.86 (s, 1H), 3.79 (s, 3H).

Synthesis Example 44. Synthesis of Compound IIIf-2

Synthesis of 1-(6-(4-chlorophenoxy)pyridine-3-yl)ethan-1-on 0.998 g of 2-chloro-5-acetyl pyridine commercially available was dissolved in 13 ml of DMF, and the mixture was added with 0.908 g of 4-chlorophenol and 2.51 g of potassium carbonate and stirred in an oil bath of 80° C. for 1.5 hours. After the completion of the reaction, the mixture was added with ethyl acetate, and the organic layer was washed with a sodium hydroxide aqueous solution, water, and a saturated saline solution and dried with anhydrous sodium sulfate. A solvent is distilled off, and the residue was purified by column chromatography (silica gel, chloroform/ethyl acetate=50/1), thereby obtaining 1.33 g of the title compound as a colorless liquid. A yield was 83.9%.

$^1$HNMR (400 MHz, CDCl$_3$) δ: 8.74 (d, J=2.3 Hz, 1H), 8.29 (dd, J=8.7, 2.3 Hz, 1H), 7.40 (d, J=8.8 Hz, 2H), 7.10 (d, J=8.8 Hz, 2H), 7.00 (d, J=8.7 Hz, 1H), 2.57 (s, 3H).

Synthesis of 2-(6-(4-chlorophenoxy)pyridine-3-yl)-2-methyl oxoacetate 1.00 g of 1-(6-(4-chlorophenoxy)pyridine-3-yl)ethan-1-on synthesized in the preceding paragraph was weighed and was added with 6 ml of DMSO to be dissolved. The mixture was added with 3.26 g of iodine and stirred at 100° C. for 0.5 hours in an oil bath. After the completion of the reaction, the mixture was cooled to 60° C., added with 3.93 g of potassium carbonate, and stirred at 100° C. for 0.5 hours. The mixture was cooled to 35° C., added with 0.303 mL of iodomethane, and stirred at 35° C. for 2.5 hours. After the completion of the reaction, a saturated sodium sulfite aqueous solution and toluene were added to the mixture, and the precipitated solution was filtrated with celite. The organic layer of the solution was separated and a water layer was extracted with toluene. The organic layers were combined and washed with water and a saturated saline solution. The organic layers were dried with anhydrous sodium sulfate, and the solvent was distilled off. The residue was purified by column chromatography (silica gel, hexane/ethyl acetate=5/1), thereby obtaining 0.156 g of the title compound as a light yellow solid. A yield was 51.3%.

$^1$HNMR (400 MHz, CDCl$_3$) δ: 8.88 (dd, J=2.4, 0.7 Hz, 1H), 8.38 (dd, J=8.7, 2.4 Hz, 1H), 7.39 (d, J=8.9 Hz, 2H), 7.11 (d, J=8.9 Hz), 7.04 (dd, J=8.7, 0.7 Hz, 1H), 3.97 (s, 3H).

Synthesis of 2-(6-(4-chlorophenoxy)pyridine-3-yl)methyl acrylate 24.7 mg of sodium hydride was weighed in a 20 mL eggplant flask, decantated with hexane, and suspended in 1 mL of DMSO After the mixture was added with 0.270 mg of methyltriphenylphosphine iodide, and stirred at a room temperature for 30 minutes, 0.148 g of methyl 2-(6-(4-chlorophenoxy)pyridin-3-yl)-2-oxoacetate synthesized in the preceding paragraph was dissolved in 1.5 mL of DMSO and dropped for 2 minutes, and the mixture was stirred at a room temperature for 3 hours After the completion of the reaction, the mixture was added with a 1 mol/L hydrochloric acid and extracted with ethyl acetate. The organic layer was washed with water and a saturated salt solution and dried with anhydrous sodium sulfate. A solvent is distilled off, and the residue was purified by column chromatography (silica gel, hexane/ethyl acetate=5/1), thereby obtaining 55.1 mg of the title compound as a colorless liquid. A yield was 37.6%.

$^1$HNMR (400 MHz, CDCl$_3$) δ: 8.20 (d, J=2.5 Hz, 1H), 7.79 (dd, J=8.6, 2.5 Hz, 1H), 7.36 (d, J=8.7 Hz, 2H), 7.09 (d, J=8.7 Hz, 2H), 6.92 (d, J=8.6 Hz, 1H), 6.43 (d, J=0.6 Hz, 1H), 5.92 (d, J=0.6 Hz, 1H), 3.83 (s, 3H).

Synthesis of 2-(6-(4-chlorophenoxy)pyridine-3-yl) oxirane-2-methyl carboxylate 55.1 mg of 2-(6-(4-chlorophenoxy)pyridin-3-yl)methyl acrylate synthesized in the preceding paragraph was dissolved in 0.5 mL of acetonitrile and 0.5 mL of methanol, and the mixture was added with 56.7 mg of hydrogen peroxide-urea adduct (UHP) and 25.9 mg of potassium carbonate under ice bath cooling and stirred at a room temperature for 3 hours. After the completion of the reaction, the mixture was added with an ammonium chloride aqueous solution and then extracted with ethyl acetate. After the organic layer was washed with water and a saturated saline solution, the organic layer was dried with anhydrous sodium sulfate, and the solvent was distilled off. A solvent is distilled off, and the residue was purified by column chromatography (silica gel, hexane/ethyl acetate=3/1), thereby obtaining 28.7 mg of the title compound as a colorless liquid. A yield was 49.4%.

$^1$HNMR (400 MHz, CDCl$_3$) δ: 8.31 (d, J=2.5, 0.7 Hz, 1H), 7.85 (dd, J=8.6, 2.5 Hz, 1H), 7.36 (d, J=8.9 Hz, 2H), 7.09 (d, J=8.9 Hz, 2H), 6.93 (dd, J=8.6, 0.7 Hz, 1H), 3.80 (s, 3H), 3.46 (d, J=6.3 Hz, 1H), 2.97 (d, J=6.3 Hz, 1H).

Synthesis of 2-(6-(4-chlorophenoxy)pyridine-3-yl)-2-hydroxy-3-(1H-1,2,4-triazol-1-yl)methyl propionate (compound IIIf-2)

28.7 mg of 2-(6-(4-chlorophenoxy)pyridine-3-yl)oxirane-2-carboxylate synthesized in the preceding paragraph was dissolved in 0.5 ml of DMF, and the mixture was added with 7.4 mg of triazole and 9.6 mg of triazole sodium and stirred at 50° C. for 40 minutes. After the completion of the reaction, the mixture was added with a saturated ammonium chloride aqueous solution and extracted with ethyl acetate. The organic layer was washed with water and a saturated saline solution, and then dried with anhydrous sodium sulfate. A solvent is distilled off, and the residue was purified by column chromatography (silica gel, hexane/ethyl acetate=1/5), thereby obtaining 23.7 mg of the title compound as a white solid. A yield was 67.4%.

$^1$HNMR (400 MHz, CDCl$_3$) δ: 8.47 (d, J=2.5, 0.6 Hz, 1H), 8.18 (s, 1H), 8.01 (dd, J=8.7, 2.5 Hz, 1H), 7.91 (s, 1H), 7.37 (d, J=8.9 Hz, 2H), 7.08 (d, J=8.9 Hz, 2H), 6.96 (dd, J=8.7, 0.6 Hz, 1H), 4.99 (d, J=14.0 Hz, 1H), 4.45 (s, 1H), 4.40 (d, J=14.0 Hz, 1H), 3.84 (s, 3H).

Synthesis Example 45. Synthesis of Compound I-63

Synthesis of methyl 2-(2-chloro-4-(4-chlorophenoxy)phenyl)-2-methoxy-3-(1H-1,2,4-triazol-1-yl) propinate (I-63)

After 2-(2-chloro-4-(4-chlorophenoxy)phenyl)2-hydroxy-3-(1H-1,2,4-triazol-1-yl)propinate synthesized in the Synthesis Example 11 was dissolved in 1 ml of DMF, the mixture was added with cesium carbonate and iodomethane and stirred. After 3 hours, the mixture was added with saturated ammonium chloride aqueous solution and extracted with chloroform. The extract was washed with water and washed with saturated saline solution. After the extract was dried with anhydrous sodium sulfate, a solvent was distilled off to obtain a brown liquid crude product of azole. By purification by column chromatography (silica gel, hexane/ethyl acetate=9/1®0/1), the title compound was obtained.

$^1$HNMR (400 MHz, CDCl$_3$) δ: 7.71 (s, 1H), 7.67 (s, 1H), 7.33 (d, J=9.2 Hz, 2H), 7.10 (d, J=8.8 Hz, 1H), 6.99-6.94 (m, 3H), 6.71 (dd, J=8.8, 2.8 Hz, 1H), 5.03 (d, J=15.2 Hz, 1H), 4.99 (d, J=14.8 Hz, 1H), 3.85 (s, 3H), 3.53 (s, 3H).

Synthesis Example 46. Synthesis of Compound I-440

Synthesis of N-benzyl-2-(2-chloro-4-(4-chlorophenoxy)phenyl)-2-hydroxy-3-(1H-1,2,4-triazol-1-yl) propanamide (I-440)

After 91 mg of compound (I-1) synthesized in Synthesis Example 5 was dissolved in 1 mL of DMF, the mixture was added with 30 mg of benzylamine, 77 mg of 4-(4,6-dimethoxy-1,3,5-triazin-2-yl)-4-methyl morpholinium chloride hydrate (DMT-MM) and left at a room temperature for 12 hours and then stirred for 12 hours and left for 12 hours again. After a solvent is distilled off, the mixture was added with water and extracted with chloroform, dried with anhydrous sodium sulfate, the crude product obtained by distilling off the solvent was purified by column chromatography (silica gel, chloroform:methanol=39:1) to obtain 12.2 mg of the title compound as a colorless solid. A yield was 12%.

$^1$HNMR (400 MHz, CDCl$_3$) δ: 8.24 (s, 1H), 7.95 (t, J=6 Hz, 1H), 7.73 (s, 1H), 7.48 (d, J=2.2 Hz, 2H), 7.44 (d, J=8.8 Hz, 1H), 7.28 (t, J=7.0 Hz, 2H), 7.22 (d, J=7.4 Hz, 2H), 7.21 (t, J=9.3 Hz, 1H), 7.08 (d, J=2.5 Hz, 1H), 7.04 (d, J=8.9 Hz, 2H), 6.86 (dd, J=8.8, 2.5 Hz, 1H), 6.80 (s, 1H), 5 (d, J=14.3 Hz, 1H), 4.91 (d, J=14.4 Hz, 1H), 4.28 (dd, J=14.9, 6.3 Hz, 1H), 4.20 (dd, J=15, 5.9 Hz, 1H).

Synthesis Example 47. Synthesis of Compound I-64

Synthesis of methyl 2-acetoxy-2-(2-chloro-4-(4-chlorophenoxy)phenyl)-3-(1H-1,2,4-triazol-1-yl) propanoate (I-1)

83.0 mg of compound (I-1) synthesized in Synthesis Example 5 and 0.2 mL of pyridine were added to and dissolved in 10 mL eggplant flask, and 28 of acetyl chloride was added and stirred. After 6 hours, the mixture was added with 2.8 mg of N,N-dimethylaminopyridine and continuously stirred. After 5 hours, the mixture was added with a saturated ammonium chloride aqueous solution to stop the reaction and extracted with toluene three times. The extract was washed with water once and was washed with a saturated saline solution once. After the extract was dried with anhydrous sodium sulfate, a solvent was distilled off to obtain 107 mg of brown liquid crude product. By purification by column chromatography (silica gel, chloroform:ethyl acetate=72:28→21:79), 7.7 mg of the title compound was obtained as a white solid. A yield was 5.6%.

$^1$HNMR (400 MHz, CDCl$_3$) δ: 7.81 (s, 1H), 7.54 (s, 1H), 7.34 (d, J=8.9 Hz, 2H), 7.28 (d, J=9.0 Hz, 1H), 7.00-6.94 (m, 3H), 6.77 (dd, J=9.0, 2.6 Hz, 1H), 5.38 (d, J=15.1 Hz, 1H), 5.28 (d, J=15.1 Hz, 1H), 3.84 (s, 3H), 2.24 (s, 3H).

Synthesis Example 48. Synthesis of Compound I-441

Synthesis of methyl 2-(2-chloro-4-(4-chlorophenoxy)phenyl)-2-((phenylcarbamoyl)oxy-3-(1H-1,2,4-triazol-1-yl)propanoate (compound I-441)

After 82.2 mg of compound (I-1) synthesized in Synthesis Example 5 and 0.2 mL of N,N-dimethylformamide were added to and dissolved in 10 mL eggplant flask, the mixture was added with 26 µL of phenyl isocyanate and stirred at a room temperature. After 7.5 hours, the mixture was added with a saturated ammonium chloride aqueous solution to stop the reaction and extracted with toluene three times. The extract was washed with water once and was washed with a saturated saline solution once. After the extract was dried with anhydrous sodium sulfate, a solvent was distilled off to obtain 114 mg of white solid crude product. By purification by column chromatography (chloroform:ethyl acetate=100:0→70:30), 16.1 mg of the title compound was obtained as a white solid. A yield was 15%.

$^1$HNMR (400 MHz, CDCl$_3$) δ: 7.79 (s, 1H), 7.77 (s, 1H), 7.44-7.31 (m, 7H), 7.16-7.10 (m, 2H), 7.00-6.94 (m, 3H), 6.78 (br, 1H), 5.50 (d, J=15.1 Hz, 1H), 5.42 (d, J=15.1 Hz, 1H), 3.87 (s, 3H).

Synthesis Example 49. Synthesis of Compound I-442

Synthesis of methyl 2-((tert-butoxycarbonyl)oxy)-2-(2-chloro-4-(4-chlorophenoxy)phenyl)-3-(1H-1,2,4-triazol-1-yl)propanoate (Compound I-442)

81.6 mg of the compound (I-1) synthesized in Synthesis Example 5 was dissolved in 0.2 mL of N,N-dimethylformamide, and the mixture was added with 11.0 mg of sodium hydride, 92 µL of di-tert-butyl dicarbonate and 5.6 mg of dimethylaminopyridine and stirred at a room temperature for 0.5 hours. After the completion of the reaction, the mixture was added with a saturated ammonium chloride aqueous solution, extracted with toluene, and washed with water and a saturated saline solution. After the organic layer was dried with anhydrous sodium sulfate, the solvent was distilled off and the residue was purified by silica gel column chromatography (chloroform/ethyl acetate) to obtain 105 mg of the title compound as a colorless viscous liquid. A yield was 100%.

$^1$HNMR (400 MHz, CDCl$_3$) δ: 7.77 (s, 1H), 7.69 (s, 1H), 7.35 (d, J=9.0 Hz, 1H), 7.33 (d, J=8.9 Hz, 2H), 6.98-6.94 (m, 1H), 6.96 (d, J=8.9 Hz, 2H), 6.77 (dd, J=9.0, 2.6 Hz, 1H), 5.39 (d, J=15.1 Hz, 1H), 5.34 (d, J=15.1 Hz, 1H), 3.84 (s, 3H), 1.54 (s, 9H).

Synthesis Example 50. Synthesis of Compound I-54

Synthesis of methyl 2-((tert-butoxycarbonyl)oxy)-2-(2-chloro-4-(4-chlorophenoxy)phenyl)-3-(1H-1,2,4-triazol-1-yl)propanoate (Compound I-54)

75.0 mg of compound (I-1) synthesized in Synthesis Example 5 was weighed in a pressure-resistant reaction tube, and added with 4 mL of a 2 mol/L methylamine, and the mixture was reacted at 80° C. for 21 hours and at a room temperature for 8 days. After the completion of the reaction, the solvent and excess amine were distilled off under reduced pressure, and the residue was purified by silica gel column chromatography (chloroform/ethanol=15/1) to obtain 9.0 mg of the title compound as a colorless viscous liquid. A yield was 12%.

$^1$HNMR (400 MHz, CDCl$_3$) δ: 8.10 (s, 1H), 7.93 (s, 1H), 7.49 (d, J=8.8 Hz, 1H), 7.34 (d, J=8.9 Hz, 2H), 7.00 (d, J=2.6 Hz, 1H), 6.96 (d, J=8.9 Hz, 2H), 6.82 (dd, J=8.8, 2.6 Hz, 1H), 6.56 (brq, J=5.0 Hz, 1H), 5.38 (s, 1H), 5.12 (d, J=14.1 Hz, 1H), 5.04 (d, J=14.1 Hz, 1H), 2.78 (d, J=5.0 Hz, 3H).

Preparation Example

Hydrates and emulsions were formulated as follows using any synthesized azole derivative described here.

Preparation Example 1 (Wettable Agent)

21.4 parts of azole derivative
2 parts of sodium lauryl sulfate
5 parts of sodium salt of alkyl naphthalene sulfonic acid formalin condensate
0.2 parts of zinc stearate
3 parts of white carbon, and
68.4 parts of clay
were pulverized and mixed to prepare a wettable agent, which was used with diluted with water.

Preparation Example 2 (Emulsion)

5.4 parts of azole derivative
3.7 parts of Polyoxyalkylene alkyl ether.alkylbenzene sulfonic acid metal salt.alkylbenzene mixture
11.2 parts of polyoxyalkylene alkyl ether, and
47.8 parts of N,N-dimethyloctanamide.N,N-dimethyldecanamide
31.9 parts of soybean fatty acid methyl ester
were uniformly mixed and dissolved to prepare an emulsion.

Test Example 1: Antimicrobial Activity Test on Plant Pathogenic Germs

By the petri dish test, antimicrobial properties of compounds according to the present invention against various plant pathogenic germs were tested. A control compound A and a control compound B synthesized in the above production example were used as a control compound. The control compound A is a compound described in Patent Literature 1 and is represented by the following chemical formula (A). In addition, the control compound B is a compound described in Patent Literature 2 and is represented by the following chemical formula (B).

[Chemical Formula 23]

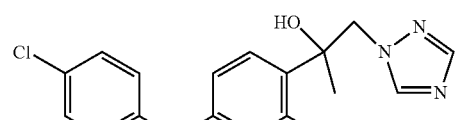

(A)

[Chemical Formula 24]

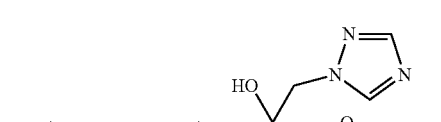

(B)

After autoclave sterilization, the compounds of the present invention were dissolved in dimethyl sulfoxide so as to have a predetermined agent concentration in a PDA medium (potato-dextrose-agar medium) which was cooled to about 60° C., and 1% (V/V) was added to the PDA medium. The compounds were mixed well so that the agent concentration was uniform in the PDA medium, and the medium was poured into the petri dish to prepare a plating medium containing the compounds according to the present invention.

On the other hand, flora of various plant pathogenic germs previously cultured on the PDA medium was punched out with a cork borer having a diameter of 4 mm and inoculated into the above-mentioned agent containing plating medium. After the culturing for a predetermined period of time and at a temperature in accordance with Table 2, the diameter of the flora on the agent-treated plate was measured. Compared to the diameter of the flora on an untreated flat plate containing no agent, a mycelium elongation inhibition rate (%) was calculated by the following Equation.

$$R=100(dc-dt)/dc$$

(In the above Equation, R=mycelium elongation inhibition rate (%), dc=flora diameter on untreated plate, dt=flora diameter on agent-treated plate)

The obtained results were evaluated in 5 stages according to the criteria shown in Table 9. The larger the antimicrobial index, the better the antimicrobial property.

TABLE 9

| Mycelium elongation inhibition rate | Antimicrobial index |
|---|---|
| 80% or more | 5 |
| Less than 80% and 60% or more | 4 |
| Less than 60% and 40% or more | 3 |
| Less than 40% and 20% or more | 2 |
| Less than 20% | 1 |

Test Example A: *Fusarium graminearum*

An antimicrobial test was carried out using *Fusarium graminearum* by the method described above. In the tested substance of 5 mg/L, any of the compounds I-1, I-122, I-228, I-334, I-20, I-21, I-23, I-25, I-24, I-47, I-48, I-7, I-29, I-236, I-130, I-234, I-128, I-40, I-133, and IIId-1 had an antimicrobial index of 5. In contrast, the control compound B had an antimicrobial index of 3. In addition, at 1.25 mg/L, the control compound A had an antimicrobial index of 4, while the compounds I-1, I-25, I-122, and I-130 had an antimicrobial index of 5.

Test Example B: *Pyrenophora teres*

An antimicrobial test was carried out using *Pyrenophora teres* by the method described above. In the tested substance of 5 mg/L, the control compound A had an antimicrobial index of 2, while the compounds I-1, I-228, I-3, I-27, I-29, I-236, and I-130 had an antimicrobial index of 5. At this time, the control compound B had an antimicrobial index of 2.

Test Example C: *Pyricularia oryzae*

An antimicrobial test was carried out using *Pyricularia oryzae* by the method described above. In the tested substance of 5 mg/L, any of the compounds I-1, I-122, I-228, I-334, I-20, I-21, I-23, I-25, I-26, I-52, I-27, I-28, I-47, I-48, I-7, I-29, I-31, I-236, I-130, II-1, and IIIc-1 had an antimicrobial index of 5. At this time, the control compound B had an antimicrobial index of 2. In addition, at 0.63 mg/L, the control compound A had an antimicrobial index of 3, while the compounds I-1, I-122, and 1-228 had an antimicrobial index of 5.

Test Example D: *Gaeumannomyces graminis*

An antimicrobial test was carried out using *Gaeumannomyces graminis* by the method described above. In the tested substance of 5 mg/L, any of the compounds I-1, I-122, I-228, I-334, I-2, I-5, I-18, I-19, I-20, I-21, I-23, I-24, I-25, I-26, I-52, I-27, I-28, I-47, I-48, I-7, I-29, I-35, I-33, I-31, I-236, I-130, II-1, IIIb-9, and IIIc-1 had an antimicrobial index of 5. In addition, at 0.08 mg/L, the control compound A had an antimicrobial index of 3 and the control compound B had an antimicrobial index of 1, while the compounds I-1, I-23, I-25, I-1222, I-128, I-27, I-29, I-236, and 1-130 had an antimicrobial index of 5.

Test Example E: *Ustilago nuda*

An antimicrobial test was carried out using *Ustilago nuda* by the method described above. In the tested substance of 5 mg/L, any of the compounds I-1, I-122, I-228, I-334, I-19, I-20, I-21, I-25, I-27, I-7, I-29, I-236, and 1-130 had an antimicrobial index of 5. At this time, the control compound B had an antimicrobial index of 1. In addition, at 1.25 mg/L, the control compound A had an antimicrobial index of 3, while the compounds I-1, I-122, I-228, I-334, I-236, and I-130 had an antimicrobial index of 5.

Test Example F: *Rhizoctonia solani*

An antimicrobial test was carried out using *Rhizoctonia solani* by the method described above. In the tested substance of 5 mg/L, any of the compounds I-5, I-6, I-22, I-334, I-27, I-236, and I-130 had an antimicrobial index of 5. At this time, the control compound B had an antimicrobial index of 2.

Test Example G: *Sclerotinia sclerotiorum*

An antimicrobial test was carried out using *Sclerotinia sclerotiorum* by the method described above. In the tested substance of 5 mg/L, any of the compounds I-1, I-122, I-228, I-334, I-18, I-20, I-21, I-23, I-25, I-26, I-27, I-47, I-48, I-7, I-29, I-33, I-31, I-236, I-130, and IIIc-1 had an antimicrobial index of 5. At this time, the control compound B had an antimicrobial index of 2.

Test Example H: *Microdochium nivale*

An antimicrobial test was carried out using *Microdochium nivale* by the method described above. In the tested substance of 5 mg/L, any of the compounds I-1, I-122, I-228, I-21, I-25, I-52, I-27, I-47, I-48, I-29, I-236, and I-130 had an antimicrobial index of 5. At this time, the control compound B had an antimicrobial index of 1.

Test Example I: *Gibberella fujikuroi*

An antimicrobial test was carried out using *Gibberella fujikuroi* by the method described above.

In the tested substance of 5 mg/L, any of the compounds I-1, I-122, I-228, I-334, I-19, I-20, I-21, I-23, I-25, I-26, I-27, I-47, I-48, I-7, I-29, I-31, I-236, I-130, and IIIc-1 had an antimicrobial index of 5. At this time, the control compound B had an antimicrobial index of 2.

Test Example J: *Zymoseptoria tritici*

An antimicrobial test was carried out using *zymoseptoria tritici* by the method described above. In the tested substance of 5 mg/L, any of the compounds I-1, I-122, I-228, I-334, I-20, I-21, I-52, I-47, I-7, I-29, I-236, I-130, and IIIc-1 had an antimicrobial index of 5. At this time, the control compound A had an antimicrobial index of 4 and the control compound B had an antimicrobial index of 1.

[Culture Temperature and Culture Day of Pathogenic Germs]

TABLE 10

| Abbreviation | Germ name | Culture temperature ion | Culture days (day) |
| --- | --- | --- | --- |
| F.g | *Fusarium graminearum* | 25 | 3 |
| p.t | *Pyrenophora teres* | 25 | 3 |
| p.o | *Pyricularia oryzae* | 25 | 7 |
| G.g | *Gaeumannomyces graminis* | 20 | 3 |
| U.n | *Ustilago nuda* | 25 | 7 |
| R.s | *Rhizoctonia solani* | 25 | 1 |
| M.n | *Microdochium nivale* | 25 | 3 |
| G.f | *Gibberella fujikuroi* | 25 | 3 |
| Z.t | *Zymoseptoria tritici* | 25 | 14 |

Test Example 2: *Puccinia* Recondite Control Effect Test

The compounds of the present invention were dissolved in acetone so as to have a predetermined agent concentration, and 5% (V/V) was added to ion exchanged water containing Gramin S (final concentration 60 ppm of Gramin S). The prepared liquid medicine was sprayed in a second leaf stage wheat (variety: agriculture No. 61) cultivated in a rectangular plastic pot (6 cm×6 cm) at a rate of 1000 L/ha (agent treated area). In addition, the untreated area was prepared in which ion exchanged water (final concentration of 60 ppm of Gramin S) containing 5% of acetone which did not contain the compound was sprayed to wheat. After the spraying, the spray solution on a wheat leaf was air-dried, and a spore fluid (adjusted to 200 spores/field of view, Gramin S of 60 ppm) of a *puccinia* recondite-causing germs was inoculated with spraying and kept for 48 hours under high humidity conditions of 25° C. Thereafter, the wheat leaf was managed in a greenhouse. On 14 days after the inoculation, a morbidity of the *puccinia* recondite was examined, and a control value was calculated by the following Equation.

Control value (%)=(1−average morbidity of agent treated area/average morbidity of untreated area)×100

In addition, the morbidity was determined based on the following Table 11.

TABLE 11

| Rust disease damage level scale from Mr. Peterson | |
| --- | --- |
| Morbidity | Pathogenic area ratio |
| 0 | Nonpathogenic one |
| 0.5 | One less than 1% |
| 1 | One 1% or more and less than 5% |
| 2 | One 5% or more and less than 10% |
| 3 | One 10% or more and less than 30% |
| 4 | One 30% or more and less than 50% |
| 5 | One 50% or more |

In the above tests, for example, at a concentration of 100 g/ha, any of the compounds I-1, I-122, I-228, I-334, I-2, I-5, I-20, I-22, I-23, I-25, I-26, I-19, I-52, I-27, I-28, I-47, I-48, I-29, I-31, II-1 and IIIb-9 had a control value of 70% or more.

In addition, at 3.13 g/ha, the control value of the compound I-1 was 73% and the control value of I-20 was 80%, while the control compound A was 20%.

Test Example 3: Cucumber Gray Mold Disease Control Effect Test

The compounds of the present invention were adjusted to a predetermined concentration (100 g/l) according to Test Example 2 in a cotyledon cucumber (variety: Sagami Hanjiro Cucumber) cultivated using a rectangular plastic pot (6 cm×6 cm), and sprayed at a ratio of 1,000 L/ha. After air-drying the spray leaves, a paper disc (8 mm in diameter) impregnated with the spore solution of gray mold fungi was placed and kept at 20° C. under high humidity conditions. On 4 days after the inoculation, a morbidity of cucumber gray mold disease was examined, and a control value was calculated by the following Equation.

Control value (%)=(1−average morbidity of sprayed area/average morbidity of unsprayed area)×100

In addition, the morbidity was determined based on the following Table 12.

TABLE 12

| Morbidity | Pathogenic area ratio |
| --- | --- |
| 0 | Nonpathogenic one |
| 0.5 | Pathological punctum area ratio less than 5% |
| 1 | Pathological punctum area ratio 5% or more and less than 10% |
| 2 | Pathological punctum area ratio 10% or more and less than 25% |
| 3 | Pathological punctum area ratio 25% or more and less than 50% |
| 4 | Pathological punctum area ratio 50% or more and less than 80% |
| 5 | Pathological punctum area ratio 80% or more |

In the above tests, for example, at a concentration of 100 g/ha, the control compound B had a control value of 0%, while any of the compounds I-1, I-122, I-228, I-334, I-20, and I-25 had a control value of 90% or more.

Test Example 4: Wheat Growth Influence by Seed Treatment and Control Effect Test on *Puccinia* Recondite The wheat growth influence by the seed treatment and the control effect on *puccinia* recondite were evaluated. After a compound dissolved in DMSO was smeared into wheat seed (variety: agriculture No. 61) in a plastic tube so that the throughput was 200 g ai/100 kg seeds, 20 g ai/100 kg seeds, or 2 g ai/100 kg seeds, 8-grain wheat seeds were seeded in a 80 cm² pot. The lower feedwater was managed in the greenhouse, a plant height of the wheat was examined 16 days after the seeding, a growth degree (%) against the wheat was examined by the following Equation, and the growth degree was calculated by the following Equation.

Growth degree (%)=(plant height in agent treated area/plant height in untreated area)×100

The results of the growth degree are shown in Table 13 below.

TABLE 13

| Compound | I-1 | Control compound A |
|---|---|---|
| Throughput (g ai/100 kg seeds) | 20 | 20 |
| Growth degree (%) | 100 | 90 |

The spore fluid of the *puccinia* recondite-causing germs (adjusted to 200 spores/field of view, Gramin S of 60 ppm) was inoculated by the spraying and kept for 48 hours under high humidity conditions of 25° C. Thereafter, it was managed in a greenhouse. On 11 days after the inoculation, the morbidity of the *puccinia* recondite was examined, and the control value was calculated by the following Equation. The morbidity was examined on the same scale as that of Test Example 2.

Control value (%)=(1−average morbidity of agent treated area/average morbidity of untreated area)×100

The results of the control value are shown in Table 14 below.

TABLE 14

| Compound | I-1 | Control compound A |
|---|---|---|
| Throughput (g ai/100 kg seeds) | 20 | 20 |
| Control value (%) | 99 | 86 |

As described above, Compound I-1 was superior in effect of controlling disease than the control compound A by the seed treatment. It was also found that the growth influence on wheat was weak and phytotoxicity was weak.

Test Example 5: Field Test of *Septoria Tritici*

The control effect test on the *Septoria tritici* was tested in the UK test field using the emulsion (prepared in accordance with Preparation Example 2) containing the compound (I-1) and the control compound A as the active ingredients. The amount of agent contained in each emulsion was adjusted to the amount shown in Table 15 and sprayed twice in with growth stages BBCH 31-32 and 37-39 (200 L/ha). The severity of flag leaf and second leaf was evaluated after 50 days lapsed after the second spraying. The control value was calculated from the average severity of the flag leaf and the second leaf.

Control value (%)=(1−average severity of treated area/average severity of untreated area)×100

The above results are shown in Table 15 below.

TABLE 15

| Trial compound | Dosage | Control value |
|---|---|---|
| Compound (I-1) | 150 | 93 |
| Compound (I-1) | 90 | 92 |
| Control compound A | 150 | 88 |

As described above, it was revealed that the emulsion containing the compound I-1 as the active ingredient had a higher control value for the *Septoria tritici* than the emulsion containing the control compound A as the active ingredient.

INDUSTRIAL APPLICABILITY

The azole derivative according to the present invention can be suitably used as an active ingredient of an agricultural and horticultural germicide, a plant growth regulator and a protective agent for industrial materials.

The invention claimed is:

1. A compound represented by Formula (I),

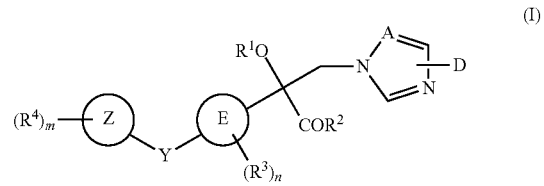

or an N-oxide or agrochemically acceptable salt thereof, wherein:

A is N;

D is a hydrogen, a halogen group, or $SR^D$;

where $R^D$ is a hydrogen, a cyano group, a $C_1$-$C_6$-alkyl group, a $C_1$-$C_6$-haloalkyl group, a $C_2$-$C_6$-alkenyl group, a $C_2$-$C_6$-haloalkenyl group, a $C_2$-$C_6$-alkynyl group or a $C_2$-$C_6$-haloalkynyl group;

$R^1$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, a phenyl-$C_2$-$C_4$-alkynyl group, or $COXR^5$;

where $R^5$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group;

X is a single bond, —O—, or —$NR^6$—;

$R^6$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group; and $R^5$ and $R^6$ may form a ring;

$R^2$ is —$OR^7$ or —$NR^8R^9$;

$R^7$, $R^8$ and $R^9$ are each independently a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group, and $R^8$ and $R^9$ may form a ring, where aliphatic groups in $R^1$, $R^2$, $R^5$, $R^6$, $R^7$, $R^8$, and $R^9$ may have 1, 2, 3 or the possible maximum number of the same or different groups $R^a$, and $R^a$ is independently selected from a halogen group, a cyano group, a nitro group, a $C_1$-$C_4$-alkoxy group, and a $C_1$-$C_4$-haloalkoxy group;

$R^4$ is a halogen group, a cyano group, a nitro group, an amino group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$;

the cycloalkyl group or phenyl group parts in $R^1$, $R^2$, $R^5$, $R^6$, $R^7$, $R^8$, and $R^9$, or the phenyl group part in $R^4$ may have 1, 2, 3, 4, 5, or the possible maximum number of the same or different groups $R^b$, and $R^b$ is independently selected from a halogen group, a cyano group, a nitro group, a $C_1$-$C_4$-alkyl group, a $C_1$-$C_4$-alkoxy group, a $C_1$-$C_4$-haloalkyl group, and a $C_1$-$C_4$-haloalkoxy group;

$R^3$ is a halogen group, a cyano group, a nitro group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, —$SOR^{10}$, or —$SF_5$;

where $R^{10}$ is a $C_1$-$C_4$-alkyl group or a $C_1$-$C_4$-haloalkyl group;

E is a phenyl group or a 6-membered heteroaromatic ring containing 1 or 2 N atoms;

n $R^3$ are bonded to any substitution sites;

when E is a phenyl group, then n is 0, 1, 2, 3, or 4, and when E is a 6-membered heteroaromatic ring containing 1 or 2 N atoms, then n is 0, 1, or 2;

Y is an oxygen atom, —$CH_2O$—, —$OCH_2$—, —NH—, —N(—$C_1$-$C_4$-alkyl)-, —N(—$C_3$-$C_6$-cycloalkyl)-, or —$S(O)_p$—, which bonds to any sites of E;

where p is 0, 1, or 2;

Z is an aromatic hydrocarbon group which is a phenyl group or a naphthyl group, or a 5-membered or 6-membered heteroaromatic ring or 9-membered or 10-membered heteroaromatic ring formed of 2 rings, containing 1 to 4 heteroatoms selected from O, N, and S; and m $R^4$ are bonded to any substitution sites;

when Z is a phenyl group, then m is 1, 2, 3, 4, or 5 and when Z is a naphthyl group or a heteroaromatic ring, then m is 0, 1, 2, 3, or 4.

2. The compound or the salt thereof according to claim 1, wherein in the general formula (I), $R^1$ is a hydrogen, a $C_1$-$C_6$-alkyl group, a $C_2$-$C_6$-alkenyl group, a $C_2$-$C_6$-alkynyl group, or $COXR^5$;

$R^2$ is —$OR^7$;

$R^5$ is a hydrogen, a $C_1$-$C_6$-alkyl group, a $C_2$-$C_6$-alkenyl group, or a $C_2$-$C_6$-alkynyl group;

$R^6$ is a hydrogen, a $C_1$-$C_6$-alkyl group, a $C_2$-$C_6$-alkenyl group, or a $C_2$-$C_6$-alkynyl group;

$R^3$ is a halogen group, a cyano group, a $C_1$-$C_4$-alkyl group, a $C_1$-$C_4$-haloalkyl group, a $C_1$-$C_4$-alkoxy group, —$SOR^{10}$, or —$SF_5$; and $R^4$ is a halogen group, a nitro group, a cyano group, an amino group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$.

3. The compound or the salt thereof according to claim 1, wherein in the general formula (I), $R^1$ is a hydrogen, a $C_1$-$C_6$-alkyl group, or $COXR^5$;

$R^5$ is a hydrogen, or $C_1$-$C_6$-alkyl group;

$R^6$ is a hydrogen;

$R^3$ is a halogen group, a cyano group, a $C_1$-$C_4$-alkyl group, a $C_1$-$C_4$-haloalkyl group, a $C_1$-$C_4$-alkoxy group, —$SOR^{10}$, or —$SF_5$; and $R^4$ is a halogen group, a nitro group, a cyano group, an amino group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —$SOR^{10}$, or —$SF_5$.

4. The compound or the salt thereof according to claim 1, wherein in the general formula (I), $R^1$ is a hydrogen, or a $C_1$-$C_6$-alkyl group;

$R^7$ is a $C_1$-$C_6$-alkyl group;

$R^3$ is a halogen group, a cyano group, a $C_1$-$C_4$-alkyl group, a $C_1$-$C_4$-haloalkyl group, or a $C_1$-$C_4$-alkoxy group; and $R^4$ is a halogen group, a cyano group, a $C_1$-$C_4$-alkyl group, a $C_1$-$C_4$-haloalkyl group, a $C_1$-$C_4$-alkoxy group, or a $C_1$-$C_4$-haloalkoxy group.

5. The compound or the salt thereof according to claim 1, wherein in the general formula (I), E is a phenyl group.

6. The compound or the salt thereof according to claim 1, wherein in the general formula (I), Z is a phenyl group, a naphthyl group, or a 5-membered or 6-membered heteroaromatic ring containing 1 to 3 heteroatoms selected from N and S.

7. The compound or the salt thereof according to claim 1, wherein in the general formula (I), Z is a phenyl group.

8. The compound or the salt thereof according to claim 1, wherein in the general formula (I), Y is an oxygen atom.

9. The compound or the salt thereof according to claim 1, wherein in the general formula (I), A is N, and D is a hydrogen.

10. The compound or the salt thereof according to claim 1, wherein the compound is represented by Formula (II),

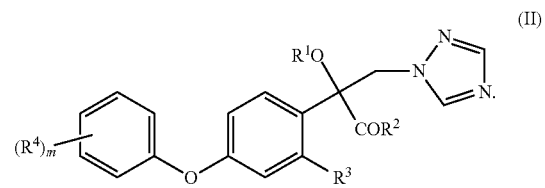

11. A method for producing a compound represented by Formula (I) according to claim 1, the method comprising a step of converting a compound represented by Formula (V),

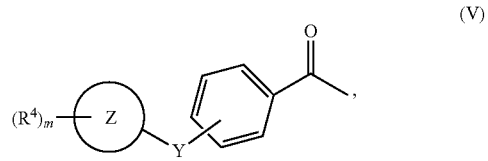

into a compound represented by Formula (VI),

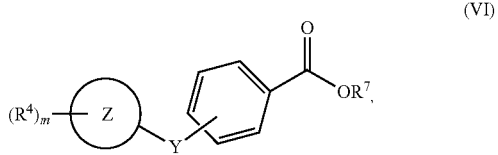

by using a dialkyl sulfate represented by Formula (VII),

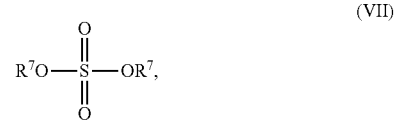

or $R^7$-LG, with LG being a nucleophilically substitutable leaving group, and iodine and a carbonate in dimethyl sulfoxide.

12. The production method according to claim 11, wherein LG in $R^7$-LG is a halogen group.

13. The production method for producing the compound represented by the general formula (VI) described above according to claim 11, the method comprising a step of converting the compound represented by the general formula (V) into the compound represented by the general formula (VI) by using $R^7$-LG, with LG being a nucleophilically substitutable leaving group, and iodine and a carbonate in dimethyl sulfoxide.

14. An agricultural or horticultural chemical agent, or a protective agent for industrial material comprising a compound represented by Formula (I) according to claim 1 as an active ingredient.

15. A compound represented by Formula (I),

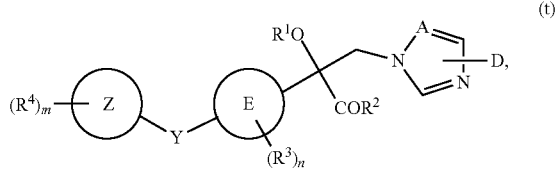

(t)

or agrochemically acceptable salt thereof, wherein:

A is N;

D is a hydrogen;

$R^1$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, a phenyl-$C_2$-$C_4$-alkynyl group, or COX$R^5$;

where $R^5$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group;

X is a single bond, —O—, or —NR$^6$—;

$R^6$ is a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group; and $R^5$ and $R^6$ may form a ring;

$R^2$ is —OR$^7$ or —NR$^8$R$^9$;

$R^7$, $R^8$ and $R^9$ are each independently a hydrogen, a $C_1$-$C_6$-alkyl group, a $C_2$-$C_6$-alkenyl group, a $C_2$-$C_6$-alkynyl group, a $C_3$-$C_8$-cycloalkyl group, a $C_3$-$C_8$-cycloalkyl-$C_1$-$C_4$-alkyl group, a phenyl group, a phenyl-$C_1$-$C_4$-alkyl group, a phenyl-$C_2$-$C_4$-alkenyl group, or a phenyl-$C_2$-$C_4$-alkynyl group, and $R^8$ and $R^9$ may form a ring, where aliphatic groups in $R^1$, $R^2$, $R^5$, $R^6$, $R^7$, $R^8$, and $R^9$ may have 1, 2, 3 or the possible maximum number of the same or different groups $R^a$, and $R^a$ is independently selected from a halogen group, a cyano group, a nitro group, a $C_1$-$C_4$-alkoxy group, and a $C_1$-$C_4$-haloalkoxy group;

$R^4$ is a halogen group, a cyano group, a nitro group, an amino group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, a $C_1$-$C_4$-alkylamino group, a $C_1$-$C_4$-dialkylamino group, a $C_1$-$C_4$-alkylacylamino group, —SOR$^{10}$, or —SF$_5$;

the cycloalkyl group or phenyl group parts in $R^1$, $R^2$, $R^5$, $R^6$, $R^7$, $R^8$, and $R^9$, or the phenyl group part in $R^4$ may have 1, 2, 3, 4, 5, or the possible maximum number of the same or different groups $R^b$, and $R^b$ is independently selected from a halogen group, a cyano group, a nitro group, a $C_1$-$C_4$-alkyl group, a $C_1$-$C_4$-alkoxy group, a $C_1$-$C_4$-haloalkyl group, and a $C_1$-$C_4$-haloalkoxy group;

$R^3$ is a halogen group, a cyano group, a nitro group, a phenyl group, a phenyl-oxy group, a $C_1$-$C_4$-alkyl group, a $C_1$-$C_4$-haloalkyl group, a $C_1$-$C_4$-alkoxy group, a $C_1$-$C_4$-haloalkoxy group, —SOR$^{10}$, or —SF$_5$;

where $R^m$ is a $C_1$-$C_4$-alkyl group or a $C_1$-$C_4$-haloalkyl group;

E is a phenyl group or a 6-membered heteroaromatic ring containing 1 or 2 N atoms;

n $R^3$ are bonded to any substitution sites;

when E is a phenyl group, then n is 0, 1, 2, 3, or 4, and when E is a 6-membered heteroaromatic ring containing 1 or 2 N atoms, then n is 0, 1, or 2;

Y is an oxygen atom;

Z is an aromatic hydrocarbon group which is a phenyl group or a naphthyl group, or a 5-membered or 6-membered heteroaromatic ring or 9-membered or 10-membered heteroaromatic ring formed of 2 rings, containing 1 to 4 heteroatoms selected from O, N, and S; and m $R^4$ are bonded to any substitution sites;

when Z is a phenyl group, then m is 1, 2, 3, 4, or 5 and when Z is a naphthyl group or a heteroaromatic ring, then m is 0, 1, 2, 3, or 4.

* * * * *